US012698259B2

(12) United States Patent
Gray et al.

(10) Patent No.: US 12,698,259 B2
(45) Date of Patent: Aug. 4, 2026

(54) TRANSCRIPTIONAL ENHANCED ASSOCIATE DOMAIN (TEAD) TRANSCRIPTION FACTOR INHIBITORS AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US); Yao Liu, Brookline, MA (US); Mengyang Fan, Allston, MA (US); Yang Gao, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 828 days.

(21) Appl. No.: 17/285,791

(22) PCT Filed: Oct. 15, 2019

(86) PCT No.: PCT/US2019/056347
§ 371 (c)(1),
(2) Date: Apr. 15, 2021

(87) PCT Pub. No.: WO2020/081572
PCT Pub. Date: Apr. 23, 2020

(65) Prior Publication Data

US 2022/0402869 A1 Dec. 22, 2022

Related U.S. Application Data

(60) Provisional application No. 62/745,942, filed on Oct. 15, 2018.

(51) Int. Cl.

| | |
|---|---|
| ***C07D 205/04*** | (2006.01) |
| ***A61K 45/06*** | (2006.01) |
| ***C07C 233/44*** | (2006.01) |
| ***C07D 207/14*** | (2006.01) |
| ***C07D 209/12*** | (2006.01) |
| ***C07D 211/42*** | (2006.01) |
| ***C07D 211/56*** | (2006.01) |
| ***C07D 223/12*** | (2006.01) |
| ***C07D 401/06*** | (2006.01) |
| ***C07D 401/12*** | (2006.01) |
| ***C07D 403/04*** | (2006.01) |
| ***C07D 405/14*** | (2006.01) |

(Continued)

(52) U.S. Cl.

CPC ............ *C07D 205/04* (2013.01); *A61K 45/06* (2013.01); *C07C 233/44* (2013.01); *C07D 207/14* (2013.01); *C07D 209/12* (2013.01); *C07D 211/42* (2013.01); *C07D 211/56* (2013.01); *C07D 223/12* (2013.01); *C07D 401/06* (2013.01); *C07D 401/12* (2013.01); *C07D 403/04* (2013.01); *C07D 405/14* (2013.01); *C07D 413/04* (2013.01); *C07D 471/04* (2013.01); *C07D 487/04* (2013.01); *C07D 487/10* (2013.01); *C07D 495/04* (2013.01)

(58) Field of Classification Search

CPC .. C07D 205/04; C07D 207/14; C07D 209/12; C07D 211/42; C07D 211/56; C07D 223/12; C07D 401/06; C07D 401/12; C07D 403/04; C07D 405/14; C07D 413/04; C07D 471/04; C07D 487/04; C07D 487/10; C07D 495/04; A61K 45/06; C07C 233/44

See application file for complete search history.

(56) References Cited

U.S. PATENT DOCUMENTS 4,824,468 A * 4/1989 Teach .................. C07D 263/04 548/215
6,004,948 A 12/1999 Blaschke et al.

(Continued)

FOREIGN PATENT DOCUMENTS

CN 106187919 A 12/2016
WO WO1997038983 A1 * 10/1997

(Continued)

OTHER PUBLICATIONS

Richie et al. (European Journal of Medicinal Chemistry 124 (2016) 1057e1068). (Year: 2016).*

(Continued)

*Primary Examiner* — Clinton A Brooks
*Assistant Examiner* — Jerica Katlynn Wilson
(74) *Attorney, Agent, or Firm* — Nielsen IP Law LLC

(57) ABSTRACT

Provided herein are compounds of Formula (I), and pharmaceutically acceptable salts, solvates, hydrates, polymorphs, co-crystals, tautomers, stereoisomers, isotopically labeled derivatives, prodrugs, compositions, and mixtures thereof. Also provided are methods and kits involving the inventive compounds or compositions for treating and/or preventing diseases (e.g., proliferative diseases (e.g., cancers, such as carcinoma, sarcoma, lung cancer, thyroid cancer, skin cancer, ovarian cancer, colorectal cancer, prostate cancer, pancreatic cancer, esophageal cancer, liver cancer, breast cancer)) in a subject. Provided are methods of inhibiting a TEAD transcription factors (e.g., TEAD1, TEAD2, TEAD3, TEAD4) in a subject.

(I)

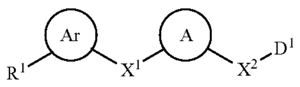

13 Claims, 6 Drawing Sheets

(51) Int. Cl.

| | |
|---|---|
| ***C07D 413/04*** | (2006.01) |
| ***C07D 471/04*** | (2006.01) |
| ***C07D 487/04*** | (2006.01) |
| ***C07D 487/10*** | (2006.01) |
| ***C07D 495/04*** | (2006.01) |

(56) References Cited

U.S. PATENT DOCUMENTS

| | | | |
|---|---|---|---|
| 6,344,459 | B1 | 2/2002 | Bridges et al. |
| 6,972,288 | B1 | 12/2005 | Himmelsbach et al. |
| 9,388,170 | B2 | 7/2016 | Xia et al. |
| 9,908,884 | B2 | 3/2018 | Gray et al. |
| 2014/0309249 | A1 | 10/2014 | Gray et al. |
| 2018/0215721 | A1 | 8/2018 | Wu |

FOREIGN PATENT DOCUMENTS

| | | | | |
|---|---|---|---|---|
| WO | WO 2005/000824 | A1 | 1/2005 | |
| WO | WO 2009/150129 | A1 | 12/2009 | |
| WO | WO 2010/135360 | A1 | 11/2010 | |
| WO | WO 2013/074986 | A1 | 5/2013 | |
| WO | WO-2013144180 | A1 * | 10/2013 | ........... C07D 213/74 |
| WO | WO 2015/047973 | A1 | 4/2015 | |
| WO | WO 2016/182780 | A1 | 11/2016 | |
| WO | WO 2017/053706 | A1 | 3/2017 | |
| WO | WO 2017/111076 | A1 | 6/2017 | |
| WO | WO 2018/098367 | A1 | 5/2018 | |
| WO | WO-2019075386 | A1 * | 4/2019 | ............. A61K 31/00 |
| WO | 2020/087063 | A1 | 4/2020 | |
| WO | 2020/243423 | A1 | 12/2020 | |

OTHER PUBLICATIONS

Jornada et al. Molecules 2016, 21, 42 (Year: 2016).*

International Search Report and Written Opinion for PCT/US2019/056347, mailed Feb. 19, 2020.

Invitation to Pay Additional Fees for PCT/US2019/056347 mailed Dec. 13, 2019.

International Preliminary Report on Patentability for PCT/US2019/056347 mailed Apr. 29, 2021.

International Search Report and Written Opinion for PCT/US2020/066811, mailed May 3, 2021.

Invitation to Pay Additional Fees for PCT/US2020/066811 mailed Mar. 8, 2021.

Pubchem-CID 22760155. Dec. 5, 2007.

Pubchem-CID 68394104. Nov. 30, 2012.

Pubchem-CID 96700286. Jul. 19, 2010.

Pubchem-CID 86839629. Jan. 5, 2010.

CAS Registry No. 2189498-81-3. Mar. 12, 2018.

Chen, Computational study of the binding mode of epidermal growth factor receptor kinase inhibitors. Chem Biol Drug Des. May 2008;71(5):434-446. doi: 10.1111/j.1747-0285.2008.00656.x. Epub Mar. 25, 2008. PMID: 18373549.

Hamada et al., Preparations of Aminosubstituted-acetanilide derivatives and their pharmacological actions. Yakugaku Zasshi 1980;100(5):565-571.

Smaill et al., Tyrosine kinase inhibitors. 15. 4-(Phenylamino)quinazoline and 4-(phenylamino)pyrido[d]pyrimidine acrylamides as irreversible inhibitors of the ATP binding site of the epidermal growth factor receptor. J Med Chem. May 20, 1999;42(10):1803-15. doi: 10.1021/jm9806603. PMID: 10346932.

Tumkevicius et al., A simple synthesis of novel 6,7,8,9-tetrahydro-2-thia-3,5,6,9-tetraazabenz[cd]azulenes. J. Chem. Res. (S) 2000:287-289.

Van Antwerpen et al., Conception of myeloperoxidase inhibitors derived from flufenamic acid by computational docking and structure modification. Bioorg Med Chem. Feb. 15, 2008;16(4):1702-20. doi: 10.1016/j.bmc.2007.11.025. Epub Nov. 13, 2007. PMID: 18063373.

Bum-Erdene, Khuchtumur et al., Small-Molecule Covalent Modification of Conserved Cysteine Leads to Allosteric Inhibition of the TEAD Yap Protein-Protein Interaction, Cell Chemical Biology, Mar. 2019, 378-389, 26.

Gibault, Floraine et al., Toward the Discovery of a Novel Class of YAP-TEAD Interaction Inhibitors by Virtual Screening Approach Targeting YAP-TEAD Protein-Protein Interface, Cancers, 2018, 14 pages, 10, 140.

Supplementary European search report dated Jun. 15, 2022, EP Application No. 19872571.5, 4 pages.

European search opinion dated Jun. 15, 2022, EP Application No. 19872571.5, 5 pages.

* cited by examiner

NSAID starting point
Flufenamic acid

Molecular Weight: 317.31

TEAD2 + I-34
2 Hr RT 10x
~33% labeling

TRANSCRIPTIONAL ENHANCED ASSOCIATE DOMAIN (TEAD) TRANSCRIPTION FACTOR INHIBITORS AND USES THEREOF

RELATED APPLICATIONS

The present application is a national stage filing under 35 U.S.C. § 371 of International Application, PCT/US2019/056347, filed Oct. 15, 2019, which claims priority under 35 U.S.C. § 119(e) to U.S. provisional application, U.S. Ser. No. 62/745,942, filed Oct. 15, 2018, each of which is incorporated herein by reference.

BACKGROUND OF THE INVENTION

The hippo signaling pathway has key roles in organ size control and tumor suppression. Signal transduction involves a core kinase cascade, leading to YAP/TAZ phosphorylation. Physiological or pathological inactivation leads to dephosphorylation and nuclear accumulation. Nuclear YAP/TAZ binds to transcriptional enhanced associate domains (TEADs) to mediate the target gene expression. The TEAD-YAP complex regulates organ development and amplification of oncogenic factors in many cancers (e.g., sarcoma, lung cancer, thyroid cancer, skin cancer, ovarian cancer, colorectal cancer, prostate cancer, pancreatic cancer, esophageal cancer, liver cancer, breast cancer). Several genes in the hippo signaling pathway have been identified as tumor suppressors, and mutations in these genes have been associated with different human cancers. Additionally, elevated YAP levels have been associated with certain human cancers.

The attachment of fatty acid palmitate to cysteine residues regulates protein trafficking, membrane localization and signaling activities. TEAD transcription factors have been found to possess intrinsic palmitoylating enzyme-like activity and undergo autopalmitoylation.

SUMMARY OF THE INVENTION

Described herein are compounds of Formula (I), and pharmaceutically acceptable salts, solvates, hydrates, polymorphs, co-crystals, tautomers, stereoisomers, isotopically labeled derivatives, prodrugs, compositions, and mixtures thereof. The compounds of Formula (I), and pharmaceutically acceptable salts, solvates, hydrates, polymorphs, co-crystals, tautomers, stereoisomers, isotopically labeled derivatives, prodrugs, compositions, and mixtures thereof, may inhibit the activity of a transcription factor (e.g., a TEAD family transcription factor) in a cell, biological sample, tissue, or subject. Disclosed herein are compounds that bind to a cysteine located in the central pocket of a YAP-binding domain (YBD) on a transcription factor (e.g. a TEAD transcription factor). Methods of using the disclosed compounds, and pharmaceutically acceptable salts, solvates, hydrates, polymorphs, co-crystals, tautomers, stereoisomers, isotopically labeled derivatives, prodrugs, compositions, and mixtures thereof, to study the inhibition of a transcription factor (e.g., TEAD1, TEAD2, TEAD3, TEAD4) are also described. The compounds described herein may be useful as therapeutics for the prevention and/or treatment of diseases associated with the overexpression and/or aberrant (e.g., increased or unwanted) activity of a transcription factor (e.g., TEAD1, TEAD2, TEAD3, or TEAD4). The compounds described herein may be useful in treating and/or preventing a disease or condition, e.g., a proliferative disease (e.g., cancers), in a subject in need thereof. Also provided are uses, pharmaceutical compositions, and kits including a compound described herein.

In one aspect, the present disclosure provides compounds of Formula (I):

(I)

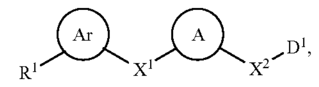

and pharmaceutically acceptable salts, solvates, hydrates, polymorphs, co-crystals, tautomers, stereoisomers, isotopically labeled derivatives, prodrugs, compositions, and mixtures thereof, wherein $R^1$, Ar, $X^1$, $X^2$, A, and $D^1$ are as defined herein. $D^1$ is a warhead which in some embodiments covalently binds a TEAD transcription factor (e.g., TEAD1, TEAD2, TEAD3, or TEAD4). In certain embodiments, the warhead covalently binds to a TEAD transcription factor, e.g., TEAD1, TEAD2, TEAD3, or TEAD4.

In one aspect, the present disclosure provides compounds of Formula (I), of the formula:

(I-a)

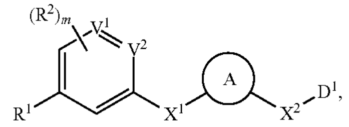

and pharmaceutically acceptable salts, solvates, hydrates, polymorphs, co-crystals, tautomers, stereoisomers, isotopically labeled derivatives, prodrugs, compositions, and mixtures thereof, wherein $R^1$, Ar, $X^1$, $X^2$, A, and $D^1$ are as defined herein.

In another aspect, the present disclosure provides compounds of Formula (I), of the formula:

(I-b)

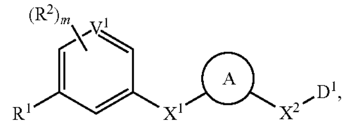

or a pharmaceutically acceptable salt, solvate, hydrate, polymorph, co-crystal, tautomer, stereoisomer, isotopically labeled derivative, prodrug, compositions, and mixtures thereof, wherein $R^1$, Ar, $X^1$, $X^2$, A, and $D^1$ are as defined herein.

Exemplary compounds of Formula (I) include, but are not limited to:

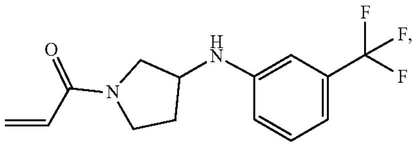

-continued

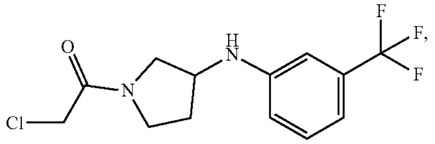

,

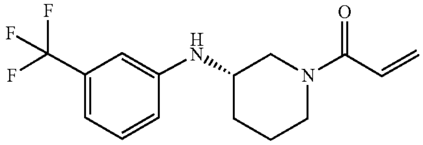

,

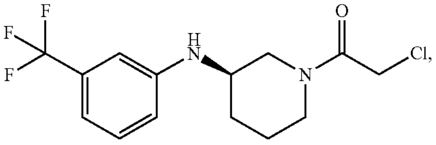

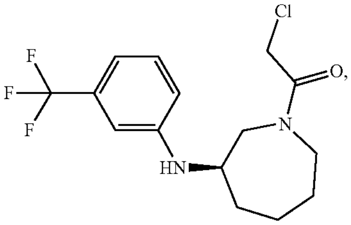

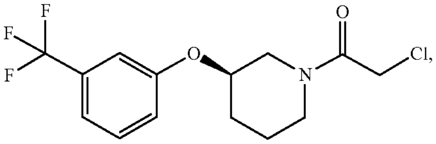

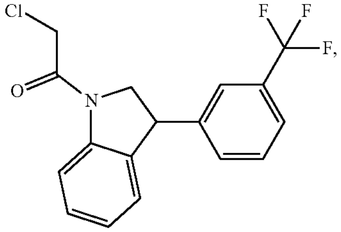

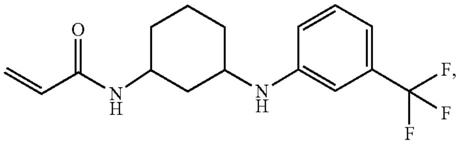

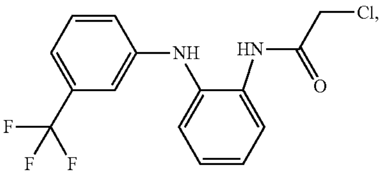

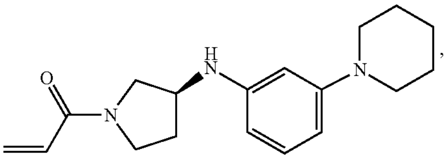

-continued

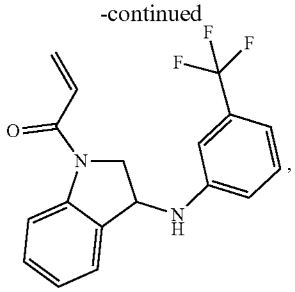

and pharmaceutically acceptable salts, solvates, hydrates, polymorphs, co-crystals, tautomers, stereoisomers, isotopically labeled derivatives, prodrugs, compositions, and mixtures thereof.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease (e.g., a proliferative disease) in a subject in need thereof. The pharmaceutical composition may be useful for inhibiting the activity of TEAD family transcription factor (e.g., TEAD1, TEAD2, TEAD3, or TEAD4) in a subject, biological sample, tissue, or cell. The compounds described herein may be useful in treating and/or preventing a disease or condition, e.g., a proliferative disease (e.g., cancers (e.g., sarcoma, carcinoma, lung cancer, thyroid cancer, skin cancer, ovarian cancer, colorectal cancer, prostate cancer, pancreatic cancer, esophageal cancer, liver cancer, breast cancer)).

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a disease (e.g., a proliferative disease) in a subject in need thereof, or inhibiting the activity of a TEAD family transcription factor (e.g., TEAD1, TEAD2, TEAD3, or TEAD4) in a subject, biological sample, tissue, or cell. In certain embodiments, the disease is a proliferative disease (e.g., cancer (e.g., carcinoma, sarcoma, carcinoma, lung cancer, thyroid cancer, skin cancer, ovarian cancer, colorectal cancer, prostate cancer, pancreatic cancer, esophageal cancer, liver cancer, breast cancer)).

In another aspect, described herein are methods for treating and/or preventing a disease (e.g., a proliferative disease). Exemplary proliferative diseases which may be treated include diseases associated with the overexpression or increased activity of a TEAD transcription factor, (e.g., cancer (e.g., carcinoma, sarcoma, lung cancer, thyroid cancer, skin cancer, ovarian cancer, colorectal cancer, prostate cancer, pancreatic cancer, esophageal cancer, liver cancer, breast cancer)).

Another aspect relates to methods of inhibiting the activity of a transcription factor (e.g., TEAD (e.g., TEAD1, TEAD2, TEAD3, or TEAD4)) using a compound described herein in a biological sample (e.g., cell, tissue). In another aspect, described herein are methods of inhibiting the activity of a transcription factor (e.g., TEAD (e.g., TEAD1, TEAD2, TEAD3, or TEAD4)) using a compound described herein in a subject. In certain embodiments, the method involves the inhibition of TEAD1, TEAD2, TEAD3, or TEAD4

Described herein are methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent (e.g., an anti-proliferative agent).

In yet another aspect, the present disclosure provides compounds of Formula (I), and pharmaceutically acceptable salts, solvates, hydrates, polymorphs, co-crystals, tautomers, stereoisomers, isotopically labeled derivatives, prodrugs, compositions, and mixtures thereof, for use in the treatment of a disease (e.g., a proliferative disease) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿ is a single bond where the stereochemistry of the moieties immediately attached thereto is not specified, --- is absent or a single bond, and ⎓ or ⎓ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $—CF_3$, —Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $—CHF_2$, $—CH_2F$, $—CF_3$, $—CH_2CF_3$, $—CF_2CF_3$, $—CF_2CF_2CF_3$, $—CCl_3$, $—CFCl_2$, $—CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., $—CH═CHCH_3$ or

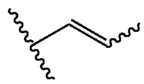

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and lor 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2 -propynyl ($C_3$), 1-butynyl ($C_4$), 2-butynyl ($C_4$), and the like. Examples of $C_{2-6}$ alkenyl groups include the aforementioned $C_{24}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and lor 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$)

and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl. In certain embodiments, the heteroaryl group is thiophene, benzothiophene, furan, isobenzofuran, pyrrole, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, triazole, tetrazole, oxazole, isoxazole, thiazole, oxazole, or the like.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R)_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{aa})_2$, —P(═O)$(OR^{cc})_2$, —OP(═O)$(R^{aa})_2$, —OP(═O)$(OR^{cc})_2$, —P(═O)$(N(R^{bb})_2)_2$, —OP(═O)$(N(R^{bb})_2)_2$, —$NR^{bb}$P(═O)$(R^{aa})_2$, —$NR^{bb}$P(═O)$(OR^{cc})_2$, —$NR^{bb}$P(═O)$(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, ═$NN(R^{bb})_2$, ═$NNR^{bb}$C(═O)$R^{aa}$, =$NNR^{bb}$C(═O)$OR^{aa}$, =$NNR^{bb}S$(═O)$_2R^{aa}$, ═$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)N(Ra)$_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), $—OCO_2(C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)($OC_{1-6}$ alkyl)$_2$, —P(=O)($C_{1-6}$ alkyl)$_2$, —OP(=O)($C_{1-6}$ alkyl)$_2$, —OP(=O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)Rt, —$OSO_2R^{aa}$, —OSi($R^{aa}$)$_3$, —OP($R^{cc}$)$_2$, —OP($R^{cc}$)$_3^+X^-$, —OP($OR^{cc}$)$_2$, —OP($OR^{cc}$)$_3^+X^-$, —OP(=O)($R^{aa}$)$_2$, —OP(=O)($OR^{cc}$)$_2$, and —OP(=O)(N($R^{bb}$))$_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —$SO_2$N($R^{bb}$)$_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)$OR^{X1}$, —C(=O)—O—C(=O)$R^{X1}$, —C(=O)$SR^{X1}$, —C(=O)N($R^{X1}$)$_2$, —C(=S)$R^{X1}$, —C(=S)N($R^{X1}$)$_2$, —C(=S)S($R^{X1}$), —C(=$NR^{X1}$)$R^{X1}$, —C(=$NR^{X1}$)$OR^{X1}$, —C(=NRx)$SR^{X1}$, and —C(=$NR^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$), —C(=$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quintenary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{aa}$, —$SO_2OR^{cc}$, —$SOR^{aa}$, —C(=S)N($R^{cc}$)$_2$, —C(═O)SR$^{cc}$, —C(═S)SR$^{cc}$, —P(═O)(OR$^{cc}$)$_2$, —P(═O)(R$^{aa}$)$_2$, —P(═O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(═O)R$^{aa}$, —C(═O)N(R$^{cc}$)$_2$, —CO$_2$R$^{aa}$, —SO$_2$R$^{aa}$, —C(═NR$^{cc}$)R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{aa}$, —SO$_2$OR$^{cc}$, —SOR$^{aa}$, —C(═S)N(R$^{cc}$)$_2$, —C(═O)SR$^{cc}$, —C(═S)SR$^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(═O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5- dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as a "hydroxyl protecting group"). Oxygen protecting groups include, but are not limited to, —$R^{aa}$, —$N(R^{bb})_2$, —C(═O)S$R^{aa}$, —C(═O)$R^{aa}$, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)$R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1 -(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N' -tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)S$R^{aa}$, —C(═O)$R^{aa}$, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)$R^{aa}$, —$SO_2R^{aa}$, —$Si(R^{aa})_3$, —$P(R^{cc})_2$, —$P(R^{cc})_3^+X^-$, —$P(O^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., $—OC(═O)SR^{aa}$, $—OC(═O)R^{aa}$, $—OCO_2R^{aa}$, $—OC(═O)N(R^{bb})_2$, $—OC(═NR^{bb})R^{aa}$, $—OC(═NR^{bb})OR^{aa}$, $—OC(═NR^{bb})N(R^{bb})_2$, $—OS(═O)R^{aa}$, $—OSO_2R^{aa}$, $—OP(R^{cc})_2$, $—OP(R^{cc})_3$, $—OP(═O)_2R^{aa}$, $—OP(═O)(R^{aa})_2$, $—OP(═O)(OR^{cc})_2$, $—OP(═O)_2N(R^{bb})_2$, and $—OP(═O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the $—CH_2OH$ side branch. The alternative form, in which the $—CH_2OH$ substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$—includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH$(C_2H_5)$— is a $C_1$ hydrocarbon chain, and

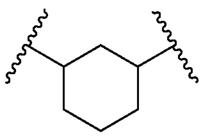 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C═C and/or C≡C bonds anywhere in the hydrocarbon chain. For instance, —CH═CH—$(CH_2)_2$—, —$CH_2$—C≡C—$CH_2$—, and —C≡C—CH═CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —CH$(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For insurance,

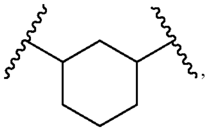, 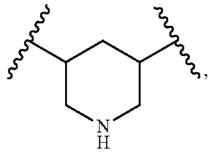,

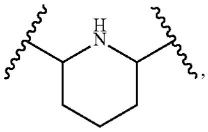, 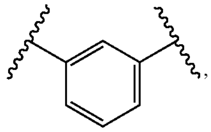,

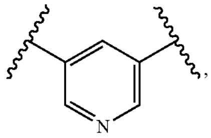, and 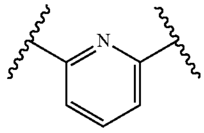

are all examples of a hydrocarbon chain. In contrast, in certain embodiments,

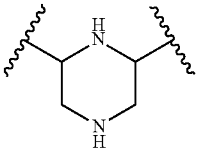 and 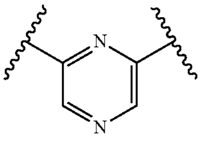

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

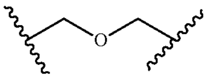 [SMILES: *COC*]

is a $C_3$ hydrocarbon chain wherein one chain atom is replaced with an oxygen atom.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibition of a TEAD transcription factor. In certain embodiments, a therapeutically effective amount is an amount sufficient for treating a proliferative disease.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for inhibition of a TEAD transcription factor. In certain embodiments, a prophylactically effective amount is an amount sufficient for treating a proliferative disease.

As used herein the term "inhibit" or "inhibition" in the context of proteins, for example, in the context of TEAD transcription factors, refers to a reduction in the activity of the transcription factor. In some embodiments, the term refers to a reduction of the level of activity, e.g., TEAD1, TEAD2, TEAD3, or TEAD4 activity, to a level that is statistically significantly lower than an initial level, which may, for example, be a baseline level of activity. In some embodiments, the term refers to a reduction of the level of enzyme activity, e.g., TEAD1, TEAD2, TEAD3, or TEAD4 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of transcription factor activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, $25^{th}$ ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij© 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragées, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragées, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a transcription factor in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease) in a subject in need thereof. In certain embodiments, the kits are useful for preventing a disease (e.g., proliferative disease) in a subject in need thereof. In certain embodiments, the kits are useful for reducing the risk of developing a disease (e.g., proliferative disease) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease) in a subject in need thereof. In certain embodiments, the kits and instructions provide for preventing a disease (e.g., proliferative disease) in a subject in need thereof. In certain embodiments, the kits and instructions provide for reducing the risk of developing a disease (e.g., proliferative disease) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

A "transcription factor" is a type of protein that is involved in the process of transcribing DNA into RNA. Transcription factors can work independently or with other proteins in a complex to either stimulate or repress transcription. Transcription factors contain at least one DNA-binding domain that give them the ability to bind to specific sequences of DNA. Other proteins such as coactivators, chromatin remodelers, histone acetyltransferases, histone deacetylases, kinases, and methylases are also essential to gene regulation, but lack DNA-binding domains, and therefore are not transcription factors. These exemplary human transcription factors include, but are not limited to, AC008770.3, AC023509.3, AC092835.1, AC138696.1, ADNP, ADNP2, AEBP1, AEBP2, AHCTF1, AHDC1, AHR, AHRR, AIRE, AKAP8, AKAP8L, AKNA, ALX1, ALX3, ALX4, ANHX, ANKZF1, AR, ARGFX, ARHGAP35, ARID2, ARID3A, ARID3B, ARID3C, ARID5A, ARID5B, ARNT, ARNT2, ARNTL, ARNTL2, ARX, ASCL1, ASCL2, ASCL3, ASCL4, ASCL5, ASH1L, ATF1, ATF2, ATF3, ATF4, ATF5, ATF6, ATF6B, ATF7, ATMIN, ATOH1, ATOH7, ATOH8, BACH1, BACH2, BARHL1, BARHL2, BARX1, BARX2, BATF, BATF2, BATF3, BAZ2A, BAZ2B, BBX, BCL11A, BCL11B, BCL6, BCL6B, BHLHA15, BHLHA9, BHLHE22, BHLHE23, BHLHE40, BHLHE41, BNC1, BNC2, BORCS-MEF2B, BPTF, BRF2, BSX, C11 orf95, CAMTA1, CAMTA2, CARF, CASZ1, CBX2, CC2D1A, CCDC169-SOHLH2, CCDC17, CDC5L, CDX1, CDX2, CDX4, CEBPA, CEBPB, CEBPD, CEBPE, CEBPG, CEBPZ, CENPA, CENPB, CENPBD1, CENPS, CENPT, CENPX, CGGBP1, CHAMP1, CHCHD3, CIC, CLOCK, CPEB1, CPXCR1, CREB1, CREB3, CREB3L1, CREB3L2, CREB3L3, CREB3L4, CREB5, CREBL2, CREBZF, CREM, CRX, CSRNP1, CSRNP2, CSRNP3, CTCF, CTCFL, CUX1, CUX2, CXXC1, CXXC4, CXXC5, DACH1, DACH2, DBP, DBX1, DBX2, DDIT3, DEAFI, DLX1, DLX2, DLX3, DLX4, DLX5, DLX6, DMBX1, DMRT1, DMRT2, DMRT3, DMRTA1, DMRTA2, DMRTB1, DMRTC2, DMTF1, DNMT1, DNTTIP1, DOT1L, DPF1, DPF3, DPRX, DR1, DRAP1, DRGX, DUX1, DUX3, DUX4, DUXA, DZIP1, E2F1, E2F2, E2F3, E2F4, E2F5, E2F6, E2F7, E2F8, E4F1, EBF1, EBF2, EBF3, EBF4, EEA1, EGR1, EGR2, EGR3, EGR4, EHF, ELF1, ELF2, ELF3, ELF4, ELF5, ELK1, ELK3, ELK4, EMX1, EMX2, EN1, EN2, EOMES, EPAS1, ERF, ERG, ESR1, ESR2, ESRRA, ESRRB, ESRRG, ESX1, ETS1, ETS2, ETV1, ETV2, ETV3, ETV3L, ETV4, ETV5, ETV6, ETV7, EVX1, EVX2, FAM170A, FAM200B, FBXL19, FERD3L, FEV, FEZF1, FEZF2, FIGLA, FIZ1, FLI1, FLYWCH1, FOS, FOSB, FOSL1, FOSL2, FOXA1, FOXA2, FOXA3, FOXB1, FOXB2, FOXC1, FOXC2, FOXD1, FOXD2, FOXD3, FOXD4, FOXD4L1, FOXD4L3, FOXD4L4, FOXD4L5, FOXD4L6, FOXE1, FOXE3, FOXF1, FOXF2, FOXG1, FOXH1, FOXI1, FOXI2, FOXI3, FOXJ1, FOXJ2, FOXJ3, FOXK1, FOXK2, FOXL1, FOXL2, FOXM1, FOXN1, FOXN2, FOXN3, FOXN4, FOXO1, FOXO3, FOXO4, FOXO6, FOXP1, FOXP2, FOXP3, FOXP4, FOXQ1, FOXR1, FOXR2, FOXS1, GABPA, GATA1, GATA2, GATA3, GATA4, GATA5, GATA6, GATAD2A, GATAD2B, GBX1, GBX2, GCM1, GCM2, GFI1, GFI1B, GLI1, GLI2, GLI3, GLI4, GLIS1, GLIS2, GLIS3, GLMP, GLYR1, GMEB1, GMEB2, GPBP1, GPBP1L1, GRHL1, GRHL2, GRHL3, GSC, GSC2, GSX1, GSX2, GTF2B, GTF2I, GTF2IRD1, GTF2IRD2, GTF2IRD2B, GTF3A, GZF1, HAND1, HAND2, HBP1, HDX, HELT, HES1, HES2, HES3, HES4, HES5, HES6, HES7, HESX1, HEY1, HEY2, HEYL, HHEX, HIC1, HIC2, HIF1A, HIF3A, HINFP, HIVEP1, HIVEP2, HIVEP3, HKR1, HLF, HLX, HMBOX1, HMG20A, HMG20B, HMGA1, HMGA2, HMGN3, HMX1, HMX2, HMX3, HNF1A, HNF1B, HNF4A, HNF4G, HOMEZ, HOXA1, HOXA10, HOXA11, HOXA13, HOXA2, HOXA3, HOXA4, HOXA5, HOXA6, HOXA7, HOXA9, HOXB1, HOXB13, HOXB2, HOXB3, HOXB4, HOXB5, HOXB6, HOXB7, HOXB8, HOXB9, HOXC10, HOXC11, HOXC12, HOXC13, HOXC4, HOXC5, HOXC6, HOXC8, HOXC9, HOXD1, HOXD10, HOXD11, HOXD12, HOXD13, HOXD3, HOXD4, HOXD8, HOXD9, HSF1, HSF2, HSF4, HSF5, HSFX1, HSFX2, HSFY1, HSFY2, IKZF1, IKZF2, IKZF3, IKZF4, IKZF5, INSM1, INSM2, IRF1, IRF2, IRF3, IRF4, IRF5, IRF6, IRF7, IRF8, IRF9, IRX1, IRX2, IRX3, IRX4, IRX5, IRX6, ISL1, ISL2, ISX, JAZF1, JDP2, JRK, JRKL, JUN, JUNB, JUND, KAT7, KCMF1, KCNIP3, KDM2A, KDM2B, KDM5B, KIN, KLF1, KLF10, KLF11, KLF12, KLF13, KLF14, KLF15, KLF16, KLF17, KLF2, KLF3, KLF4, KLF5, KLF6, KLF7, KLF8, KLF9, KMT2A, KMT2B, L3MBTL1, L3MBTL3, L3MBTL4, LBX1, LBX2, LCOR, LCORL, LEF1, LEUTX, LHX1, LHX2, LHX3, LHX4, LHX5, LHX6, LHX8, LHX9, LIN28A, LIN28B, LIN54, LMX1A, LMX1B, LTF, LYL1, MAF, MAFA, MAFB, MAFF, MAFG, MAFK, MAX, MAZ, MBD1, MBD2, MBD3, MBD4, MBD6, MBNL2, MECOM, MECP2, MEF2A, MEF2B, MEF2C, MEF2D, MEIS1, MEIS2, MEIS3, MEOX1, MEOX2, MESP1, MESP2, MGA, MITF, MIXL1, MKX, MLX, MLXIP, MLXIPL, MNT, MNX1, MSANTD1, MSANTD3, MSANTD4, MSC, MSGN1, MSX1, MSX2, MTERF1, MTERF2, MTERF3, MTERF4, MTF1, MTF2, MXD1, MXD3, MXD4, MXII, MYB, MYBL1, MYBL2, MYC, MYCL, MYCN, MYF5, MYF6, MYNN, MYOD1, MYOG, MYPOP, MYRF, MYRFL, MYSM1, MYT1, MYT1L, MZF1, NACC2, NAIF1, NANOG, NANOGNB, NANOGP8, NCOA1, NCOA2, NCOA3, NEUROD1, NEUROD2, NEUROD4, NEUROD6, NEUROG1, NEUROG2, NEUROG3, NFAT5, NFATC1, NFATC2, NFATC3, NFATC4, NFE2, NFE2L1, NFE2L2, NFE2L3, NFE4, NFIA, NFIB, NFIC, NFIL3, NFIX, NFKB1, NFKB2, NFX1, NFXL1, NFYA, NFYB, NFYC, NHLH1, NHLH2, NKRF, NKX1-1, NKX1-2, NKX2-1, NKX2-2, NKX2-3, NKX2-4, NKX2-5, NKX2-6, NKX2-8, NKX3-1, NKX3-2, NKX6-1, NKX6-2, NKX6-3, NME2, NOBOX, NOTO, NPAS1, NPAS2, NPAS3, NPAS4, NR0B1, NR1D1, NR1D2, NR1H2, NR1H3, NR1H4, NR1I2, NR1I3, NR2C1, NR2C2, NR2E1, NR2E3, NR2F1, NR2F2, NR2F6, $NR3C_1$, $NR3C_2$, NR4A1, NR4A2, NR4A3, NR5A1, NR5A2, NR6A1, NRF1, NRL, OLIG1, OLIG2, OLIG3, ONECUT1, ONECUT2, ONECUT3, OSR1, OSR2, OTP, OTX1, OTX2, OVOL1, OVOL2, OVOL3, PA2G4, PATZ1, PAX1, PAX2, PAX3, PAX4, PAX5, PAX6, PAX7, PAX8, PAX9, PBX1, PBX2, PBX3, PBX4, PCGF2, PCGF6, PDX1, PEG3, PGR, PHF1, PHF19, PHF20, PHF21A, PHOX2A, PHOX2B, PIN1, PITX1, PITX2, PITX3, PKNOX1, PKNOX2, PLAG1, PLAGL1, PLAGL2, PLSCR1, POGK, POU1F1, POU2AF1, POU2F1, POU2F2, POU2F3, POU3F1, POU3F2, POU3F3, POU3F4, POU4F1, POU4F2, POU4F3, POU5F1, POU5F1B, POU5F2, POU6F1, POU6F2, PPARA, PPARD, PPARG, PRDM1, PRDM10, PRDM12, PRDM13, PRDM14, PRDM15, PRDM16, PRDM2, PRDM4, PRDM5, PRDM6, PRDM8, PRDM9, PREB, PRMT3, PROP1, PROX1, PROX2, PRR12, PRRX1, PRRX2, PTF1A, PURA, PURB, PURG, RAG1, RARA, RARB, RARG, RAX, RAX2, RBAK, RBCK1, RBPJ, RBPJL, RBSN, REL, RELA, RELB, REPINi, REST, REXO4, RFX1, RFX2, RFX3, RFX4, RFX5, RFX6, RFX7, RFX8, RHOXF1, RHOXF2, RHOXF2B, RLF, RORA, RORB, RORC, RREB1, RUNX1, RUNX2, RUNX3, RXRA, RXRB, RXRG, SAFB, SAFB2, SALL1, SALL2, SALL3, SALL4, SATB1, SATB2, SCMH1, SCML4, SCRT1, SCRT2, SCX, SEBOX, SETBP1, SETDB1, SETDB2, SGSM2, SHOX, SHOX2, SIM1, SIM2, SIX1, SIX2, SIX3, SIX4, SIX5, SIX6, SKI, SKIL, SKOR1, SKOR2, SLC2A4RG, SMAD1, SMAD3, SMAD4, SMAD5, SMAD9, SMYD3, SNAI1, SNAI2, SNAI3, SNAPC2, SNAPC4, SNAPC5, SOHLH1, SOHLH2, SON, SOX1, SOX10, SOX11, SOX12, SOX13, SOX14, SOX15, SOX17, SOX18, SOX2, SOX21, SOX3, SOX30, SOX4, SOX5, SOX6, SOX7, SOX8, SOX9, SP1, SP100, SP110, SP140, SP140L, SP2, SP3, SP4, SP5, SP6, SP7, SP8, SP9, SPDEF, SPEN, SPI1, SPIB, SPIC, SPZ1, SRCAP, SREBF1, SREBF2, SRF, SRY, ST18, STAT1, STAT2, STAT3, STAT4, STAT5A, STA5B, STT6, T, TAL1, TAL2, TBP, TBPL1, TBPL2, TBR1, TBX1, TBX10, TBX15, TBX18, TBX19, TBX2, TBX20, TBX21, TBX22, TBX3, TBX4, TBX5, TBX6, TCF12, TCF15, TCF20, TCF21, TCF23, TCF24, TCF3, TCF4, TCF7, TCF7L1, TCF7L2, TCFL5, TEAD1, TEAD2, TEAD3, TEAD4, TEF, TERB1, TERF1, TERF2, TET1, TET2, TET3, TFAP2A, TFAP2B, TFAP2C, TFAP2D, TFAP2E, TFAP4, TFCP2, TFCP2L1, TFDP1, TFDP2, TFDP3, TFE3, TFEB, TFEC, TGIF1, TGIF2, TGIF2LX, TGIF2LY, THAP1, THAP10, THAP11, THAP12, THAP2, THAP3, THAP4, THAP5, THAP6, THAP7, THAP8, THAP9, THRA, THRB, THYN1, TIGD1, TIGD2, TIGD3, TIGD4, TIGD5, TIGD6, TIGD7, TLX1, TLX2, TLX3, TMF1, TOPORS, TP53, TP63, TP73, TPRX1, TRAFD1, TRERF1, TRPS1, TSC22D1, TSHZ1, TSHZ2, TSHZ3, TTF1, TWIST1, TWIST, UBP1, UNCX, USF1, USF2, USF3, VAX1, VAX2, VDR, VENTX, VEZF1, VSX1, VSX2, WIZ, WT1, XBP1, XPA, YBX1, YBX2, YBX3, YY1, YY2, ZBED1, ZBED2, ZBED3, ZBED4, ZBED5, ZBED6, ZBED9, ZBTB1, ZBTB10, ZBTB11, ZBTB12, ZBTB14, ZBTB16, ZBTB17, ZBTB18, ZBTB2, ZBTB20, ZBTB21, ZBTB22, ZBTB24, ZBTB25, ZBTB26, ZBTB3, ZBTB32, ZBTB33, ZBTB34, ZBTB37, ZBTB38, ZBTB39, ZBTB4, ZBTB40, ZBTB41, ZBTB42, ZBTB43, ZBTB44, ZBTB45, ZBTB46, ZBTB47, ZBTB48, ZBTB49, ZBTB5, ZBTB6, ZBTB7A, ZBTB7B, ZBTB7C, ZBTB8A, ZBTB8B, ZBTB9, ZC3H8, ZEB1, ZEB2, ZFAT, ZFHX2, ZFHX3, ZFHX4, ZFP1, ZFP14, ZFP2, ZFP28, ZFP3, ZFP30, ZFP37, ZFP41, ZFP42, ZFP57, ZFP62, ZFP64, ZFP69, ZFP69B, ZFP82, ZFP90, ZFP91, ZFP92, ZFPM1, ZFPM2, ZFX, ZFY, ZGLP1, ZGPAT, ZHX1, ZHX2, ZHX3, ZIC1, ZIC2, ZIC3, ZIC4, ZIC5, ZIK1, ZIM2, ZIM3, ZKSCAN1, ZKSCAN2, ZKSCAN3, ZKSCAN4, ZKSCAN5, ZKSCAN7, ZKSCAN8, ZMAT1, ZMAT4, ZNF10, ZNF100, ZNF101, ZNF107, ZNF112, ZNF114, ZNF117, ZNF12, ZNF121, ZNF124, ZNF131, ZNF132, ZNF133, ZNF134, ZNF135, ZNF136, ZNF138, ZNF14, ZNF140, ZNF141, ZNF142, ZNF143, ZNF146, ZNF148, ZNF154, ZNF155, ZNF157, ZNF16, ZNF160, ZNF165, ZNF169, ZNF17, ZNF174, ZNF175, ZNF177, ZNF18, ZNF180, ZNF181, ZNF182, ZNF184, ZNF189, ZNF19, ZNF195, ZNF197, ZNF2, ZNF20, ZNF200, ZNF202, ZNF205, ZNF207, ZNF208, ZNF211, ZNF212, ZNF213, ZNF214, ZNF215, ZNF217, ZNF219, ZNF22, ZNF221, ZNF222, ZNF223, ZNF224, ZNF225, ZNF226, ZNF227, ZNF229, ZNF23, ZNF230, ZNF232, ZNF233, ZNF234, ZNF235, ZNF236, ZNF239, ZNF24, ZNF248, ZNF25, ZNF250, ZNF251, ZNF253, ZNF254, ZNF256, ZNF257, ZNF26, ZNF260, ZNF263, ZNF264, ZNF266, ZNF267, ZNF268, ZNF273, ZNF274, ZNF275, ZNF276, ZNF277, ZNF28, ZNF280A, ZNF280B, ZNF280C, ZNF280D, ZNF281, ZNF282, ZNF283, ZNF284, ZNF285, ZNF286A, ZNF286B, ZNF287, ZNF292, ZNF296, ZNF3, ZNF30, ZNF300, ZNF302, ZNF304, ZNF311, ZNF316, ZNF317, ZNF318, ZNF319, ZNF32, ZNF320, ZNF322, ZNF324, ZNF324B, ZNF326, ZNF329, ZNF331, ZNF333, ZNF334, ZNF335, ZNF337, ZNF33A, ZNF33B, ZNF34, ZNF341, ZNF343, ZNF345, ZNF346, ZNF347, ZNF35, ZNF350, ZNF354A, ZNF354B, ZNF354C, ZNF358, ZNF362, ZNF365, ZNF366, ZNF367, ZNF37A, ZNF382, ZNF383, ZNF384, ZNF385A, ZNF385B, ZNF385C, ZNF385D, ZNF391, ZNF394, ZNF395, ZNF396, ZNF397, ZNF398, ZNF404, ZNF407, ZNF408, ZNF41, ZNF410, ZNF414, ZNF415, ZNF416, ZNF417, ZNF418, ZNF419, ZNF420, ZNF423, ZNF425, ZNF426, ZNF428, ZNF429, ZNF43, ZNF430, ZNF431, ZNF432, ZNF433, ZNF436, ZNF438, ZNF439, ZNF44, ZNF440, ZNF441, ZNF442, ZNF443, ZNF444, ZNF445, ZNF446, ZNF449, ZNF45, ZNF451, ZNF454, ZNF460, ZNF461, ZNF462, ZNF467, ZNF468, ZNF469, ZNF470, ZNF471, ZNF473, ZNF474, ZNF479, ZNF48, ZNF480, ZNF483, ZNF484, ZNF485, ZNF486, ZNF487, ZNF488, ZNF490, ZNF491, ZNF492, ZNF493, ZNF496, ZNF497, ZNF500, ZNF501, ZNF502, ZNF503, ZNF506, ZNF507, ZNF510, ZNF511, ZNF512, ZNF512B, ZNF513, ZNF514, ZNF516, ZNF517, ZNF518A, ZNF518B, ZNF519, ZNF521, ZNF524, ZNF525, ZNF526, ZNF527, ZNF528, ZNF529, ZNF530, ZNF532, ZNF534, ZNF536, ZNF540, ZNF541, ZNF543, ZNF544, ZNF546, ZNF547, NF548, ZNF549, ZNF550, ZNF551, ZNF552, ZNF554, ZNF555, ZNF556, ZNF557, ZNF558, ZNF559, ZNF560, ZNF561, ZNF562, ZNF563, ZNF564, ZNF565, ZNF566, ZNF567, ZNF568, ZNF569, ZNF57, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF587B, ZNF589, ZNF592, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF614, ZNF615, ZNF616, ZNF618, ZNF619, ZNF620, ZNF621, ZNF623, ZNF624, ZNF625, ZNF626, ZNF627, ZNF628, ZNF629, ZNF630, ZNF639, ZNF641, ZNF644, ZNF645, ZNF646, ZNF648, ZNF649, ZNF652, ZNF653, ZNF654, ZNF655, ZNF658, ZNF66, ZNF660, ZNF662, ZNF664, ZNF665, ZNF667, ZNF668, ZNF669, ZNF670, ZNF671, ZNF672, ZNF674, ZNF675, ZNF676, ZNF677, ZNF678, ZNF679, ZNF680, ZNF681, ZNF682, ZNF683, ZNF684, ZNF687, ZNF688, ZNF689, ZNF69, ZNF691, ZNF692, ZNF695, ZNF696, ZNF697, ZNF699, ZNF7, ZNF70, ZNF700, ZNF701, ZNF703, ZNF704, ZNF705A, ZNF705B, ZNF705D, ZNF705E, ZNF705G, ZNF706, ZNF707, ZNF708, ZNF709, ZNF71, ZNF710, ZNF711, ZNF713, ZNF714, ZNF716, ZNF717, ZNF718, ZNF721, ZNF724, ZNF726, ZNF727, ZNF728, ZNF729, ZNF730, ZNF732, ZNF735, ZNF736, ZNF737, ZNF74, ZNF740, ZNF746, ZNF747, ZNF749, ZNF750, ZNF75A, ZNF75D, ZNF76, ZNF761, ZNF763, ZNF764, ZNF765, ZNF766, ZNF768, ZNF77, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF785, ZNF786, ZNF787, ZNF788, ZNF789, ZNF79, ZNF790, ZNF791, ZNF792, ZNF793, ZNF799, ZNF8, ZNF80, ZNF800, ZNF804A, ZNF804B, ZNF805, ZNF808, ZNF81, ZNF813, ZNF814, ZNF816, ZNF821, ZNF823, ZNF827, ZNF829, ZNF83, ZNF830, ZNF831, ZNF835, ZNF836, ZNF837, ZNF84, ZNF841, ZNF843, ZNF844, ZNF845, ZNF846, ZNF85, ZNF850, ZNF852, ZNF853, ZNF860, ZNF865, ZNF878, ZNF879, ZNF880, ZNF883, ZNF888, ZNF891, ZNF90, ZNF91, ZNF92, ZNF93, ZNF98, ZNF99, ZSCAN1, ZSCAN10, ZSCAN12, ZSCAN16, ZSCAN18, ZSCAN2, ZSCAN20, ZSCAN21, ZSCAN22, ZSCAN23, ZSCAN25, ZSCAN26, ZSCAN29, ZSCAN30, ZSCAN31, ZSCAN32, ZSCAN4, ZSCAN5A, ZSCAN5B, ZSCAN5C, ZSCAN9, ZUFSP, ZXDA, ZXDB, ZXDC, and ZZZ3.

The term "inhibition," "inhibiting," "inhibit," or "inhibitor" refer to the ability of a compound to reduce, slow, halt, or prevent activity of a particular biological process (e.g., a transcription factor) in a cell relative to vehicle.

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g. HERCEPTIN (trastuzumab), T-DMT, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (HTTP://EN.WIKIPEDIA.ORG/WIKI/ABRAXANE"\O" ABRAXANE), http://en.wikipedia.org/wiki/Docosahexaenoic_acid"\o" Docosahexaenoic acid, bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) http://en.wikipedia.org/wiki/ANG1005"\o" ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA@), semaxanib (semaxinib, SU5416), sunitinib (SUTENT®, SU11248), toceranib (PALLADIA@), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA@), sorafenib (NEXAVAR®), everolimus (AFINITOR®), alemtuzumab (CAMPATH®), gemtuzumab ozogamicin (MYLOTARG@), temsirolimus (TORISEL@), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

DETAILED DESCRIPTION OF CERTAIN EMBODIMENTS OF THE INVENTION

Figure 1:
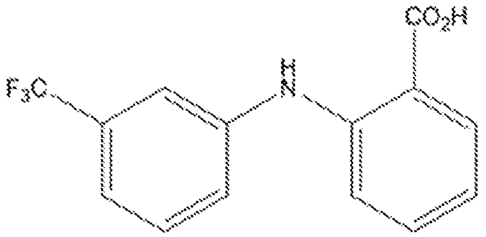
FIG. 1 shows the NSAID starting point-flufenamic acid.
Figure 2:
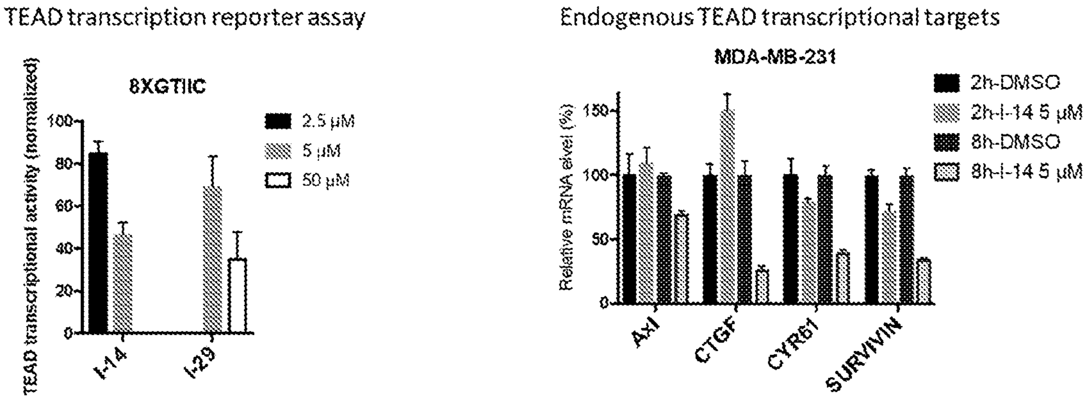
FIG. 2 shows preliminary data for the lead compound, including the TEAD transcription reporter assay and endogenous TEAD transcription targets.
Figure 3:
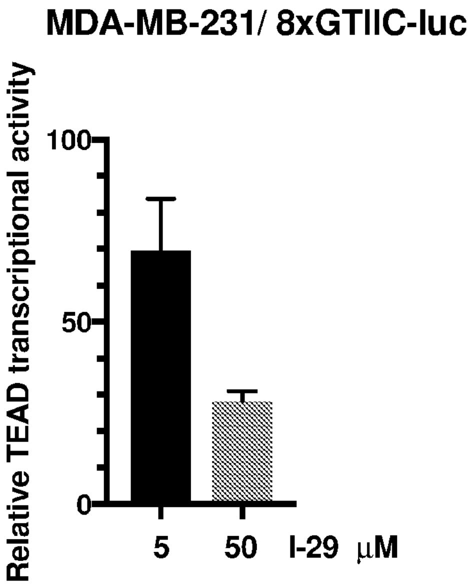
FIG. 3 shows relative TEAD transcriptional activity for MDA-MB-231/8×G TIIC-luc.
Figure 4:
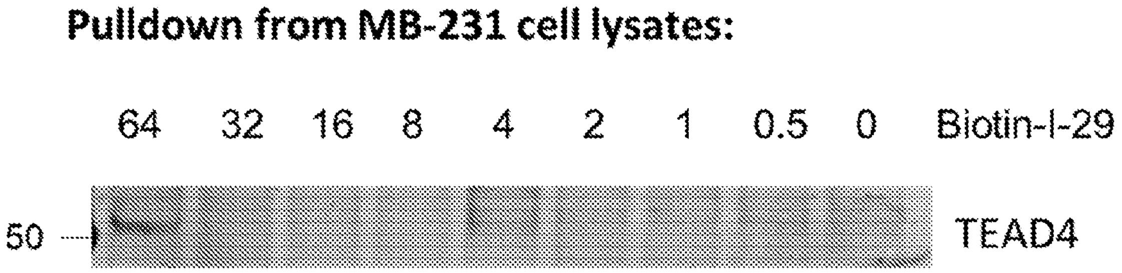
FIG. 4 shows pulldown from MB-231 cell lysates.
Figure 5:
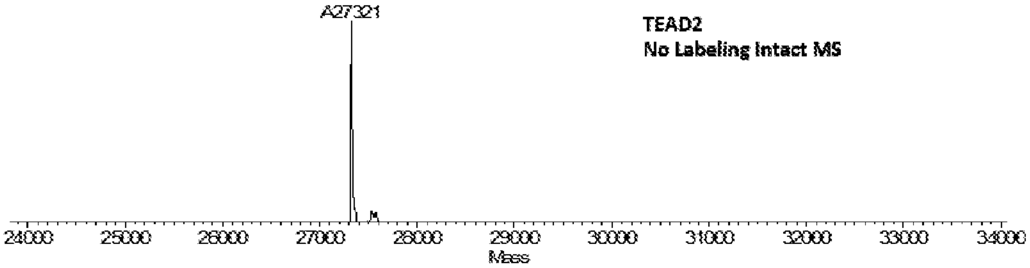
FIG. 5 shows mass spectrometry labeling of TEAD2 with 1-34.
Figure 5:
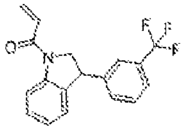
Figure 5:
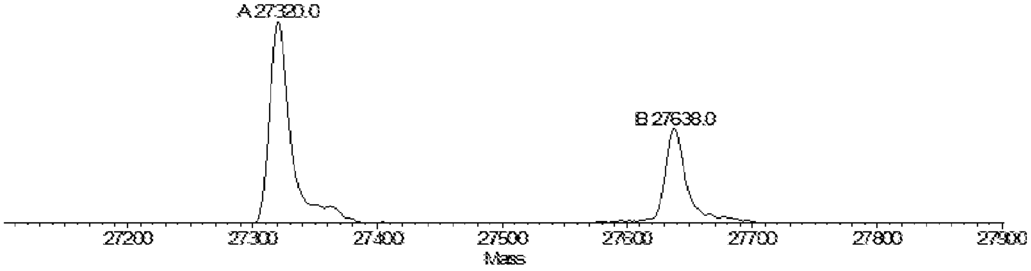
Figure 6:
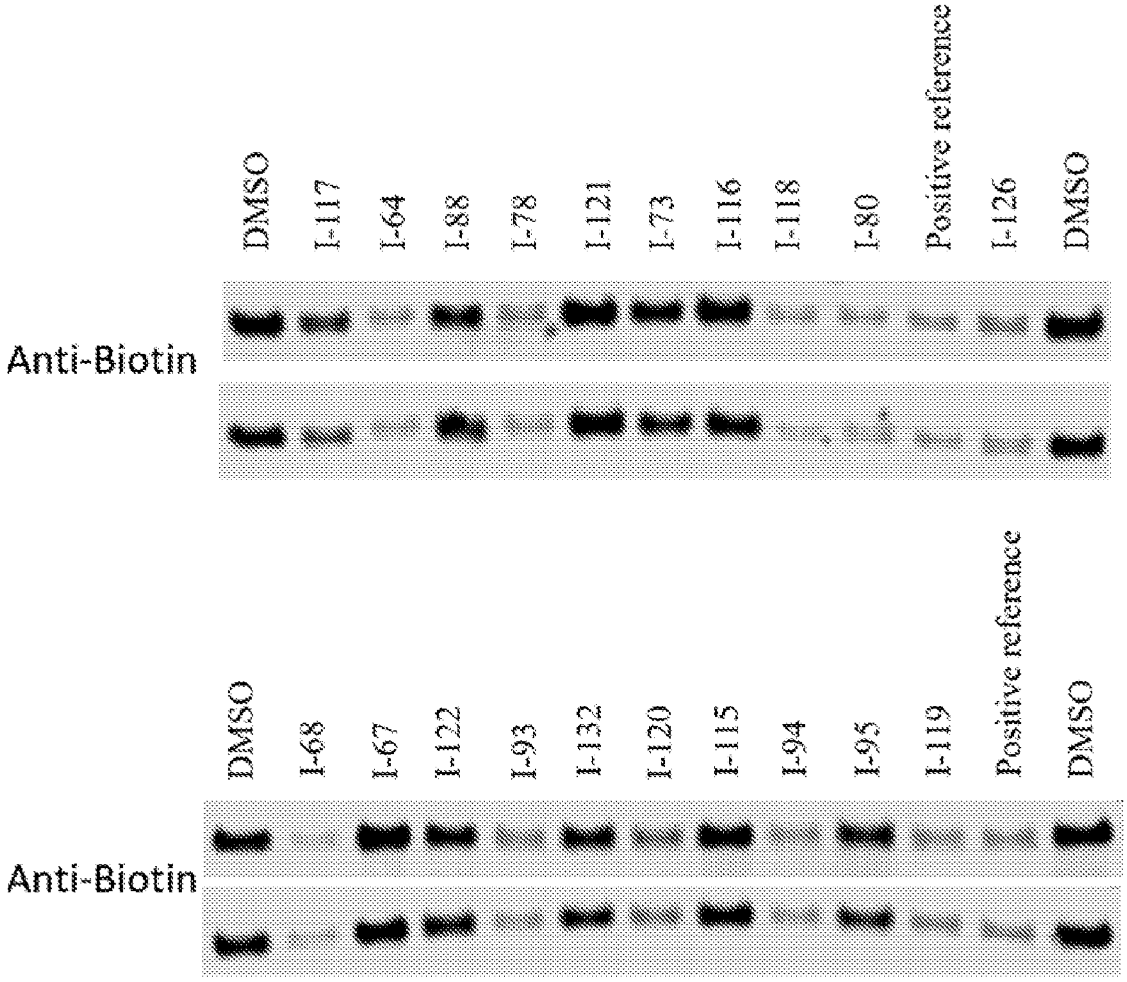
FIG. 6 shows the in vitro inhibition of palmitoylation of TEAD2 protein using the disclosed compounds.

The present disclosure provides pharmaceutical compositions comprising a compound of Formula (I), or a pharmaceutically acceptable salt thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

Compounds

In certain embodiments, a compound described herein is of Formula (I):

(I)

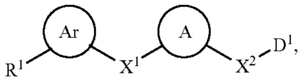

or a pharmaceutically acceptable salt, solvate, hydrate, polymorph, co-crystal, tautomer, stereoisomer, isotopically labeled derivative, prodrug, composition, or mixture thereof, wherein:

Ar is an optionally substituted bicyclic or monocyclic aryl, or an optionally substituted bicyclic or monocyclic heteroaryl;

$R^1$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^f$, —$N(R^f)_2$, —$SR^f$, —$C(=O)R^f$, —$C(=O)OR^f$, —$C(=O)SR^f$, —$C(=O)N(R^f)_2$, —$OC(=O)R^f$, —$OC(=O)OR^f$, —$OC(=O)SR^f$, —$OC(=O)N(R^f)_2$, —$N(R^f)C(=O)R^f$, —$N(R^f)C(=O)OR^f$, —$N(R^f)C(=O)SR^f$, —$N(R^f)C(=O)N(R^f)_2$, —$SC(=O)R^f$, —$SC(=O)OR^f$, —$SC(=O)SR^f$, —$SC(=O)N(R^f)_2$, —$C(=NR^f)R^f$, —$C(=NR^f)OR^f$, —$C(=NR^f)SR^f$, —$C(=NR^f)N(R^f)_2$, —$OC(=NR^f)R^f$, —$OC(=NR^f)OR^f$, —$OC(=NR^f)SR^f$, —$OC(=NR^f)N(R^f)_2$, —$NR^fC(=NR^f)R^f$, —$NR^fC(=NR^f)OR^f$, —$NR^fC(=NR^f)SR^f$, —$NR^fC(=NR^f)N(R^f)_2$, —$SC(=NR^f)R^f$, —$SC(=NR^f)OR^f$, —$SC(=NR^f)SR^f$, —$SC(=NR^f)N(R^f)_2$, —$C(=S)R^f$, —$C(=S)OR^f$, —$C(=S)SR^f$, —$C(=S)N(R^f)_2$, —$S(=O)R^f$, —$SO_2R^f$, —$NR^fSO_2R^f$, —$SO_2N(R^f)_2$, —CN, —SCN, or —$NO_2$;

each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or two instances of $R^f$, when present, can be joined together with the heteroatom to which they are attached to form an optionally substituted heterocyclic ring;

A is an optionally substituted carbocyclic ring, an optionally substituted aryl ring, or an optionally substituted heterocyclic ring;

$X^1$ is a bond, —O—, optionally substituted $C_{1-6}$alkyl, —$N(R^d)$—, —$C(R^d)_2N(R^d)$—, —$C(=O)N(R^d)$—, —$N(R^d)C(=O)$—, —$C(R^d)_2O$—, —$OC(R^d)_2$—, —$C(=O)$—, —$C(=O)O$—, —$C(=O)S$—, —$C(=O)N(R^d)$—, —$OC(=O)$—, —$OC(=O)O$—, —$OC(=O)N(R^d)$—, —$NR^dC(=O)$—, —$N(R^d)C(=O)O$—, —$N(R^d)C(=O)N(R^d)$—, —$C(=NR^d)$—, —$C(=NR^d)O$—, —$C(=NR^d)N(R^d)$—, —$OC(=NR^d)$—, —$OC(=NR^d)O$—, —$OC(=NR^d)S$—, —$OC(=NR^d)N(R^d)$—, —NRdC(=$NR^d$)—, —NRdC(=$NR^d$)O—, —S—, —S(=O)—, or —$SO_2$—, wherein $R^d$ is independently a bond, hydrogen, substituted or unsubstituted $C_{1-6}$alkyl, or a nitrogen protecting group;

$X^2$ is a bond, —O—, optionally substituted $C_{1-6}$alkyl, —N(Ra)—, —$C(R^{da})_2N(R^{da})$—, —$C(=O)N(R^{da})$—, —$N(R^{da})C(=O)$—, —$C(R^{da})_2O$—, —$OC(R^{aa})_2$—, —$C(=O)$—, —$C(=O)O$—, —$C(=O)S$—, —$C(=O)N(R^{da})$, —$OC(=O)$—, —$OC(=O)O$—, —$OC(=O)S$—, —$OC(=O)N(R^{da})$—, —$NR^{da}C(=O)$—, —$N(R^{da})C(=O)O$—, —$N(R^{da})C(=O)S$—, —$N(R^{da})C(=O)N(R^{da})$—, —$SC(=O)$—, —$SC(=O)O$—, —$SC(=O)S$—, —$SC(=O)N(R^{da})$—, —$C(=NR^{da})$—, —$C(=NR^{da})O$—, —$C(=NR^{da})S$—, —$C(=NR^{da})N(R^{da})$—, —$OC(=NR^{da})$—, —$OC(=NR^{da})O$—, —$OC(=NR^{da})S$—, —$OC(=NR^{da})N(R^{da})$, $NR^{da}C(=NR^{da})$—, —$NR^{da}C(=NR^{da})O$—, —$NR^{da}C(=NR^{da})S$—, —$NR_{da}C(=NR^{da})N(R^{da})$—, —$SC(=NR^{da})$—, —$SC(=NR^{da})O$—, —$SC(=NR^{da})S$—, —$SC(=NR^{da})N(R^{da})$—, —S—, —S(=O)—, or —$SO_2$—, wherein $R^{da}$ is independently a bond, hydrogen, substituted or unsubstituted $C_{1-6}$alkyl, or a nitrogen protecting group;

$D^1$ is a warhead of any one of Formulae (i-1) to (i-42):

(i-1)

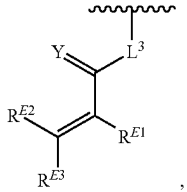

, (i-2)

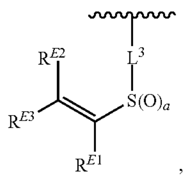

,

-continued
(i-3)
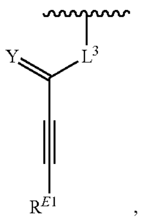
,
(i-4)
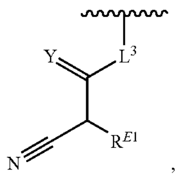
,
(i-5)
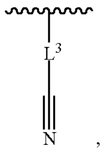
,
(i-6)
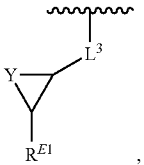
,
(i-7)
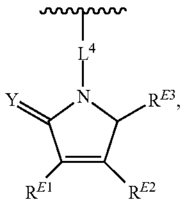
(i-8)
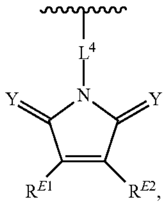
(i-9)
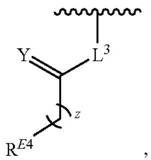
,
(i-10)
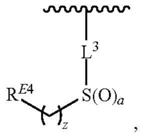
,
-continued
(i-11)
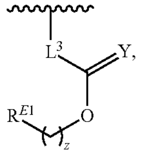
(i-12)
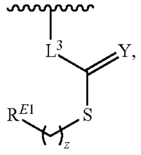
(i-13)
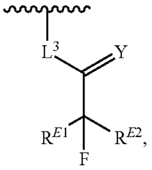
(i-14)
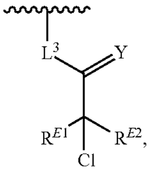
(i-15)
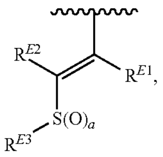
(i-16)
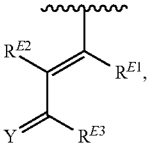
(i-17)
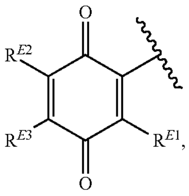
(i-18)
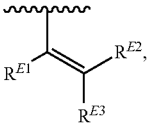
(i-19)
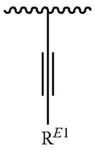
, and -continued
(i-20)
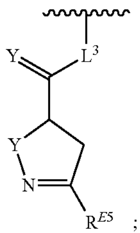
;
(i-21)
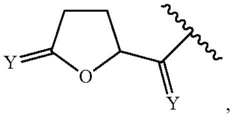
,
(i-22)
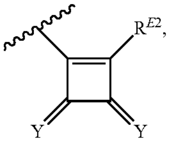
(i-23)
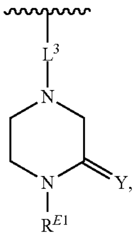
(i-24)
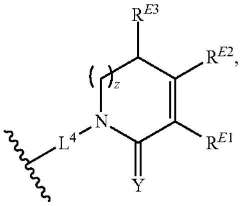
(i-25)
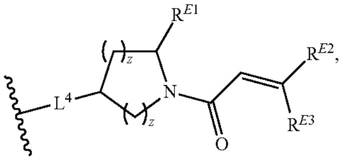
(i-26)
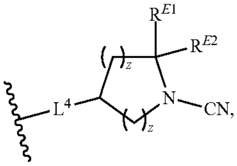
(i-27)
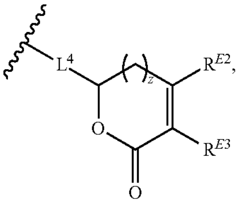
-continued
(i-28)
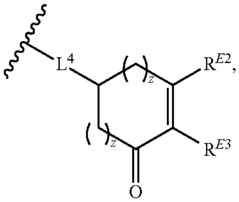
(i-29)
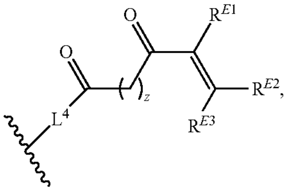
(i-30)
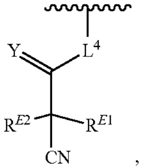
,
(i-31)
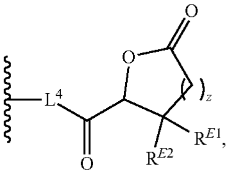
(i-32)
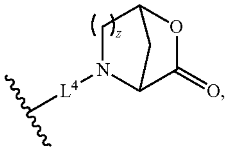
(i-33)
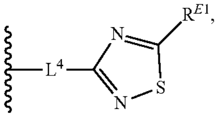
(i-34)
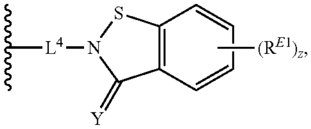
(i-35)
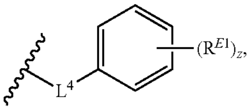
(i-36)
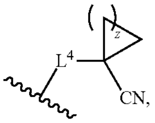
(i-37)
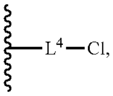

-continued (i-38)

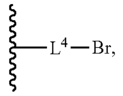

(i-39)

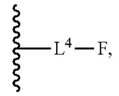

(i-40)

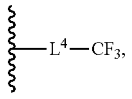

(i-41)

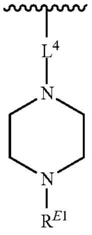

, and (i-42)

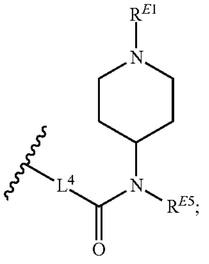

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}$C(═O)—, —C(═O)$NR^{L3a}$—, —SC(═O)—, —C(═O)S—, —OC(═O)—, —C(═O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —$S(═O)_2$—, —$S(═O)_2$O—, —$OS(═O)_2$—, —$S(═O)_2NR^{L3a}$—, or —$NR^{L3a}$$S(═O)_2$—, wherein $R^{L3a}$ is hydrogen, substituted or unsubstituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, and —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, and —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E3a}$, —$CH_2N(R^{E3a})_2$, —$CH_2SR^{E3a}$, —$OR^{E3a}$, —$N(R^{E3a})_2$, and —$SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is —O—, —S—, or —$NR^{E6}$—, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

Formula (I) contains the substituent $R^1$. In certain embodiments, $R^1$ is hydrogen. In certain embodiments, $R^1$ is haloalkyl. In certain embodiments, $R^1$ is trihalomethyl. In certain embodiments, $R^1$ is trifluoromethyl. In certain embodiments, $R^1$ is trichloromethyl. In certain embodiments, $R^1$ is dihalomethyl. In certain embodiments, $R^1$ is difluoromethyl. In certain embodiments, $R^1$ is halomethyl. In certain embodiments, $R^1$ is fluoromethyl. In certain embodiments, $R^1$ is halogen. In certain embodiments, $R^1$ is —F. In certain embodiments, $R^1$ is —Cl. In certain embodiments, $R^1$ is —Br. In certain embodiments, $R^1$ is optionally substituted alkyl. In certain embodiments, $R^1$ is optionally substituted $C_1$-$C_6$alkyl. In certain embodiments, $R^1$ is -Me. In certain embodiments, $R^1$ is

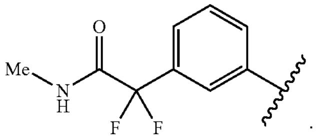 [SMILES: *c1cccc(C(F)(F)C(=O)NC)c1]

In certain embodiments, $R^1$ is optionally substituted alkenyl. In certain embodiments, $R^1$ is optionally substituted alkynyl. In certain embodiments, $R^1$ is optionally substituted carbocyclyl. In certain embodiments, $R^1$ is optionally substituted heterocyclyl. In certain embodiments, $R^1$ is optionally substituted aryl. In certain embodiments, $R^1$ is optionally substituted heteroaryl. In certain embodiments, $R^1$ is $—OR^f$, wherein each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or two instances of $R^f$, when present, can be joined together with the heteroatom to which they are attached to form an optionally substituted heterocyclic ring. In certain embodiments, $R^f$ is optionally substituted alkyl. In certain embodiments, $R^f$ is

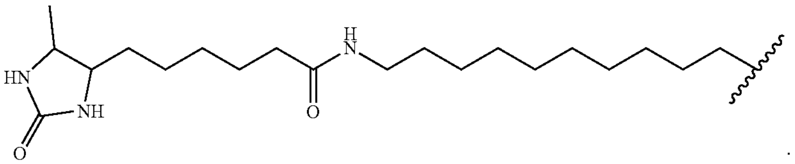 [SMILES: *CCCCCCCCCCNC(=O)CCCCCC1NC(=O)NC1C]

In certain embodiments, $R^f$ is optionally substituted $C_1$-$C_6$alkyl. In certain embodiments, $R^f$ is $C_1$-$C_6$ haloalkyl. In certain embodiments, $R^1$ is $—OCF_3$. In certain embodiments, $R^1$ is —OMe. In certain embodiments, $R^1$ is $—OCH_2CF_3$. In certain embodiments, $R^1$ is $—OCH_2CCH$. In certain embodiments, $R^1$ is —OPh.

In certain embodiments, $R^1$ is $—N(R^f)_2$, wherein each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or two instances of $R^f$, when present, can be joined together with the heteroatom to which they are attached to form an optionally substituted heterocyclic ring. In certain embodiments, $R^1$ is $—SR^f$. In certain embodiments, $R^1$ is $—SCF_3$. In certain embodiments, $R^1$ is $—C(═O)R^f$. In certain embodiments, $R^1$ is $—C(═O)OR^f$. In certain embodiments, $R^1$ is $—C(═O)SR^f$. In certain embodiments, $R^1$ is $—C(═O)N(R^f)_2$. In certain embodiments, $R^1$ is $—OC(═O)R^f$. In certain embodiments, $R^1$ is $—OC(═O)OR^f$. In certain embodiments, $R^1$ is $—OC(═O)SR^f$. In certain embodiments, $R^1$ is $—OC(═O)N(R^f)_2$. In certain embodiments, $R^1$ is $—N(R^f)C(═O)R^f$. In certain embodiments, $R^1$ is $—N(R^f)C(═O)OR^f$. In certain embodiments, $R^1$ is $—N(R^f)C(═O)SR^f$. In certain embodiments, $R^1$ is $—N(R^f)C(═O)N(R^f)_2$. In certain embodiments, $R^1$ is $—SC(═O)R^f$. In certain embodiments, $R^1$ is $—SC(═O)OR^f$. In certain embodiments, $R^1$ is $—SC(═O)SR^f$. In certain embodiments, $R^1$ is $—SC(═O)N(R^f)_2$. In certain embodiments, $R^1$ is $—C(═NR^f)R^f$. In certain embodiments, $R^1$ is $—C(═NR^f)OR^f$. In certain embodiments, $R^1$ is $—C(═NR^f)SR^f$. In certain embodiments, $R^1$ is $—C(═NR^f)N(R^f)_2$. In certain embodiments, $R^1$ is $—OC(═NR^f)R^f$. In certain embodiments, $R^1$ is $—OC(═NR^f)OR^f$. In certain embodiments, $R^1$ is $—OC(═NR^f)SR^f$. In certain embodiments, $R^1$ is $—OC(═NR^f)N(R^f)_2$. In certain embodiments, $R^1$ is $—NR^fC(═NR^f)R^f$. In certain embodiments, $R^1$ is $—NR^fC(═NR^f)OR^f$. In certain embodiments, $R^1$ is $—NR^fC(═NR^f)SR^f$. In certain embodiments, $R^1$ is $—NR^fC(═NR^f)N(R^f)_2$. In certain embodiments, $R^1$ is $—SC(═NR^f)R^f$. In certain embodiments, $R^1$ is $—SC(═NR^f)OR^f$. In certain embodiments, $R^1$ is $—SC(═NR^f)SR^f$. In certain embodiments, $R^1$ is $—SC(═NR^f)N(R^f)_2$. In certain embodiments, $R^1$ is $—S(═O)R^f$. In certain embodiments, $R^1$ is $—SO_2R^f$. In certain embodiments, $R^1$ is $—NR^fSO_2R^f$. In certain embodiments, $R^1$ is $—SO_2N(R^f)_2$. In certain embodiments, $R^1$ is —CN. In certain embodiments, $R^1$ is —SCN. In certain embodiments, $R^1$ is $—NO_2$. In certain embodiments, $R^f$ is substituted or unsubstituted acyl. In certain embodiments, $R^f$ contains a biotin-derivative. In certain embodiments, $R^1$ is

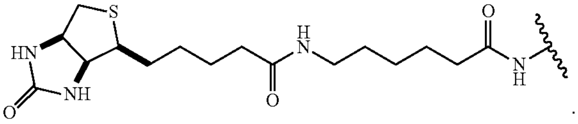

In certain embodiments, $R^f$ is substituted or unsubstituted $C_{1-6}$ alkyl. In certain embodiments, $R^f$ is substituted or unsubstituted $C_{2-6}$ alkenyl. In certain embodiments, $R^f$ is substituted or unsubstituted $C_{2-6}$ alkynyl. In certain embodiments, $R^f$ is substituted or unsubstituted carbocyclyl. In certain embodiments, $R^f$ is substituted or unsubstituted heterocyclyl. In certain embodiments, $R^f$ is substituted or unsubstituted aryl. In certain embodiments, $R^f$ is substituted or unsubstituted heteroaryl. In certain embodiments, $R^f$ is hydrogen. In certain embodiments, $R^f$ is substituted or unsubstituted acyl. In certain embodiments, $R^f$ is substituted or unsubstituted $C_{1-6}$ alkyl. In certain embodiments, $R^f$ is substituted or unsubstituted $C_{1-6}$ alkyl and $R^f$ is substituted or unsubstituted acyl. In certain embodiments, $R^f$ is substituted or unsubstituted $C_{2-6}$ alkenyl. In certain embodiments, $R^f$ is substituted or unsubstituted $C_{2-6}$ alkynyl. In certain embodiments, $R^f$ is substituted or unsubstituted carbocyclyl. In certain embodiments, $R^f$ is substituted or unsubstituted heterocyclyl. In certain embodiments, $R^f$ is substituted or unsubstituted aryl. In certain embodiments, $R^f$ is substituted or unsubstituted heteroaryl. In certain embodiments, there are two instances of $R^f$ and each is alkyl. In certain embodiments, there are two instances of $R^f$ and each is methyl. In certain embodiments, $R^1$ is dimethylamine. In certain embodiments, two instances of $R^f$ are joined to form a substituted or unsubstituted heterocycle. In certain embodiments, $R^1$ is a substituted or unsubstituted piperidine ring. In certain embodiments, $R^1$ is a substituted or unsubstituted piperazine ring. In certain embodiments, $R^1$ is a substituted or unsubstituted morpholine ring.

In certain embodiments, $R^1$ is of Formula (V):

(V-a)

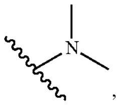

, (V-b)

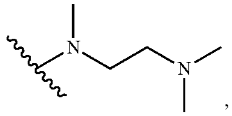

, (V-c)

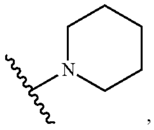

, (V-d)

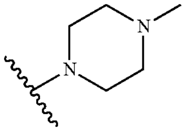

, or (V-e)

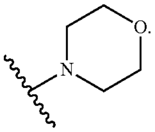

In certain embodiments, $R^1$ is $—NH_2$. In certain embodiments, $R^1$ is

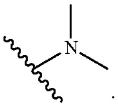

.

In certain embodiments, $R^1$ is

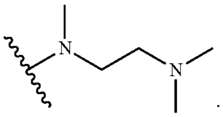 [SMILES: *N(C)CCN(C)C]

.

In certain embodiments, $R^1$ is

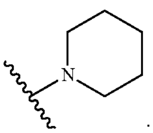 [SMILES: *N1CCCCC1]

.

In certain embodiments, $R^1$ is

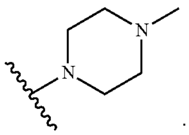 [SMILES: *N1CCN(C)CC1]

.

In certain embodiments, $R^1$ is

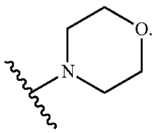 [SMILES: *N1CCOCC1]

Formula (I) includes an aryl ring (Ar). In certain embodiments, the aryl ring is bicyclic or monocyclic aryl, or bicyclic or monocyclic heteroaryl. In certain embodiments, the aryl ring is monocyclic aryl. In certain embodiments, the aryl ring is substituted phenyl. In certain embodiments, the aryl ring is of the formula:

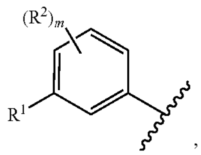

, wherein $R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, $—OR^c$, —NO2, $—N(R^c)_2$, or $—SR^c$, wherein $R^c$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined with together with X1 to form an optionally substituted heterocyclic ring. In certain embodiments, the aryl ring is of the formula:

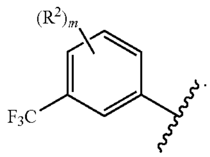

.

In certain embodiments, the aryl ring is of the formula:

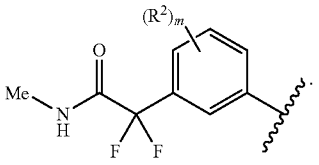

In certain embodiments, the aryl ring is of the formula:

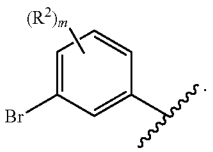

In certain embodiments, the aryl ring is of the formula:

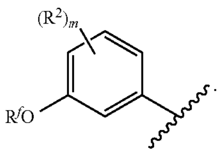

In certain embodiments, the aryl ring is of the formula:

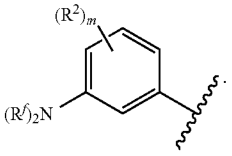

In certain embodiments, the aryl ring is of the formula:

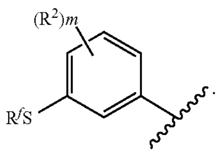

In certain embodiments, the aryl ring is of the formula:

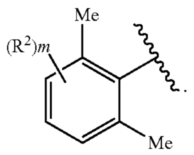

In certain embodiments, the aryl ring is of the formula:

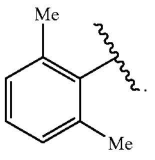 [SMILES: *c1c(C)cccc1C]

In certain embodiments, the aryl ring is of the formula:

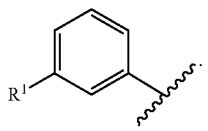

In certain embodiments, the aryl ring is of the formula:

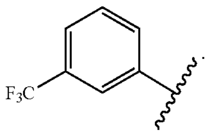

In certain embodiments, the aryl ring is of the formula:

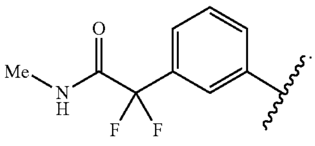 [SMILES: *c1cccc(C(F)(F)C(=O)NC)c1]

In certain embodiments, the aryl ring is of the formula:

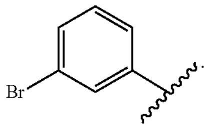 [SMILES: *c1cccc(Br)c1]

In certain embodiments, the aryl ring is of the formula:

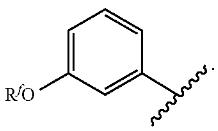

In certain embodiments, the aryl ring is of the formula:

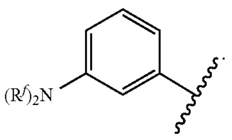

In certain embodiments, the aryl ring is of the formula:

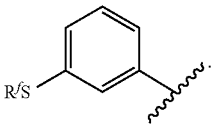

In certain embodiments, the aryl ring is of the formula:

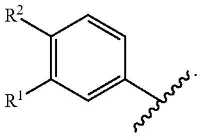

In certain embodiments, the aryl ring is of the formula:

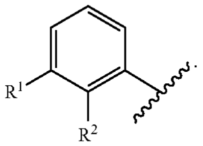

In certain embodiments, the aryl ring is of the formula:

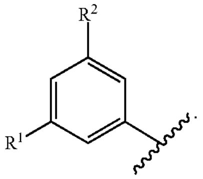

In certain embodiments, the aryl ring is of the formula:

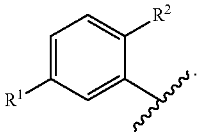

In certain embodiments, the aryl ring is of the formula:

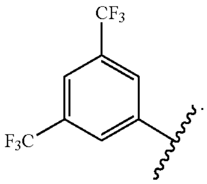

In certain embodiments, the aryl ring is of the formula:

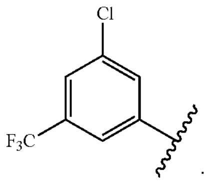

In certain embodiments, the aryl ring is of the formula:

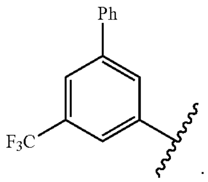

In certain embodiments, the aryl ring is of the formula:

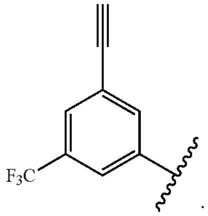 [SMILES: *c1cc(C#C)cc(C(F)(F)F)c1]

In certain embodiments, the aryl ring is of the formula:

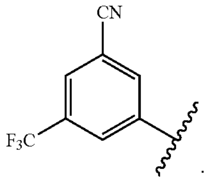

In certain embodiments, the aryl ring is of the formula:

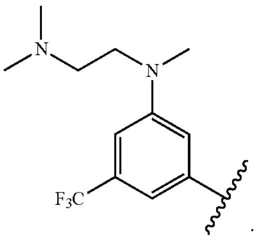 [SMILES: *c1cc(N(C)CCN(C)C)cc(C(F)(F)F)c1]

In certain embodiments, the aryl ring is of the formula:

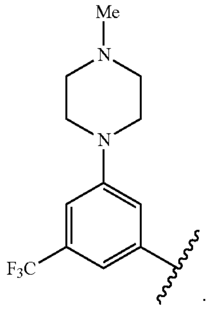

In certain embodiments, the aryl ring is of the formula:

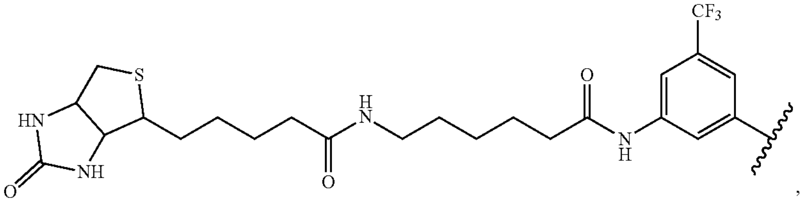 [SMILES: *c1cc(NC(=O)CCCCCNC(=O)CCCCC2SCC3NC(=O)NC32)cc(C(F)(F)F)c1]
,

In certain embodiments, the aryl ring is of the formula:

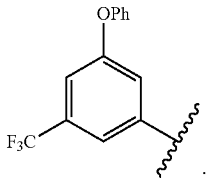

In certain embodiments, the aryl ring is of the formula:

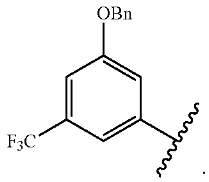

In certain embodiments, the aryl ring is of the formula:

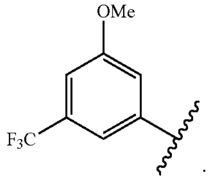

In certain embodiments, the aryl ring is of the formula:

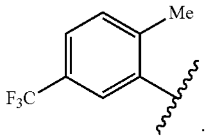

In certain embodiments, the aryl ring is of the formula:

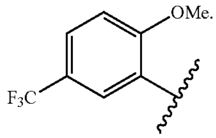 [SMILES: *c1cc(C(F)(F)F)ccc1OC]

In certain embodiments, the aryl ring is of the formula:

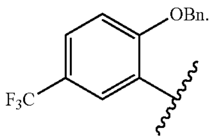 [SMILES: *c1cc(C(F)(F)F)ccc1OCc1ccccc1]

In certain embodiments, the aryl ring is of the formula:

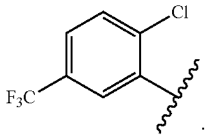 [SMILES: *c1cc(C(F)(F)F)ccc1Cl]

In certain embodiments, the aryl ring is of the formula:

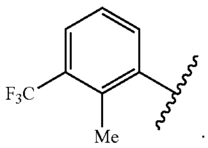

In certain embodiments, the aryl ring is of the formula:

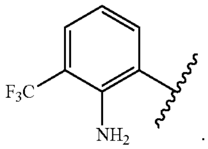

In certain embodiments, the aryl ring is of the formula:

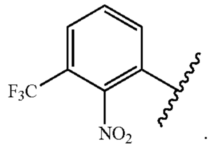

In certain embodiments, the aryl ring is of the formula:

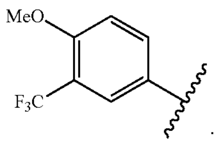

In certain embodiments, the aryl ring is of the formula:

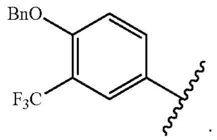 [SMILES: *c1ccc(OCc2ccccc2)c(C(F)(F)F)c1]

In certain embodiments, the aryl ring is of the formula:

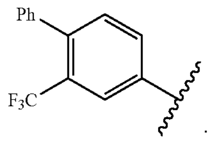

In certain embodiments, the aryl ring is of the formula:

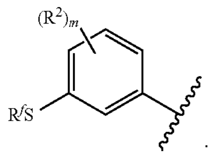

In certain embodiments, the aryl ring is of the formula:

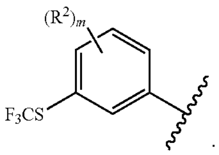

In certain embodiments, the aryl ring is of the formula:

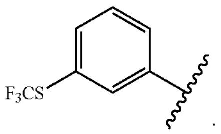

In certain embodiments, the aryl ring is of the formula:

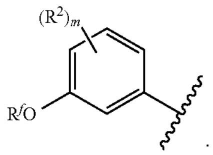

In certain embodiments, the aryl ring is of the formula:

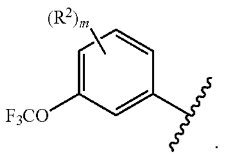

In certain embodiments, the aryl ring is of the formula:

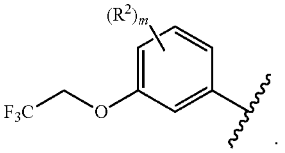

In certain embodiments, the aryl ring is of the formula:

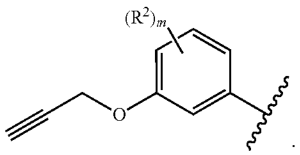

In certain embodiments, the aryl ring is of the formula:

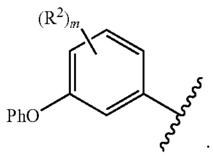

In certain embodiments, the aryl ring is of the formula:

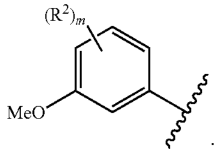

In certain embodiments, the aryl ring is of the formula:

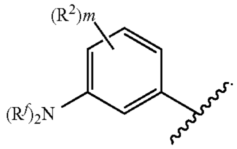

In certain embodiments, the aryl ring is of the formula:

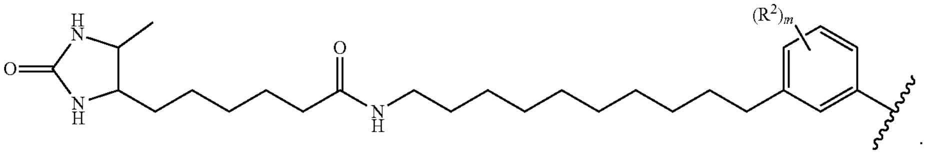

In certain embodiments, the aryl ring is of the formula:

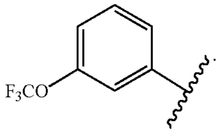 [SMILES: *c1cccc(OC(F)(F)F)c1]

In certain embodiments, the aryl ring is of the formula:

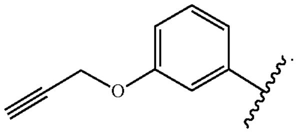 [SMILES: *c1cccc(OCC#C)c1]

In certain embodiments, the aryl ring is of the formula:

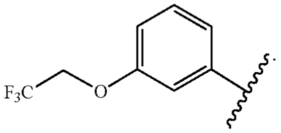 [SMILES: *c1cccc(OCC(F)(F)F)c1]

In certain embodiments, the aryl ring is of the formula:

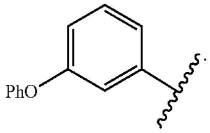

In certain embodiments, the aryl ring is of the formula:

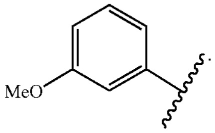 [SMILES: *c1cccc(OC)c1]

In certain embodiments, the aryl ring is of the formula:

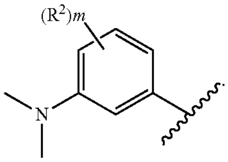

In certain embodiments, the aryl ring is of the formula:

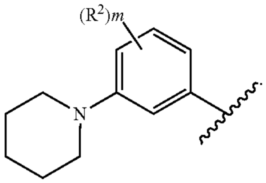

In certain embodiments, the aryl ring is of the formula:

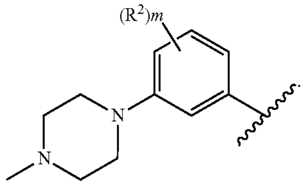

In certain embodiments, the aryl ring is of the formula:

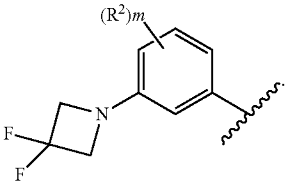

In certain embodiments, the aryl ring is of the formula:

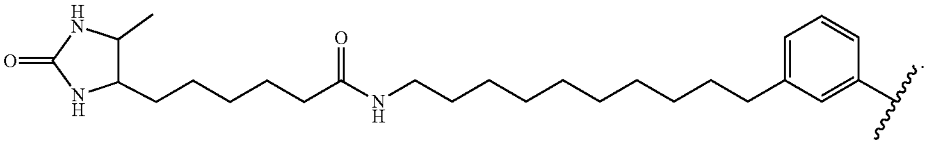

In certain embodiments, the aryl ring is of the formula:

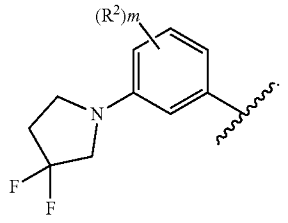

In certain embodiments, the aryl ring is of the formula:

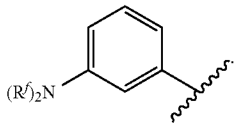

In certain embodiments, the aryl ring is of the formula:

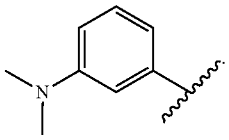 [SMILES: *c1cccc(N(C)C)c1]

In certain embodiments, the aryl ring is of the formula:

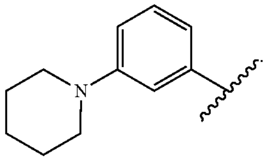 [SMILES: *c1cccc(N2CCCCC2)c1]

In certain embodiments, the aryl ring is of the formula:

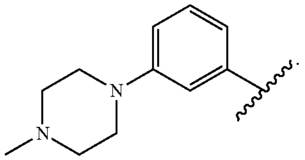 [SMILES: *c1cccc(N2CCN(C)CC2)c1]

In certain embodiments, the aryl ring is of the formula:

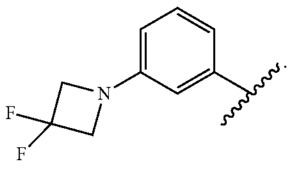 [SMILES: *c1cccc(N2CC(F)(F)C2)c1]

In certain embodiments, the aryl ring is of the formula:

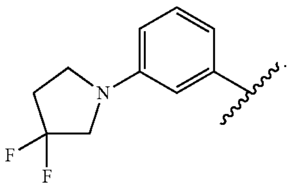

In certain embodiments, the aryl ring is of the formula:

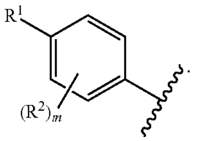

In certain embodiments, the aryl ring is of the formula:

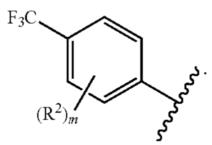

In certain embodiments, the aryl ring is of the formula:

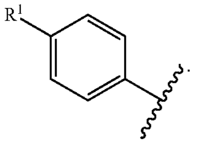

In certain embodiments, the aryl ring is of the formula:

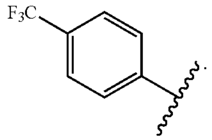

In certain embodiments, the aryl ring is a bicyclic aryl. In certain embodiments, the aryl ring is of the formula:

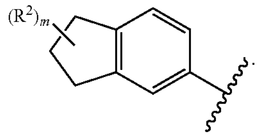

In certain embodiments, the aryl ring is of the formula:

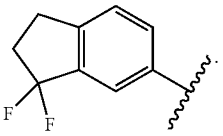 [SMILES: *c1ccc2c(c1)C(F)(F)CC2]

In certain embodiments, the aryl ring is a heteroaryl. In certain embodiments, the aryl ring is pyridine. In certain embodiments, the aryl ring is of the formula:

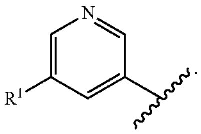

In certain embodiments, the aryl ring is of the formula:

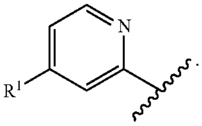

In certain embodiments, the aryl ring is of the formula:

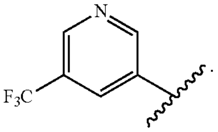 [SMILES: *c1cncc(C(F)(F)F)c1]

In certain embodiments, the aryl ring is of the formula:

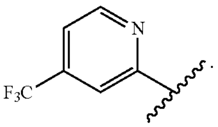 [SMILES: *c1cc(C(F)(F)F)ccn1]

In certain embodiments, the aryl ring is bicyclic heteroaryl. In certain embodiments, the aryl ring is of the formula:

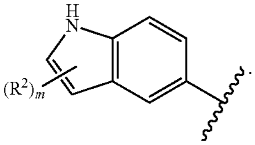

In certain embodiments, the aryl ring is of the formula:

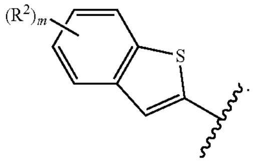

In certain embodiments, the aryl ring is of the formula:

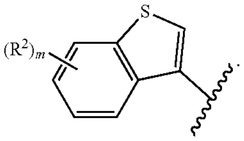

In certain embodiments, the aryl ring is of the formula:

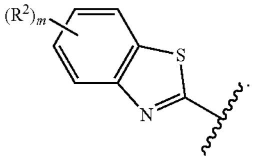

In certain embodiments, the aryl ring is of the formula:

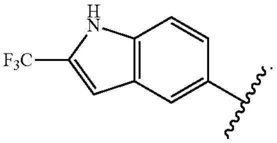 [SMILES: *c1ccc2[nH]c(C(F)(F)F)cc2c1]

In certain embodiments, the aryl ring is of the formula:

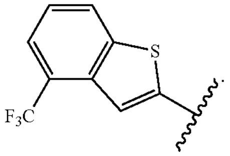 [SMILES: *c1cc2c(C(F)(F)F)cccc2s1]

In certain embodiments, the aryl ring is of the formula:

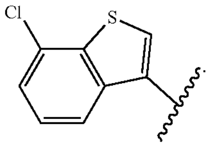 [SMILES: *c1csc2c(Cl)cccc12]

In certain embodiments, the aryl ring is of the formula:

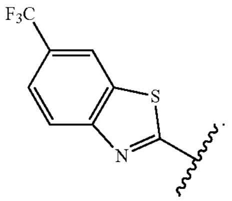 [SMILES: *c1nc2ccc(C(F)(F)F)cc2s1]

In certain embodiments, the aryl ring is of the formula:

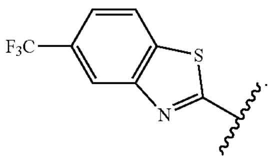 [SMILES: *c1nc2cc(C(F)(F)F)ccc2s1]

As generally defined herein, the aryl ring may be substituted with the substituent $R^2$. In certain embodiments, the aryl ring includes one or more instances of substituent $R^2$. In certain embodiments, m is 1. In certain embodiments, m is 2. In certain embodiments, m is 3. In certain embodiments, m is 4. In certain embodiments, $R^2$ is —H. In certain embodiments, $R^2$ is substituted or unsubstituted alkyl. In certain embodiments, $R^2$ is substituted or unsubstituted methyl. In certain embodiments, $R^2$ is unsubstituted methyl. In certain embodiments, $R^2$ is haloalkyl. In certain embodiments, $R^2$ is —$CF_3$. In certain embodiments, $R^2$ is —CC13. In certain embodiments, $R^2$ is —$CHF_2$. In certain embodiments, $R^2$ is —$CH_2F$. In certain embodiments, $R^2$ is substituted or unsubstituted alkenyl. In certain embodiments, $R^2$ is substituted or unsubstituted alkynyl. In certain embodiments, $R^2$ is a terminal alkyne. In certain embodiments, $R^2$ is substituted or unsubstituted carbocyclyl. In certain embodiments, $R^2$ is substituted or unsubstituted heterocyclyl. In certain embodiments, $R^2$ is substituted or unsubstituted aryl. In certain embodiments, $R^2$ is substituted or unsubstituted heteroaryl. In certain embodiments, $R^2$ optionally substituted acyl. In certain embodiments, $R^2$ is —$N(R^c)_2$, wherein on instance of RC is hydrogen. In certain embodiments, $R^2$ is —$N(R^c)_2$, wherein one instance of $R^c$ is optionally substituted acyl. In certain embodiments, $R^c$ optionally substituted alkyl. In certain embodiments, both instances of $R^c$ are the same. In certain embodiments, each instance of RC is different. In certain embodiments, $R^c$ optionally substituted alkenyl. In certain embodiments, $R^2$ is —OMe. In certain embodiments, $R^2$ is a halogen. In certai embodiments, $R^2$ is —Cl. In certain embodiments, $R^2$ is —$NO_2$.

In certain embodiments, $R^2$ is substituted or unsubstituted heteroalkyl. In certain embodiments, $R^2$ is

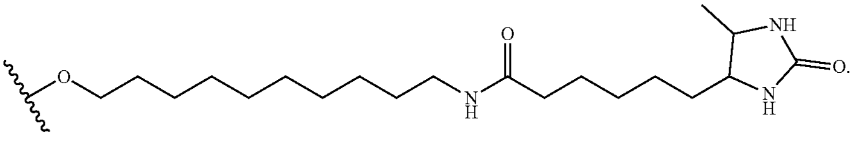 [SMILES: *OCCCCCCCCCCNC(=O)CCCCCC1NC(=O)NC1C]

In certain embodiments, $R^2$ is

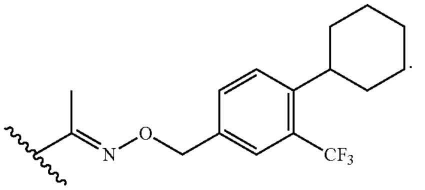 [SMILES: */C(C)=N/OCc1ccc(C2CCCCC2)c(C(F)(F)F)c1]

Formula (I) includes substituent $X^1$. In certain embodiments, $X^1$ is a bond. In certain embodiments, $X^1$ is —O—. In certain embodiments, $X^1$ is S—. In certain embodiments, $X^1$ is optionally substituted $C_{1-6}$alkyl. In certain embodiments, $X^1$ is —$N(R^d)$— as valency permits, wherein $R^d$ is a bond, hydrogen, substituted or unsubstituted $C_{1-6}$ alkyl, or a nitrogen protecting group. In certain embodiments, $X^1$ is C(═O)$N(R^d)$—. In certain embodiments, $X^1$ is —$N(R^d)$C(═O)—. In certain embodiments, $X^1$ is —$C(R^d)_2N(R^d)$—. In certain embodiments, $X^1$ is —$CH_2N(R^d)$—. In certain embodiments, $X^1$ is —$N(R^d)$C(═O)—. In certain embodiments, $X^1$ is —$C(R^d)_2$O—. In certain embodiments, $X^1$ is —$OC(R^d)_2$—. In certain embodiments, $X^1$ is —C(═O)—. In certain embodiments, $X^1$ is —C(═O)O—. In certain embodiments, $X^1$ is —C(═O)S—. In certain embodiments, $X^1$ is —C(═O)$N(R^d)$—. In certain embodiments, $X^1$ is —OC(═O)—. In certain embodiments, $X^1$ is —OC(═O)O—. In certain embodiments, $X^1$ is —OC(═O)S—. In certain embodiments, $X^1$ is —OC(═O)$N(R^d)$—. In certain embodiments, $X^1$ is —$N(R^d)$C(═O)O—. In certain embodiments, $X^1$ is —$N(R^d)$C(═O)S—. In certain embodiments, $X^1$ is —$N(R^d)$C(═O)$N(R^d)$—. In certain embodiments, $X^1$ is —C(═$NR^d$)—. In certain embodiments, $X^1$ is —C(═$NR^d$)O—. In certain embodiments, $X^1$ is —C(═$NR^d$)$N(R^d)$—. In certain embodiments, $X^1$ is —OC(═$NR^d$)—. In certain embodiments, $X^1$ is —OC(═$NR^d$)O—. In certain embodiments, $X^1$ is —OC(═$NR^d$)S—. In certain embodiments, $X^1$ is —OC(═$NR^d$)$N(R^d)$—. In certain embodiments, $X^1$ is —$NR^d$C(═$NR^d$)—. In certain embodiments, $X^1$ is —$NR^d$C(═$NR^d$)O—. In certain embodiments, $X^1$ is —S(═O)—. In certain embodiments, $X^1$ is —$SO_2$—. In certain embodiments, $R^d$ is hydrogen. In certain embodiments, $R^d$ is $C_{1-6}$ alkyl. In certain embodiments, $R^d$ is substituted or unsubstituted methyl. In certain embodiments, $R^d$ is unsubstituted methyl. In certain embodiments, $X^1$ is —C(═O)N(H)—. In certain embodiments, $X^1$ is —N(H)C(═O)—. In certain embodiments, $X^1$ is —$CH_2$N(H)—. In certain embodiments, $R^2$ is joined together with $X^1$ to form an optionally substituted heterocyclic ring. In certain embodiments, $R^2$ is joined together with $X^1$ to form a pyrroline ring. In certain embodiments, $R^1$ is —$CF_3$, $R^2$ is —$CH_2$—, and $X^1$ is —$CH_2N(R^d)$—.

Formula (I) includes substituent $X^2$. In certain embodiments, $X^2$ is a bond. In certain embodiments, $X^2$ is —O—. In certain embodiments, $X^2$ is optionally substituted $C_1$-alkyl. In certain embodiments, $X^2$ is —N($R^{da}$)—, wherein $R^{da}$ is independently a bond, hydrogen, substituted or unsubstituted $C_1$-alkyl, or a nitrogen protecting group. In certain embodiments, $X^2$ is —C($R^d$)$_2$N($R^{da}$)—. In certain embodiments, $X^2$ is —C(=O)N($R^{da}$)—. In certain embodiments, $X^2$ is —C(=O)N(H)—. In certain embodiments, $X^2$ is —N(Ra)C(=O)—. In certain embodiments, $X^2$ is —C($R^{da}$)$_2$O—. In certain embodiments, $X^2$ is —OC(Ra)$_2$—. In certain embodiments, $X^2$ is —C(=O)—. In certain embodiments, $X^2$ is —C(=O)O—. In certain embodiments, $X^2$ is —C(=O)S—. In certain embodiments, $X^2$ is —C(=O)N($R^d$)—. In certain embodiments, $X^2$ is —OC(=O)—. In certain embodiments, $X^2$ is —OC(=O)O—. In certain embodiments, $X^2$ is —OC(=O)S—. In certain embodiments, $X^2$ is —OC(=O)N($R^d$)—. In certain embodiments, $X^2$ is —N$R^{da}$C(=O)—. In certain embodiments, $X^2$ is —N($R^{da}$)C(=O)O—. In certain embodiments, $X^2$ is —N($R^{da}$)C(=O)S—. In certain embodiments, $X^2$ is —N($R^{da}$)C(=O)N($R^{da}$)—. In certain embodiments, $X^2$ is —SC(=O)—. In certain embodiments, $X^2$ is —SC(=O)O—. In certain embodiments, $X^2$ is —SC(=O)S—. In certain embodiments, $X^2$ is —SC(=O)N($R^{da}$)—. In certain embodiments, $X^2$ is —C(=N$R^{da}$)—. In certain embodiments, $X^2$ is —C(=N$R^{da}$)O—. In certain embodiments, $X^2$ is —C(=N$R^{da}$)S—. In certain embodiments, $X^2$ is —C(=N$R^{da}$)N($R^{da}$)—. In certain embodiments, $X^2$ is —OC(=N$R^{da}$)—. In certain embodiments, $X^2$ is —OC(=N$R^{da}$)O—. In certain embodiments, $X^2$ is —OC(=N$R^{da}$)S—. In certain embodiments, $X^2$ is —OC(=N$R^{da}$)N($R^{da}$)—. In certain embodiments, $X^2$ is —N$R^{da}$C(=N$R^{da}$)—. In certain embodiments, $X^2$ is —N$R^{da}$C(=N$R^{da}$)O—. In certain embodiments, $X^2$ is —N$R^{da}$C(=N$R^{da}$)S—. In certain embodiments, $X^2$ is —N$R^{da}$C(=N$R^{da}$)N($R^{da}$)—. In certain embodiments, $X^2$ is —SC(=N$R^{da}$)—. In certain embodiments, $X^2$ is —SC(=N$R^{da}$)O—. In certain embodiments, $X^2$ is —SC(=N$R^{da}$)S—. In certain embodiments, $X^2$ is —SC(=N$R^{da}$)N($R^{da}$)—. In certain embodiments, $X^2$ is —S—. In certain embodiments, $X^2$ is —S(=O)—. In certain embodiments, $X^2$ is —SO$_2$—. In certain embodiments, $R^{da}$ is hydrogen. In certain embodiments, Ra is $C_{1-6}$ alkyl. In certain embodiments, $R^{da}$ is substituted or unsubstituted methyl.

In certain embodiments, $X^1$ and $X^2$ are the same. In certain embodiments, $X^1$ and $X^2$ are different. In certain embodiments, $X^1$ is a bond; and $X^2$ is a bond. In certain embodiments, $X^1$ is —N($R^d$)—; and $X^2$ is a bond. In certain embodiments, $X^1$ is —N(H)—; and $X^2$ is a bond. In certain embodiments, $X^1$ is —N($R^d$)—; and $X^2$ is —N($R^{da}$)—. In certain embodiments, $X^1$ is —N(H)—; and $X^2$ is —N($R^{da}$)—. In certain embodiments, $X^1$ is —N($R^d$)—; and $X^2$ is —N(H)—. In certain embodiments, $X^1$ is —N(H)—; and $X^2$ is —N(H)—. In certain embodiments, $X^1$ is —O—; and $X^2$ is a bond. In certain embodiments, $X^1$ is —O—; and $X^2$ is —N($R^{da}$)—. In certain embodiments, $X^1$ is —O—; and $X^2$ is —N(H)—. In certain embodiments, $X^1$ is —CH$_2$N($R^d$)—; and $X^2$ is a bond. In certain embodiments, $X^1$ is —N($R^d$)C(=O)—; and $X^2$ is a bond. In certain embodiments, $X^1$ is —N(H)C(=O)—; and $X^2$ is a bond. In certain embodiments, $X^1$ is —N(Me)C(=O)—; and $X^2$ is a bond. In certain embodiments, $X^1$ is —C(=O)N($R^d$)—; and $X^2$ is a bond. In certain embodiments, $X^1$ is —C(=O)N(H)—; and $X^2$ is a bond. In certain embodiments, $X^1$ is a bond; and $X^2$ is N($R^A$). In certain embodiments, $X^1$ is a bond; and $X^2$ is N(H). In certain embodiments, $X^1$ is —C($R^d$)$_2$O—; and $X^2$ is a bond. In certain embodiments, $X^1$ is —CH$_2$O—; and $X^2$ is a bond. In certain embodiments, $X^1$ is —N($R^d$)C($R^d$)$_2$—; and $X^2$ is a bond. In certain embodiments, $X^1$ is —N(H)CH$_2$—; and $X^2$ is a bond. In certain embodiments, $X^1$ is —C(R)$_2$—; and $X^2$ is a bond. In certain embodiments, $X^1$ is —CH$_2$—; and $X^2$ is a bond.

Formula (I) includes ring

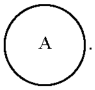.

In certain embodiments, ring

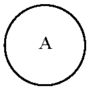

is optionally substituted carbocyclyl (e.g., substituted or unsubstituted, 5- to 6-membered, monocyclic carbocyclyl comprising zero, one, or two double bonds in the carbocyclic ring system). In certain embodiments, ring

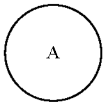

is substituted or unsubstituted cyclohexane. In certain embodiments, ring

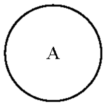

is substituted or unsubstituted cyclopentane. In certain embodiments, $X^1$ is —N(H)—; and ring

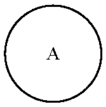

is substituted or unsubstituted cyclohexane. In certain embodiments, $X^1$ is —O—; and ring

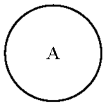

is substituted or unsubstituted cyclohexane. In certain embodiments, $X^1$ is —N(H)—; and ring

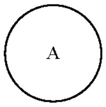

is substituted or unsubstituted cyclopentane. In certain embodiments, $X^1$ is —O—; and ring

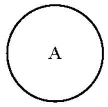

is substituted or unsubstituted cyclopentane.

In certain embodiments, ring A is of the Formula (IV):

(IV-a)

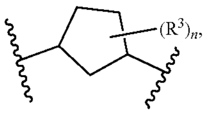

(IV-b)

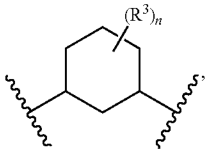

(IV-c)

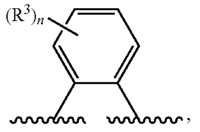

(IV-d)

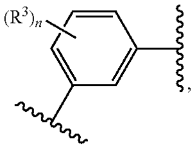

(IV-e)

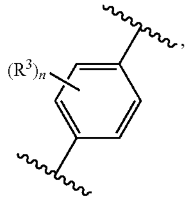

(IV-f)

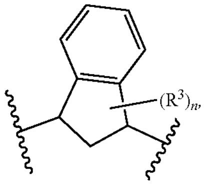

wherein:

$R^3$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)OH, —$OR^{ee}$, —$N(R^e)_2$, —$SR^e$, or —$S(═O)_2R^e$ wherein $R^e$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom;

n is 0, 1, 2, 3, 4, 5, 6, 7, or 8 as valency permits; or optionally, two instances of $R^3$ can be joined together to form an optionally substituted carbocyclic or heterocyclic fused ring.

As generally defined herein, ring A may include the substituent $R^3$. In certain embodiments, $R^3$ is hydrogen. In certain embodiments, $R^3$ is halogen. In certain embodiments, $R^3$ is —Cl. In certain embodiments, $R^3$ is —Br. In certain embodiments, $R^3$ is —I. In certain embodiments, $R^3$ is optionally substituted acyl. In certain embodiments, $R^3$ is optionally substituted alkyl. In certain embodiments, $R^3$ is optionally substituted $C_1$-$C_6$ alkyl. In certain embodiments, $R^3$ is -Me. In certain embodiments, $R^3$ is —$CF_3$. In certain embodiments, $R^3$ is optionally substituted alkenyl. In certain embodiments, $R^3$ is optionally substituted alkynyl. In certain embodiments, $R^3$ is optionally substituted carbocyclyl. In certain embodiments, $R^3$ is optionally substituted heterocyclyl. In certain embodiments, $R^3$ is optionally substituted aryl. In certain embodiments, $R^3$ is substituted or unsubstituted phenyl. In certain embodiments, $R^3$ is optionally substituted heteroaryl. In certain embodiments, $R^3$ is substituted or unsubstituted pyridine. In certain embodiments, $R^3$ is substituted or unsubstituted pyrimidine. In certain embodiments, $R^3$ is substituted or unsubstituted pyrazine. In certain embodiments, $R^3$ is substituted or unsubstituted pyrrole. In certain embodiments, $R^3$ is a substituted or unsubstituted azole. In certain embodiments, $R^3$ is substituted or unsubstituted pyrazole. In certain embodiments, $R^3$ is substituted or unsubstituted imidazole. In certain embodiments, $R^3$ is substituted or unsubstituted triazole. In certain embodiments, the triazole is further substituted with an optionally substituted heteroaryl. In certain embodiments, $R^3$ is substituted or unsubstituted tetrazole. In certain embodiments, $R^3$ is substituted or unsubstituted pyrazole. In certain embodiments, $R^3$ is —C(═O)$OR^e$. In certain embodiments, $R^3$ is —C(═O)OH. In certain embodiments, $R^3$ is —C(═O)OMe. In certain embodiments, $R^3$ is —CN. In certain embodiments, $R^3$ is —C(═O)$N(R^e)_2$. In certain embodiments, $R^3$ is —C(═O)$NH_2$. In certain embodiments, $R^3$ is —C(═O)$NMe_2$. In certain embodiments, $R^3$ is —$OR^e$. In certain embodiments, $R^3$ is —$N(R^e)_2$. In certain embodiments, $R^3$ is —$SR^e$. In certain embodiments, $R^3$ is —$N(R^e)SO_2R^e$. In certain embodiments, $R^3$ is $N(H)SO_2R^e$. In certain embodiments, $R^3$ is —$N(H)SO_2R^e$, wherein $R^e$ is optionally substituted aryl or heteroaryl. In certain embodiments, $R^e$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom; and n is 0, 1, 2, 3, 4, 5, 6, 7, or 8 as valency permits. Optionally, two instances of $R^3$ can be joined together to form an optionally substituted carbocyclic or heterocyclic fused ring In certain embodiments, ring

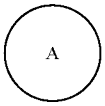

is an optionally substituted heteroaryl ring. In certain embodiments, ring

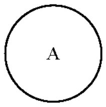

is an optionally substituted heterocyclic ring. In certain embodiments, A is substituted or unsubstituted azetidine. In certain embodiments, ring

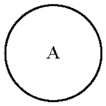

is substituted or unsubstituted pyrrolidine. In certain embodiments, ring

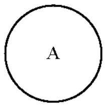

is substituted or unsubstituted indoline. In certain embodiments, ring

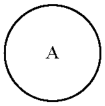

is substituted or unsubstituted piperidine. In certain embodiments, ring

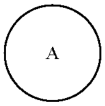

is substituted or unsubstituted azepane. In certain embodiments, ring

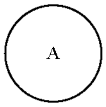

is of the formula:

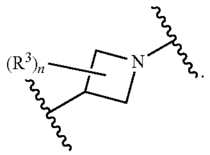

In certain embodiments, $X^1$ is —N(H)—, $X^2$ is —N(H)—, and ring

is of the formula:

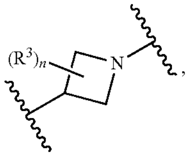

wherein n is 0. In certain embodiments, $X^1$ is —N(H)—, $X^2$ is a bond, and ring

is of the formula:

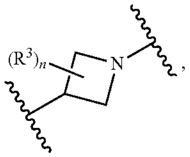

wherein n is 0. In certain embodiments, ring

is of the formula:

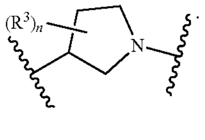

In certain embodiments, ring A is of the formula:
(II-a)
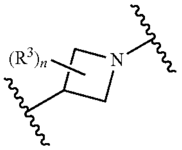
,
(II-b)
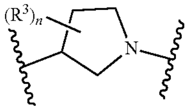
,
(II-c)
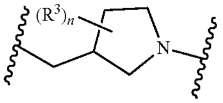
,
(II-d)
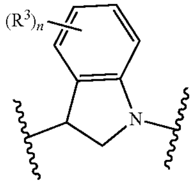
,
(II-e)
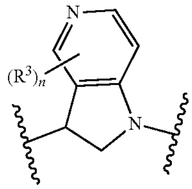
,
(II-f)
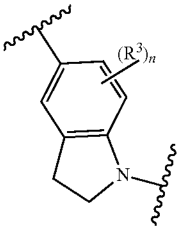
,
(II-g)
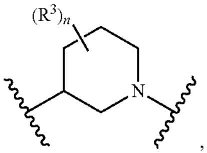
,
(II-h)
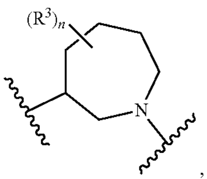
,
-continued
(II-i)
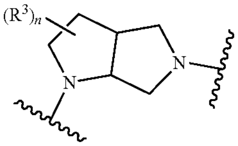
, or
(II-j)
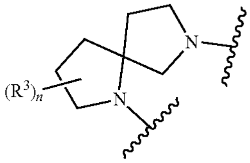
.
In other embodiments, ring A is of the Formula (III):
(III-a)
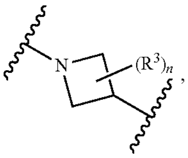
,
(III-b)
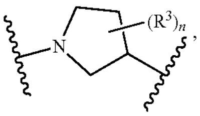
,
(III-c)
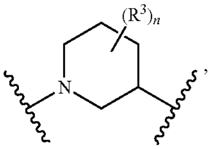
,
(III-d)
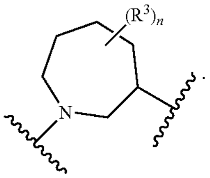
.
In certain embodiments, ring
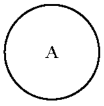
is of the formula:
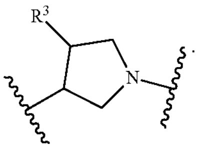
.

In certain embodiments, ring
is of the formula:
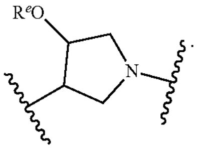
In certain embodiments, ring
is of the formula:
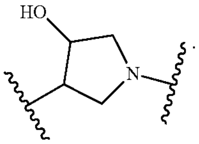 [SMILES: *C1CN(*)CC1O]
In certain embodiments, ring
is of the formula:
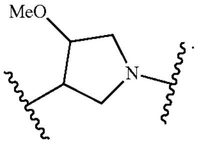
In certain embodiments, ring
is of the formula:
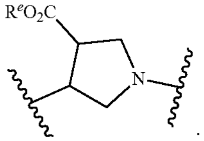
In certain embodiments, ring
is of the formula:
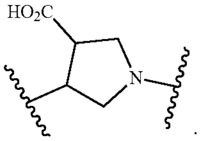 [SMILES: *C1CN(*)CC1C(=O)O]
In certain embodiments, ring
is of the formula:
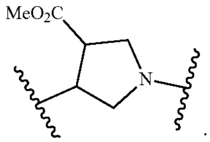 [SMILES: *C1CN(*)CC1C(=O)OC]
In certain embodiments, ring
is of the formula:
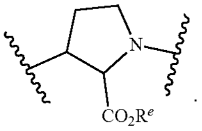
In certain embodiments, ring

is of the formula:

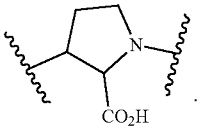 [SMILES: *C1CCN(*)C1C(=O)O]

In certain embodiments, ring

is of the formula:

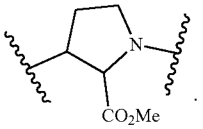 [SMILES: *C1CCN(*)C1C(=O)OC]

In certain embodiments, ring

is of the formula:

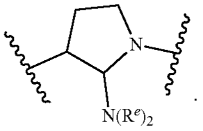

In certain embodiments, ring

is of the formula:

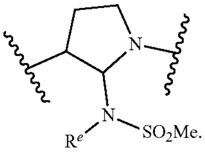

In certain embodiments, ring

is of the formula:

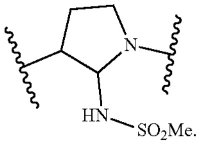

In certain embodiments, ring

is of the formula:

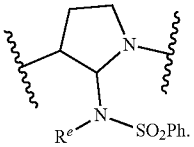

In certain embodiments, ring

is of the formula:

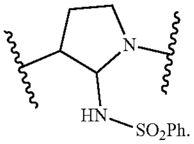

In certain embodiments, ring

is of the formula:

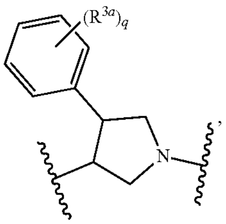

wherein $R^{3a}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{3aa}$, —$NO_2$, —$N(R^{3aa})_2$, or —$SR^{3aa}$, wherein $R^{3aa}$, is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, and q is 0, 1, 2, 3, 4, or 5. In certain embodiments, ring

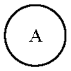

is of the formula:

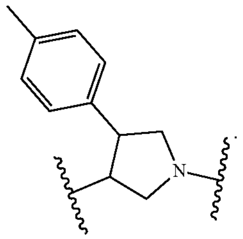 [SMILES: *C1CN(*)CC1c1ccc(C)cc1]

In certain embodiments, ring

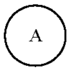

is of the formula:

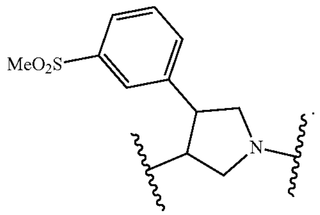 [SMILES: *C1CN(*)CC1c1cccc(S(C)(=O)=O)c1]

In certain embodiments, ring

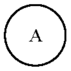

is of the formula:

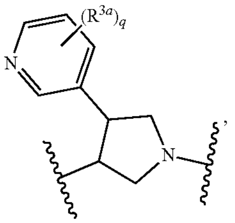

wherein $R^{3a}$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^{3a1}$, —$NO_2$, —$N(R^{3a1})_2$, or —$SR^{3a1}$, wherein $R^{3a1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and q is 0, 1, 2, 3 or 4, as valency permits. In certain embodiments, ring

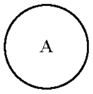

is of the formula:

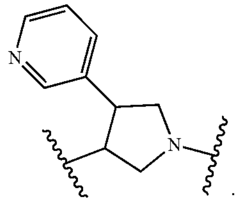 [SMILES: *C1CN(*)CC1c1cccnc1]

In certain embodiments, ring

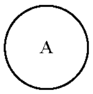

is of the formula:

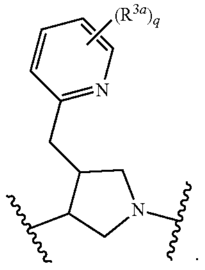

In certain embodiments, ring

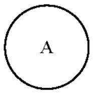

is of the formula:

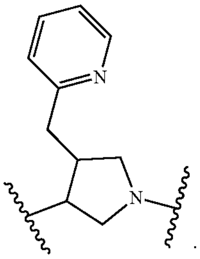 [SMILES: *C1CN(*)CC1Cc1ccccn1]
.

In certain embodiments, ring

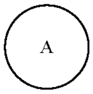

is of the formula:

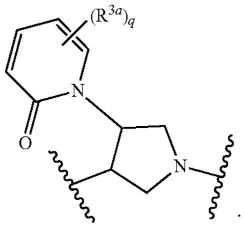
.

In certain embodiments, ring

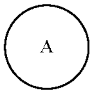

is of the formula:

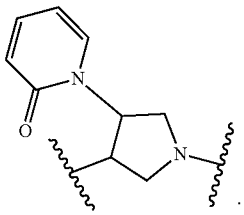 [SMILES: *C1CN(*)CC1n1ccccc1=O]
.

In certain embodiments, ring

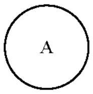

is of the formula:

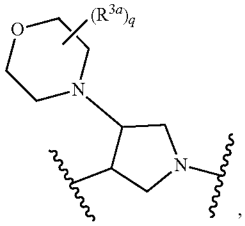
, wherein $R^{3a}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{3aa}$, —$NO_2$, —$N(R^{3aa})_2$, or —$SR^{3aa}$, wherein $R^{3aa}$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, and q is 0, 1, 2, 3, 4, 5, 6, 7, or 8. In certain embodiments, ring

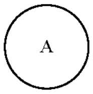

is of the formula:

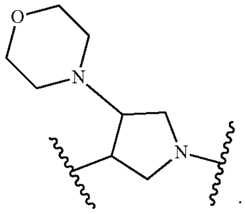 [SMILES: *C1CN(*)CC1N1CCOCC1]
.

In certain embodiments, ring

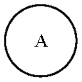

is of the formula:
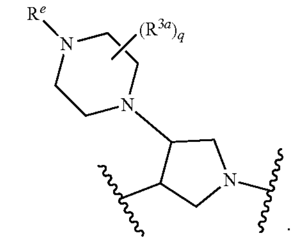
In certain embodiments, ring
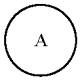
is of the formula:
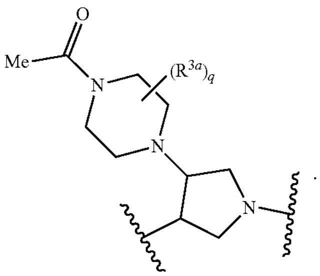
In certain embodiments, ring
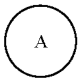
is of the formula:
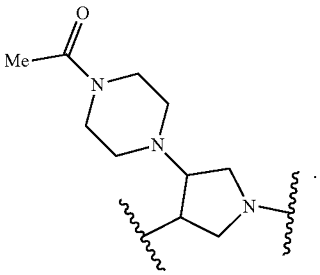 [SMILES: *C1CN(*)CC1N1CCN(C(C)=O)CC1]
In certain embodiments, ring
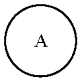
is of the formula:
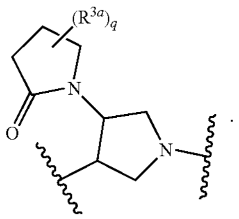
In certain embodiments, ring
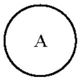
is of the formula:
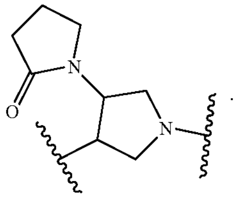 [SMILES: *C1CN(*)CC1N1CCCC1=O]
In certain embodiments, ring
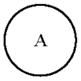
is of the formula:
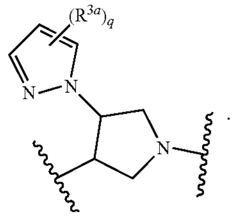
In certain embodiments, ring
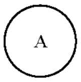

is of the formula:
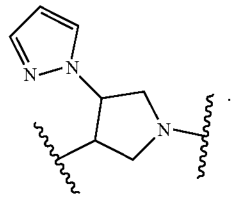 [SMILES: *C1CN(*)CC1n1cccn1]
In certain embodiments, ring
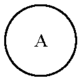
is of the formula:
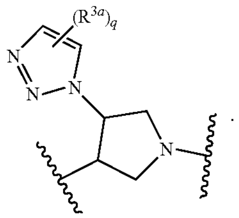
In certain embodiments, ring
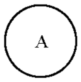
is of the formula:
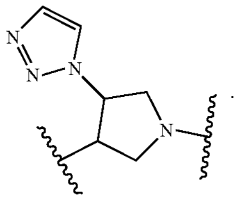 [SMILES: *C1CN(*)CC1n1ccnn1]
In certain embodiments, ring
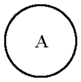
is of the formula:
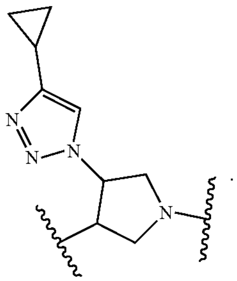 [SMILES: *C1CN(*)CC1n1cc(C2CC2)nn1]
In certain embodiments, ring
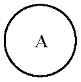
is of the formula:
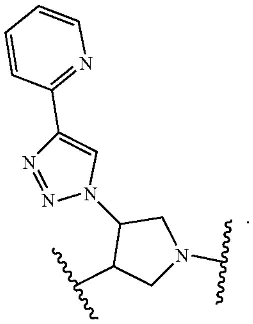 [SMILES: *C1CN(*)CC1n1cc(-c2ccccn2)nn1]
In certain embodiments, ring
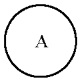
is of the formula:
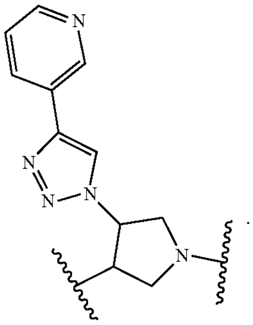 [SMILES: *C1CN(*)CC1n1cc(-c2cccnc2)nn1]

In certain embodiments, ring
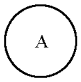
is of the formula:
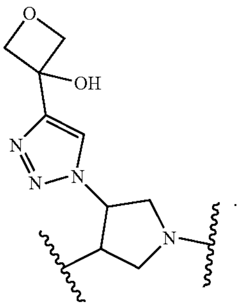 [SMILES: *C1CN(*)CC1n1cc(C2(O)COC2)nn1]
In certain embodiments, ring
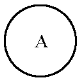
is of the formula:
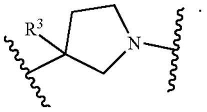
In certain embodiments, ring
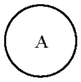
is of the formula:
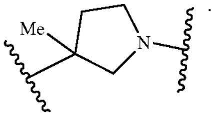 [SMILES: *N1CCC(*)(C)C1]
In certain embodiments, ring
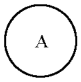
is of the formula:
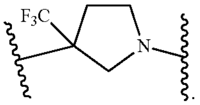 [SMILES: *N1CCC(*)(C(F)(F)F)C1]
In certain embodiments, ring
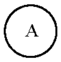
is of the formula:
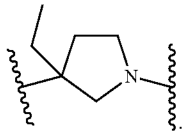 [SMILES: *N1CCC(*)(CC)C1]
In certain embodiments, ring
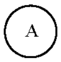
is of the formula:
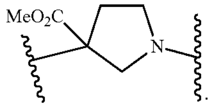
In certain embodiments, ring
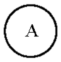
is of the formula:
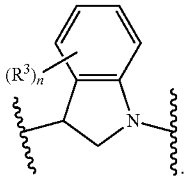
In certain embodiments, ring
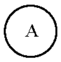

is of the formula:
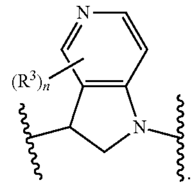
In certain embodiments, ring
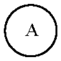
is of the formula:
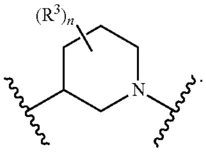
In certain embodiments, ring
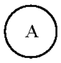
is of the formula:
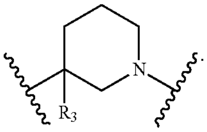
In certain embodiments, ring
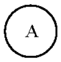
is of the formula:
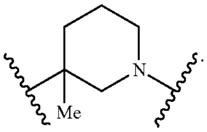 [SMILES: *N1CCCC(*)(C)C1]
As generally defined herein, Formula (I) includes the substituent $D^1$, wherein $D^1$ is a warhead of formula:
(i-1)
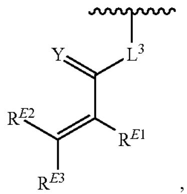
,
(i-2)
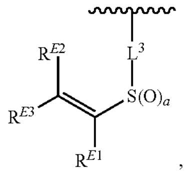
,
(i-3)
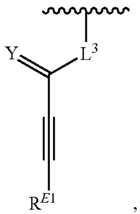
,
(i-4)
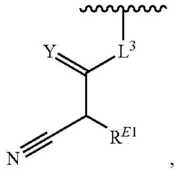
,
(i-5)
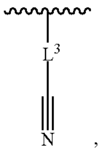
,
(i-6)
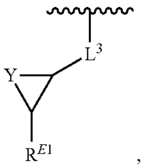
,
(i-7)
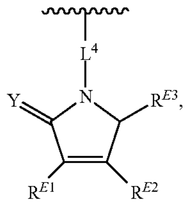
(i-8)
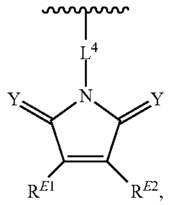

-continued
(i-9)
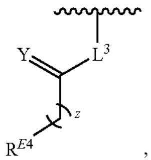
,
(i-10)
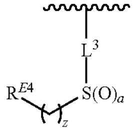
,
(i-11)
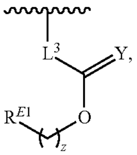
(i-12)
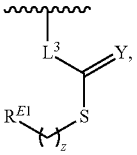
(i-13)
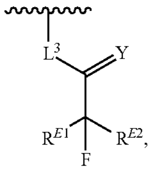
(i-14)
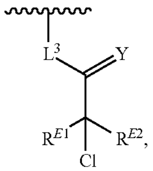
(i-15)
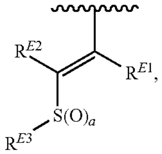
(i-16)
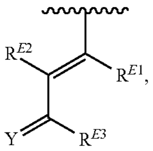
(i-17)
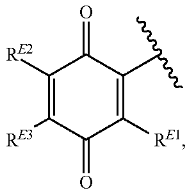
-continued
(i-18)
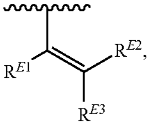
(i-19)
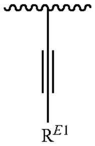
, and
(i-20)
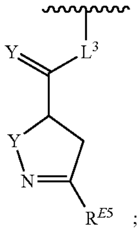
;
(i-21)
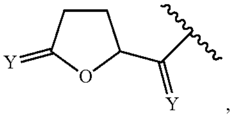
,
(i-22)
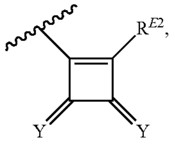
(i-23)
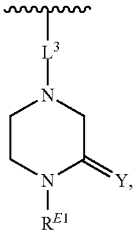
(i-24)
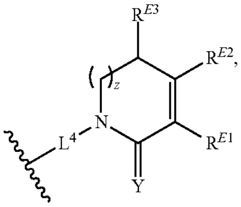
(i-25)
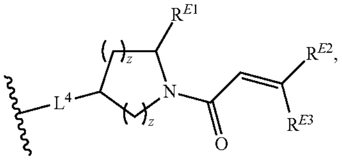
(i-26)
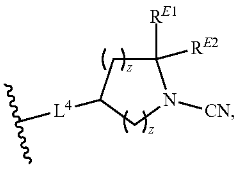

-continued (i-27)

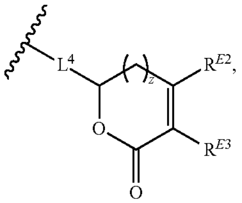

(i-28)

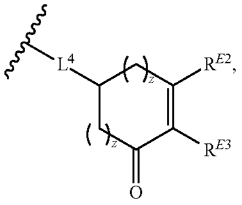

(i-29)

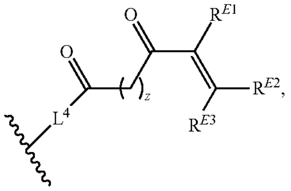

(i-30)

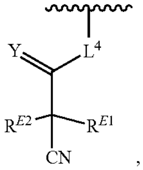

, (i-31)

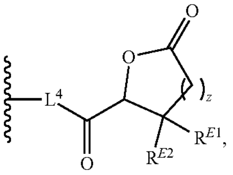

(i-32)

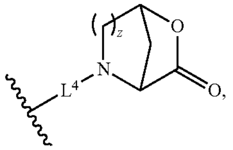

(i-33)

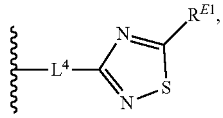

(i-34)

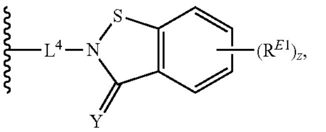

(i-35)

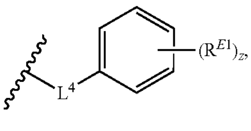

-continued (i-36)

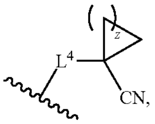

(i-37)

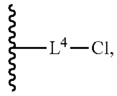

(i-38)

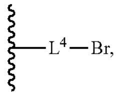

(i-39)

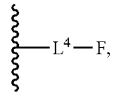

(i-40)

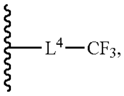

(i-41)

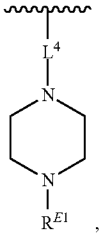

, and (i-42)

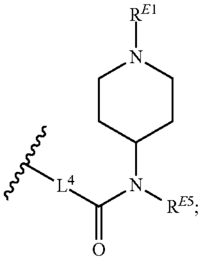

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —$S(═O)_2$—, —$S(═O)_2O$—, —$OS(═O)_2$—, —$S(═O)_2NR^{L3a}$—, or —$NR^{L3a}S(═O)_2$—, wherein $R^{L3a}$ is hydrogen, substituted or unsubstituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, and —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, and —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E3a}$, —$CH_2N(R^{E3a})_2$, —$CH_2SR^{E3a}$, —$OR^{E3a}$, —$N(R^{E3a})_2$, and —$SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or $NR^{E6}$, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

In certain embodiments, $D^1$ is a warhead of formula (i-1) through (i-42). In certain embodiments, the warhead is of formula (i-1)

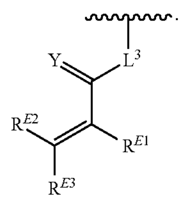

In certain embodiments, $D^1$ is a warhead of formula

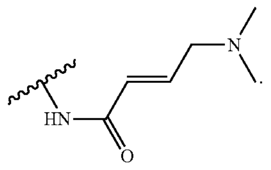 [SMILES: *NC(=O)/C=C/CN(C)C]

In certain embodiments, $D^1$ is a warhead of formula

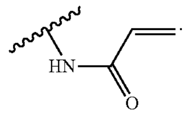

In certain embodiments, $D^1$ is a warhead of formula

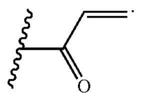

In certain embodiments, $D^1$ is of formula:

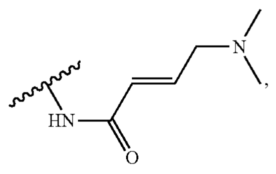
,
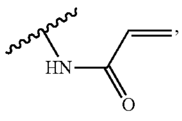 [SMILES: *NC(=O)C=C]
, or
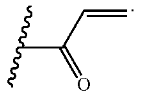

In certain embodiments, $D^1$ is of formula:

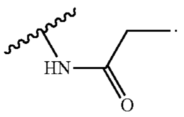 [SMILES: *NC(=O)CC]

In certain embodiments, $L^3$ is a bond. In certain embodiments, $L^3$ is —NH—. In certain embodiments, $R^{E1}$ and $R^{E2}$ are hydrogen. In certain embodiments, $R^{E1}$, $R^{E2}$, and $R^{E3}$ are all hydrogen. In certain embodiments, $R^{E3}$ is —$CH_2NMe_2$.

In certain embodiments, the warhead is of formula:

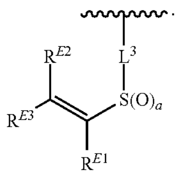
(i-2)

In certain embodiments, the warhead is of formula:

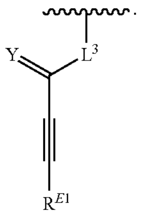
(i-3)

In certain embodiments, the warhead is of formula:

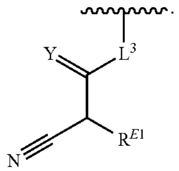
(i-4)

In certain embodiments, the warhead is of formula:

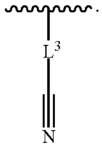
(i-5)

In certain embodiments, the warhead is of formula:

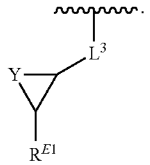
(i-6)

In certain embodiments, the warhead is of formula:

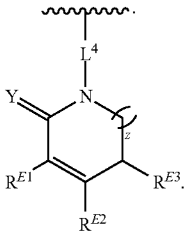
(i-7)

In certain embodiments, the warhead is of formula:

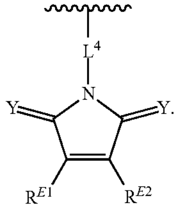
(i-8)

In certain embodiments, the warhead is of formula:

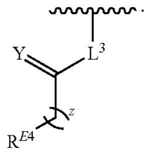
(i-9)

In certain embodiments, the warhead is of formula:

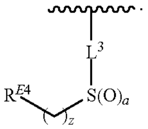
(i-10)

In certain embodiments, the warhead is

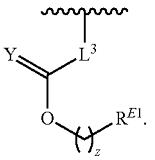
(i-11)

In certain embodiments, the warhead is of formula:

(i-12)

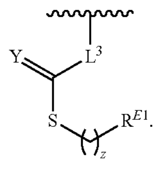

In certain embodiments, the warhead is of formula:

(i-13)

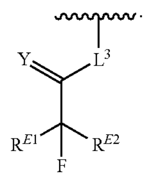

In certain embodiments, the warhead is of formula:

(i-14)

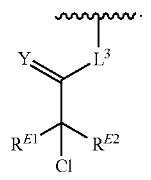

In certain embodiments, the warhead is of formula:

(i-15)

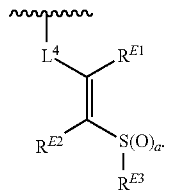

In certain embodiments, the warhead is of formula:

(i-16)

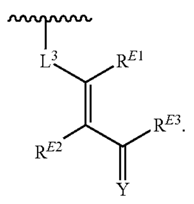

In certain embodiments, the warhead is of formula:

(i-17)

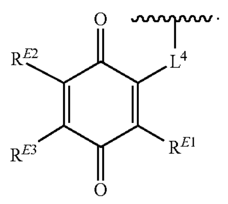

In certain embodiments, the warhead is of formula:

(i-18)

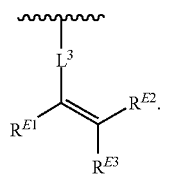

In certain embodiments, the warhead is of formula (i-19)

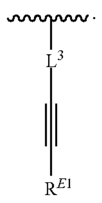

In certain embodiments, the warhead is of formula:

(i-20)

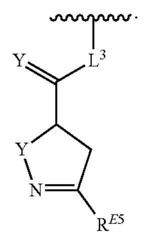

In certain embodiments, the warhead is of formula:

(i-21)

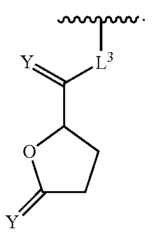

In certain embodiments, the warhead is of formula:

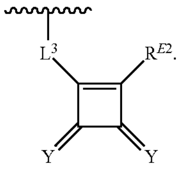

(i-22)

In certain embodiments, the warhead is of formula:

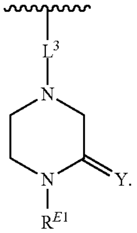

(i-23)

In certain embodiments, the warhead is of formula:

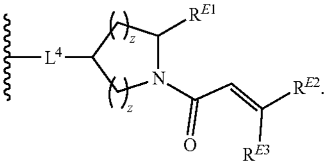

(i-24)

In certain embodiments, the warhead is of formula:

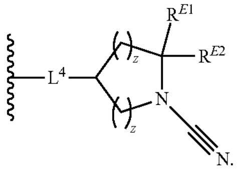

(i-25)

In certain embodiments, the warhead is of formula:

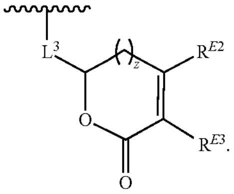

(i-26)

In certain embodiments, the warhead is of formula:

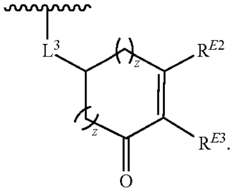

(i-27)

In certain embodiments, the warhead is of formula:

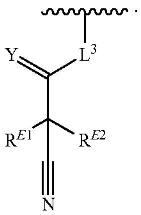

(i-28)

In certain embodiments, the warhead is of formula:

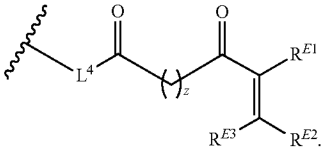

(i-29)

In certain embodiments, the warhead is of formula:

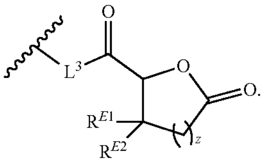

(i-30)

In certain embodiments, the warhead is of formula:

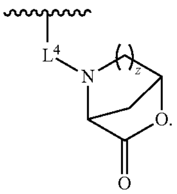

(i-31)

In certain embodiments, the warhead is of formula:

(i-32)

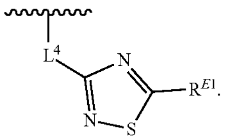

In certain embodiments, the warhead is of formula:

(i-33)

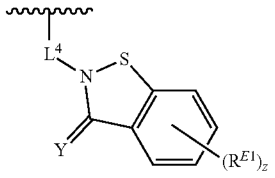

In certain embodiments, the warhead is of formula:

(i-34)

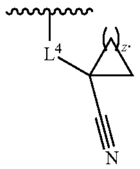

In certain embodiments, the warhead is of formula:

(i-35)

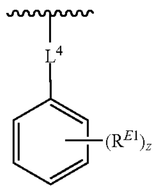

In certain embodiments, the warhead is of formula:

(i-36)

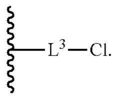

In certain embodiments, the warhead is of formula:

(i-37)

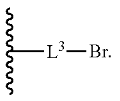

In certain embodiments, the warhead is of formula:

(i-38)

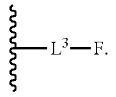

In certain embodiments, the warhead is of formula:

(i-39)

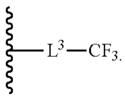

In certain embodiments, the warhead is of formula:

(i-40)

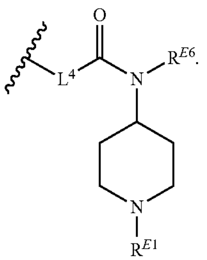

In certain embodiments, the warhead is of formula:

(i-41)

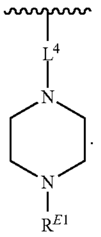

In certain embodiments, the warhead is of formula:

(i-42)

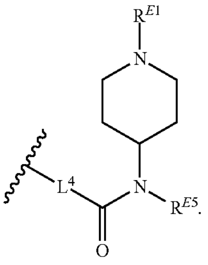

In certain embodiments, the warhead is of the formula:

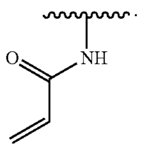 [SMILES: *NC(=O)C=C]

In certain embodiments, the warhead is of the formula:

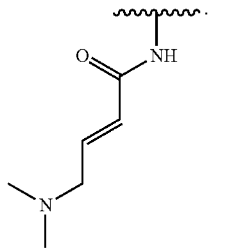 [SMILES: *NC(=O)/C=C/CN(C)C]

In certain embodiments, the warhead is of the formula:

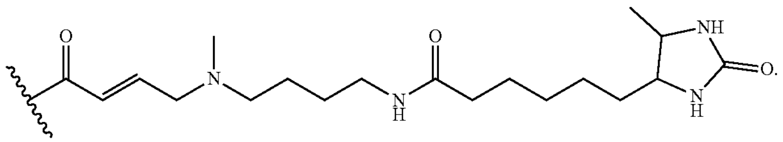 [SMILES: *C(=O)/C=C/CN(C)CCCCNC(=O)CCCCCC1NC(=O)NC1C]

In certain embodiments, the warhead is of the formula:

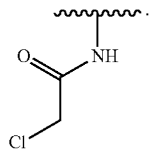

In certain embodiments, $L^3$ is a bond (e.g., a single bond, a double bond, or a triple bond). In certain embodiments, $L^3$ is a single bond. In certain embodiments, $L^3$ is a double bond. In certain embodiments, $L^3$ is a triple bond. In certain embodiments, $L^3$ is an optionally substituted $C_{1-4}$ hydrocarbon chain, optionally wherein one or more carbon units of the hydrocarbon chain are independently replaced with $-C{=}O-$, $-O-$, $-S-$, $-NR^{L3a}-$, $-NR^{L3a}C(=O)-$, $-C(=O)NR^{L3a}-$, $-SC(=O)-$, $-C(=O)S-$, $-OC(=O)-$, $C(=O)O$, $-NR^{L3a}C(=S)-$, $-C(=S)NR^{L3a}-$, trans-$CR^{L3b}{=}CR^{L3b}-$, cis-$CR^{L3b}{=}CR^{L3b}-$, $-C{\equiv}C-$, $-S(=O)-$, $-S(=O)O-$, $-OS(=O)-$, $-S(=O)NR^{L3a}-$, $-NR^{L3a}S(=O)-$, $-S(=O)_2-$, $-S(=O)_2O-$, $-OS(=O)_2-$, $-S(=O)_2NR^{L3a}-$, or $-NR^{L3a}S(=O)_2-$, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{L3b}$ groups are joined to form an optionally substituted carbocyclic or optionally substituted heterocyclic ring. In certain embodiments, $L^4$ is a bond (e.g., a single bond, a double bond, or a triple bond). In certain embodiments, $L^4$ is an optionally substituted branched $C_{1-6}$ hydrocarbon chain (e.g., i-Pr). In certain embodiments, $L^4$ is an optionally substituted unbranched $C_{1-4}$ hydrocarbon chain (e.g., n-Pr, or n-Bu). In certain embodiments, at least one instance of $R^{E1}$ is H. In certain embodiments, at least one instance of $R^{E1}$ is halogen (e.g., F, Cl, Br, or I). In certain embodiments, at least one instance of $R^{E1}$ is optionally substituted alkyl (e.g., Me, or Et). In certain embodiments, at least one instance of $R^{E1}$ is optionally substituted alkenyl (e.g., optionally substituted vinyl). In certain embodiments, at least one instance of $R^{E1}$ is optionally substituted alkynyl. In certain embodiments, at least one instance of $R^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E1}$ is substituted or unsubstituted aryl (e.g., substituted or unsubstituted, 6- to 10-membered aryl). In certain embodiments, at least one instance of $R^{E1}$ is substituted or unsubstituted phenyl. In certain embodiments, at least one instance of $R^{E1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E1}$ is $-CN$. In certain embodiments, at least one instance of $R^{E1}$ is $-CH_2OR^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E1}$ is $-CH_2N(R^{EF})_2$ or $-N(R^{EF})_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E1}$ is $-CH_2SREE$ or $-SR^{EE}$ (e.g., $-CH_2SMe$ or $-SMe$). In certain embodiments, at least one instance of $R^{E1}$ is $-OR^{EE}$ (e.g., $-OMe$). In certain embodiments, at least one instance of $R^{E1}$ is $-Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$).

In certain embodiments, at least one instance of $R^{E2}$ is H. In certain embodiments, at least one instance of $R^{E2}$ is halogen (e.g., F, Cl, Br, or I). In certain embodiments, at least one instance of $R^{E2}$ is optionally substituted alkyl (e.g., Me, or Et). In certain embodiments, at least one instance of $R^{E2}$ is optionally substituted alkenyl (e.g., optionally substituted vinyl). In certain embodiments, at least one instance of $R^{E2}$ is optionally substituted alkynyl. In certain embodiments, at least one instance of $R^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E2}$ is —CN. In certain embodiments, at least one instance of $R^{E2}$ is —$CH_2OR^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E2}$ is —$CH_2N(R^{EF})_2$ or $N(R^{EF})_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E2}$ is —$CH_2SR^{EE}$ or —$SR^{EE}$ (e.g., —$CH_2SMe$ or —SMe). In certain embodiments, at least one instance of $R^{E2}$ is —ORE (e.g., —OMe). In certain embodiments, at least one instance of $R^{E2}$ is —$Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$). In certain embodiments, at least one instance of $R^{E3}$ is H. In certain embodiments, at least one instance of $R^{E3}$ is halogen (e.g., F, Cl, Br, or I). In certain embodiments, at least one instance of $R^{E3}$ is optionally substituted alkyl (e.g., Me, or Et). In certain embodiments, at least one instance of $R^{E3}$ is optionally substituted alkenyl (e.g., optionally substituted vinyl). In certain embodiments, at least one instance of $R^{E3}$ is optionally substituted alkynyl. In certain embodiments, at least one instance of $R^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of $R^{E3}$ is —CN. In certain embodiments, at least one instance of $R^{E3}$ is —$CH_2OR^{EE}$, wherein each instance of $R^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{E3}$ is —$CH_2N(R^EF)_2$ or —$N(R^{EF})_2$, wherein each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two $R^{EF}$ groups are joined to form an optionally substituted heterocyclic ring. In certain embodiments, at least one instance of $R^{E3}$ is —$CH_2SR^{EE}$ or —$SR^{EE}$ (e.g., —$CH_2SMe$ or —SMe). In certain embodiments, at least one instance of $R^{E3}$ is —$OR^{EE}$ (e.g., —OMe). In certain embodiments, at least one instance of $R^{E3}$ is — $Si(R^{EG})_3$, wherein each instance of $R^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —$Si(Me)_3$). In certain embodiments, $R^{E1}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E2}$ and $R^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E2}$ and $R^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E1}$ and $R^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, $R^{E1}$ and $R^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{E4}$ is a leaving group (e.g., halogen, or a sulfonic acid ester, e.g., —O(tosylate) or —O(mesylate)). In certain embodiments, $R^{E5}$ is halogen (e.g., F, Cl, Br, or I). In certain embodiments, $R^{E6}$ is H. In certain embodiments, $R^{E6}$ is substituted or unsubstituted $C_{1-6}$ alkyl (e.g., Me, is —$CF_3$, Bn, Et, perfluoroethyl, Pr, perfluoropropyl, Bu, or perfluorobutyl). In certain embodiments, $R^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is $NR^{E7}$, wherein $R^{E7}$ is hydrogen, substituted or unsubstituted $C_{1-6}$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

In certain embodiments, Formula (I) is of the formula:

(VI-a)

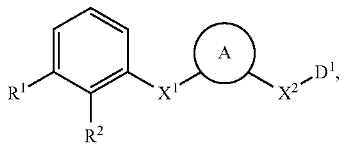

(VI-b)

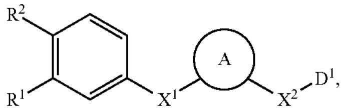

(VI-c)

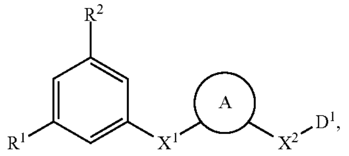

(VI-d)

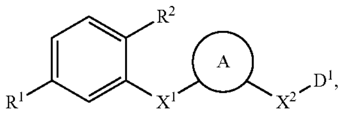

or (VI-e)

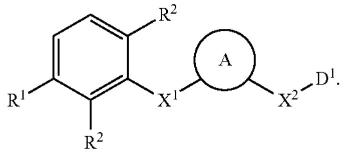

or a pharmaceutically acceptable salt, solvate, hydrate, polymorph, co-crystal, tautomer, stereoisomer, isotopically labeled derivative, prodrug, composition, or mixture thereof.

In certain embodiments, Formula (I) is of the formula:

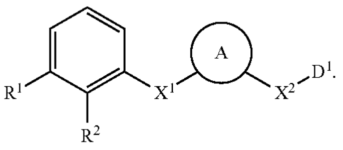

In certain embodiments, Formula (I) is of the formula:

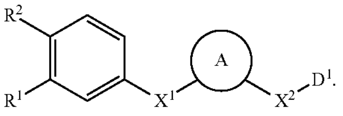

In certain embodiments, Formula (I) is of the formula:

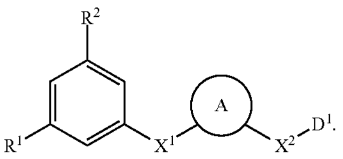

In certain embodiments, Formula (I) is of the formula:

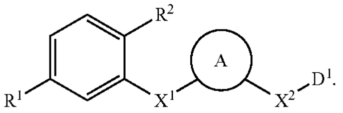

In certain embodiments, Formula (I) is of the formula:

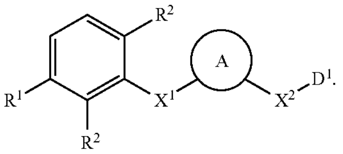

In certain embodiments, Formula (I) is of the formula:

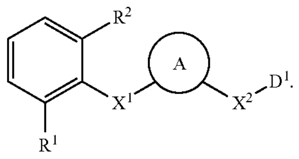

In certain embodiments, Formula (I) is of the formula:

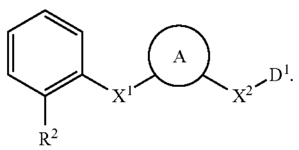

In certain embodiments, Formula (I) is of the formula:

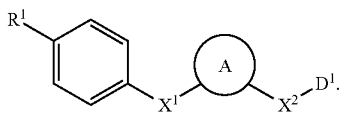

In certain embodiments, Formula (I) is of the formula:

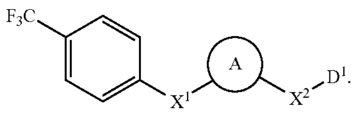

In certain embodiments, Formula (I) is of the formula:

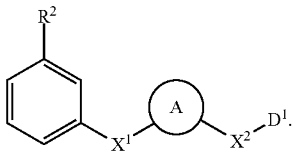

In certain embodiments, Formula (I) is of the formula:

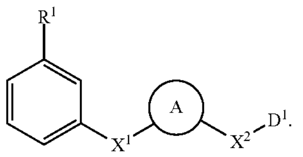

In certain embodiments, $R^1$ is —$CF_3$; and $R^2$ is haloalkyl. In certain embodiments, $R^1$ is —$CF_3$; and $R^2$ is —$CF_3$. In certain embodiments, $R^1$ is —$CF_3$; and $R^2$ is H. In certain embodiments, $R^1$ is —$CF_3$; and $R^2$ is —OMe. In certain embodiments, $R^1$ is —$CF_3$; and $R^2$ is a halogen. In certain embodiments, $R^1$ is —$CF_3$; and $R^2$ is —Cl. In certain embodiments, $R^1$ is —$CF_3$; and $R^2$ is —$NO_2$. In certain embodiments, $R^1$ is —$CF_3$; and $R^2$ is substituted or unsubstituted alkyl. In certain embodiments, $R^1$ is —$CF_3$; and $R^2$ is substituted or unsubstituted methyl. In certain embodiments, $R^1$ is —$CF_3$; and $R^2$ is unsubstituted methyl. In certain embodiments, $R^1$ is —$CF_3$; and $R^2$ is substituted or unsubstituted alkynyl. In certain embodiments, $R^1$ is —$CF_3$; and $R^2$ is alkynyl. In certain embodiments, $R^1$ is —$CF_3$; and $R^2$ is —$N(R^c)_2$, wherein $R^c$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or two instances of $R^c$ together with the nitrogen atom to which they are attached can be joined to form a heterocyclic ring. In certain embodiments, $R^1$ is —$CF_3$, $R^2$ is —$N(R^c)_2$, and $R^c$ is H. In certain embodiments, $R^1$ is —$N(Rb)_2$; and $R^2$ is haloalkyl. In certain embodiments, $R^1$ is —$N(R^b)_2$; and $R^2$ is —$CF_3$. In certain embodiments, $R^1$ is

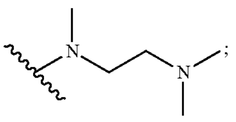 [SMILES: *N(C)CCN(C)C]

and $R^2$ is $CF_3$. In certain embodiments, $R^1$ is

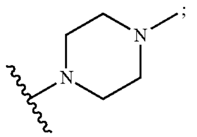 [SMILES: *N1CCN(C)CC1]

and $R^2$ is $CF_3$. In certain embodiments, $R^1$ is

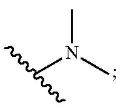 [SMILES: *N(C)C]

and $R^2$ is $CF_3$. In certain embodiments, $R^1$ is

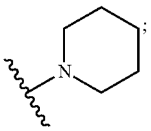 [SMILES: *N1CCCCC1]

and $R^2$ is $CF_3$. In certain embodiments, $R^1$ is

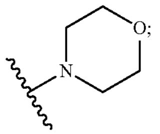 [SMILES: *N1CCOCC1]

and $R^2$ is $CF_3$. In certain embodiments, $R^1$ is —$N(R^b)_2$; and $R^2$ is H. In certain embodiments, $R^1$ is

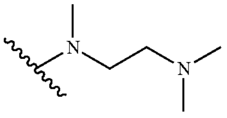 [SMILES: *N(C)CCN(C)C]

and $R^2$ is H. In certain embodiments, $R^1$ is

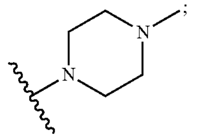 [SMILES: *N1CCN(C)CC1]

and $R^2$ is H. In certain embodiments, $R^1$ is

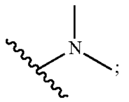 [SMILES: *N(C)C]

and $R^2$ is H. In certain embodiments, $R^1$ is

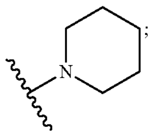 [SMILES: *N1CCCCC1]

and $R^2$ is H. In certain embodiments, $R^1$ is

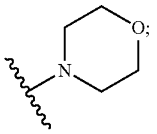 [SMILES: *N1CCOCC1]

and $R^2$ is H. In certain embodiments, $R^1$ is H; and $R^2$ is H. In certain embodiments, $R^1$ is H; and $R^2$ is substituted or unsubstituted alkyl. In certain embodiments, $R^1$ is H; and $R^2$ is substituted or unsubstituted methyl. In certain embodiments, $R^1$ is H; and $R^2$ is unsubstituted methyl. In certain embodiments, $R^1$ is H; and there are two instances of $R^2$, wherein $R^2$ is methyl.

In certain embodiments, Formula (I) is of the formula

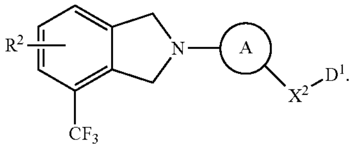

In certain embodiments, Formula (I) is of the formula:

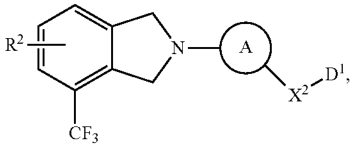

and $X^2$ is a bond.

In certain embodiments, $X^1$ is —N(H)—, $X^2$ is a bond, and ring

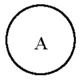

is substituted or unsubstituted cyclohexane. In certain embodiments, $X^1$ is —O—, $X^2$ is a bond, and ring

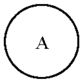

is substituted or unsubstituted cyclohexane. In certain embodiments, $X^1$ is —N(H)—, $X^2$ is a bond, and ring

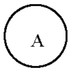

is substituted or unsubstituted cyclopentane. In certain embodiments, $X^1$ is —O—, $X^2$ is a bond, and ring

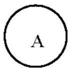

is substituted or unsubstituted cyclopentane. In certain embodiments, $X^1$ is —N(H)—, $X^2$ is —N(H)—, and ring

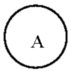

is substituted or unsubstituted cyclohexane. In certain embodiments, $X^1$ is —O—, $X^2$ is —N(H)—, and ring

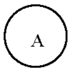

is substituted or unsubstituted cyclohexane. In certain embodiments, $X^1$ is —N(H)—, $X^2$ is —N(H)—, and ring

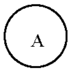

is substituted or unsubstituted cyclopentane. In certain embodiments, $X^1$ is —O—, $X^2$ is —N(H)—, and ring

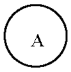

is substituted or unsubstituted cyclopentane. In certain embodiments, ring

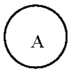

is of the formula:

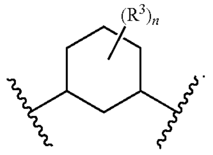

In certain embodiments, ring

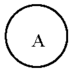

is of the formula:

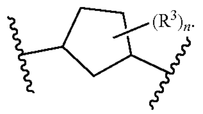

In certain embodiments, $X^1$ is —N(H)—, $X^2$ is a bond, and ring

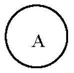

is of the formula:

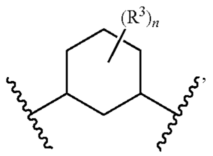

wherein $R^3$ is hydrogen. In certain embodiments, $X^1$ is —N(H)—, $X^2$ is —N(H)—, and ring

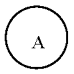

is of the formula:

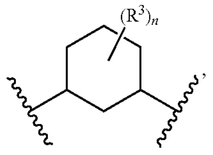

wherein $R^3$ is hydrogen. In certain embodiments, $X^1$ is —N(H)—, $X^2$ is a bond, and ring

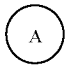

is of the formula:

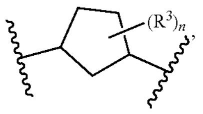

wherein $R^3$ is hydrogen. In certain embodiments, $X^1$ is —N(H)—, $X^2$ is —N(H)—, and ring

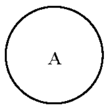

is of the formula:

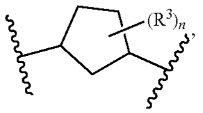

wherein $R^3$ is hydrogen.

In certain embodiments, or Formula (I) is of the formula:

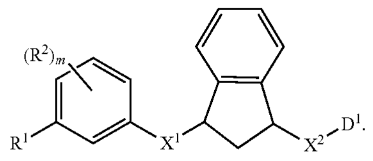

In certain embodiments, Formula (I) is of the formula:

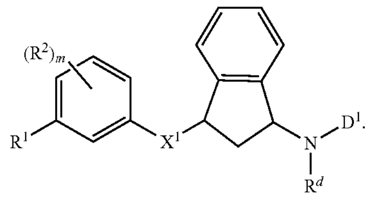

In certain embodiments, Formula (I) is of the formula

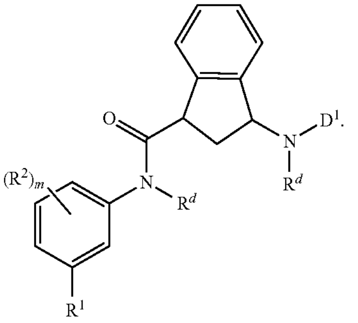

In certain embodiments, Formula (I) is of the formula:

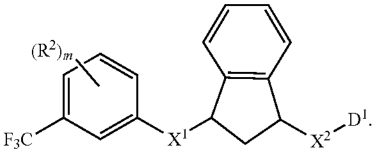

In certain embodiments, Formula (I) is of the formula:

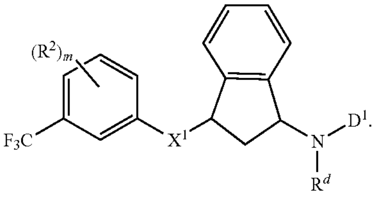

In certain embodiments, Formula (I) is of the formula:

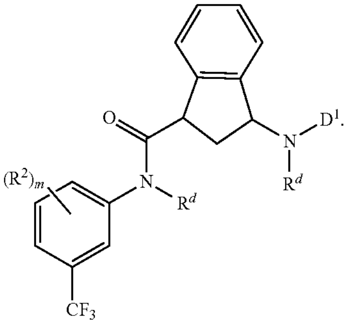

In certain embodiments, Formula (I) is of the formula:

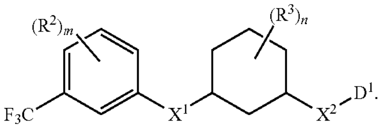

In certain embodiments, Formula (I) is of the formula:

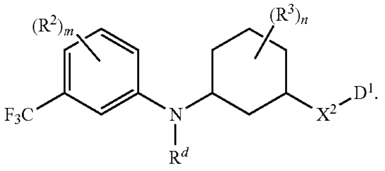

In certain embodiments, Formula (I) is of the formula:

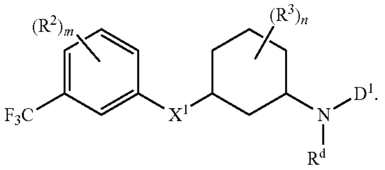

In certain embodiments, Formula (I) is of the formula:

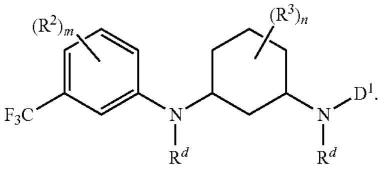

In certain embodiments, ring

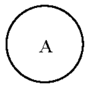

is an optionally substituted aryl ring. In certain embodiments, ring

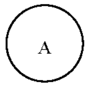

is substituted or unsubstituted phenyl. In certain embodiments, ring

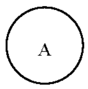

is of the formula:

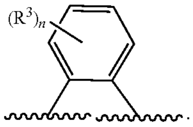

In certain embodiments, $X^1$ is NH, $X^2$ is NH, and ring

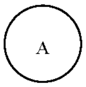

is of the formula:

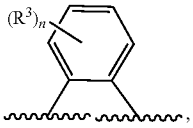, wherein n is 0. In certain embodiments, $X^1$ is —N(H)—, $X^2$ is a bond, and ring

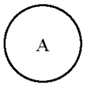

is of the formula:

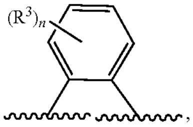, wherein n is 0. In certain embodiments, ring

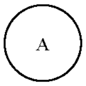

is of the formula:

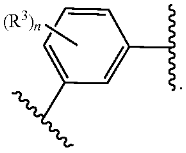.

In certain embodiments, $X^1$ is —N(H)—, $X^2$ is —N(H)—, and ring

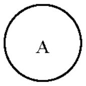

is of the formula:

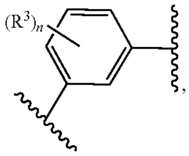, wherein $R^3$ is hydrogen. In certain embodiments, $X^1$ is —N(H)—, $X^2$ is a bond, and ring

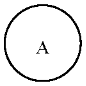

is of the formula:

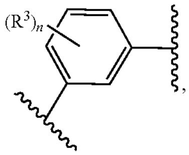, wherein $R^3$ is hydrogen. In certain embodiments, $X^1$ is —N(H)—, $X^2$ is —N(H)—, and ring

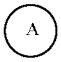

is of the formula:

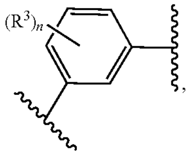, wherein n is 1 and $R^3$ is —C(═O)OH. In certain embodiments, $X^1$ is —N(H)—, $X^2$ is a bond, and ring

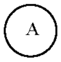

is of the formula:

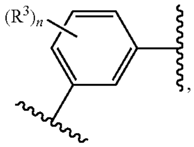, wherein n is 1 and $R^3$ is —C(═O)OH. In certain embodiments, ring

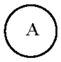

is of the formula:

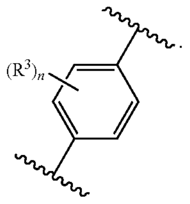

In certain embodiments, $X^1$ is —N(H)—, $X^2$ is —N(H)—, and ring

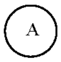

is of the formula:

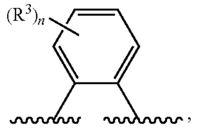

wherein n is 0. In certain embodiments, $X^1$ is —N(H)—, $X^2$ is a bond, and ring

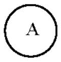

is of the formula:

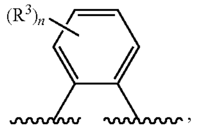

wherein n is 0.

In certain embodiments, Formula (I) is of the formula:

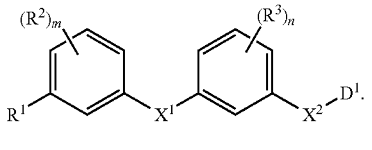

In certain embodiments, Formula (I) is of the formula:

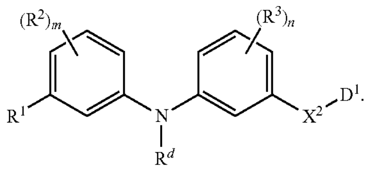

In certain embodiments, Formula (I) is of the formula:

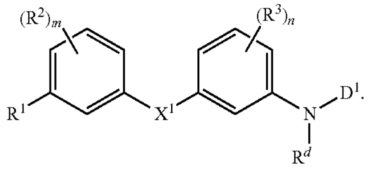

In certain embodiments, Formula (I) is of the formula:

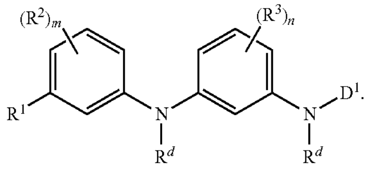

In certain embodiments, Formula (I) is of the formula:

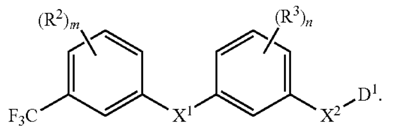

In certain embodiments, Formula (I) is of the formula:

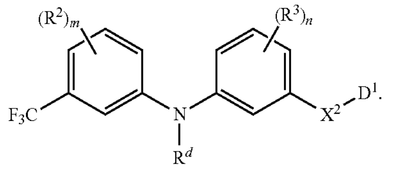

In certain embodiments, Formula (I) is of the formula:

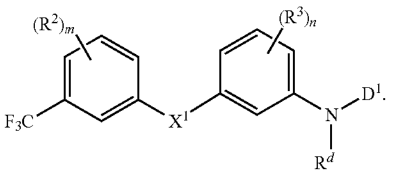

In certain embodiments, Formula (I) is of the formula:

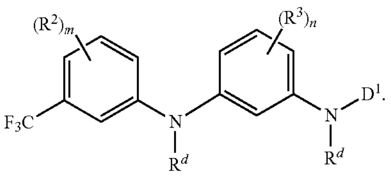

In certain embodiments, $X^1$ is —N(H)—, $X^2$ is —N(H)—, and ring

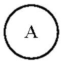

is of the formula:

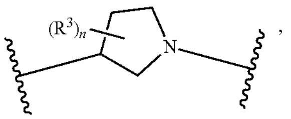

wherein n is 0. In certain embodiments, $X^1$ is —N(H)—, $X^2$ is a bond, and ring

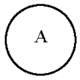

is of the formula:

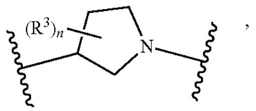

wherein n is 0.

In certain embodiments, Formula (I) is of the formula:

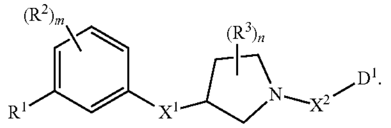

In certain embodiments, Formula (I) is of the formula:

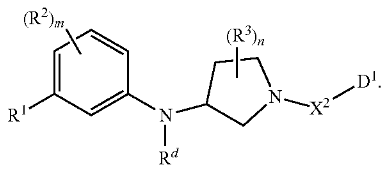

In certain embodiments, Formula (I) is of the formula:

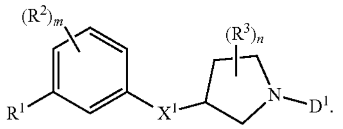

In certain embodiments, Formula (I) is of the formula:

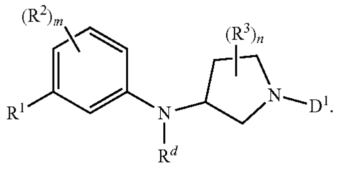

In certain embodiments, Formula (I) is of the formula:

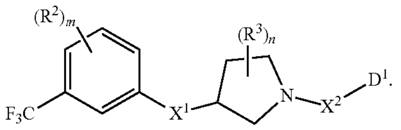

In certain embodiments, Formula (I) is of the formula:

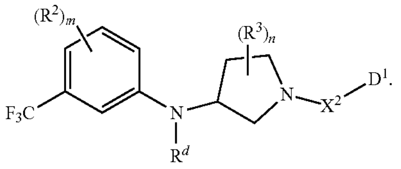

In certain embodiments, Formula (I) is of the formula:

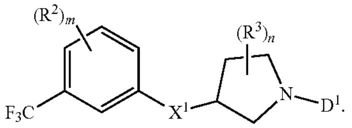

In certain embodiments, Formula (I) is of the formula:

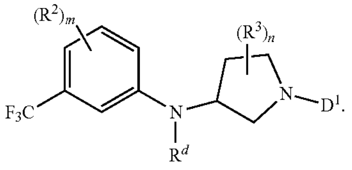

In certain embodiments, Formula (I) is of the formula:

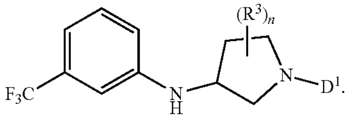

In certain embodiments, Formula (I) is of the formula:

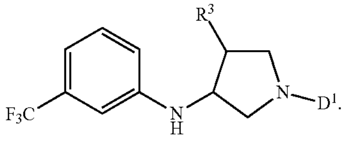

In certain embodiments, Formula (I) is of the formula:

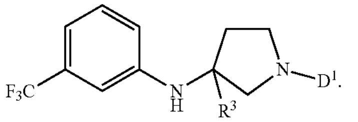

In certain embodiments, Formula (I) is of the formula:

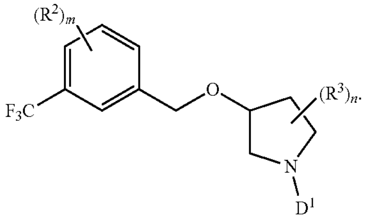

In certain embodiments, Formula (I) is of the formula:

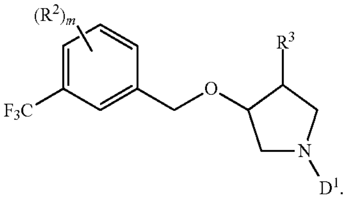

In certain embodiments, Formula (I) is of the formula:

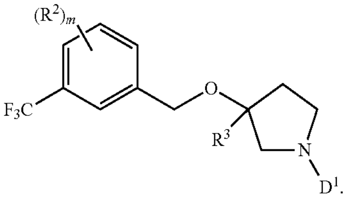

In certain embodiments, Formula (I) is of the formula:

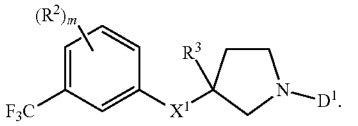

In certain embodiments, Formula (I) is of the formula:

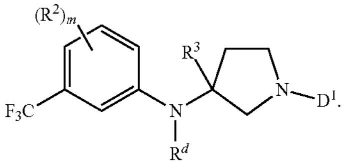

In certain embodiments, Formula (I) is of the formula:

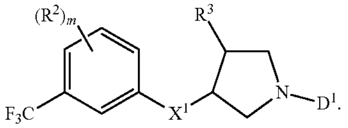

In certain embodiments, Formula (I) is of the formula:

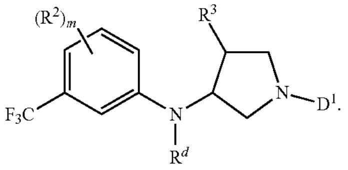

In certain embodiments, Formula (I) is of the formula:

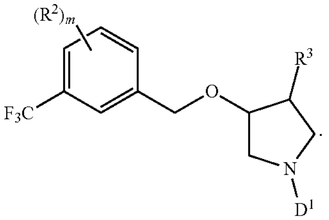

In certain embodiments, Formula (I) is of the formula:

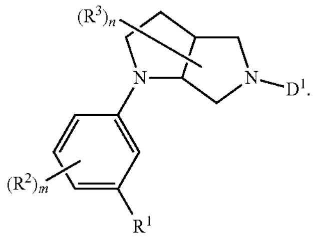

In certain embodiments, Formula (I) is of the formula:

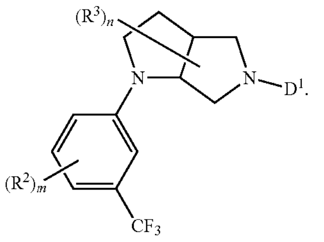

In certain embodiments, Formula (I) is of the formula:

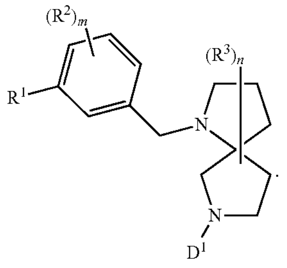

In certain embodiments, Formula (I) is of the formula:

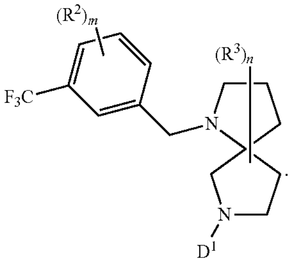

In certain embodiments, $X^1$ is —N(H)—, $X^2$ is —N(H)—, and ring

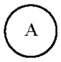

is of the formula:

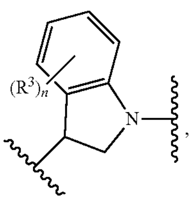

wherein n is 0. In certain embodiments, $X^1$ is —N(H)—, $X^2$ is a bond, and ring

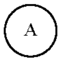

is of the formula:

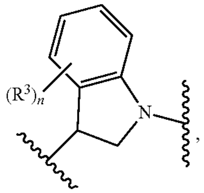

wherein n is 0. In certain embodiments, $X^1$ is a bond, $X^2$ is a bond, and ring

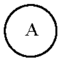

is of the formula:

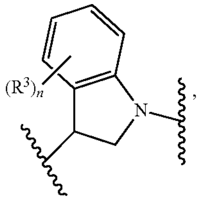

wherein n is 0. In certain embodiments, $X^1$ is —N(H)—, $X^2$ is —N(H)—, and ring

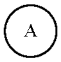

is of the formula:

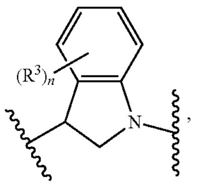

wherein $R^3$ is $OR^e$ and n is 1. In certain embodiments, $X^1$ is —N(H)—, $X^2$ is a bond, and ring

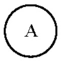

is of the formula:

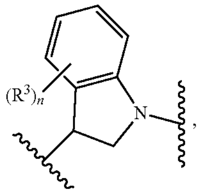

wherein $R^3$ is —$OR^e$ and n is 1. In certain embodiments, $X^1$ is a bond, $X^2$ is a bond, and ring

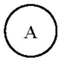

is of the formula:

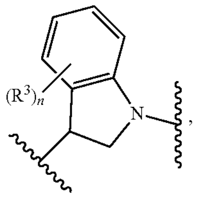

wherein $R^3$ is —$OR^e$ and n is 1. In certain embodiments, $X^1$ is —N(H)—, $X^2$ is —N(H)—, and ring

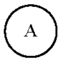

is of the formula:

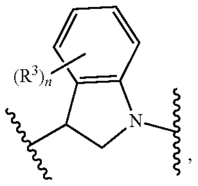

wherein $R^3$ is —OMe and n is 1. In certain embodiments, $X^1$ is —N(H)—, $X^2$ is a bond, and ring

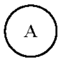

is of the formula:

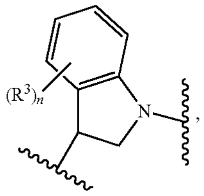

wherein $R^3$ is —OMe; and n is 1. In certain embodiments, $X^1$ is a bond, $X^2$ is a bond, and ring

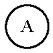

is of the formula:

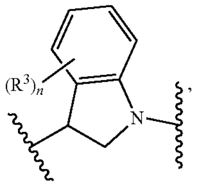

wherein $R^3$ is —OMe; and n is 1. In certain embodiments, $X^1$ is —N(H)—, $X^2$ is —N(H)—, and ring

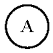

is of the formula:

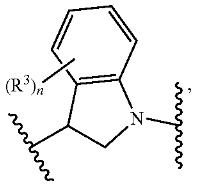

wherein $R^3$ is —$N(R^e)_2$; and n is 1. In certain embodiments, $X^1$ is —N(H)—, $X^2$ is a bond, and ring

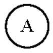

is of the formula:

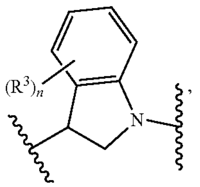

wherein $R^3$ is —$N(R^e)_2$; and n is 1.

In certain embodiments, $X^1$ is a bond, $X^2$ is a bond, and ring

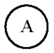

is of the formula:

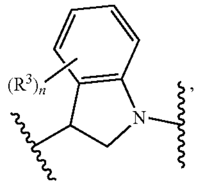

wherein $R^3$ is —$N(R^e)_2$; and n is 1. In certain embodiments, $X^1$ is —N(H)—, $X^2$ is —N(H)—, and ring

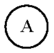

is of the formula:

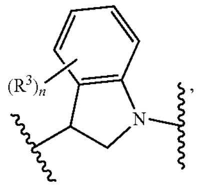

wherein $R^3$ is —$N(Me)_2$; and n is 1. In certain embodiments, $X^1$ is —N(H)—, $X^2$ is a bond, and ring

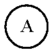

is of the formula:

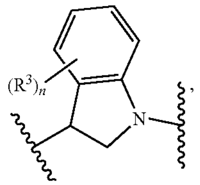

wherein $R^3$ is —$N(Me)_2$; and n is 1. In certain embodiments, $X^1$ is a bond, $X^2$ is a bond, and ring

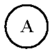

is of the formula:

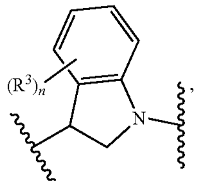

wherein $R^3$ is —$N(Me)_2$; and n is 1.

In certain embodiments, Formula (I) is of the formula:

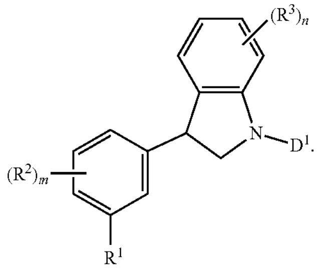

In certain embodiments, Formula (I) is of the formula:

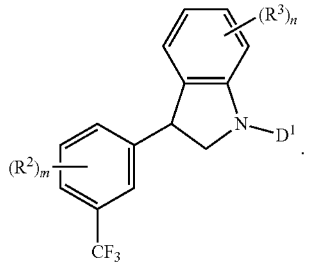

In certain embodiments, or Formula (I) is of the formula:

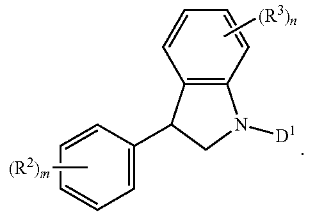

In certain embodiments, or Formula (I) is of the formula:

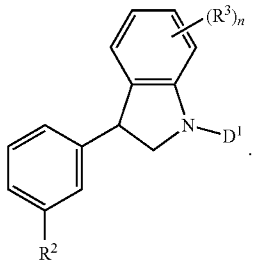

In certain embodiments, Formula (I) is of the formula:

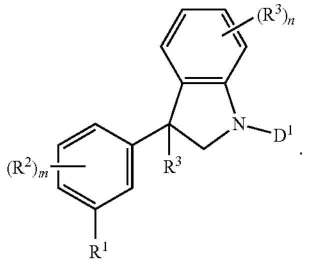

In certain embodiments, Formula (I) is of the formula:

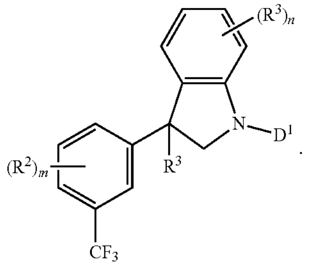

In certain embodiments, Formula (I) is of the formula:

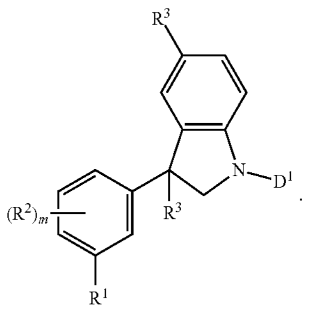

In certain embodiments, Formula (I) is of the formula:

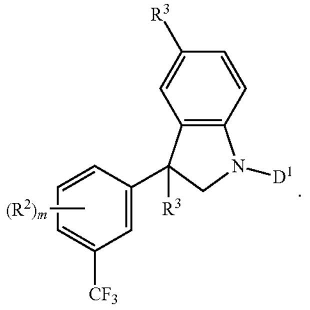

In certain embodiments, Formula (I) is of the formula:

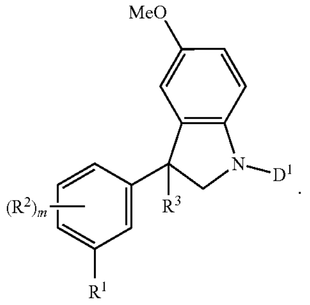

In certain embodiments, Formula (I) is of the formula:

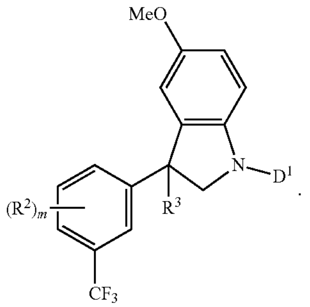

In certain embodiments, Formula (I) is of the formula:

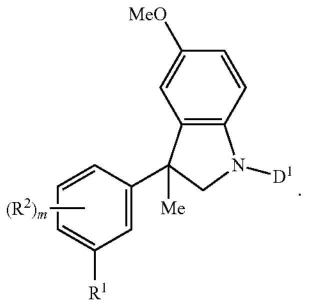

In certain embodiments, Formula (I) is of the formula:

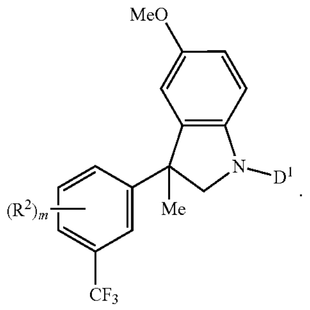

In certain embodiments, or Formula (I) is of the formula:

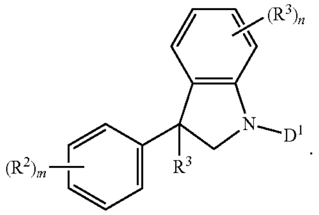

In certain embodiments, or Formula (I) is of the formula:

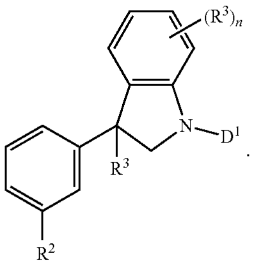

In certain embodiments, Formula (I) is of the formula:

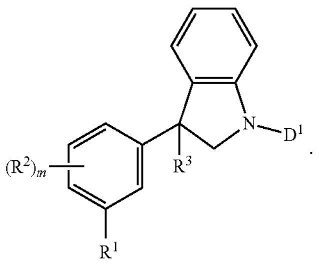

In certain embodiments, Formula (I) is of the formula:

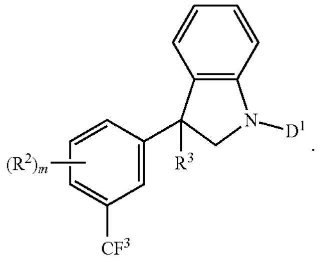

In certain embodiments, or Formula (I) is of the formula:

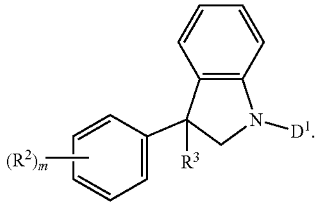

In certain embodiments, or Formula (I) is of the formula:

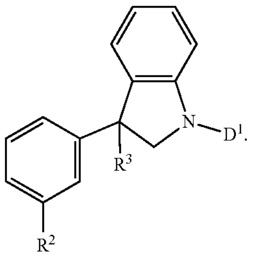

In certain embodiments, Formula (I) is of the formula:

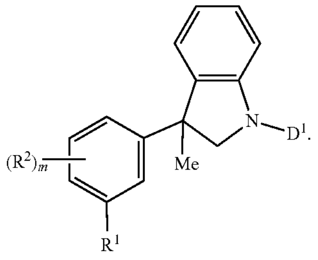

In certain embodiments, Formula (I) is of the formula:

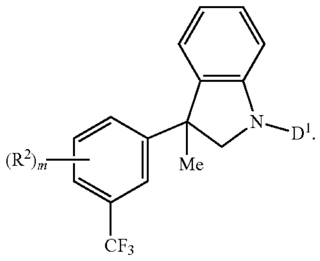

In certain embodiments, or Formula (I) is of the formula:

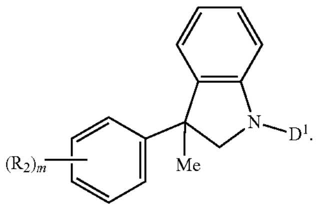

In certain embodiments, or Formula (I) is of the formula:

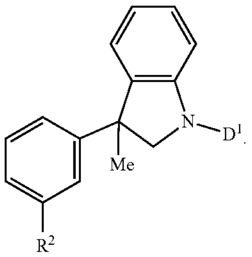

In certain embodiments, $X^1$ is —N(H)—, $X^2$ is —N(H)—, and ring

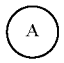

is of the formula:

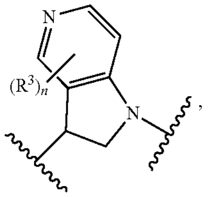

wherein n is 0. In certain embodiments, $X^1$ is —N(H)—, $X^2$ is a bond, and ring

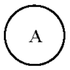

is of the formula:

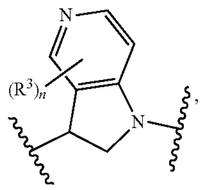

wherein n is 0. In certain embodiments, $X^1$ is a bond, $X^2$ is a bond, and ring

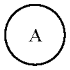

is of the formula:

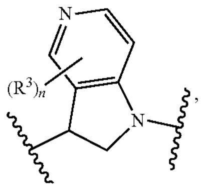

wherein n is 0. In certain embodiments, $X^1$ is —N(H)—, $X^2$ is —N(H)—, and ring

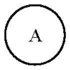

is of the formula:

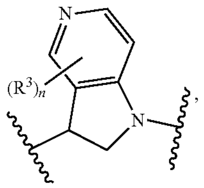

wherein $R^3$ is —$OR^e$; and n is 1. In certain embodiments, $X^1$ is —N(H)—, $X^2$ is a bond, and ring

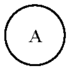

is of the formula:

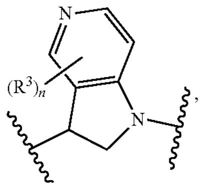

wherein $R^3$ is —$OR^e$; and n is 1. In certain embodiments, $X^1$ is a bond, $X^2$ is a bond, and ring

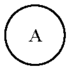

is of the formula:

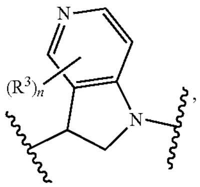

wherein $R^3$ is —$OR^e$; and n is 1. In certain embodiments, $X^1$ is —N(H)—, $X^2$ is —N(H)—, and ring

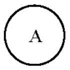

is of the formula:

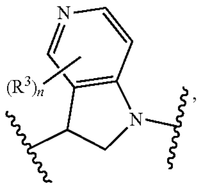

wherein $R^3$ is —OMe and n is 1. In certain embodiments, $X^1$ is —N(H)—, $X^2$ is a bond, and ring

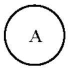

is of the formula:

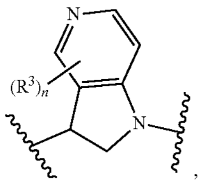

wherein $R^3$ is —OMe; and n is 1. In certain embodiments, $X^1$ is a bond, $X^2$ is a bond, and ring

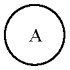

is of the formula:

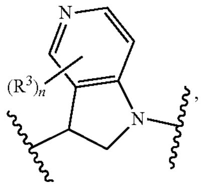

wherein $R^3$ is —OMe; and n is 1. In certain embodiments, $X^1$ is —N(H)—, $X^2$ is —N(H)—, and ring

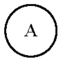

is of the formula:

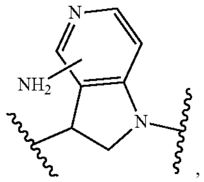

wherein $R^3$ is —$N(R^e)_2$ and n is 1. In certain embodiments, $X^1$ is —N(H)—, $X^2$ is a bond, and ring

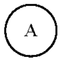

is of the formula:

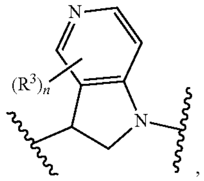

wherein $R^3$ is —$N(R^e)_2$; and n is 1. In certain embodiments, $X^1$ is a bond, $X^2$ is a bond, and ring

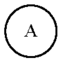

is of the formula:

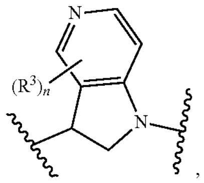

wherein $R^3$ is —N($R^e$)$_2$; and n is 1. In certain embodiments, $X^1$ is —N(H)—, $X^2$ is —N(H)—, and ring

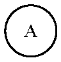

is of the formula:

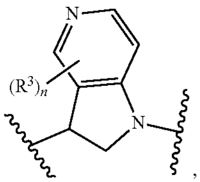

, wherein $R^3$ is —N(Me)$_2$; and n is 1. In certain embodiments, $X^1$ is —N(H)—, $X^2$ is a bond, and ring

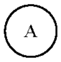

is of the formula:

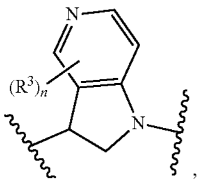

, wherein $R^3$ is —N(Me)$_2$; and n is 1. In certain embodiments, $X^1$ is a bond, $X^2$ is a bond, and ring

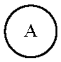

is of the formula:

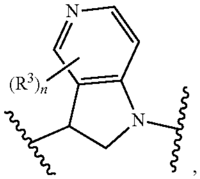

, wherein $R^3$ is —N(Me)$_2$; and n is 1. In certain embodiments, Formula (I) is of the formula:

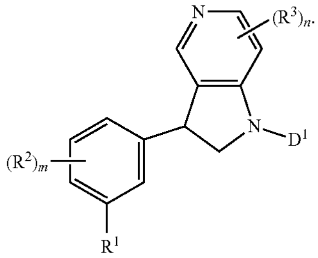

.

In certain embodiments, Formula (I) is of the formula:

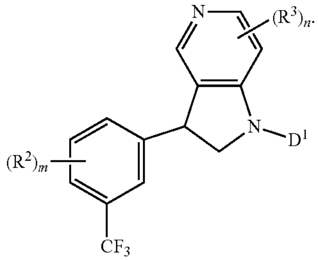

.

In certain embodiments, $X^1$ is —N(H)—, $X^2$ is —N(H)—, and ring

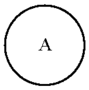

is of the formula:

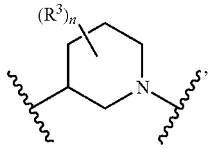

, wherein n is 0. In certain embodiments, $X^1$ is —O—, $X^2$ is —N(H)—, and ring

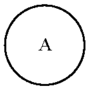

is of the formula:

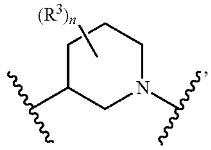

, wherein n is 0. In certain embodiments, $X^1$ is —N(H)—, $X^2$ is a bond, and ring

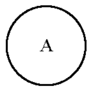

is of the formula:

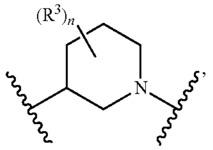

wherein n is 0. In certain embodiments, $X^1$ is —O—, $X^2$ is a bond, and ring

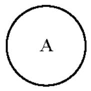

is of the formula:

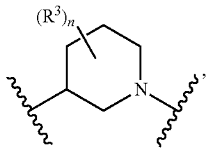

wherein n is 0.

In certain embodiments, Formula (I) is of the formula:

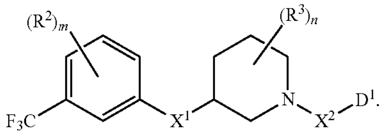

In certain embodiments, Formula (I) is of the formula:

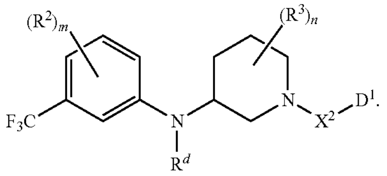

In certain embodiments, Formula (I) is of the formula:

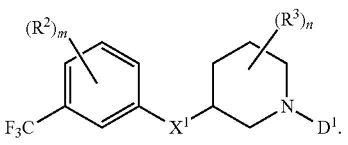

In certain embodiments, Formula (I) is of the formula:

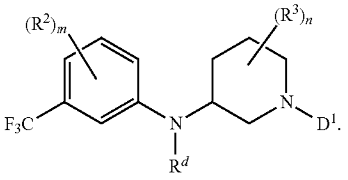

In certain embodiments, ring

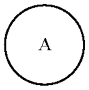

is of the formula:

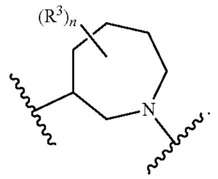

In certain embodiments, $X^1$ is —N(H)—, $X^2$ is —N(H)—, and ring

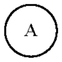

is of the formula:

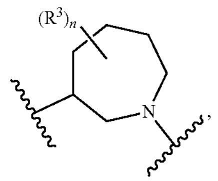

wherein n is 0. In certain embodiments, $X^1$ is —N(H)—, $X^2$ is a bond, and ring

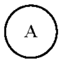

is of the formula:

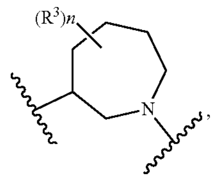

wherein n is 0.

In certain embodiments, a compound of Formula (I) is of the formula:

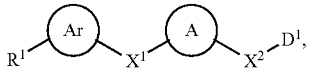

(I)

or a pharmaceutically acceptable salt, solvate, hydrate, polymorph, co-crystal, tautomer, stereoisomer, isotopically labeled derivative, prodrug, composition, or mixture thereof, wherein:

Ar is bicyclic aryl or bicyclic heteroaryl.

In certain embodiments, a compound of Formula (I) is of the formula:

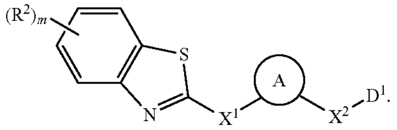

In certain embodiments, a compound of Formula (I) is of the formula:

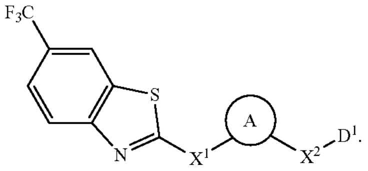

In certain embodiments, a compound of Formula (I) is of the formula:

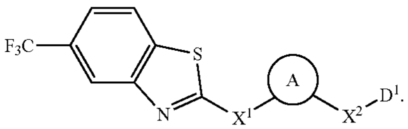

In certain embodiments, a compound of Formula (I) is of the formula:

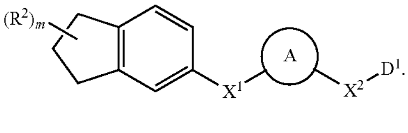

In certain embodiments, a compound of Formula (I) is of the formula:

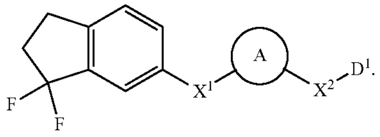

In certain embodiments, a compound of Formula (I) is of the formula:

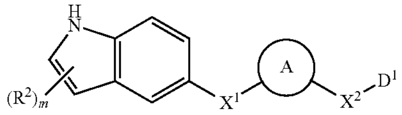

In certain embodiments, a compound of Formula (I) is of the formula:

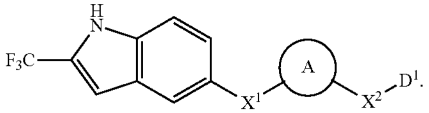

In certain embodiments, a compound of Formula (I) is of the formula:

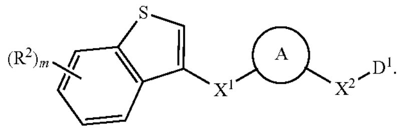

In certain embodiments, a compound of Formula (I) is of the formula:

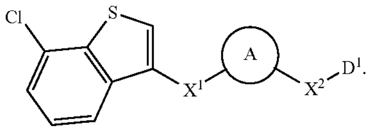

In certain embodiments, a compound of Formula (I) is of the formula:

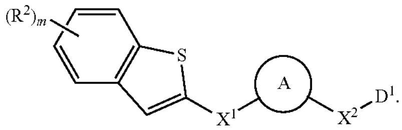

In certain embodiments, a compound of Formula (I) is of the formula:

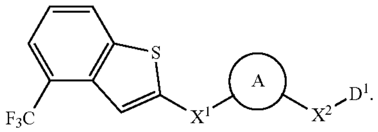

In certain embodiments, Formula (I) is of the Formula (I-a):

(I-a)

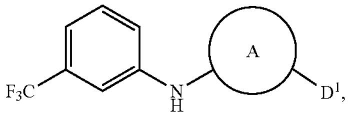

or a pharmaceutically acceptable salt, solvate, hydrate, polymorph, co-crystal, tautomer, stereoisomer, isotopically labeled derivative, prodrug, composition, or mixture thereof.

In certain embodiments, Formula (I) is of the Formula (I-b):

(I-b)

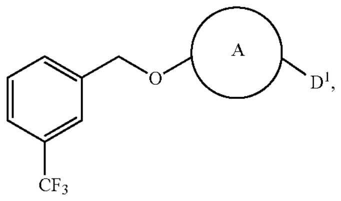

or a pharmaceutically acceptable salt, solvate, hydrate, polymorph, co-crystal, tautomer, stereoisomer, isotopically labeled derivative, prodrug, composition, or mixture thereof.

In certain embodiments, Formula (I) is of the Formula (I-c):

(I-c)

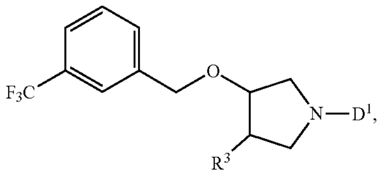

or a pharmaceutically acceptable salt, solvate, hydrate, polymorph, co-crystal, tautomer, stereoisomer, isotopically labeled derivative, prodrug, composition, or mixture thereof.

In certain embodiments a compound of Formula (I) is of the Formula (I-d):

(I-d)

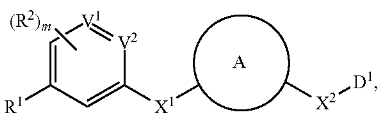

or a pharmaceutically acceptable salt, solvate, hydrate, polymorph, co-crystal, tautomer, stereoisomer, isotopically labeled derivative, prodrug, composition, or mixture thereof, wherein:

$R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^c$, —$NO_2$, —$N(R^c)_2$, or —$SR^c$, wherein $R^c$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined with together with $X^1$ to form an optionally substituted heterocyclic ring;

$V^1$ is —N— or —$C(R^2)$—; and $V^2$ is —N— or —$C(R^2)$—.

In certain embodiments, Formula (I) is of the Formula (I-e):

(I-e)

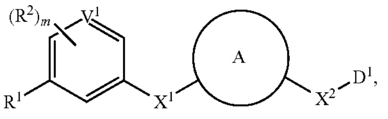

or a pharmaceutically acceptable salt, solvate, hydrate, tautomer, or stereoisomer thereof, wherein:

$R^1$ is hydrogen, trifluoromethyl or $N(R^a)(R^b)$, wherein $R^a$ is selected from optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl;

$R^b$ is selected from optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or $R^a$ and $R^b$ together with the nitrogen atom to which they are attached form a heterocycle;

$R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^c$, —$NO_2$, —$N(R^c)_2$, or —$SR^c$, wherein $R^c$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined with together with $X^1$ to form an optionally substituted heterocyclic ring;

A is an optionally substituted carbocyclic ring, an optionally substituted aryl ring, or an optionally substituted heterocyclic ring;

$V^1$ is N or —$C(R^2)$—;

$X^1$ is a bond or O, S, —$CH_2N(R^d)$—, or —$N(R^d)$—, wherein $R^d$ is a bond, hydrogen, substituted or unsubstituted $C_{1-6}$ alkyl, or a nitrogen protecting group, or $R^d$ can be joined together with one instance of $R^2$ to form an optionally substituted heterocyclic ring;

$X^2$ is a bond or O, S, or $N(R^d)$;
m is 0, 1, 2, 3 or 4;
$D^1$ is a warhead of any one of Formulae (i-1) to (i-42):
(i-1)
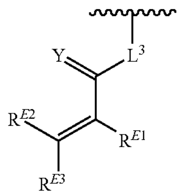
,
(i-2)
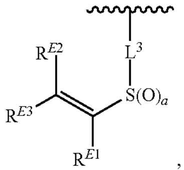
,
(i-3)
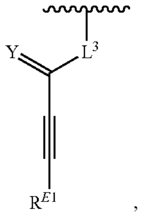
,
(i-4)
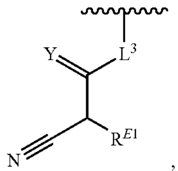
,
(i-5)
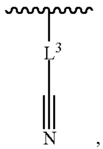
,
(i-6)
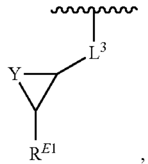
,
(i-7)
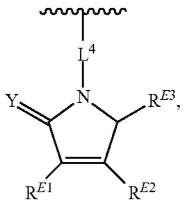
-continued
(i-8)
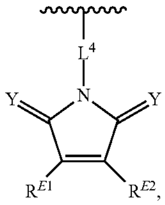
(i-9)
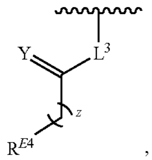
,
(i-10)
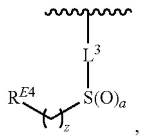
,
(i-11)
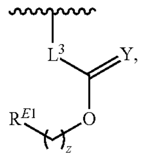
(i-12)
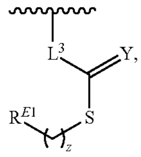
(i-13)
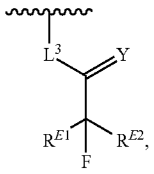
(i-14)
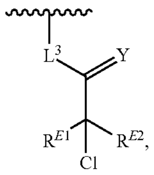
(i-15)
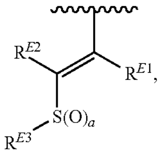
(i-16)
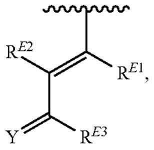

-continued
(i-17)
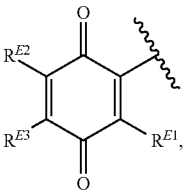
(i-18)
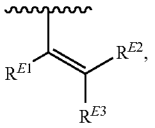
(i-19)
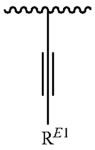
, and
(i-20)
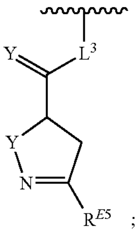
;
(i-21)
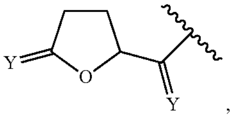
,
(i-22)
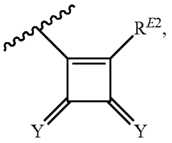
(i-23)
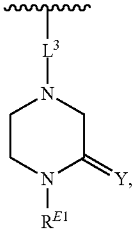
(i-24)
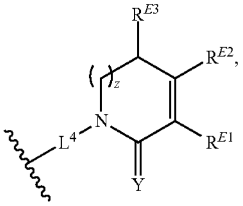
-continued
(i-25)
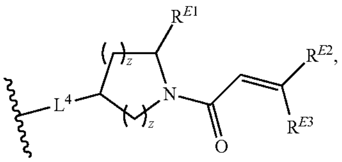
(i-26)
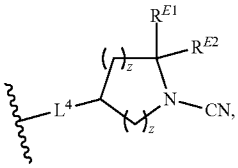
(i-27)
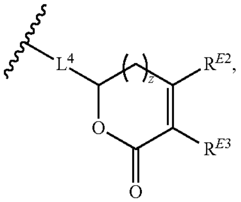
(i-28)
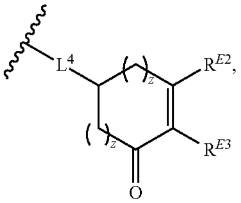
(i-29)
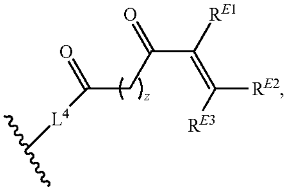
(i-30)
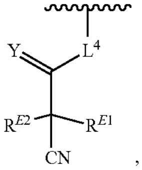
,
(i-31)
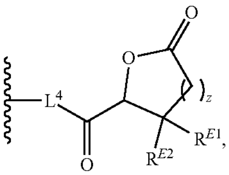
(i-32)
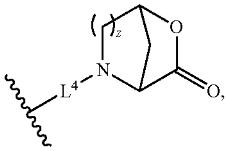

-continued (i-33)

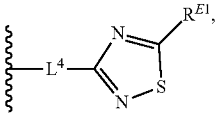

(i-34)

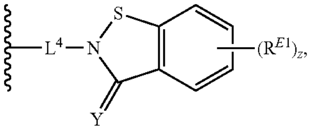

(i-35)

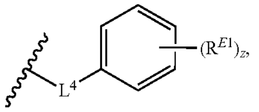

(i-36)

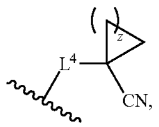

(i-37)

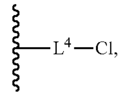

(i-38)

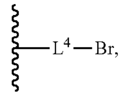

(i-39)

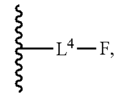

(i-40)

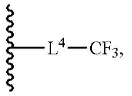

(i-41)

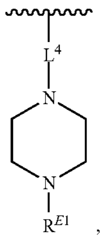

, and (i-42)

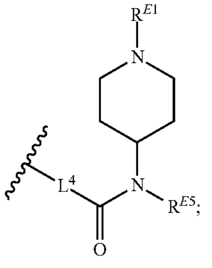

wherein:

$L^3$ is a bond or an optionally substituted $C_{1-4}$ hydrocarbon chain, optionally wherein one or more carbon units of the hydrocarbon chain are independently replaced with —O—, —S—, —$NR^{L3a}$—, —$NR^{L3a}C(=O)$—, —$C(=O)NR^{L3a}$—, —SC(=O)—, —C(=O)S—, —OC(=O)—, —C(=O)O—, —$NR^{L3a}C(=S)$—, —$C(=S)NR^{L3a}$—, trans-$CR^{L3b}$=$CR^{L3b}$—, cis-$CR^{L3b}$=$CR^{L3b}$—, —C≡C—, —S(=O)—, —S(=O)O—, —OS(=O)—, —$S(=O)NR^{L3a}$—, —$NR^{L3a}S(=O)$—, —$S(=O)_2$—, —$S(=O)_2O$—, —$OS(=O)_2$—, —$S(=O)_2NR^{L3a}$—, or —$NR^{L3a}S(=O)_2$—, wherein $R^{L3a}$ is hydrogen, substituted or unsubstituted $C_{1-6}$ alkyl, or a nitrogen protecting group, and wherein each occurrence of $R^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L3b}$ groups are joined to form an optionally substituted carbocyclic or optionally substituted heterocyclic ring;

$L^4$ is a bond or an optionally substituted $C_{1-4}$ hydrocarbon chain;

$R^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E1a}$, —$CH_2N(R^{E1a})_2$, —$CH_2SR^{E1a}$, —$OR^{E1a}$, —$N(R^{E1a})_2$, —$Si(R^{E1a})_3$, and —$SR^{E1a}$, wherein each occurrence of $R^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E1a}$ groups are joined to form an optionally substituted heterocyclic ring;

$R^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E2a}$, —$CH_2N(R^{E2a})_2$, —$CH_2SR^{E2a}$, —$OR^{E2a}$, —$N(R^{E2a})_2$, and —$SR^{E2a}$, wherein each occurrence of $R^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E2a}$ groups are joined to form an optionally substituted heterocyclic ring;

$R^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$CH_2OR^{E3a}$, —$CH_2N(R^{E3a})_2$, —$CH_2SR^{E3a}$, —$OR^{E3a}$, —$N(R^{E3a})_2$, and —$SR^{E3a}$, wherein each occurrence of $R^{E3a}$ is independently selected from the group consisting of hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

Y is O, S, or $NR^{E6}$, wherein $R^{E6}$ is hydrogen, substituted or unsubstituted $C_{1-6}$ alkyl, or a nitrogen protecting group;

a is 1 or 2; and each instance of z is independently 0, 1, 2, 3, 4, 5, or 6.

Formula (I-e) contains the substituent $R^1$. In certain embodiments, $R^1$ is hydrogen. In certain embodiments, $R^1$ is haloalkyl. In certain embodiments, $R^1$ is trifluoromethyl. In certain embodiments, $R^1$ is —$N(R^a)(R^b)$, wherein $R^a$ and $R^b$ are as defined herein. In certain embodiments, $R^a$ and $R^b$ are the same. In certain embodiments, $R^a$ and $R^b$ are different. In certain embodiments, $R^a$ is substituted or unsubstituted acyl. In certain embodiments, $R^a$ contains a biotin-derivative. In certain embodiments, $R^1$ is

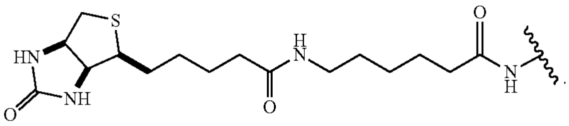

In certain embodiments, $R^a$ is substituted or unsubstituted $C_{1-6}$ alkyl. In certain embodiments, $R^a$ is substituted or unsubstituted $C_{2-6}$ alkenyl. In certain embodiments, $R^a$ is substituted or unsubstituted $C_{2-6}$ alkynyl. In certain embodiments, $R^a$ is substituted or unsubstituted carbocyclyl. In certain embodiments, $R^a$ is substituted or unsubstituted heterocyclyl. In certain embodiments, $R^a$ is substituted or unsubstituted aryl. In certain embodiments, $R^a$ is substituted or unsubstituted heteroaryl. In certain embodiments, $R^b$ is hydrogen. In certain embodiments, $R^a$ is hydrogen and $R^b$ is hydrogen. In certain embodiments, $R^b$ is hydrogen and $R^a$ is substituted or unsubstituted acyl. In certain embodiments, $R^b$ is substituted or unsubstituted acyl. In certain embodiments, $R^b$ is substituted or unsubstituted $C_{1-6}$ alkyl. In certain embodiments, $R^b$ is substituted or unsubstituted $C_{1-6}$ alkyl and $R^a$ is substituted or unsubstituted acyl. In certain embodiments, $R^b$ is substituted or unsubstituted $C_{2-6}$ alkenyl. In certain embodiments, $R^b$ is substituted or unsubstituted $C_{2-6}$ alkynyl. In certain embodiments, $R^b$ is substituted or unsubstituted carbocyclyl. In certain embodiments, $R^b$ is substituted or unsubstituted heterocyclyl. In certain embodiments, $R^b$ is substituted or unsubstituted aryl. In certain embodiments, $R^b$ is substituted or unsubstituted heteroaryl. In certain embodiments, $R^a$ and $R^b$ are alkyl. In certain embodiments, $R^a$ and $R^b$ are methyl. In certain embodiments, $R^1$ is dimethylamine. In certain embodiments, $R^a$ and $R^b$ are joined to form a substituted or unsubstituted heterocycle. In certain embodiments, $R^1$ is a substituted or unsubstituted piperidine ring. In certain embodiments, $R^1$ is a substituted or unsubstituted piperazine ring. In certain embodiments, $R^1$ is a substituted or unsubstituted morpholine ring. In certain embodiments, $R^1$ is —$NH_2$. In certain embodiments, $R^1$ is

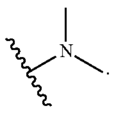 [SMILES: *N(C)C]

In certain embodiments, $R^1$ is

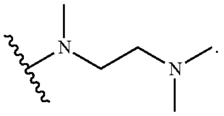 [SMILES: *N(C)CCN(C)C]

In certain embodiments, $R^1$ is

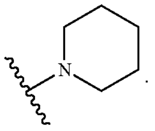

In certain embodiments, $R^1$ is

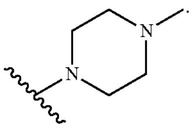 [SMILES: *N1CCN(C)CC1]

In certain embodiments, R is

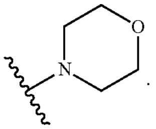 [SMILES: *N1CCOCC1]

In certain embodiments of Formula (I-e), $R^1$ is $CF_3$ and $R^2$ is haloalkyl. In certain embodiments, $R^1$ is $CF_3$; and $R^2$ is —$CF_3$. In certain embodiments, $R^1$ is $CF_3$; and $R^2$ is H. In certain embodiments, $R^1$ is $CF_3$; and $R^2$ is —OMe. In certain embodiments, $R^1$ is $CF_3$; and $R^2$ is a halogen. In certain embodiments, $R^1$ is —$CF_3$; and $R^2$ is Cl. In certain embodiments, $R^1$ is $CF_3$ and $R^2$ is $NO_2$. In certain embodiments, $R^1$ is —$CF_3$; and $R^2$ is substituted or unsubstituted alkyl. In certain embodiments, $R^1$ is $CF_3$; and $R^2$ is substituted or unsubstituted methyl. In certain embodiments, $R^1$ is —$CF_3$; and $R^2$ is unsubstituted methyl. In certain embodiments, $R^1$ is —$CF_3$; and $R^2$ is substituted or unsubstituted alkynyl. In certain embodiments, $R^1$ is —$CF_3$; and $R^2$ is alkynyl. In certain embodiments, $R^1$ is —$CF_3$; and $R^2$ is —$N(R^c)_2$, wherein RC is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or two instances of $R^c$ together with the nitrogen atom to which they are attached can be joined to form a heterocyclic ring. In certain embodiments, $R^1$ is $CF_3$, $R^2$ is —$N(R^c)_2$, and $R^c$ is H. In certain embodiments, $R^1$ is —$N(R^a)(R^b)$ and $R^2$ is haloalkyl. In certain embodiments, $R^1$ is —$N(R^a)(R^b)$ and $R^2$ is $CF_3$. In certain embodiments, $R^1$ is

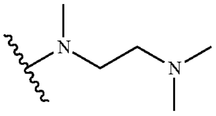 [SMILES: *N(C)CCN(C)C]

and $R^2$ is $CF_3$. In certain embodiments, $R^1$ is

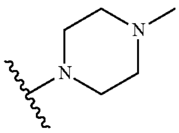 [SMILES: *N1CCN(C)CC1]

and $R^2$ is $CF_3$. In certain embodiments, $R^1$ is

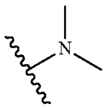 [SMILES: *N(C)C]

and $R^2$ is H. In certain embodiments, $R^1$ is

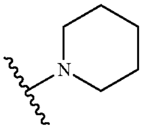 [SMILES: *N1CCCCC1]

and $R^2$ is $CF_3$. In certain embodiments, $R^1$ is

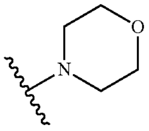 [SMILES: *N1CCOCC1]

and $R^2$ is $CF_3$. In certain embodiments, $R^1$ is —N($R^a$)($R^b$) and $R^2$ is H. In certain embodiments, $R^1$ is

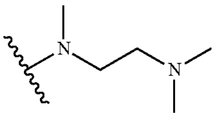 [SMILES: *N(C)CCN(C)C]

and $R^2$ is H. In certain embodiments, $R^1$ is

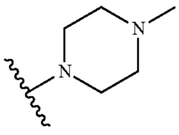 [SMILES: *N1CCN(C)CC1]

and $R^2$ is H. In certain embodiments, $R^1$ is

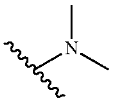 [SMILES: *N(C)C]

and $R^2$ is H. In certain embodiments, $R^1$ is

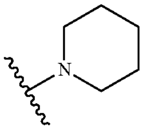 [SMILES: *N1CCCCC1]

and $R^2$ is H. In certain embodiments, $R^1$ is

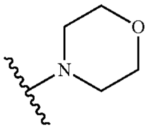 [SMILES: *N1CCOCC1]

and $R^2$ is H. In certain embodiments, $R^1$ is H and $R^2$ is H. In certain embodiments, $R^1$ is H and $R^2$ is substituted or unsubstituted alkyl. In certain embodiments, $R^1$ is H and $R^2$ is substituted or unsubstituted methyl. In certain embodiments, $R^1$ is H and $R^2$ is unsubstituted methyl. In certain embodiments, $R^1$ is H and there are two instances of $R^2$, wherein $R^2$ is methyl.

In certain embodiments, $R^a$ is selected from optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl; and $R^b$ is selected from optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or $R^a$ and $R^b$ together with the nitrogen atom to which they are attached form a heterocycle.

In certain embodiments of Formula (I-e), $R^1$ is of Formula (V):

(V-a)

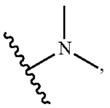

(V-b)

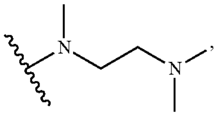

(V-c)

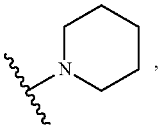

-continued (V-d)

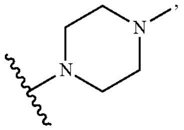

(V-e)

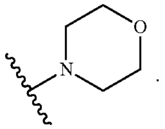

As generally defined herein, Formula (I-d) and Formula (I-e) includes the substituent $V^1$. In certain embodiments, $V^1$ is —N= or —C($R^2$)=, wherein $R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^c$, —$NO_2$, —$N(R^c)_2$, or —$SR^c$, wherein RC is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined together with $X^1$ to form an optionally substituted heterocyclic ring.

As generally defined herein, Formula (I-d) includes the substituent $V^2$. In certain embodiments, $V^2$ is —N= or —C($R^2$)=, wherein $R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^c$, —$NO_2$, —$N(R')_2$, or —$SR^c$, wherein $R^c$ is independently selected from hydrogen, optionally substituted acyl, optionally substituted alkyl, methyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined together with $X^1$ to form an optionally substituted heterocyclic ring.

In certain embodiments, $V^1$ and $V^2$ are the same. In certain embodiments, $V^1$ and $V^2$ are different. In certain embodiments, $V^1$ is —C($R^2$)—; and $V^2$ is —C($R^2$)—. In certain embodiments, $V^1$ is —C(H)—; and $V^2$ is —C($R^2$)—. In certain embodiments, $V^1$ is —C($R^2$)—; and $V^2$ is —C(H)—. In certain embodiments, $V^1$ is —C(H)—; and $V^2$ is —C(H)—. In certain embodiments, $V^1$ is N; and $V^2$ is —C($R^2$)—. In certain embodiments, $V^1$ is N; and $V^2$ is —C(H)—. In certain embodiments, $V^1$ is —C($R^2$)—; and $V^2$ is N. In certain embodiments, $V^1$ is —C(H)— and $V^2$ is N.

In certain embodiments, the compound of Formula (I) is of one of the formulae in Table 1 below:

TABLE 1

Compounds of the Disclosure

| Compound Number | Chemical Structure |
|---|---|
| I-1 | 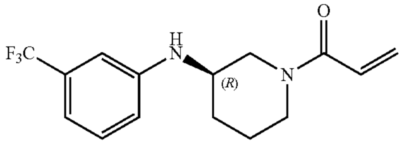 |
| I-2 | 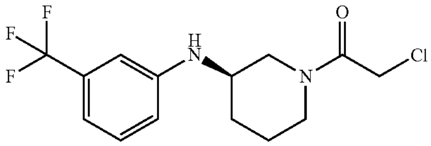 [SMILES: O=C(CCl)N1CCC[C@@H](Nc2cccc(C(F)(F)F)c2)C1] |
| I-11 | 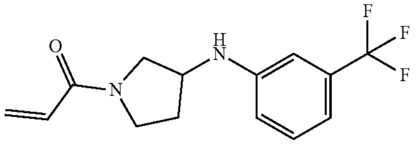 [SMILES: C=CC(=O)N1CCC(Nc2cccc(C(F)(F)F)c2)C1] |
| I-13 | 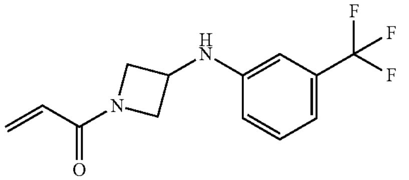 [SMILES: C=CC(=O)N1CC(Nc2cccc(C(F)(F)F)c2)C1] |

TABLE 1-continued
| Compounds of the Disclosure | |
|---|---|
| Compound Number | Chemical Structure |
| I-15 | 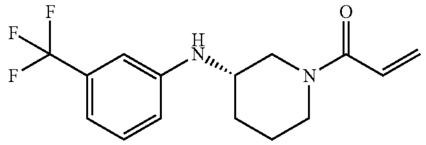 [SMILES: C=CC(=O)N1CCC[C@H](Nc2cccc(C(F)(F)F)c2)C1] |
| I-17 | 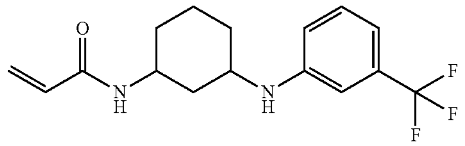 [SMILES: C=CC(=O)NC1CCCC(Nc2cccc(C(F)(F)F)c2)C1] |
| I-23 | 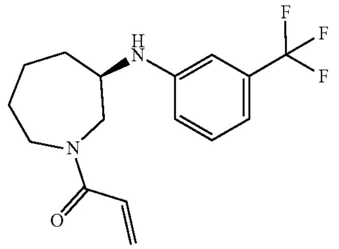 [SMILES: C=CC(=O)N1CCCC[C@@H](Nc2cccc(C(F)(F)F)c2)C1] |
| I-25 | 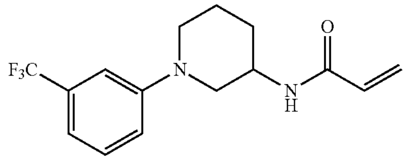 [SMILES: C=CC(=O)NC1CCCN(c2cccc(C(F)(F)F)c2)C1] |
| I-28 | 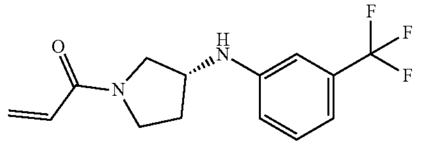 [SMILES: C=CC(=O)N1CC[C@@H](Nc2cccc(C(F)(F)F)c2)C1] |
| I-29 | 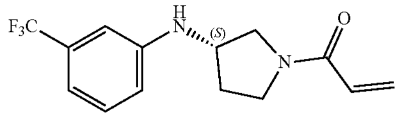 |
| I-48 | 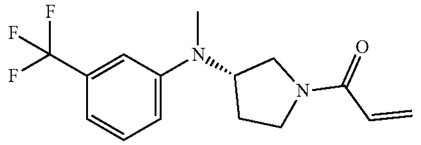 [SMILES: C=CC(=O)N1CC[C@H](N(C)c2cccc(C(F)(F)F)c2)C1] |
| I-47 | 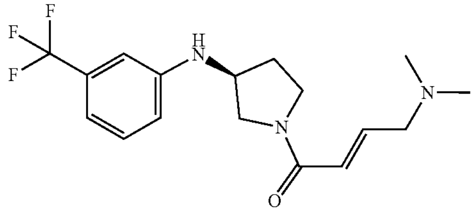 [SMILES: CN(C)C/C=C/C(=O)N1CC[C@H](Nc2cccc(C(F)(F)F)c2)C1] |

TABLE 1-continued
| Compounds of the Disclosure | |
|---|---|
| Compound Number | Chemical Structure |
| I-50 | 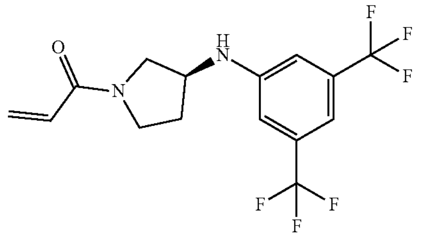 [SMILES: C=CC(=O)N1CC[C@H](Nc2cc(C(F)(F)F)cc(C(F)(F)F)c2)C1] |
| I-51 | 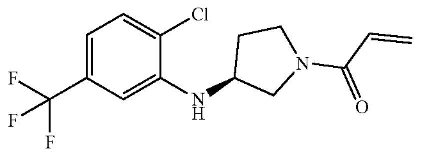 [SMILES: C=CC(=O)N1CC[C@H](Nc2cc(C(F)(F)F)ccc2Cl)C1] |
| I-52 | 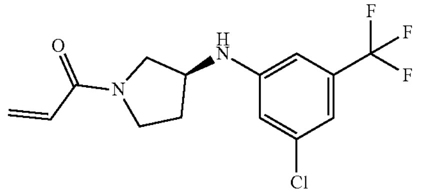 [SMILES: C=CC(=O)N1CC[C@H](Nc2cc(Cl)cc(C(F)(F)F)c2)C1] |
| I-53 | 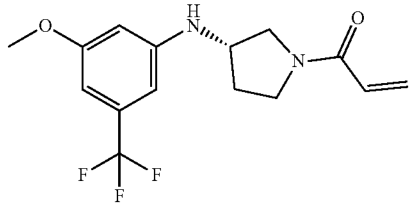 [SMILES: C=CC(=O)N1CC[C@H](Nc2cc(OC)cc(C(F)(F)F)c2)C1] |
| I-55 | 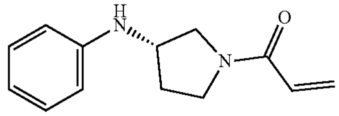 [SMILES: C=CC(=O)N1CC[C@H](Nc2ccccc2)C1] |
| I-56 | 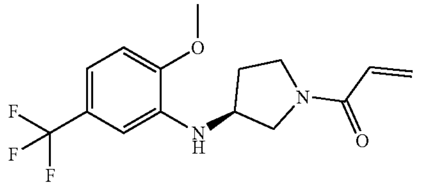 [SMILES: C=CC(=O)N1CC[C@H](Nc2cc(C(F)(F)F)ccc2OC)C1] |
| I-57 | 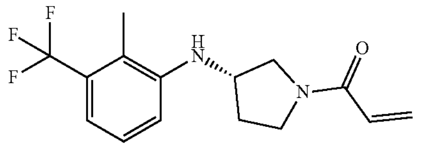 [SMILES: C=CC(=O)N1CC[C@H](Nc2cccc(C(F)(F)F)c2C)C1] |
| I-49 | 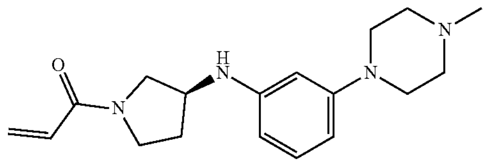 [SMILES: C=CC(=O)N1CC[C@H](Nc2cccc(N3CCN(C)CC3)c2)C1] |

TABLE 1-continued
| Compounds of the Disclosure | |
|---|---|
| Compound Number | Chemical Structure |
| I-61 | 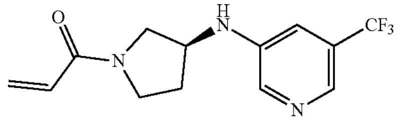 [SMILES: C=CC(=O)N1CC[C@H](Nc2cncc(C(F)(F)F)c2)C1] |
| I-62 | 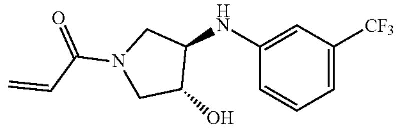 [SMILES: C=CC(=O)N1C[C@@H](O)[C@H](Nc2cccc(C(F)(F)F)c2)C1] |
| I-63 | 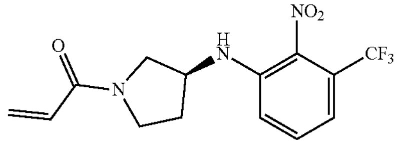 [SMILES: C=CC(=O)N1CC[C@H](Nc2cccc(C(F)(F)F)c2N)C1] |
| I-65 | 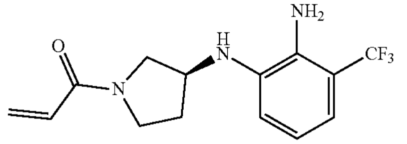 |
| I-67 | 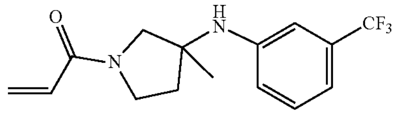 [SMILES: C=CC(=O)N1CCC(C)(Nc2cccc(C(F)(F)F)c2)C1] |
| I-9 | 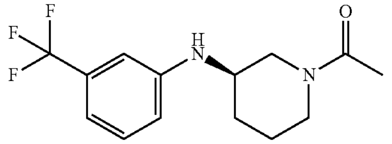 [SMILES: CC(=O)N1CCC[C@@H](Nc2cccc(C(F)(F)F)c2)C1] |
| I-10 | 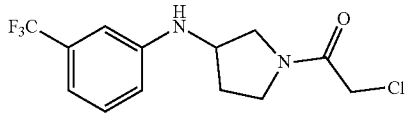 [SMILES: O=C(CCl)N1CCC(Nc2cccc(C(F)(F)F)c2)C1] |
| I-12 | 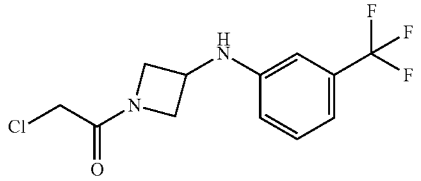 [SMILES: O=C(CCl)N1CC(Nc2cccc(C(F)(F)F)c2)C1] |
| I-14 | 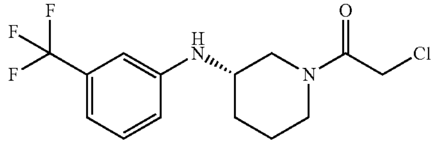 [SMILES: O=C(CCl)N1CCC[C@H](Nc2cccc(C(F)(F)F)c2)C1] |
| I-16 | 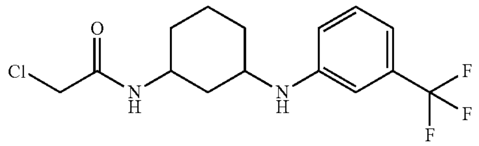 [SMILES: O=C(CCl)NC1CCCC(Nc2cccc(C(F)(F)F)c2)C1] |

TABLE 1-continued
| Compounds of the Disclosure | |
|---|---|
| Compound Number | Chemical Structure |
| I-19 | 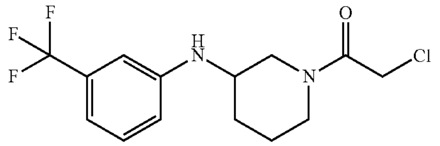 [SMILES: O=C(CCl)N1CCCC(Nc2cccc(C(F)(F)F)c2)C1] |
| I-24 | 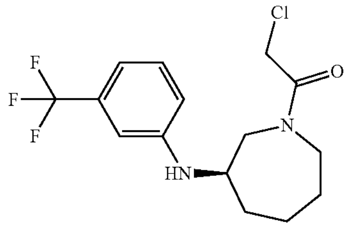 [SMILES: O=C(CCl)N1CCCC[C@@H](Nc2cccc(C(F)(F)F)c2)C1] |
| I-26 | 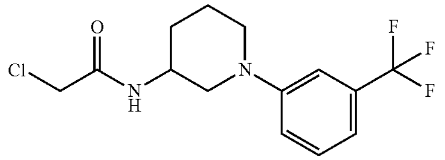 [SMILES: O=C(CCl)NC1CCCN(c2cccc(C(F)(F)F)c2)C1] |
| I-27 | 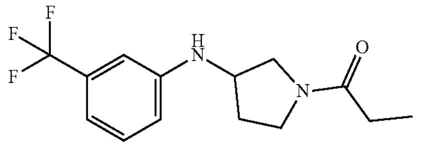 [SMILES: CCC(=O)N1CCC(Nc2cccc(C(F)(F)F)c2)C1] |
| I-21 | 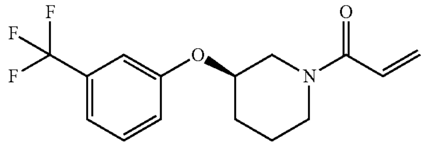 [SMILES: C=CC(=O)N1CCC[C@@H](Oc2cccc(C(F)(F)F)c2)C1] |
| I-58 | 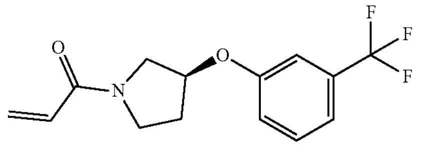 [SMILES: C=CC(=O)N1CC[C@H](Oc2cccc(C(F)(F)F)c2)C1] |
| I-20 | 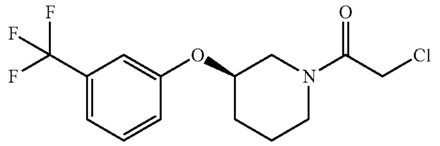 [SMILES: O=C(CCl)N1CCC[C@@H](Oc2cccc(C(F)(F)F)c2)C1] |
| I-34 | 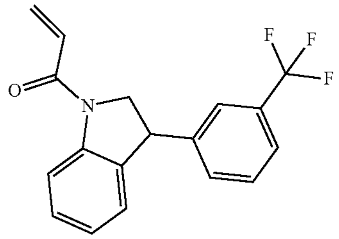 [SMILES: C=CC(=O)N1CC(c2cccc(C(F)(F)F)c2)c2ccccc21] |

TABLE 1-continued
| Compounds of the Disclosure | |
|---|---|
| Compound Number | Chemical Structure |
| I-35 | 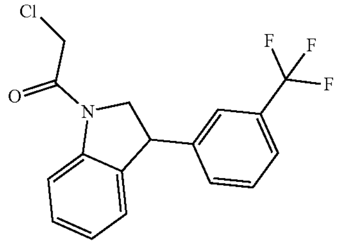 [SMILES: O=C(CCl)N1CC(c2cccc(C(F)(F)F)c2)c2ccccc21] |
| I-68 | 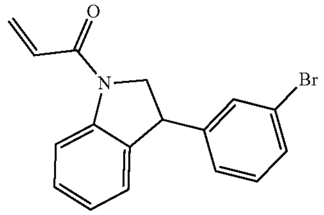 [SMILES: C=CC(=O)N1CC(c2cccc(Br)c2)c2ccccc21] |
| I-22 | 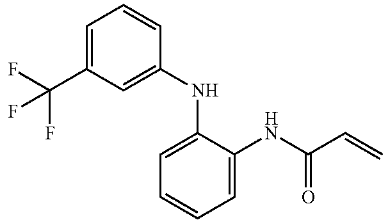 [SMILES: C=CC(=O)Nc1ccccc1Nc1cccc(C(F)(F)F)c1] |
| I-31 | 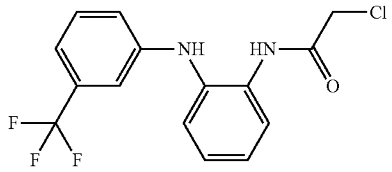 [SMILES: O=C(CCl)Nc1ccccc1Nc1cccc(C(F)(F)F)c1] |
| I-64 | 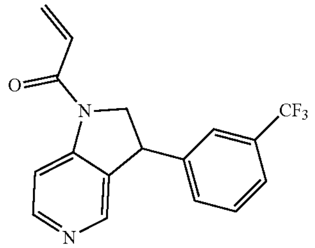 [SMILES: C=CC(=O)N1CC(c2cccc(C(F)(F)F)c2)c2cnccc21] |
| I-66 | 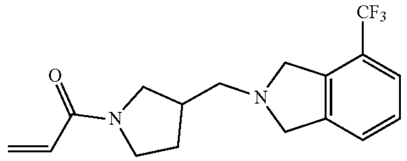 [SMILES: C=CC(=O)N1CCC(CN2Cc3cccc(C(F)(F)F)c3C2)C1] |
| I-4 | 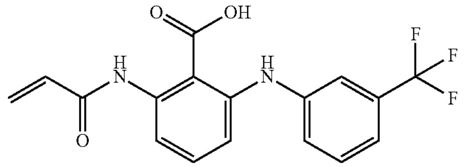 [SMILES: C=CC(=O)Nc1cccc(Nc2cccc(C(F)(F)F)c2)c1C(=O)O] |

TABLE 1-continued
| Compounds of the Disclosure | |
|---|---|
| Compound Number | Chemical Structure |
| I-3 | 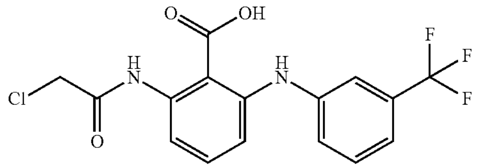 [SMILES: O=C(CCl)Nc1cccc(Nc2cccc(C(F)(F)F)c2)c1C(=O)O] |
| I-59 | 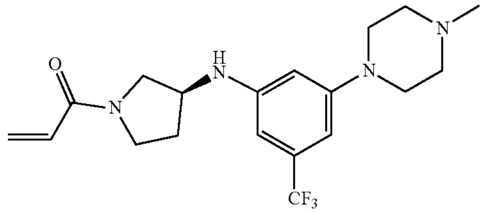 [SMILES: C=CC(=O)N1CC[C@H](Nc2cc(N3CCN(C)CC3)cc(C(F)(F)F)c2)C1] |
| I-60 | 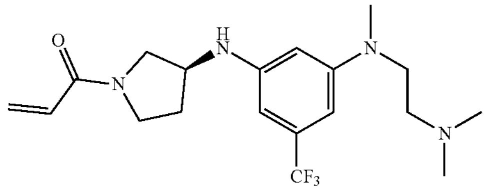 [SMILES: C=CC(=O)N1CC[C@H](Nc2cc(N(C)CCN(C)C)cc(C(F)(F)F)c2)C1] |
| I-18 | 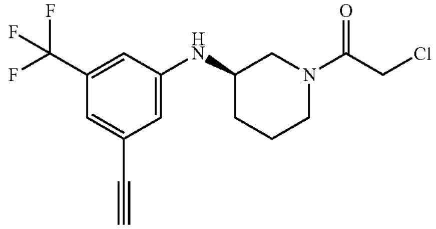 [SMILES: C#Cc1cc(N[C@@H]2CCCN(C(=O)CCl)C2)cc(C(F)(F)F)c1] |
| I-30 | 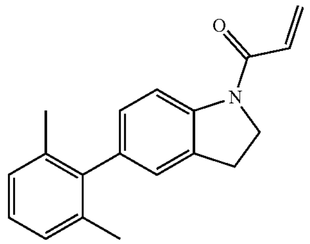 [SMILES: C=CC(=O)N1CCc2cc(-c3c(C)cccc3C)ccc21] |
| I-32 | 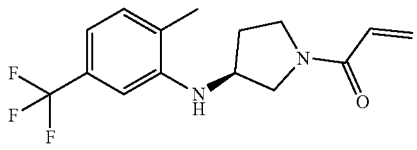 [SMILES: C=CC(=O)N1CC[C@H](Nc2cc(C(F)(F)F)ccc2C)C1] |
| I-33 | 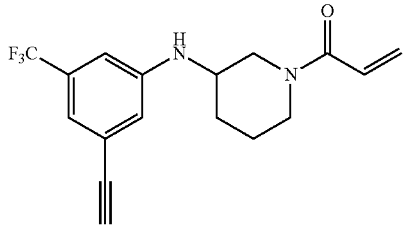 [SMILES: C#Cc1cc(NC2CCCN(C(=O)C=C)C2)cc(C(F)(F)F)c1] |

TABLE 1-continued
| Compounds of the Disclosure | |
|---|---|
| Compound Number | Chemical Structure |
| I-36 | 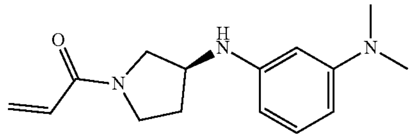 [SMILES: C=CC(=O)N1CC[C@H](Nc2cccc(N(C)C)c2)C1] |
| I-37 | 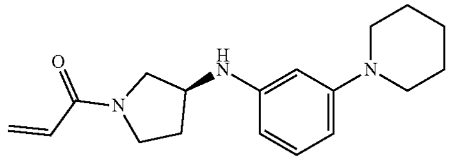 [SMILES: C=CC(=O)N1CC[C@H](Nc2cccc(N3CCCCC3)c2)C1] |
| I-38 | 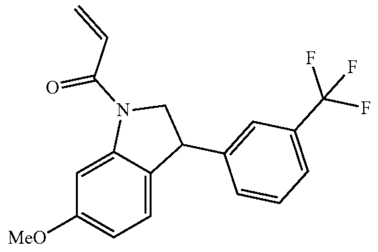 [SMILES: C=CC(=O)N1CC(c2cccc(C(F)(F)F)c2)c2ccc(OC)cc21] |
| I-39 | 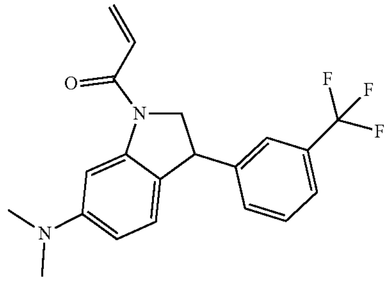 [SMILES: C=CC(=O)N1CC(c2cccc(C(F)(F)F)c2)c2ccc(N(C)C)cc21] |
| I-40 | 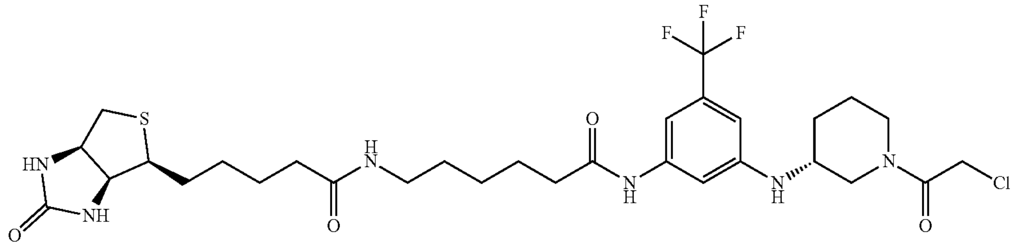 [SMILES: O=C(CCCC[C@@H]1SC[C@@H]2NC(=O)N[C@@H]21)NCCCCCC(=O)Nc1cc(N[C@@H]2CCCN(C(=O)CCl)C2)cc(C(F)(F)F)c1] |
| I-69 | 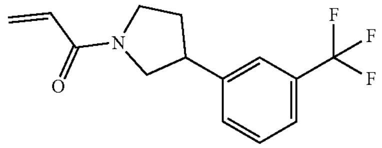 [SMILES: C=CC(=O)N1CCC(c2cccc(C(F)(F)F)c2)C1] |
| I-70 | 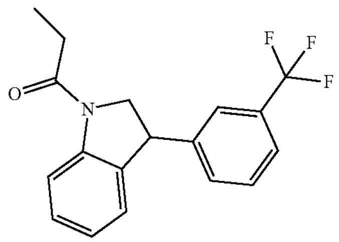 [SMILES: CCC(=O)N1CC(c2cccc(C(F)(F)F)c2)c2ccccc21] |

TABLE 1-continued
| Compounds of the Disclosure | |
|---|---|
| Compound Number | Chemical Structure |
| I-71 | 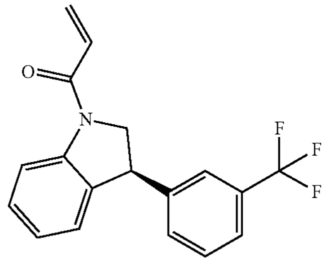 [SMILES: C=CC(=O)N1C[C@@H](c2cccc(C(F)(F)F)c2)c2ccccc21] |
| I-72 | 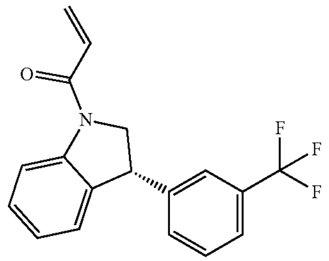 [SMILES: C=CC(=O)N1C[C@H](c2cccc(C(F)(F)F)c2)c2ccccc21] |
| I-73 | 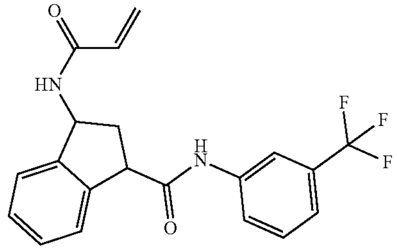 [SMILES: C=CC(=O)NC1CC(C(=O)Nc2cccc(C(F)(F)F)c2)c2ccccc21] |
| I-74 | 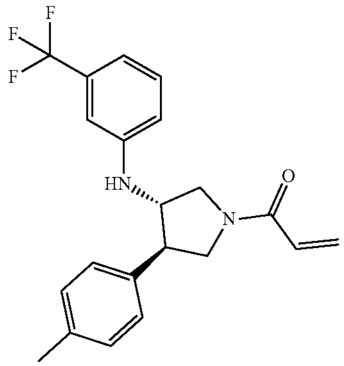 [SMILES: C=CC(=O)N1C[C@@H](Nc2cccc(C(F)(F)F)c2)[C@H](c2ccc(C)cc2)C1] |
| I-75 | 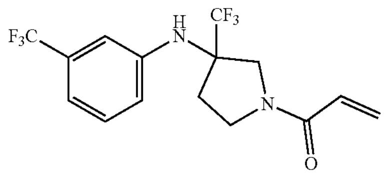 [SMILES: C=CC(=O)N1CCC(Nc2cccc(C(F)(F)F)c2)(C(F)(F)F)C1] |
| I-76 | 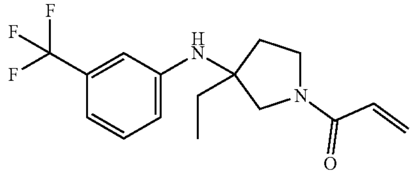 [SMILES: C=CC(=O)N1CCC(CC)(Nc2cccc(C(F)(F)F)c2)C1] |

TABLE 1-continued
| Compounds of the Disclosure | |
|---|---|
| Compound Number | Chemical Structure |
| I-77 | 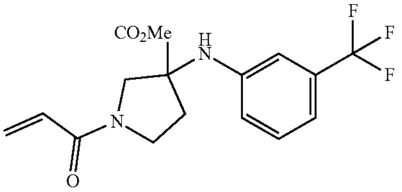 [SMILES: C=CC(=O)N1CCC(Nc2cccc(C(F)(F)F)c2)(C(=O)OC)C1] |
| I-78 | 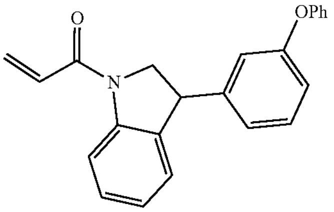 [SMILES: C=CC(=O)N1CC(c2cccc(Oc3ccccc3)c2)c2ccccc21] |
| I-79 | 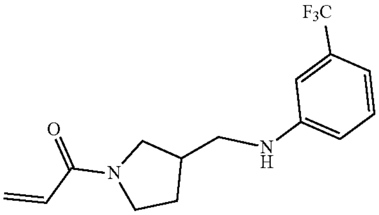 [SMILES: C=CC(=O)N1CCC(CNc2cccc(C(F)(F)F)c2)C1] |
| I-80 | 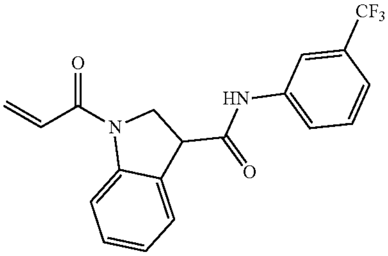 [SMILES: C=CC(=O)N1CC(C(=O)Nc2cccc(C(F)(F)F)c2)c2ccccc21] |
| I-81 | 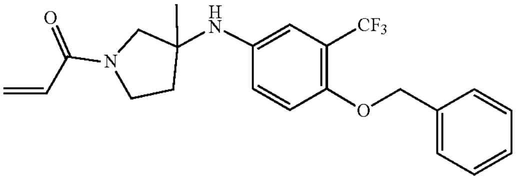 [SMILES: C=CC(=O)N1CCC(C)(Nc2ccc(OCc3ccccc3)c(C(F)(F)F)c2)C1] |
| I-82 | 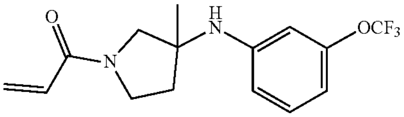 [SMILES: C=CC(=O)N1CCC(C)(Nc2cccc(OC(F)(F)F)c2)C1] |
| I-83 | 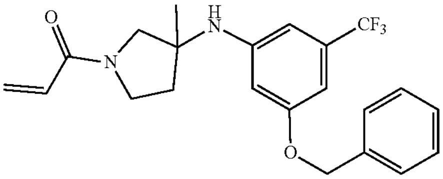 [SMILES: C=CC(=O)N1CCC(C)(Nc2cc(OCc3ccccc3)cc(C(F)(F)F)c2)C1] |

TABLE 1-continued
Compounds of the Disclosure
| Compound Number | Chemical Structure |
|---|---|
| I-84 | 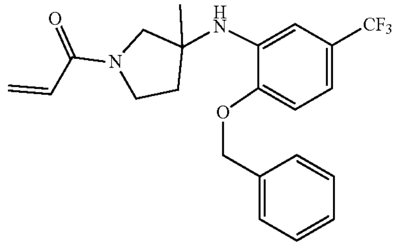 [SMILES: C=CC(=O)N1CCC(C)(Nc2cc(C(F)(F)F)ccc2OCc2ccccc2)C1] |
| I-85 | 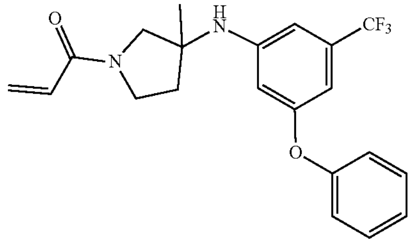 [SMILES: C=CC(=O)N1CCC(C)(Nc2cc(Oc3ccccc3)cc(C(F)(F)F)c2)C1] |
| I-86 | 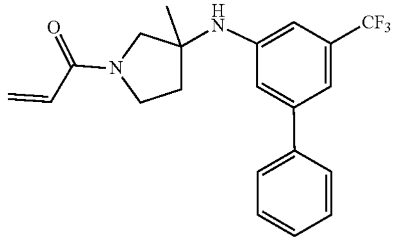 [SMILES: C=CC(=O)N1CCC(C)(Nc2cc(-c3ccccc3)cc(C(F)(F)F)c2)C1] |
| I-87 | 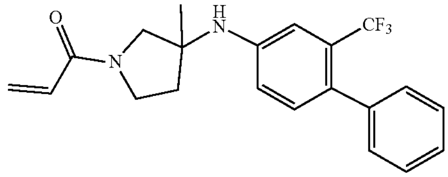 [SMILES: C=CC(=O)N1CCC(C)(Nc2ccc(-c3ccccc3)c(C(F)(F)F)c2)C1] |
| I-88 | 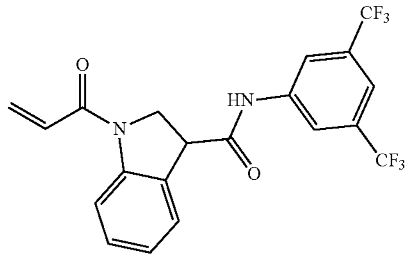 [SMILES: C=CC(=O)N1CC(C(=O)Nc2cc(C(F)(F)F)cc(C(F)(F)F)c2)c2ccccc21] |
| I-89 | 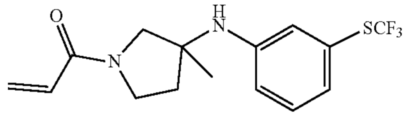 |
| I-90 | 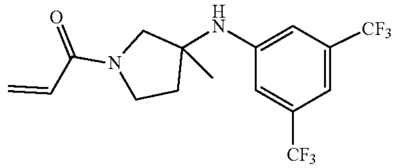 [SMILES: C=CC(=O)N1CCC(C)(Nc2cc(C(F)(F)F)cc(C(F)(F)F)c2)C1] |

TABLE 1-continued
| Compounds of the Disclosure | |
|---|---|
| Compound Number | Chemical Structure |
| I-91 | 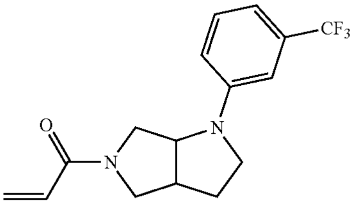 [SMILES: C=CC(=O)N1CC2CCN(c3cccc(C(F)(F)F)c3)C2C1] |
| I-92 | 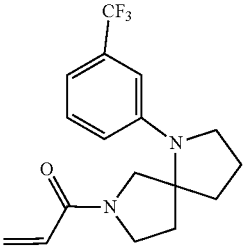 [SMILES: C=CC(=O)N1CCC2(CCCN2c2cccc(C(F)(F)F)c2)C1] |
| I-93 | 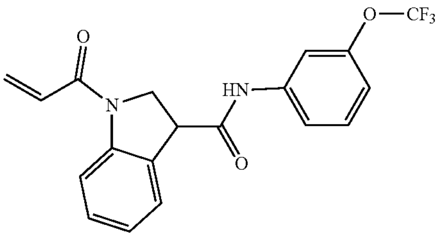 [SMILES: C=CC(=O)N1CC(C(=O)Nc2cccc(OC(F)(F)F)c2)c2ccccc21] |
| I-94 | 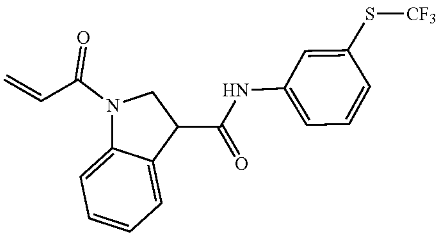 [SMILES: C=CC(=O)N1CC(C(=O)Nc2cccc(SC(F)(F)F)c2)c2ccccc21] |
| I-95 | 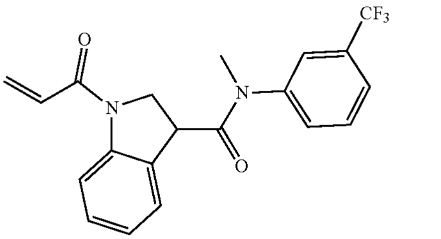 [SMILES: C=CC(=O)N1CC(C(=O)N(C)c2cccc(C(F)(F)F)c2)c2ccccc21] |
| I-97 | 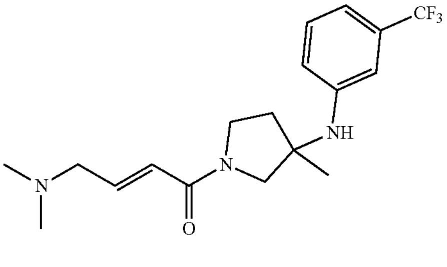 [SMILES: CN(C)C/C=C/C(=O)N1CCC(C)(Nc2cccc(C(F)(F)F)c2)C1] |

TABLE 1-continued
| Compounds of the Disclosure | |
|---|---|
| Compound Number | Chemical Structure |
| I-98 | 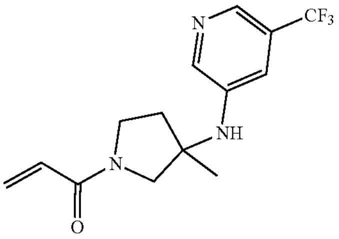 [SMILES: C=CC(=O)N1CCC(C)(Nc2cncc(C(F)(F)F)c2)C1] |
| I-99 | 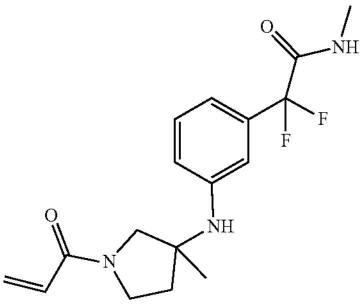 [SMILES: C=CC(=O)N1CCC(C)(Nc2cccc(C(F)(F)C(=O)NC)c2)C1] |
| I-100 | 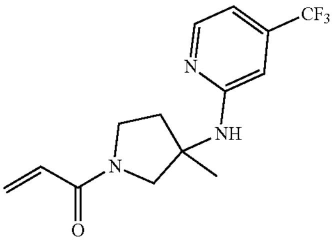 [SMILES: C=CC(=O)N1CCC(C)(Nc2cc(C(F)(F)F)ccn2)C1] |
| I-101 | 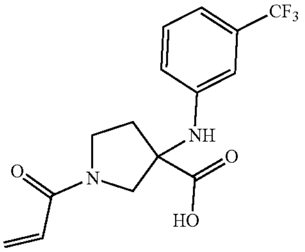 [SMILES: C=CC(=O)N1CCC(Nc2cccc(C(F)(F)F)c2)(C(=O)O)C1] |
| I-102 | 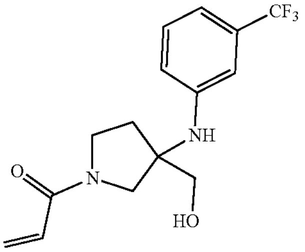 [SMILES: C=CC(=O)N1CCC(CO)(Nc2cccc(C(F)(F)F)c2)C1] |

TABLE 1-continued
| Compounds of the Disclosure | |
|---|---|
| Compound Number | Chemical Structure |
| I-103 | 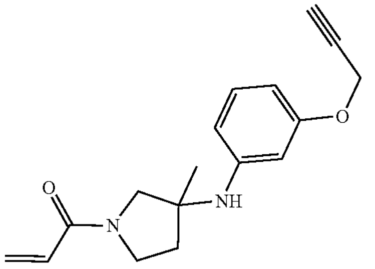 [SMILES: C#CCOc1cccc(NC2(C)CCN(C(=O)C=C)C2)c1] |
| I-104 | 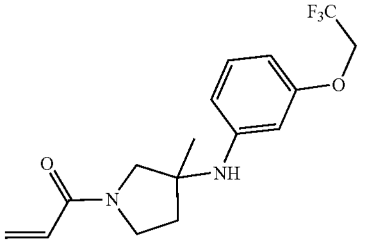 [SMILES: C=CC(=O)N1CCC(C)(Nc2cccc(OCC(F)(F)F)c2)C1] |
| I-105 | 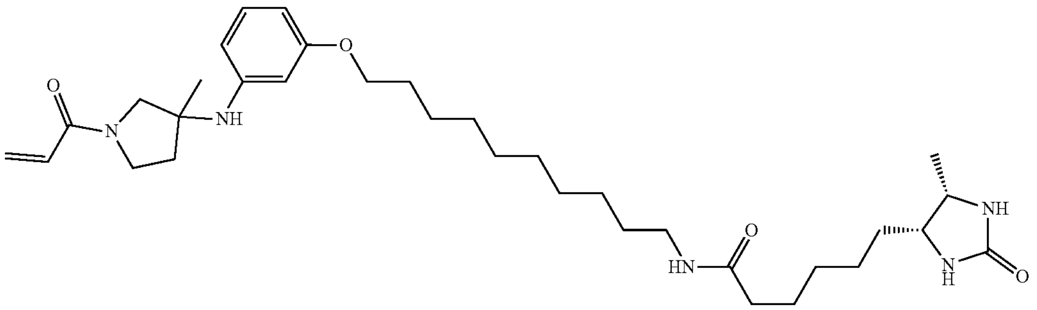 [SMILES: C=CC(=O)N1CCC(C)(Nc2cccc(OCCCCCCCCCCNC(=O)CCCCC[C@H]3NC(=O)N[C@H]3C)c2)C1] |
| I-106 | 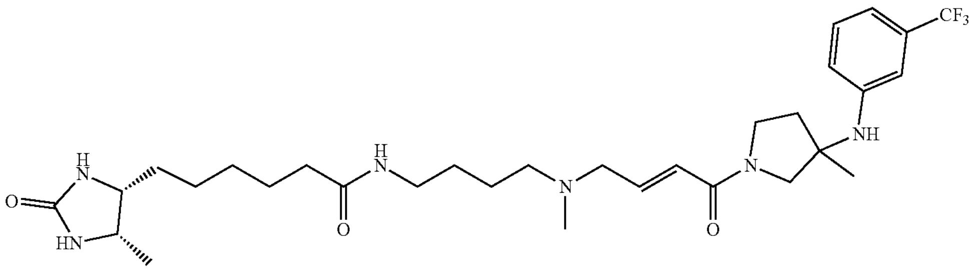 [SMILES: C[C@@H]1NC(=O)N[C@@H]1CCCCCC(=O)NCCCCN(C)C/C=C/C(=O)N1CCC(C)(Nc2cccc(C(F)(F)F)c2)C1] |
| I-107 | 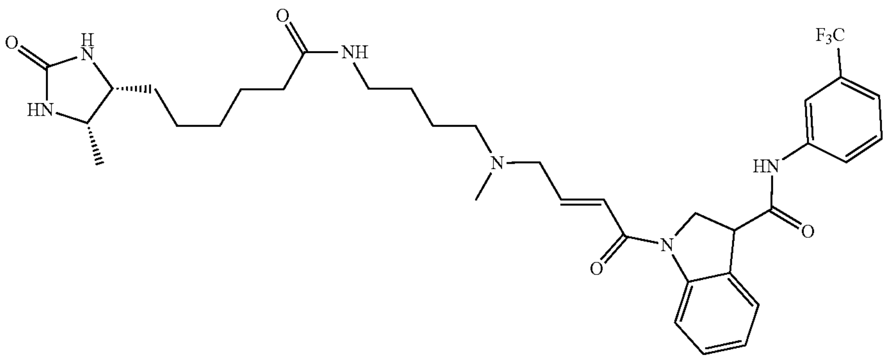 [SMILES: C[C@@H]1NC(=O)N[C@@H]1CCCCCC(=O)NCCCCN(C)C/C=C/C(=O)N1CC(C(=O)Nc2cccc(C(F)(F)F)c2)c2ccccc21] |

TABLE 1-continued
| Compounds of the Disclosure | |
|---|---|
| Compound Number | Chemical Structure |
| I-108 | 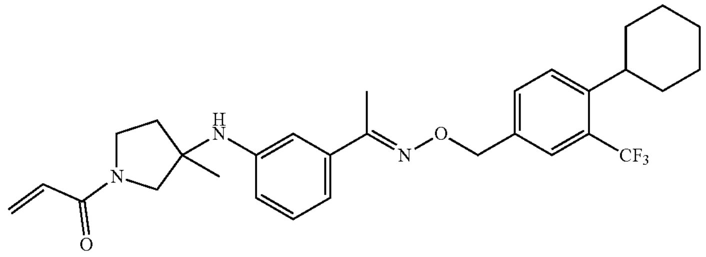 [SMILES: C=CC(=O)N1CCC(C)(Nc2cccc(/C(C)=N/OCc3ccc(C4CCCCC4)c(C(F)(F)F)c3)c2)C1] |
| I-109 | 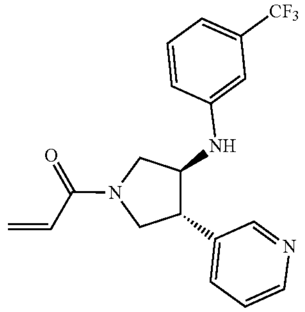 [SMILES: C=CC(=O)N1C[C@@H](Nc2cccc(C(F)(F)F)c2)[C@H](c2cccnc2)C1] |
| I-110 | 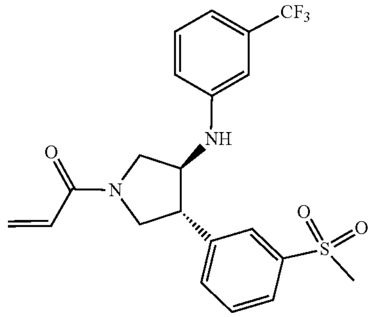 [SMILES: C=CC(=O)N1C[C@@H](Nc2cccc(C(F)(F)F)c2)[C@H](c2cccc(S(C)(=O)=O)c2)C1] |
| I-111 | 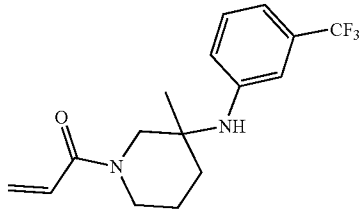 [SMILES: C=CC(=O)N1CCCC(C)(Nc2cccc(C(F)(F)F)c2)C1] |
| I-112 | 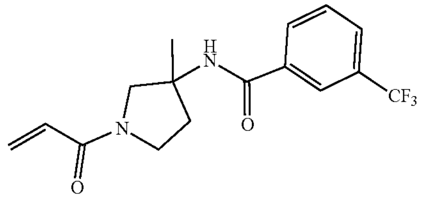 [SMILES: C=CC(=O)N1CCC(C)(NC(=O)c2cccc(C(F)(F)F)c2)C1] |
| I-113 | 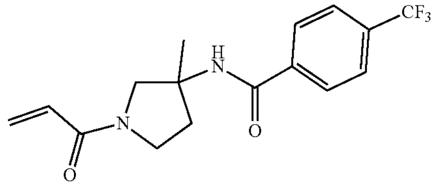 [SMILES: C=CC(=O)N1CCC(C)(NC(=O)c2ccc(C(F)(F)F)cc2)C1] |

TABLE 1-continued
Compounds of the Disclosure
| Compound Number | Chemical Structure |
|---|---|
| I-114 | 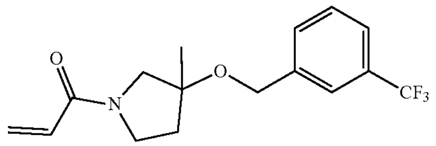 [SMILES: C=CC(=O)N1CCC(C)(OCc2cccc(C(F)(F)F)c2)C1] |
| I-115 | 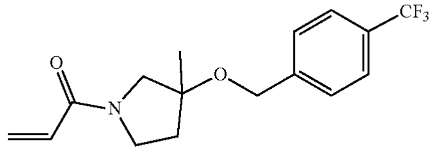 [SMILES: C=CC(=O)N1CCC(C)(OCc2ccc(C(F)(F)F)cc2)C1] |
| I-116 | 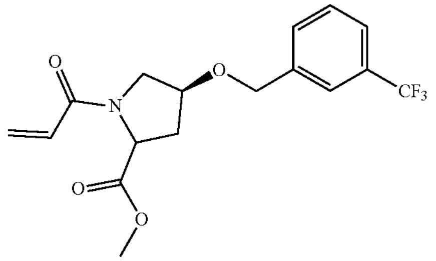 [SMILES: C=CC(=O)N1C[C@@H](OCc2cccc(C(F)(F)F)c2)CC1C(=O)OC] |
| I-117 | 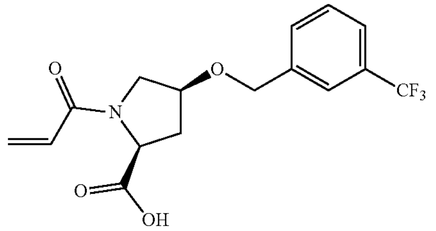 [SMILES: C=CC(=O)N1C[C@@H](OCc2cccc(C(F)(F)F)c2)C[C@H]1C(=O)O] |
| I-118 | 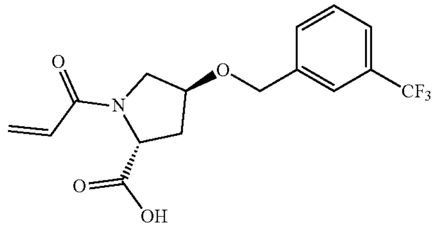 [SMILES: C=CC(=O)N1C[C@@H](OCc2cccc(C(F)(F)F)c2)C[C@@H]1C(=O)O] |
| I-119 | 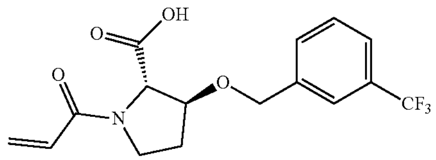 [SMILES: C=CC(=O)N1CC[C@H](OCc2cccc(C(F)(F)F)c2)[C@H]1C(=O)O] |
| I-120 | 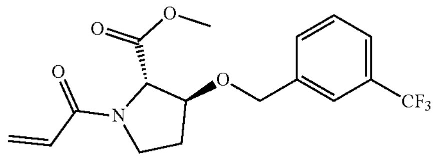 [SMILES: C=CC(=O)N1CC[C@H](OCc2cccc(C(F)(F)F)c2)[C@H]1C(=O)OC] |

TABLE 1-continued
| Compounds of the Disclosure | |
|---|---|
| Compound Number | Chemical Structure |
| I-121 | 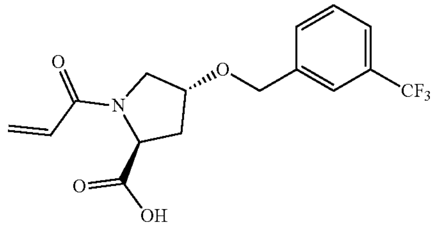 [SMILES: C=CC(=O)N1C[C@H](OCc2cccc(C(F)(F)F)c2)C[C@H]1C(=O)O] |
| I-122 | 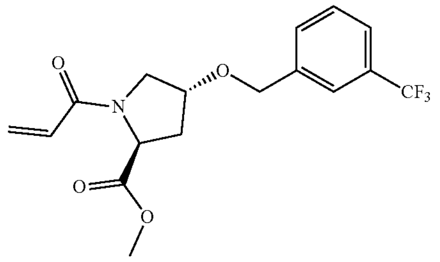 [SMILES: C=CC(=O)N1C[C@H](OCc2cccc(C(F)(F)F)c2)C[C@H]1C(=O)OC] |
| I-123 | 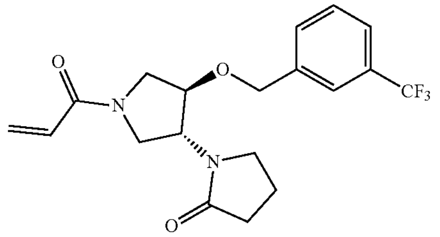 [SMILES: C=CC(=O)N1C[C@@H](N2CCCC2=O)[C@H](OCc2cccc(C(F)(F)F)c2)C1] |
| I-124 | 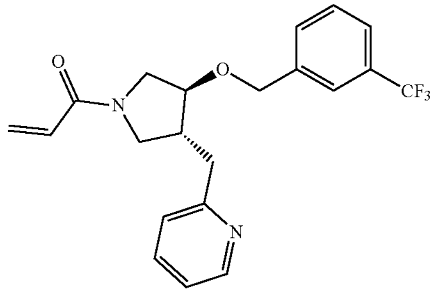 [SMILES: C=CC(=O)N1C[C@@H](Cc2ccccn2)[C@H](OCc2cccc(C(F)(F)F)c2)C1] |
| I-125 | 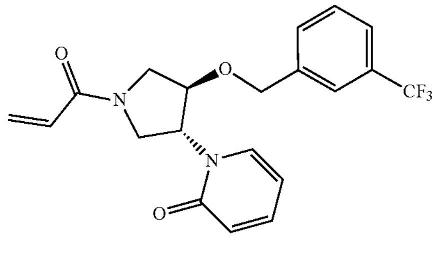 [SMILES: C=CC(=O)N1C[C@@H](n2ccccc2=O)[C@H](OCc2cccc(C(F)(F)F)c2)C1] |
| I-126 | 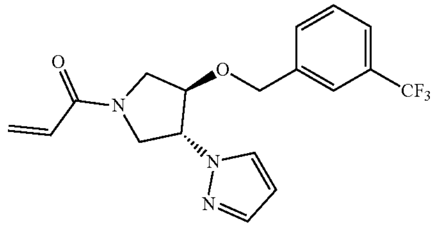 [SMILES: C=CC(=O)N1C[C@@H](n2cccn2)[C@H](OCc2cccc(C(F)(F)F)c2)C1] |

TABLE 1-continued
| Compounds of the Disclosure | |
|---|---|
| Compound Number | Chemical Structure |
| I-127 | 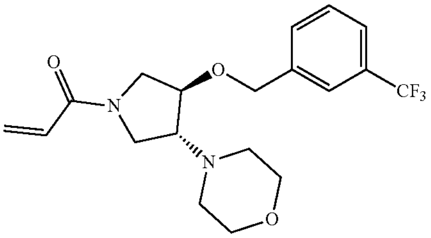 [SMILES: C=CC(=O)N1C[C@@H](N2CCOCC2)[C@H](OCc2cccc(C(F)(F)F)c2)C1] |
| I-128 | 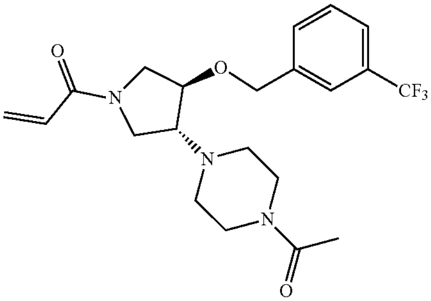 [SMILES: C=CC(=O)N1C[C@@H](N2CCN(C(C)=O)CC2)[C@H](OCc2cccc(C(F)(F)F)c2)C1] |
| I-129 | 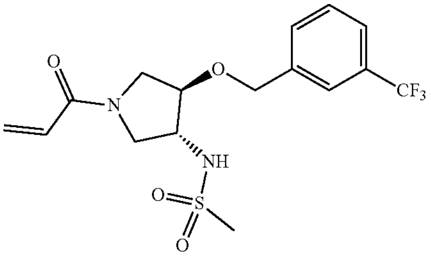 [SMILES: C=CC(=O)N1C[C@@H](NS(C)(=O)=O)[C@H](OCc2cccc(C(F)(F)F)c2)C1] |
| I-130 | 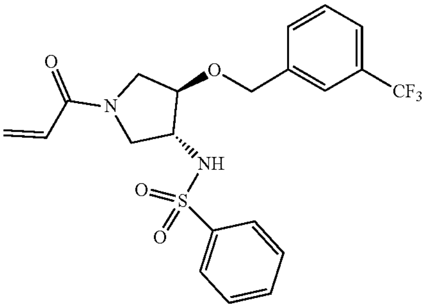 [SMILES: C=CC(=O)N1C[C@@H](NS(=O)(=O)c2ccccc2)[C@H](OCc2cccc(C(F)(F)F)c2)C1] |
| I-131 | 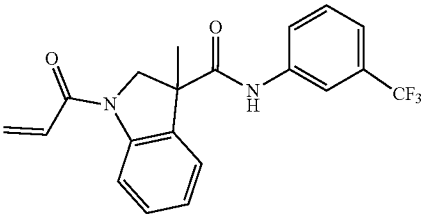 [SMILES: C=CC(=O)N1CC(C)(C(=O)Nc2cccc(C(F)(F)F)c2)c2ccccc21] |

TABLE 1-continued
| Compounds of the Disclosure | |
|---|---|
| Compound Number | Chemical Structure |
| I-132 | 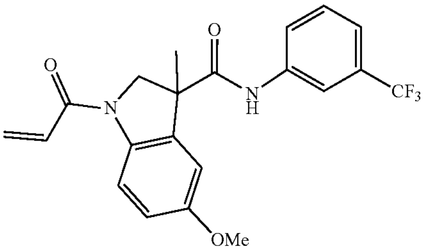 [SMILES: C=CC(=O)N1CC(C)(C(=O)Nc2cccc(C(F)(F)F)c2)c2cc(OC)ccc21] |
| I-133 | 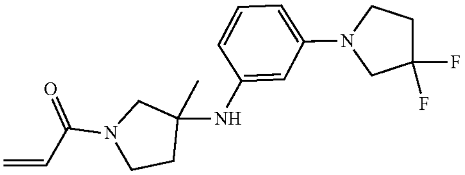 [SMILES: C=CC(=O)N1CCC(C)(Nc2cccc(N3CCC(F)(F)C3)c2)C1] |
| I-134 | 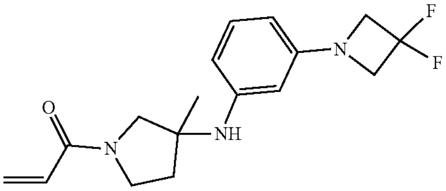 [SMILES: C=CC(=O)N1CCC(C)(Nc2cccc(N3CC(F)(F)C3)c2)C1] |
| I-135 | 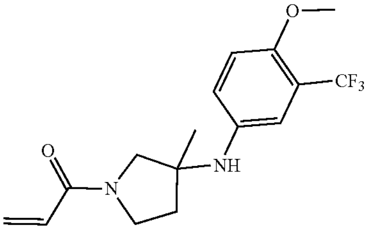 [SMILES: C=CC(=O)N1CCC(C)(Nc2ccc(OC)c(C(F)(F)F)c2)C1] |
| I-136 | 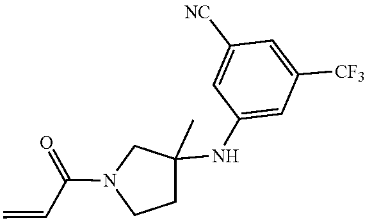 [SMILES: C=CC(=O)N1CCC(C)(Nc2cc(C#N)cc(C(F)(F)F)c2)C1] |
| I-137 | 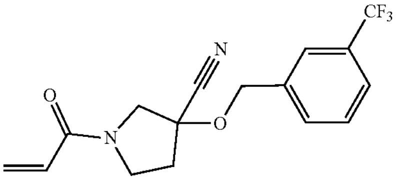 [SMILES: C=CC(=O)N1CCC(C#N)(OCc2cccc(C(F)(F)F)c2)C1] |
| I-138 | 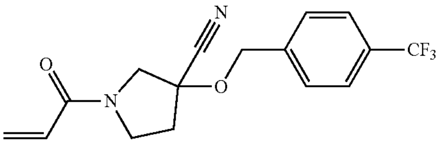 [SMILES: C=CC(=O)N1CCC(C#N)(OCc2ccc(C(F)(F)F)cc2)C1] |

TABLE 1-continued
| Compounds of the Disclosure | |
|---|---|
| Compound Number | Chemical Structure |
| I-139 | 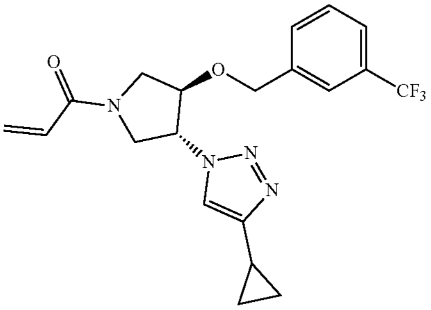 [SMILES: C=CC(=O)N1C[C@@H](n2cc(C3CC3)nn2)[C@H](OCc2cccc(C(F)(F)F)c2)C1] |
| I-140 | 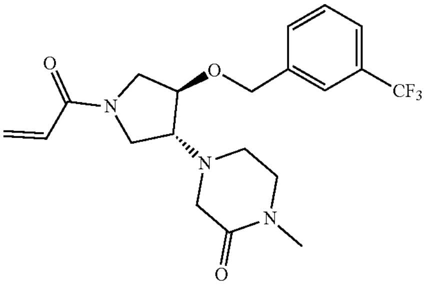 [SMILES: C=CC(=O)N1C[C@@H](N2CCN(C)C(=O)C2)[C@H](OCc2cccc(C(F)(F)F)c2)C1] |
| I-141 | 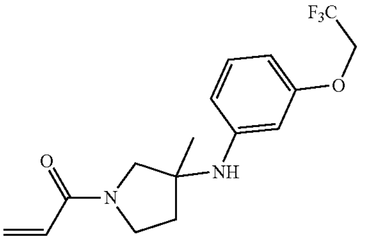 [SMILES: C=CC(=O)N1CCC(C)(Nc2cccc(OCC(F)(F)F)c2)C1] |
| I-142 | 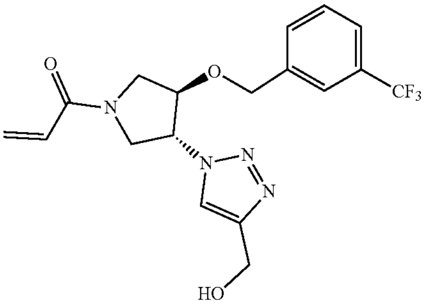 [SMILES: C=CC(=O)N1C[C@@H](n2cc(CO)nn2)[C@H](OCc2cccc(C(F)(F)F)c2)C1] |
| I-143 | 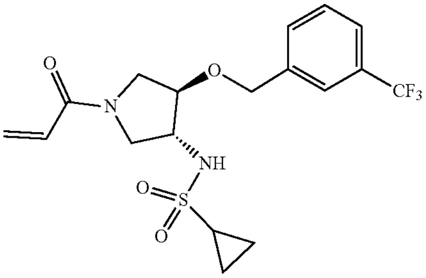 [SMILES: C=CC(=O)N1C[C@@H](NS(=O)(=O)C2CC2)[C@H](OCc2cccc(C(F)(F)F)c2)C1] |

TABLE 1-continued
| Compounds of the Disclosure | |
|---|---|
| Compound Number | Chemical Structure |
| I-144 | 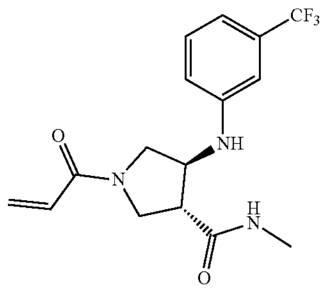 [SMILES: C=CC(=O)N1C[C@@H](Nc2cccc(C(F)(F)F)c2)[C@H](C(=O)NC)C1] |
| I-145 | 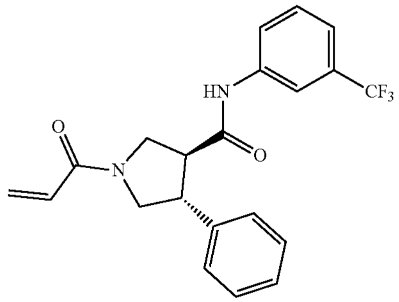 [SMILES: C=CC(=O)N1C[C@@H](C(=O)Nc2cccc(C(F)(F)F)c2)[C@H](c2ccccc2)C1] |
| I-146 | 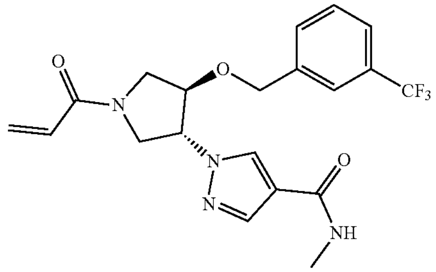 [SMILES: C=CC(=O)N1C[C@@H](n2cc(C(=O)NC)cn2)[C@H](OCc2cccc(C(F)(F)F)c2)C1] |
| I-147 | 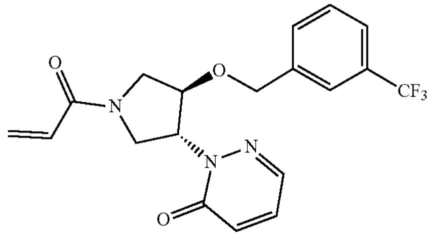 [SMILES: C=CC(=O)N1C[C@@H](n2ncccc2=O)[C@H](OCc2cccc(C(F)(F)F)c2)C1] |
| I-148 | 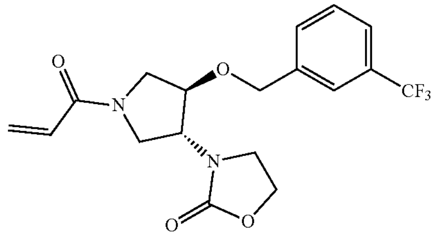 [SMILES: C=CC(=O)N1C[C@@H](N2CCOC2=O)[C@H](OCc2cccc(C(F)(F)F)c2)C1] |

TABLE 1-continued
| Compounds of the Disclosure | |
|---|---|
| Compound Number | Chemical Structure |
| I-149 | 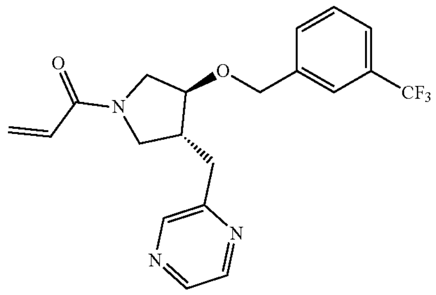 [SMILES: C=CC(=O)N1C[C@@H](Cc2cnccn2)[C@H](OCc2cccc(C(F)(F)F)c2)C1] |
| I-150 | 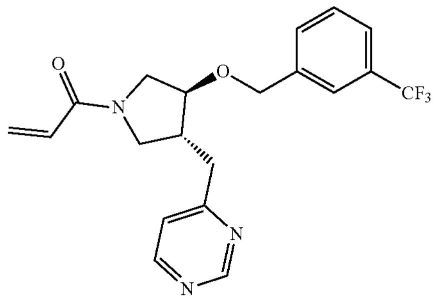 [SMILES: C=CC(=O)N1C[C@@H](Cc2ccncn2)[C@H](OCc2cccc(C(F)(F)F)c2)C1] |
| I-151 | 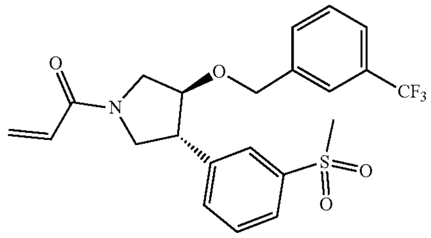 [SMILES: C=CC(=O)N1C[C@@H](OCc2cccc(C(F)(F)F)c2)[C@H](c2cccc(S(C)(=O)=O)c2)C1] |
| I-152 | 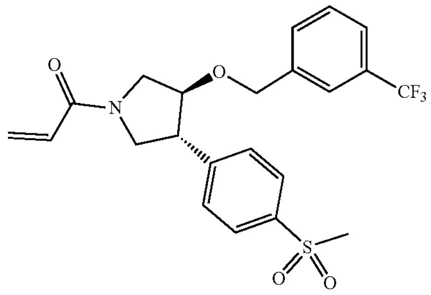 [SMILES: C=CC(=O)N1C[C@@H](OCc2cccc(C(F)(F)F)c2)[C@H](c2ccc(S(C)(=O)=O)cc2)C1] |
| I-153 | 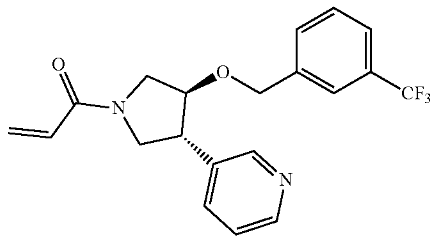 [SMILES: C=CC(=O)N1C[C@@H](OCc2cccc(C(F)(F)F)c2)[C@H](c2cccnc2)C1] |

TABLE 1-continued
| Compounds of the Disclosure | |
|---|---|
| Compound Number | Chemical Structure |
| I-154 | 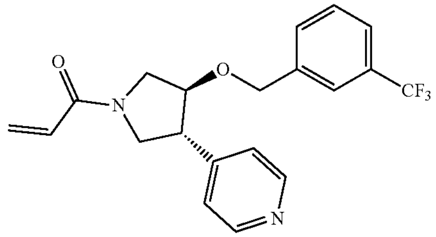 [SMILES: C=CC(=O)N1C[C@@H](OCc2cccc(C(F)(F)F)c2)[C@H](c2ccncc2)C1] |
| I-155 | 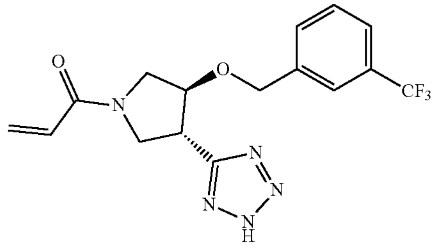 [SMILES: C=CC(=O)N1C[C@@H](OCc2cccc(C(F)(F)F)c2)[C@H](c2nn[nH]n2)C1] |
| I-156 | 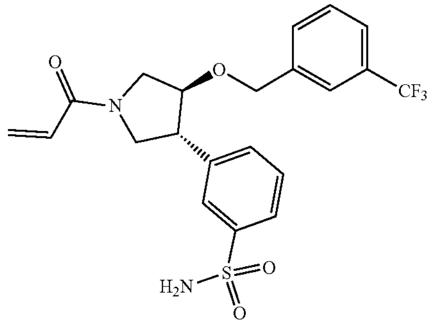 [SMILES: C=CC(=O)N1C[C@@H](OCc2cccc(C(F)(F)F)c2)[C@H](c2cccc(S(N)(=O)=O)c2)C1] |
| I-157 | 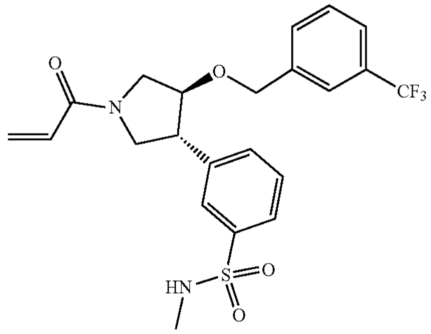 [SMILES: C=CC(=O)N1C[C@@H](OCc2cccc(C(F)(F)F)c2)[C@H](c2cccc(S(=O)(=O)NC)c2)C1] |
| I-158 | 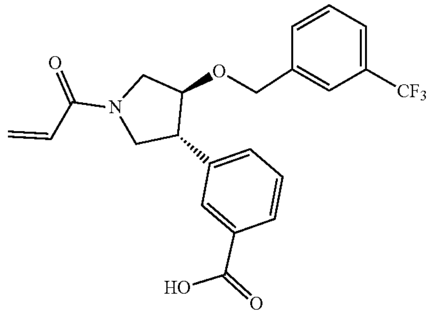 [SMILES: C=CC(=O)N1C[C@@H](OCc2cccc(C(F)(F)F)c2)[C@H](c2cccc(C(=O)O)c2)C1] |

TABLE 1-continued
Compounds of the Disclosure
| Compound Number | Chemical Structure |
| --- | --- |
| I-159 | 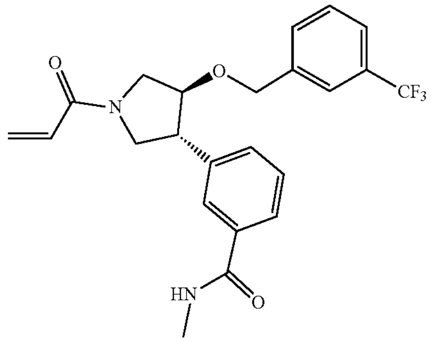 [SMILES: C=CC(=O)N1C[C@@H](OCc2cccc(C(F)(F)F)c2)[C@H](c2cccc(C(=O)NC)c2)C1] |
| I-160 | 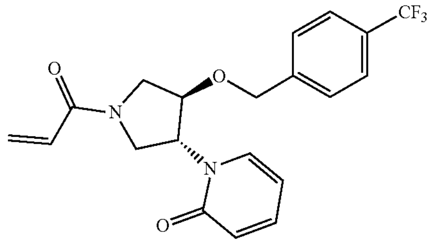 [SMILES: C=CC(=O)N1C[C@@H](n2ccccc2=O)[C@H](OCc2ccc(C(F)(F)F)cc2)C1] |
| I-161 | 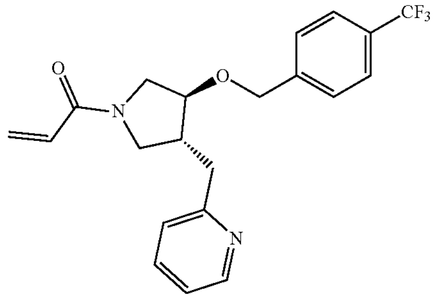 [SMILES: C=CC(=O)N1C[C@@H](Cc2ccccn2)[C@H](OCc2ccc(C(F)(F)F)cc2)C1] |
| I-162 | 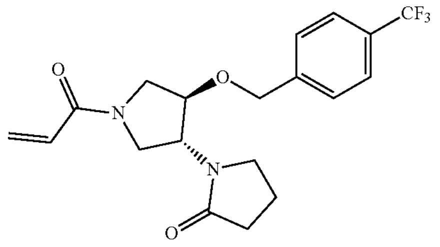 [SMILES: C=CC(=O)N1C[C@@H](N2CCCC2=O)[C@H](OCc2ccc(C(F)(F)F)cc2)C1] |
| I-163 | 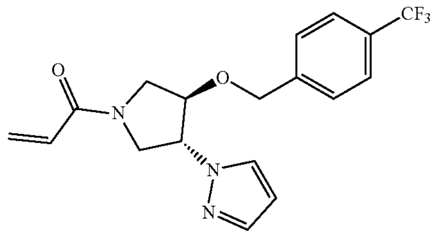 [SMILES: C=CC(=O)N1C[C@@H](n2cccn2)[C@H](OCc2ccc(C(F)(F)F)cc2)C1] |

TABLE 1-continued
| Compounds of the Disclosure | |
|---|---|
| Compound Number | Chemical Structure |
| I-164 | 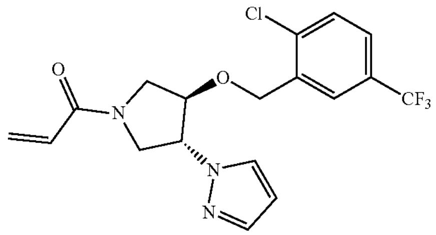 [SMILES: C=CC(=O)N1C[C@@H](n2cccn2)[C@H](OCc2cc(C(F)(F)F)ccc2Cl)C1] |
| I-165 | 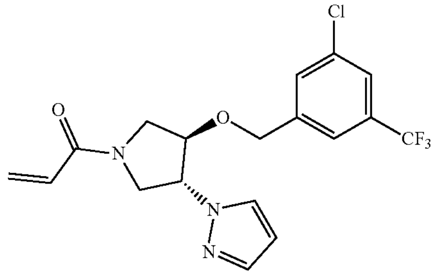 [SMILES: C=CC(=O)N1C[C@@H](n2cccn2)[C@H](OCc2cc(Cl)cc(C(F)(F)F)c2)C1] |
| I-166 | 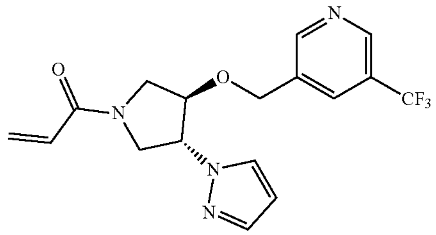 [SMILES: C=CC(=O)N1C[C@@H](n2cccn2)[C@H](OCc2cncc(C(F)(F)F)c2)C1] |
| I-167 | 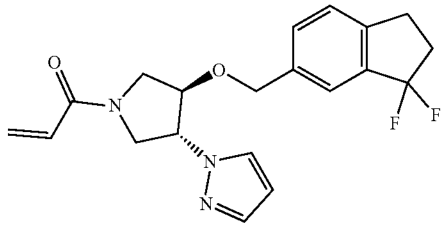 [SMILES: C=CC(=O)N1C[C@@H](n2cccn2)[C@H](OCc2ccc3c(c2)C(F)(F)CC3)C1] |
| I-168 | 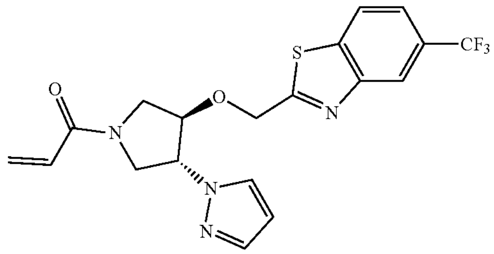 [SMILES: C=CC(=O)N1C[C@@H](n2cccn2)[C@H](OCc2nc3cc(C(F)(F)F)ccc3s2)C1] |

TABLE 1-continued
| Compounds of the Disclosure | |
|---|---|
| Compound Number | Chemical Structure |
| I-169 | 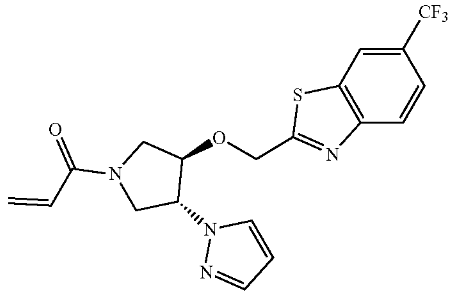 [SMILES: C=CC(=O)N1C[C@@H](n2cccn2)[C@H](OCc2nc3ccc(C(F)(F)F)cc3s2)C1] |
| I-170 | 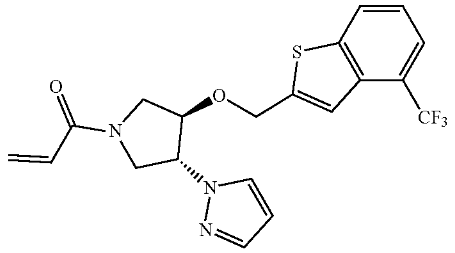 [SMILES: C=CC(=O)N1C[C@@H](n2cccn2)[C@H](OCc2cc3c(C(F)(F)F)cccc3s2)C1] |
| I-171 | 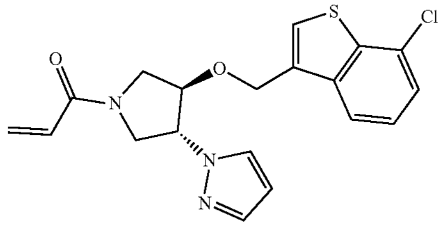 [SMILES: C=CC(=O)N1C[C@@H](n2cccn2)[C@H](OCc2csc3c(Cl)cccc23)C1] |
| I-172 | 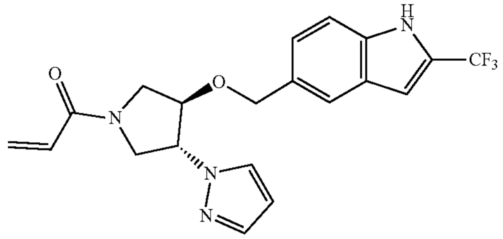 [SMILES: C=CC(=O)N1C[C@@H](n2cccn2)[C@H](OCc2ccc3[nH]c(C(F)(F)F)cc3c2)C1] |
| I-173 | 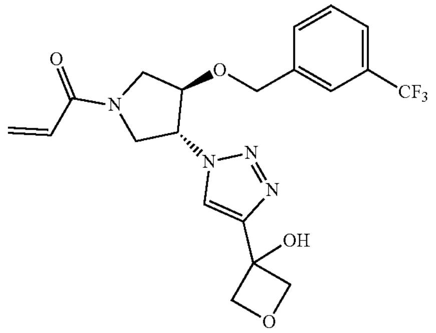 [SMILES: C=CC(=O)N1C[C@@H](n2cc(C3(O)COC3)nn2)[C@H](OCc2cccc(C(F)(F)F)c2)C1] |

TABLE 1-continued
| Compounds of the Disclosure | |
|---|---|
| Compound Number | Chemical Structure |
| I-174 | 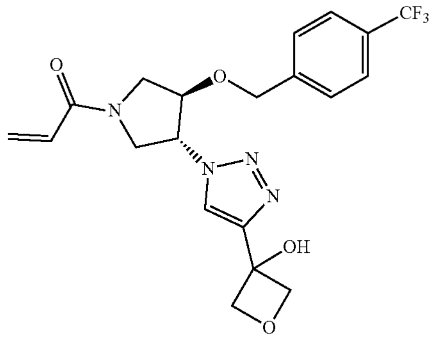 |
| I-175 | 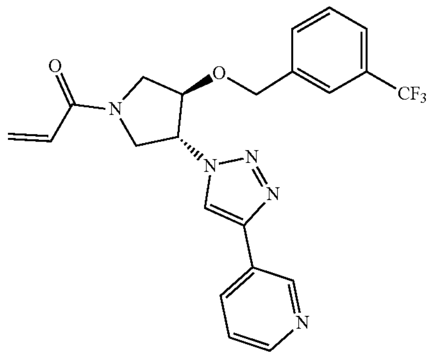 [SMILES: C=CC(=O)N1C[C@@H](n2cc(-c3cccnc3)nn2)[C@H](OCc2cccc(C(F)(F)F)c2)C1] |
| I-176 | 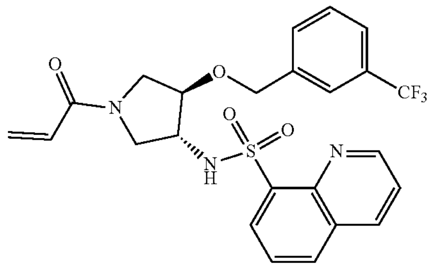 [SMILES: C=CC(=O)N1C[C@@H](NS(=O)(=O)c2cccc3cccnc23)[C@H](OCc2cccc(C(F)(F)F)c2)C1] |
| I-177 | 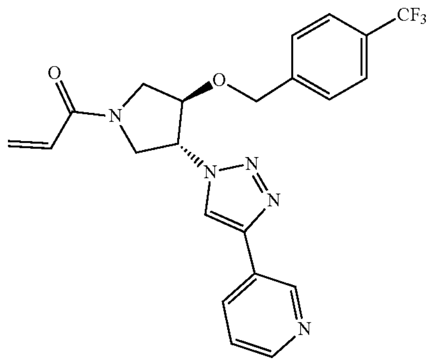 [SMILES: C=CC(=O)N1C[C@@H](n2cc(-c3cccnc3)nn2)[C@H](OCc2ccc(C(F)(F)F)cc2)C1] |

TABLE 1-continued
| Compounds of the Disclosure | |
|---|---|
| Compound Number | Chemical Structure |
| I-178 | 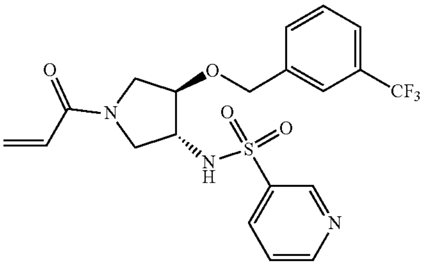 [SMILES: C=CC(=O)N1C[C@@H](NS(=O)(=O)c2cccnc2)[C@H](OCc2cccc(C(F)(F)F)c2)C1] |
| I-179 | 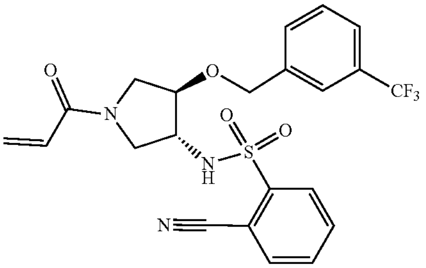 [SMILES: C=CC(=O)N1C[C@@H](NS(=O)(=O)c2ccccc2C#N)[C@H](OCc2cccc(C(F)(F)F)c2)C1] |
| I-180 | 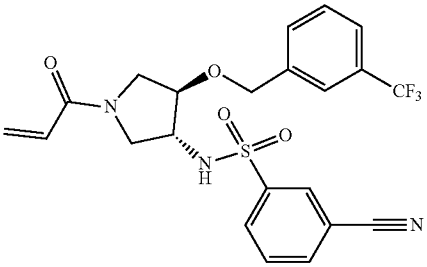 [SMILES: C=CC(=O)N1C[C@@H](NS(=O)(=O)c2cccc(C#N)c2)[C@H](OCc2cccc(C(F)(F)F)c2)C1] |
| I-181 | 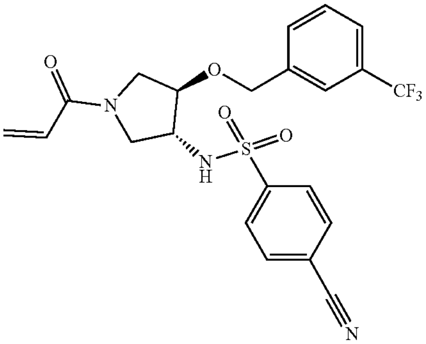 [SMILES: C=CC(=O)N1C[C@@H](NS(=O)(=O)c2ccc(C#N)cc2)[C@H](OCc2cccc(C(F)(F)F)c2)C1] |
| I-182 | 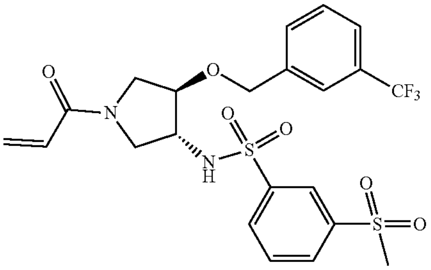 [SMILES: C=CC(=O)N1C[C@@H](NS(=O)(=O)c2cccc(S(C)(=O)=O)c2)[C@H](OCc2cccc(C(F)(F)F)c2)C1] |

TABLE 1-continued
| Compounds of the Disclosure | |
|---|---|
| Compound Number | Chemical Structure |
| I-183 | 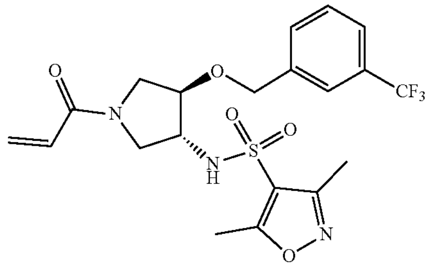 [SMILES: C=CC(=O)N1C[C@@H](NS(=O)(=O)c2c(C)noc2C)[C@H](OCc2cccc(C(F)(F)F)c2)C1] |
| I-184 | 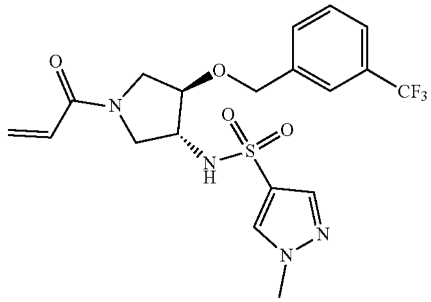 [SMILES: C=CC(=O)N1C[C@@H](NS(=O)(=O)c2cnn(C)c2)[C@H](OCc2cccc(C(F)(F)F)c2)C1] |
| I-185 | 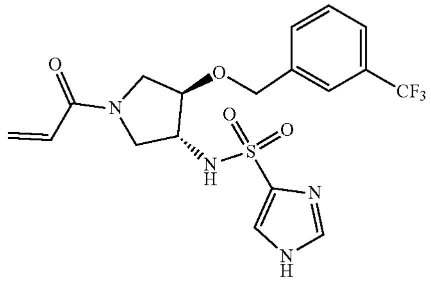 [SMILES: C=CC(=O)N1C[C@@H](NS(=O)(=O)c2c[nH]cn2)[C@H](OCc2cccc(C(F)(F)F)c2)C1] |
| I-186 | 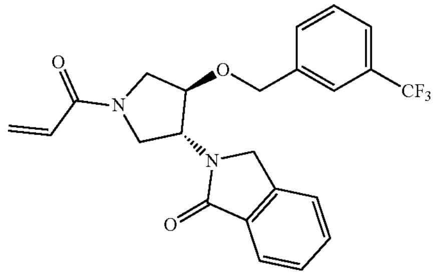 |
| I-187 | 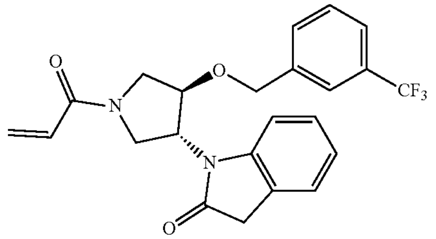 [SMILES: C=CC(=O)N1C[C@@H](N2C(=O)Cc3ccccc32)[C@H](OCc2cccc(C(F)(F)F)c2)C1] |

and pharmaceutically acceptable salts, solvates, hydrates, polymorphs, co-crystals, autoes stereoisomers, isotopically labeled derivatives, prodrugs, compositions, and mixtures thereof.

In certain embodiments, a compound described herein is a compound of Formula (I), or a pharmaceutically acceptable salt, solvate, hydrate, polymorph, co-crystal, tautomer, stereoisomer, isotopically labeled derivative, prodrug, composition, or mixture thereof. In certain embodiments, a compound described herein is a compound of Formula (I), or a pharmaceutically acceptable salt thereof.

In certain embodiments, the compounds described herein are provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for reducing the risk of developing a disease (e.g., proliferative disease) in a subject in need thereof. In certain embodiments, the effective amount is an amount effective for inhibiting the activity (e.g., aberrant activity, such as increased activity) of a transcription factor (e.g., TEAD) in a subject or cell. In certain embodiments, the effective amount is an amount effective for modulating the activity of the hippo signaling pathway in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell is present in vitro. In certain embodiments, the cell is present in vivo.

In certain embodiments, the effective amount is an amount effective for inhibiting the activity of a transcription factor by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a TEAD family transcription factor by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a TEAD family transcription factor by a range between a percentage described in this paragraph and another percentage described in this paragraph, inclusive.

In certain embodiments, the transcription factor is a TEAD family transcription factor. In certain embodiments, the TEAD is TEAD1 In certain embodiments, the TEAD is TEAD2. In certain embodiments, the TEAD is TEAD3. In certain embodiments, the TEAD is TEAD4. In certain embodiments, the present disclosure provides inhibitors of the TEAD family of transcription factors (e.g., TEAD1, TEAD2, TEAD3, TEAD4). In certain embodiments, the inventive compounds inhibit the activity of a TEAD. In certain embodiments, the inhibitor is selective for the TEAD family of transcription factors.

The present disclosure provides methods of using the compounds described herein, e.g., as biological probes to study the hippo signaling pathway or the inhibition of the activity of a transcription factor (e.g., TEAD (e.g., TEAD1, TEAD2, TEAD3, TEAD4)), and as therapeutics, e.g., in the treatment and/or prevention of diseases associated with the overexpression and/or aberrant activity of the hippo signaling pathway or a transcription factor (e.g., TEAD (e.g., TEAD1, TEAD2, TEAD3, TEAD4)). In certain embodiments, the compound covalently binds TEADs (e.g., TEAD1). In certain embodiments, the diseases treated and/or prevented include, but are not limited to, proliferative diseases. The proliferative diseases include, but are not limited to, cancer (e.g., carcinoma, sarcoma, lung cancer, thyroid cancer, skin cancer, ovarian cancer, colorectal cancer, prostate cancer, pancreatic cancer, esophageal cancer, liver cancer, breast cancer). In certain embodiments, the cancer is a sarcoma. In certain embodiments, the cancer is Kaposi's sarcoma. In certain embodiments, the cancer is associated with the overexpression and/or aberrant activity of a transcription factor (e.g., TEAD (e.g., TEAD1, TEAD2, TEAD3, TEAD4)). Also provided by the present disclosure are pharmaceutical compositions, kits, methods, and uses of a compound of Formula (I) as described herein.

Certain aspects of the present disclosure relate to the compounds described herein. The compounds described herein may be useful in treating and/or preventing diseases (e.g., proliferative diseases (e.g., cancers)) or diseases associated with the activity of a transcription factor (e.g., TEAD1, TEAD2, TEAD3, TEAD4) in a subject, or inhibiting the activity of a transcription factor (e.g., TEAD1, TEAD2, TEAD3, TEAD4) in a subject or biological sample. In certain embodiments, a compound described herein is a compound of Formula (I), or a pharmaceutically acceptable salt, solvate, hydrate, polymorph, co-crystal, tautomer, stereoisomer, isotopically labeled derivative, prodrug, composition, or mixture thereof. In certain embodiments, a compound described herein is a compound of Formula (I), or a pharmaceutically acceptable salt thereof.

Certain compounds described herein bind, covalently modify, and/or inhibit a transcription factor. In certain embodiments, the compounds described herein irreversibly inhibit a transcription factor. In certain embodiments, the compounds described herein reversibly inhibit a transcription factor. In certain embodiments, the transcription factor is a transcription enhancer factor. In certain embodiments, the transcription factor is a TEAD family transcription factor. In certain embodiments, the transcription factor is TEAD1. In certain embodiments, the transcription factor is TEAD2. In certain embodiments, the transcription factor is TEAD3. In certain embodiments, the transcription factor is TEAD4. In certain embodiments, the compounds described herein covalently bind to the transcription factor (e.g., TEAD (e.g., TEAD1, TEAD2, TEAD3, or TEAD4)). In certain embodiments, the compounds described herein reversibly bind to the transcription factor (e.g., TEAD (e.g., TEAD1, TEAD2, TEAD3, or TEAD4)). In certain embodiments, the compounds described herein non-reversibly bind to the transcription factor (e.g., TEAD (e.g., TEAD1, TEAD2, TEAD3, or TEAD4)). In certain embodiments, the compounds described herein modulate the activity of a transcription factor (e.g., TEAD (e.g., TEAD1, TEAD2, TEAD3, or TEAD4)). In certain embodiments, the compounds described herein inhibit the activity of a transcription factor (e.g., a TEAD family transcription factor (e.g., TEAD (e.g., TEAD1, TEAD2, TEAD3, or TEAD4)). In certain embodiments, the compounds described herein reversibly inhibit the activity of a transcription factor (e.g., TEAD (e.g., TEAD1, TEAD2, TEAD3, or TEAD4)). In certain embodiments, the compounds described herein irreversibly inhibit the activity of a transcription factor (e.g., TEAD (e.g., TEAD1, TEAD2, TEAD3, or TEAD4)). In certain embodiments, the compounds described herein covalently inhibit the activity of a transcription factor (e.g., TEAD (e.g., TEAD1, TEAD2, TEAD3, or TEAD4)).

The binding affinity of a compound described herein to a transcription factor (e.g., TEAD (e.g., TEAD1, TEAD2, TEAD3, or TEAD4)) may be measured by the dissociation constant ($K_d$) value of an adduct of the compound and the transcription factor (e.g., TEAD (e.g., TEAD1, TEAD2, TEAD3, or TEAD4)) using methods known in the art (e.g., isothermal titration calorimetry (ITC)). In certain embodiments, the $K_d$ value of the adduct is not more than about 100 μM, not more than about 10 μM, not more than about 1 μM, not more than about 100 nM, not more than about 10 nM, or not more than about 1 nM.

In certain embodiments, the activity of a transcription factor (e.g., TEAD (e.g., TEAD1, TEAD2, TEAD3, or TEAD4)) is inhibited by a compound described herein. The inhibition of the activity of a transcription factor (e.g., a TEAD family transcription factor (e.g., TEAD (e.g., TEAD1, TEAD2, TEAD3, or TEAD4)) by a compound described herein may be measured by determining the half maximal inhibitory concentration ($IC_{50}$) of the compound when the compound, or a pharmaceutical composition thereof, is contacted with the transcription factor (e.g., TEAD (e.g., TEAD1, TEAD2, TEAD3, or TEAD4)). The $IC_{50}$ values may be obtained using methods known in the art (e.g., by a competition binding assay). In certain embodiments, the $IC_{50}$ value of a compound described herein is not more than about 1 mM, not more than about 100 μM, not more than about 10 μM, not more than about 1 μM, not more than about 100 nM, not more than about 10 nM, or not more than about 1 nM.

The compounds described herein may selectively modulate the activity of a transcription factor (e.g., TEAD (e.g., TEAD1, TEAD2, TEAD3, or TEAD4)). In certain embodiments, the compounds selectively increase the activity of a transcription factor (e.g., TEAD (e.g., TEAD1, TEAD2, TEAD3, or TEAD4)) In certain embodiments, the compounds selectively inhibit the activity of a transcription factor (e.g., TEAD (e.g., TEAD1, TEAD2, TEAD3, or TEAD4)). In certain embodiments, the compounds inhibit the activity of two or more protein transcription factors (e.g., TEAD (e.g., TEAD1, TEAD2, TEAD3, or TEAD4)) to the same extent. In certain embodiments, the compounds increase the activity of two or more transcription factors (e.g., TEAD (e.g., TEAD1, TEAD2, TEAD3, or TEAD4)) to the same extent.

The selectivity of a compound described herein in inhibiting the activity of a first transcription factor (e.g., TEAD1, TEAD2, TEAD3, or TEAD4) over a second transcription factor may be measured by the quotient of the $IC_{50}$ value of the compound in inhibiting the activity of the second transcription factor (e.g., TEAD1, TEAD2, TEAD3, or TEAD4) over the $IC_{50}$ value of the compound in inhibiting the activity of the first transcription factor (e.g., TEAD1, TEAD2, TEAD3, or TEAD4). The selectivity of a compound described herein in modulating the activity of a first transcription factor (e.g., TEAD1, TEAD2, TEAD3, or TEAD4) over a second transcription factor may also be measured by the quotient of the $K_d$ value of an adduct of the compound and the second transcription factor over the $K_d$ value of an adduct of the compound and the first transcription factor (e.g., TEAD1, TEAD2, TEAD3, or TEAD4). In certain embodiments, the selectivity is at least about 1-fold, at least about 3-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of a transcription factor (e.g., TEAD (e.g., TEAD1, TEAD2, TEAD3, or TEAD4)). In certain embodiments, a therapeutically effective amount is an amount effective for treating a disease (e.g., a disease associated with aberrant activity of a TEAD (e.g., proliferative disease). In certain embodiments, a therapeutically effective amount is an amount effective for inhibiting the aberrant activity of a TEAD (e.g., TEAD1, TEAD2, TEAD3, or TEAD4)) and treating a disease (e.g., a disease associated with aberrant activity of a transcription factor (e.g., TEAD (e.g., TEAD1, TEAD2, TEAD3, or TEAD4)) (e.g., proliferative disease). In certain embodiments, a therapeutically effective amount is an amount effective for inducing apoptosis of a cell (e.g., cell in vivo or in vitro). In certain embodiments, a prophylactically effective amount is an amount effective for inhibiting the aberrant activity of a protein (e.g., TEAD (e.g., TEAD1, TEAD2, TEAD3, or TEAD4)). In certain embodiments, a prophylactically effective amount is an amount effective for preventing or keeping a subject in need thereof in remission of a disease (e.g., a disease associated with aberrant activity of a TEAD (e.g., proliferative disease). In certain embodiments, a prophylactically effective amount is an amount effective for inhibiting the aberrant activity of a TEAD, and preventing or keeping a subject in need thereof in remission of a disease (e.g., a disease associated with aberrant activity of a TEAD (e.g., proliferative disease).

In certain embodiments, the effective amount is an amount effective for inhibiting the activity of a transcription factor (e.g., TEAD (e.g., TEAD1, TEAD2, TEAD3, or TEAD4)) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a TEAD (e.g., TEAD1, TEAD2, TEAD3, or TEAD4)) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is in vitro. In certain embodiments, the cell being contacted with a compound or composition described herein is in vivo.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine 1131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R—CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS—777607, ABT-869, MP470, BIBF 1120 (VARGATEF®), AP24534, JNJ-26483327, MGCD265, DCC-2036, BMS—690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is ibrutinib. In certain embodiments, the additional pharmaceutical agent is a transcription factor inhibitor (e.g., a TEAD family transcription factor inhibitor). In certain embodiments, the additional pharmaceutical agent is a binder or inhibitor of a TEAD (e.g., TEAD1, TEAD2, TEAD3, or TEAD4)). In certain embodiments, the additional pharmaceutical agent is a binder or inhibitor of a TEAD. In certain embodiments, the additional pharmaceutical agent is a binder or inhibitor of TEAD1. In certain embodiments, the additional pharmaceutical agent is a binder or inhibitor of TEAD2. In certain embodiments, the additional pharmaceutical agent is a binder or inhibitor of TEAD3. In certain embodiments, the additional pharmaceutical agent is a binder or inhibitor of TEAD4. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., transcription factor inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Thus, in one aspect, provided are kits including a first container comprising a compound or pharmaceutical composition described herein. In certain embodiments, the kits are useful for treating a disease (e.g., proliferative disease) in a subject in need thereof. In certain embodiments, the kits are useful for preventing a disease (e.g., proliferative disease) in a subject in need thereof. In certain embodiments, the kits are useful for inhibiting the activity (e.g., aberrant or unwanted activity, such as increased activity) of a transcription factor (e.g., TEAD1, TEAD2, TEAD3, or TEAD4) in a subject, biological sample, tissue, or cell. In certain embodiments, the kits are useful for inducing apoptosis of a cell (e.g., cell in vivo or in vitro).

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease) in a subject in need thereof. In certain embodiments, the kits and instructions provide for preventing a disease (e.g., proliferative disease) in a subject in need thereof. In certain embodiments, the kits and instructions provide for modulating (e.g., inhibiting) the activity (e.g., aberrant activity, such as increased activity) of a transcription factor (e.g., TEAD1, TEAD2, TEAD3, TEAD4) in a subject, biological sample, tissue, or cell. In certain embodiments, the kits and instructions provide for inducing apoptosis of a cell. A kit described herein may include one or more additional pharmaceutical agents described herein as a separate composition.

Methods of Treatment and Uses

The present disclosure provides methods of modulating (e.g., inhibiting or increasing) the activity (e.g., aberrant activity, such as increased or decreased activity) of a transcription factor (e.g., TEAD (e.g., TEAD1, TEAD2, TEAD3, or TEAD4)). The present disclosure provides methods of modulating (e.g., inhibiting or increasing) the activity (e.g., aberrant activity, such as increased or decreased activity) of a TEAD (e.g., TEAD1, TEAD2, TEAD3, or TEAD4) in a subject, biological sample, tissue, or cell. The present disclosure also provides methods for the treatment of a wide range of diseases, such as diseases associated with the aberrant activity (e.g., increased activity) of a transcription factor, e.g., proliferative diseases, in a subject in need thereof. The present disclosure provides methods for the treatment and/or prevention of a proliferative disease (e.g., cancers (e.g., carcinoma, sarcoma, lung cancer, thyroid cancer, skin cancer, ovarian cancer, colorectal cancer, prostate cancer, pancreatic cancer, esophageal cancer, liver cancer, breast cancer)).

The present disclosure also provides a compound of Formula (I), or a pharmaceutically acceptable salt, co-crystal, tautomer, stereoisomer, solvate, hydrate, polymorph, isotopically enriched derivative, prodrug, composition, or mixture thereof, for use in the treatment of diseases, such as proliferative diseases, in a subject in need thereof.

The present disclosure also provides uses of a compound of Formula (I), or a pharmaceutically acceptable salt, co-crystal, tautomer, stereoisomer, solvate, hydrate, polymorph, isotopically enriched derivative, prodrug, composition, or mixture thereof, in the manufacture of a medicament for the treatment of diseases, such as proliferative diseases, in a subject in need thereof.

In another aspect, the present disclosure provides methods of modulating the activity of a transcription factor (e.g., TEAD (e.g., TEAD1, TEAD2, TEAD3, or TEAD4)) in a subject, biological sample, tissue, or cell. In certain embodiments, provided are methods of inhibiting the activity of a transcription factor in a subject. In certain embodiments, provided are methods of inhibiting the activity of a transcription factor in a cell. In certain embodiments, provided are methods of increasing the activity of a transcription factor (e.g., TEAD (e.g., TEAD1, TEAD2, TEAD3, or TEAD4)) in a subject. The compounds described herein may exhibit transcription factor inhibitory activity; the ability to inhibit a transcription enhancer factor; the ability to inhibit a TEAD family transcription factor; the ability to inhibit TEAD; the ability to inhibit TEAD1, without inhibiting another transcription factor (e.g., TEAD2, TEAD3, or TEAD4); the ability to inhibit TEAD2, without inhibiting another transcription factor (e.g., TEAD1, TEAD3, or TEAD4); the ability to inhibit TEAD3, without inhibiting another transcription factor (e.g., TEAD1, TEAD2, or TEAD4); the ability to inhibit TEAD4, without inhibiting another transcription factor (e.g., TEAD2, TEAD3, or TEAD4); a therapeutic effect and/or preventative effect in the treatment of cancers; a therapeutic effect and/or preventative effect in the treatment of proliferative diseases; and/or a therapeutic profile (e.g., optimum safety and curative effect) that is superior to existing chemotherapeutic agents.

In certain embodiments, provided are methods of decreasing the activity of a transcription factor (e.g., TEAD (e.g., TEAD1, TEAD2, TEAD3, or TEAD4)) in a subject or biological sample (e.g., cell, tissue) by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a transcription factor (e.g., TEAD (e.g., TEAD1, TEAD2, TEAD3, or TEAD4)) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a transcription factor (e.g., TEAD1 (e.g., TEAD2, TEAD3, or TEAD4)) in a subject or cell is selectively inhibited by the method. In some embodiments, the activity of a transcription factor (e.g., TEAD (e.g., TEAD1, TEAD2, TEAD3, or TEAD4)) in a subject or cell is selectively decreased by the method.

Without wishing to be bound by any particular theory, the compounds described herein are able to bind (e.g., covalently modify) the transcription factor being inhibited. In certain embodiments, a compound described herein is able to bind (e.g., covalently modify) the transcription factor. In certain embodiments, the compound described herein is able to covalently bind a cysteine residue of the transcription factor. In certain embodiments, the compound is capable of covalently binding the central pocket of the YAP/TAZ domain of a TEAD family transcription factor. In certain embodiments, the compound is capable of covalently binding TEAD1, TEAD2, TEAD3, or TEAD4. In certain embodiments, the compound is capable of covalently modifying TEAD1, TEAD2, TEAD3, or TEAD4. In certain embodiments, the compound is capable of covalently modifying YAP-binding domain of a TEAD transcription factor. In certain embodiments, the compound is capable of covalently modifying TEAD1. In certain embodiments, the compound is capable of covalently modifying TEAD2. In certain embodiments, the compound is capable of covalently modifying TEAD3. In certain embodiments, the compound is capable of covalently modifying TEAD4.

In another aspect, the present disclosure provides methods of inhibiting the activity of a transcription factor in a subject, the methods comprising administering to the subject an effective amount (e.g., therapeutically effective amount) of a compound, or pharmaceutical composition thereof, as described herein. In another aspect, the present disclosure provides methods of inhibiting the activity of a transcription factor (e.g., TEAD (e.g., TEAD1, TEAD2, TEAD3, or TEAD4)) in a biological sample, the methods comprising contacting the biological sample with an effective amount of a compound, or pharmaceutical composition thereof, as described herein. In another aspect, the present disclosure provides methods of inhibiting the activity of a transcription factor in a tissue or cell, the methods comprising contacting the tissue or cell with an effective amount of a compound, or pharmaceutical composition thereof, as described herein.

In another aspect, the present disclosure provides methods of inhibiting the activity of a transcription factor (e.g., TEAD (e.g., TEAD1, TEAD2, TEAD3, or TEAD4)) in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal, such as a transgenic mouse or transgenic pig.

In certain embodiments, the biological sample being contacted with the compound or composition is breast tissue, bone marrow, lymph node, lymph tissue, spleen, or blood. In certain embodiments, the biological sample being contacted with the compound or composition is a tumor or cancerous tissue. In certain embodiments, the biological sample being contacted with the compound or composition is serum, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

In certain embodiments, the cell or tissue being contacted with the compound or composition is present in vitro. In certain embodiments, the cell or tissue being contacted with the compound or composition is present in vivo. In certain embodiments, the cell or tissue being contacted with the compound or composition is present ex vivo. In certain embodiments, the cell or tissue being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant white blood cell. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a fallopian tube carcinoma cell. In certain embodiments, the cell being contacted with the compound or composition is a sarcoma cell. In certain embodiments, the cell being contacted with the compound or composition is a sarcoma cell from breast tissue.

The disease (e.g., proliferative disease) to be treated or prevented using the compounds described herein may be associated with increased activity of a transcription factor, such as a TEAD (e.g., TEAD1, TEAD2, TEAD3, or TEAD4). The disease (e.g., proliferative disease) to be treated or prevented using the compounds described herein may be associated with the overexpression of a transcription factor, such as a TEAD (e.g., TEAD1, TEAD2, TEAD3, or TEAD4).

In certain embodiments, the disease (e.g., proliferative disease) to be treated or prevented using the compounds described herein may be associated with the overexpression of a TEAD (e.g., TEAD1,TEAD2, TEAD3, or TEAD4). A disease (e.g., proliferative disease) may be associated with aberrant activity of a TEAD (e.g., TEAD1, TEAD2, TEAD3, or TEAD4). Aberrant activity of a TEAD (e.g., TEAD1, TEAD2, TEAD3, TEAD4) may be elevated and/or inappropriate or undesired activity of the TEAD. The compounds described herein, and pharmaceutically acceptable salts, solvates, hydrates, polymorphs, co-crystals, tautomers, stereoisomers, isotopically labeled derivatives, prodrugs, compositions, and mixtures thereof, may inhibit the activity of a TEAD (e.g., TEAD1, TEAD2, TEAD3, or TEAD4) and be useful in treating and/or preventing diseases (e.g., proliferative diseases). The compounds described herein, and pharmaceutically acceptable salts, solvates, hydrates, polymorphs, co-crystals, tautomers, stereoisomers, isotopically labeled derivatives, prodrugs, compositions, and mixtures thereof, may inhibit the activity of a TEAD and be useful in treating and/or preventing diseases (e.g., proliferative diseases). The compounds described herein, and pharmaceutically acceptable salts, solvates, hydrates, polymorphs, co-crystals, tautomers, stereoisomers, isotopically labeled derivatives, prodrugs, compositions, and mixtures thereof, may inhibit the activity of a TEAD and be useful in treating and/or preventing diseases (e.g., proliferative diseases).

All types of biological samples described herein or known in the art are contemplated as being within the scope of the invention. In certain embodiments, the disease (e.g., proliferative disease) to be treated or prevented using the compounds described herein is cancer. All types of cancers disclosed herein or known in the art are contemplated as being within the scope of the invention. In certain embodiments, the proliferative disease is carcinoma. In certain embodiments, the proliferative disease is fallopian tube carcinoma. In certain embodiments, the proliferative disease is carcinoma. In certain embodiments, the proliferative disease is Kaposi's carcinoma. In certain embodiments, the proliferative disease is colorectal cancer. In certain embodiments, the proliferative disease is colon cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the proliferative disease is triple-negative breast cancer (TNBC). In certain embodiments, the proliferative disease is lung cancer. In certain embodiments, the proliferative disease is thyroid cancer. In certain embodiments, the proliferative disease is skin cancer. In certain embodiments, the proliferative disease is ovarian cancer. In certain embodiments, the proliferative disease is prostate cancer. In certain embodiments, the proliferative disease is pancreatic cancer. In certain embodiments, the proliferative disease is esophageal cancer. In certain embodiments, the proliferative disease is liver cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention.

Another aspect of the disclosure relates to methods of inhibiting the activity of a transcription factor in a biological sample, tissue, cell, or subject. In certain embodiments, the transcription factor is a TEAD transcription factor. In certain embodiments, the TEAD is a Transcriptional Enhancer Associate Domain transcription factor. In certain embodiments, the transcription factor is TEAD1. In certain embodiments, the transcription factor is TEAD2. In certain embodiments, the transcription factor is TEAD3. In certain embodiments, the transcription factor is TEAD4. In certain embodiments, the activity of the transcription factor is aberrant activity of the transcription factor. In certain embodiments, the activity of the transcription factor is increased activity of the transcription factor. In certain embodiments, the inhibition of the activity of the transcription factor is irreversible. In other embodiments, the inhibition of the activity of the transcription factor is reversible. In certain embodiments, the methods of inhibiting the activity of the transcription factor include attaching a compound described herein to the transcription factor. In certain embodiments, the methods comprise covalently inhibiting a TEAD (e.g., TEAD1, TEAD2, TEAD3, or TEAD4). In certain embodiments, the methods comprise reversibly inhibiting a TEAD (e.g., TEAD1, TEAD2, TEAD3, or TEAD4). The present invention provides methods of inhibiting cell growth in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, prodrug, composition, or mixture thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a transcription factor inhibitor. In certain embodiments, the additional pharmaceutical agent is an inhibitor of TEAD. In certain embodiments, the additional pharmaceutical agent is an inhibitor of a transcription enhancer factor. In certain embodiments, the additional pharmaceutical agent is an inhibitor of a TEAD family transcription factor. In certain embodiments, the additional pharmaceutical agent is an inhibitor of TEAD1. In certain embodiments, the additional pharmaceutical agent is an inhibitor of TEAD2. In certain embodiments, the additional pharmaceutical agent is an inhibitor of TEAD3. In certain embodiments, the additional pharmaceutical agent is an inhibitor of TEAD4. In certain embodiments, the additional pharmaceutical agent is a selective inhibitor of TEAD1. In certain embodiments, the additional pharmaceutical agent is a selective inhibitor of TEAD2. In certain embodiments, the additional pharmaceutical agent is a selective inhibitor of TEAD3. In certain embodiments, the additional pharmaceutical agent is a selective inhibitor of TEAD4. In certain embodiments, the additional pharmaceutical agent is a non-selective inhibitor of TEAD1. In certain embodiments, the additional pharmaceutical agent is a non-selective inhibitor of TEAD2. In certain embodiments, the additional pharmaceutical agent is a non-selective inhibitor of TEAD3. In certain embodiments, the additional pharmaceutical agent is a non-selective inhibitor of TEAD4. In certain embodiments, the additional pharmaceutical agent includes an anti-cancer agent (e.g., chemotherapeutics), anti-inflammatory agent, steroids, immunosuppressant, radiation therapy, or other agents. In certain embodiments, the additional pharmaceutical agent is an anti-proliferative agent. In certain embodiments, the additional pharmaceutical agent is an inhibitor of a transcription factor. In certain embodiments, the additional pharmaceutical agent is a non-selective inhibitor of a transcription factor. In certain embodiments, the additional pharmaceutical agent is an immunotherapy agent (e.g., PD1 inhibitor, PDL1 inhibitor). In certain embodiments, the additional pharmaceutical agent is an immune checkpoint inhibitor.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-((I-1-methoxypropan-2-yl)amino)cyclohexyl)amino)-[2,4'-bi-pyridin]-6-yl)amino)methyl)tetrahydro-2H-pyran-4-carbonitrile, JIB04, or cisplatin. Exemplary chemotherapeutic agents include alkylating agents such as nitrogen mustards, ethylenimines, methylmelamines, alkyl sulfonates, nitrosoureas, and triazenes; antimetabolites such as folic acid analogs, pyrimidine analogs, in particular fluorouracil and cytosine arabinoside, and purine analogs; natural products such as vinca alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant. Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine. In certain embodiments, a pharmaceutical composition described herein further comprises a combination of the additional pharmaceutical agents described herein.

The inventive compounds or compositions may synergistically augment inhibition of TEAD induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a transcription factor is non-selectively inhibited by the compounds or pharmaceutical compositions described herein. In some embodiments, the activity of the transcription factor being inhibited is selectively inhibited by the compounds or pharmaceutical compositions described herein, compared to the activity of a different protein (e.g., a different transcription factor). In certain embodiments, the activity of a TEAD (e.g., TEAD1, TEAD2, TEAD3, or TEAD4) is selectively inhibited by a compound or pharmaceutical composition described herein, compared to the activity of a different protein. In certain embodiments, the activity of TEAD1 is selectively inhibited by a compound or pharmaceutical composition described herein, compared to the activity of another TEAD1 (e.g., TEAD2, TEAD3, or TEAD4). In certain embodiments, the activity of TEAD1 is selectively inhibited by a compound or pharmaceutical composition described herein, compared to the activity of another TEAD (e.g., TEAD2, TEAD3, or TEAD4). In certain embodiments, the activity of TEAD2 is selectively inhibited by a compound or pharmaceutical composition described herein, compared to the activity of another TEAD2 (e.g., TEAD1, TEAD3, or TEAD4). In certain embodiments, the activity of TEAD2 is selectively inhibited by a compound or pharmaceutical composition described herein, compared to the activity of another TEAD (e.g., TEAD1, TEAD3, or TEAD4). In certain embodiments, the activity of TEAD3 is selectively inhibited by a compound or pharmaceutical composition described herein, compared to the activity of another TEAD3 (e.g., TEAD1, TEAD2, or TEAD4). In certain embodiments, the activity of TEAD3 is selectively inhibited by a compound or pharmaceutical composition described herein, compared to the activity of another TEAD (e.g., TEAD1, TEAD2, or TEAD4). In certain embodiments, the activity of TEAD4 is selectively inhibited by a compound or pharmaceutical composition described herein, compared to the activity of another TEAD4 (e.g., TEAD1, TEAD2, or TEAD3). In certain embodiments, the activity of TEAD4 is selectively inhibited by a compound or pharmaceutical composition described herein, compared to the activity of another TEAD (e.g., TEAD1, TEAD2, or TEAD3).

The selectivity of a compound or pharmaceutical composition described herein in inhibiting the activity of a transcription factor over a different protein (e.g., a different transcription factor) may be measured by the quotient of the $IC_{50}$ value of the compound or pharmaceutical composition in inhibiting the activity of the different protein over the $IC_{50}$ value of the compound or pharmaceutical composition in inhibiting the activity of the transcription factor. The selectivity of a compound or pharmaceutical composition described herein for a transcription factor over a different protein may also be measured by the quotient of the $K_d$ value of an adduct of the compound or pharmaceutical composition and the different protein over the $K_d$ value of an adduct of the compound or pharmaceutical composition and the transcription factor. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating and/or preventing a disease, such as a proliferative disease (e.g., cancers (e.g., sarcoma, carcinoma, lung cancer, thyroid cancer, skin cancer, ovarian cancer, colorectal cancer, prostate cancer, pancreatic cancer, esophageal cancer, liver cancer, breast cancer)), in a subject in need thereof, inhibiting the activity of a transcription factor (e.g., a TEAD (e.g., TEAD1, TEAD2, TEAD3, or TEAD4)) in a subject, biological sample, tissue, or cell, and/or inducing apoptosis in a cell.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Inhibition of TEAD-Driven Transcription

The compounds were tested for their ability to inhibit TEAD-driven transcription. The results are summarized in Table 2.

TABLE 2

Summary of Inhibition of TEAD-driven transcription.

| ID | Inhibition of TEAD-driven transcription | ID | Inhibition of TEAD-driven transcription | ID | Inhibition of TEAD-driven transcription |
|---|---|---|---|---|---|
| I-29 | ++++ | I-50 | +++ | I-30 | N/A |
| I-28 | N/A | I-51 | +++ | I-25 | N/A |
| I-27 | ++ | I-52 | ++ | I-26 | N/A |
| I-11 | +++ | I-53 | N/A | I-57 | ++ |
| I-10 | +++ | I-54 | N/A | I-58 | ++ |
| I-9 | N/A | I-55 | N/A | I-59 | N/A |
| I-14 | ++ | I-56 | + | I-60 | N/A |
| I-15 | ++ | I-12 | N/A | I-61 | + |
| I-18 | + | I-13 | N/A | I-62 | ++ |
| I-34 | ++++ | I-16 | N/A | I-63 | N/A |
| I-35 | ++ | I-17 | N/A | I-64 | ++++ |
| I-1 | + | I-22 | N/A | I-65 | +++ |
| I-2 | + | I-23 | N/A | I-47 | + |
| I-19 | + | I-24 | N/A | I-48 | + |
| I-20 | ++ | I-66 | N/A | I-49 | + |
| I-21 | ++ | I-67 | ++++ | I-22 | N/A |
| I-3 | N/A | I-4 | N/A | I-31 | +++ |

N/A signifies that activity was undetectable, +++ signifies 90% inhibition of TEAD transcriptional activity, ++ signifies 70% inhibition, and + signifies 50% inhibition. This assay used 40 μM at 24 hour treatment.

Example 2. Bioluminescent Reporter Assay Using 8×GTIIC-luc

8×GTIIC-luciferase plasmid, containing 8 TEAD binding sites (ACATTCCA), was obtained from Addgene (Addgene #34615). MDA-MB-231 cells were transfected with 8×GTIIC-luciferase and stable clone was obtained using neomycin selection. The TEAD transcriptional activity was monitored by assessing the luciferase activity using luciferase assay system (Promega). Each data point represents mean±standard deviation.

Example 3. Endogenous TEAD Transcription Targets in MDA-MB-231 Cells

MDA-MB-231 cells were treated at indicated conditions and total RNA was extracted using RNAeasy Plus reagent (Qiagen). qRT-PCR was performed to 1 pg RNA to quantify the transcript levels of indicated TEAD-regulated targets genes. Data points represent mean±standard deviation.

Example 4. Pulldown of TEAD from MDA-MB-231 Cell Lysates

Total cell lysates from MDA-MB-231 was extracted using IP lysis buffer (Pierce). 1 mg protein lysate was combined with Biotinylated I-29 at indicated doses overnight. Streptavidin agarose beads were added to enrich the covalently engaged proteins, which were subsequently separated on Bis-Tris Plus gels (Invitrogen). TEAD4-selective antibody was used to quantify 1-29 engaged TEAD4.

Example 5. In Vitro Inhibition of Palmitoylation of TEAD2 Protein

For overnight treatment, 90 μL of recombinant His6-TEAD2 (300 nM) protein (217-447) was incubated with DMSO control or TEAD inhibitors at 40 μM. Next, 10 μL of 25 μM alkyne palmitoyl-CoA (Cayman Chemical) were added into the reaction mixture and incubated for 15 min in 20 mM Hepes, pH 7.4 and 200 mM NaCl on ice. The reaction was quenched with 1% SDS followed by Click reaction with biotin-azide. Samples were analyzed by SDS-PAGE and streptavidin HRP. Bands intensity obtained from streptavidin blot were quantified using Image Studio Lite Ver 5.2 and normalized with DMSO control.

Example 6. Exemplary Synthesis of TEAD Inhibitors

Method 1

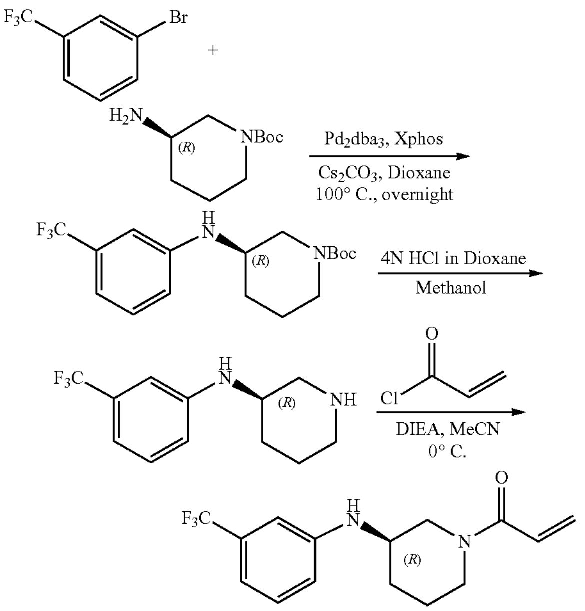

(I-1)

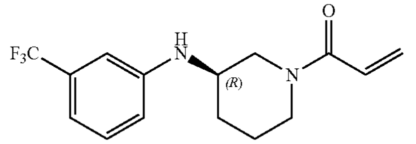

tert-butl(R)-3-((3-(trifluoromethyl)phenyl)amino)piperidine-1-carboxylate

To a solution of 1-bromo-3-(trifluoromethyl)benzene (223 mg, 1.0 mmol) and tert-lyl (R)-3-aminopiperidine-1-carboxylate (240 mg, 1.2 mmol) in 5 mL of dioxane was added $Pd_2dba_3$ (9 mg, 0.01 mmol), XPhos (14 mg, 0.03 mmol) and $Cs_2CO_3$ (652 mg, 2 mmol) under $N_2$. The mixture was stirred at 100° C. overnight. The mixture was filtered. The filtrate was concentrated in vacuo, then purified by flash chromatography on silica gel (hexane:ethyl acetate=4:1) to provide the product (240 mg, 70%). LC/MS (ESI) m/z=345 (I H)$^+$.

(R)—N-(3-(trifluoromethyl)phenyl)piperidin-3-amine

To a solution of tert-butyl (R)-3-((3-(trifluoromethyl)phenyl)amino)piperidine-1-carboxylate (240 mg, 0.7 mmol) in 3 mL of methanol was added HCl/dioxane (1 mL, 4 N) solution. The result solution was stirred at room temperature for 1 h, and then concentrated in vacuo to obtain the product as HCl salt, which was used into next step without any purification. LC/MS (ESI) m/z=245 (M+H)$^+$.

(R)-1-(3-((3-(trifluoromethyl)phenyl)amino)piperidin-1-yl)prop-2-en-1-one

To a solution of (R)—N-(3-(trifluoromethyl)phenyl)piperidin-3-amine (28 mg, 0.1 mmol) and DIEA (33 μL, 0.2 mmol) in 1 mL of acetonitrile was added acryloyl chloride dropwise at 0° C. until the reaction completed. Then the mixture was diluted with dichloromethane, washed with 1 N $NaHCO_3$ solution and brine. The organic layer was dried over sodium sulfate, concentrated in vacuo and then purified by prep-HPLC ($MeOH/H_2O$, 0-100%) to provide I-1 (23.4 mg, 56%) as TFA salt. LC/MS (ESI) m/z=299 (M+H)$^+$. $^1$H NMR (500 MHz, DMSO-d6) δ 7.29 (t, J=7.8 Hz, 1H), 6.95-6.50 (m, 4H), 6.19-5.52 (m, 2H), 4.68-3.74 (m, 2H), 3.34-2.91 (m, 3H), 2.68-2.50 (m, 1H), 1.98 (m, 1H), 1.90-1.65 (m, 1H), 1.59-1.37 (m, 2H).

(I-2)

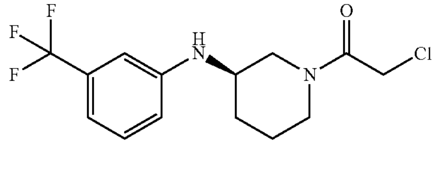

(R)-2-chloro-1-(3-((3-(trifluoromethyl)phenyl)amino)piperidin-1-yl)ethan-1-one

I-2 is prepared by using the similar procedure as for I-1. 2-chloroacetyl chloride was used in the last step. LC/MS (ESI) m/z=321 (M+H)$^+$. $^1$H NMR (500 MHz, DMSO-d6) δ 7.29 (t, J=7.9 Hz, 1H), 7.07-6.75 (m, 3H), 6.11 (br, 1H), 4.49-4.29 (m, 2H), 4.25-3.89 (m, 1H), 3.85-3.66 (m, 1H), 3.21-3.06 (m, 1H), 2.96 (dd, J=13.4, 9.0 Hz, 1H), 2.56 (dd, J=12.6, 9.5 Hz, 1H), 2.07-1.89 (m, 1H), 1.88-1.68 (m, 1H), 1.67-1.34 (m, 2H).

(I-11)

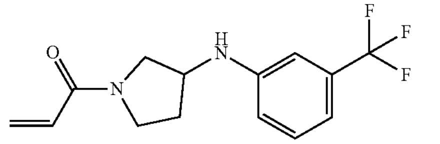

1-(3-((3-(trifluoromethyl)phenyl)amino)pyrrolidin-1-yl)prop-2-en-1-one

I-11 is prepared by using the similar procedure as for I-1. Tert-butyl 3-aminopyrrolidine-1-carboxylate was used in the first step. LC/MS (ESI) m/z=285 $(M+H)^+$. $^1H$ NMR (500 MHz, DMSO-d6) δ 7.30 (t, J=8.2 Hz, 1H), 6.90-6.82 (m, 3H), 6.59 (ddd, J=24.1, 16.8, 10.3 Hz, 1H), 6.14 (ddd, J=16.8, 7.9, 2.4 Hz, 1H), 5.67 (ddd, J=17.2, 10.3, 2.4 Hz, 1H), 4.21-4.01 (m, 1H), 3.94-3.60 (m, 2H), 3.59-3.44 (m, 2H), 3.37-3.29 (m, 1H), 2.28-2.08 (m, 1H), 1.98-1.75 (m, 1H).

(I-13)

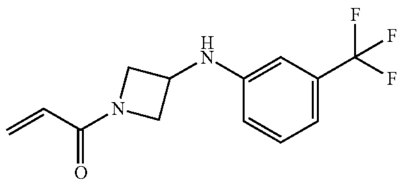

1-(3-((3-(trifluoromethyl)phenyl)amino)azetidin-1-yl)prop-2-en-1-one

I-13 is prepared by using the similar procedure as for I-1. Tert-butyl 3-aminoazetidine-1-carboxylate was used in the first step. LC/MS (ESI) m/z=271 $(M+H)^+$. $^1H$ NMR (500 MHz, DMSO-d6) δ 7.33 (t, J=8.2 Hz, 1H), 6.94-6.88 (m, 1H), 6.82-6.75 (m, 3H), 6.34 (dd, J=17.0, 10.4 Hz, 1H), 6.12 (dd, J=17.0, 2.2 Hz, 1H), 5.68 (dd, J=10.3, 2.2 Hz, 1H), 4.63-4.56 (m, 1H), 4.35-4.26 (m, 2H), 3.97-3.91 (m, 1H), 3.73 (d, J=5.4 Hz, 1H), 3.37-3.07 (m, 1H).

(I-15)

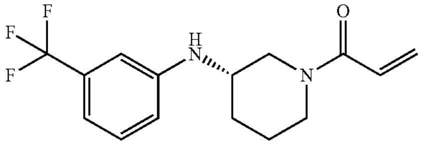

(S)-1-(3-((3-(trifluoromethyl)phenyl)amino)piperidin-1-yl)prop-2-en-1-one

I-15 is prepared by using the similar procedure as for I-1. Tert-butyl (S)-3-aminopiperidine-1-carboxylate was used in the first step. LC/MS (ESI) m/z=299 $(M+H)^+$. $^1H$ NMR (500 MHz, DMSO-d6) δ 7.29 (t, J=7.9 Hz, 1H), 6.97-6.52 (m, 4H), 6.22-5.95 (m, 1H), 5.76-5.45 (m, 1H), 4.63-4.31 (m, 1H), 4.13-3.77 (m, 2H), 3.73-3.57 (m, 1H), 3.21-3.02 (m, 2H), 2.11-1.89 (m, 1H), 1.86-1.69 (m, 1H), 1.64-1.39 (m, 2H).

(I-17)

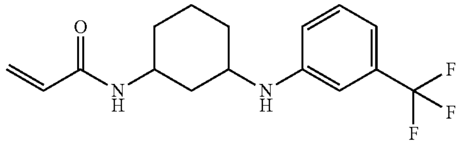

N-(3-((3-(trifluoromethyl)phenyl)amino)cyclohexyl)acrylamide

I-17 is prepared by using the similar procedure as for I-1. Tert-butyl (3-aminocyclohexyl)carbamate was used in the first step. LC/MS (ESI) m/z=313 $(M+H)^+$. $^1H$ NMR (500 MHz, DMSO-d6) δ 8.04 (d, J=7.9 Hz, 1H), 7.26 (t, J=7.8 Hz, 1H), 6.89-6.62 (m, 4H), 6.26-6.00 (m, 2H), 5.68-5.46 (m, 1H), 3.78-3.72 (m, 2H), 2.14-2.04 (m, 1H), 1.98-1.88 (m, 1H), 1.85-1.73 (m, 2H), 1.47-0.98 (m, 4H).

(I-23)

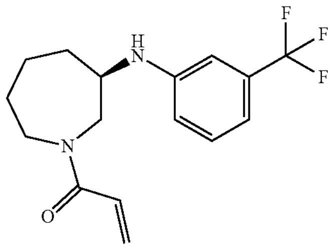

(R)-1-(3-((3-(trifluoromethyl)phenyl)amino)azepan-1-yl)prop-2-en-1-one

I-23 (21 mg, 38%) is prepared by using the similar procedure for I-1. Tert-butyl (R)-3-aminoazepane-1-carboxylate was used in the first step. LC/MS (ESI) m/z=313 $(M+H)^+$. $^1H$ NMR (500 MHz, DMSO-$d_6$) δ 7.29 (d, J=8.2 Hz, 1H), 7.00 (d, J=5.0 Hz, 2H), 6.88-6.75 (m, 3H), 6.18 (dd, J=16.7, 2.5 Hz, 1H), 5.71 (dd, J=10.5, 2.4 Hz, 1H), 4.12 (dd, J=13.3, 4.5 Hz, 1H), 3.81 (ddd, J=32.1, 14.4, 5.9 Hz, 2H), 3.73-3.64 (m, 1H), 2.86 (dd, J=13.2, 9.5 Hz, 1H), 1.90-1.70 (m, 4H), 1.55-1.38 (m, 2H).

(I-25)

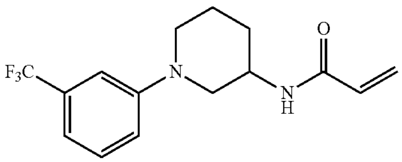

N-(1-(3-(trifluoromethyl)phenyl)piperidin-3-yl)acrylamide

I-25 (6.6 mg, 44%) is prepared by using the similar procedure as for I-1. Tert-butyl piperidin-3-ylcarbamate was used in the first step. LC/MS (ESI) m/z=299 $(M+H)^+$. $^1H$ NMR (500 MHz, DMSO-$d_6$) δ 8.17 (d, J=7.3 Hz, 1H), 7.40 (t, J=8.0 Hz, 1H), 7.22 (dd, J=8.3, 2.6 Hz, 1H), 7.15 (d, J=2.6 Hz, 2H), 7.03 (d, J=7.4 Hz, 1H), 6.12 (dd, J=17.1, 2.2 Hz, 1H), 5.61 (dd, J=10.2, 2.2 Hz, 1H), 3.86-3.80 (m, 1H), 3.70 (dd, J=12.4, 4.0 Hz, 2H), 2.90 (ddd, J=13.2, 10.5, 3.0 Hz, 1H), 2.74 (dd, J=12.3, 9.3 Hz, 1H), 1.93-1.74 (m, 2H), 1.66-1.42 (m, 2H).

(I-28)

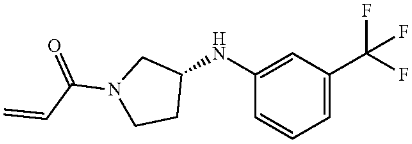

(R)-1-(3-((3-(trifluoromethyl)phenyl)amino)pyrrolidin-1-yl)prop-2-en-1-one

I-28 is prepared by using the similar procedure as for I-1. Tert-butyl (R)-3-aminopyrrolidine-1-carboxylate was used in the first step. LC/MS (ESI) m/z=285 $(M+H)^+$.

(I-29)

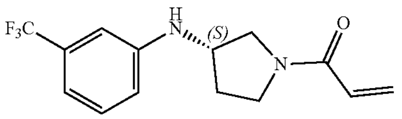

(S)-1-(3-((3-(trifluoromethyl)phenyl)amino)pyrrolidin-1-yl)prop-2-en-1-one

I-29 (8.3 mg, 19%) is prepared by using the similar procedure as for I-1. Tert-butyl (S)-3-aminopyrrolidine-1-carboxylate was used in the first step. LC/MS (ESI) m/z=285 $(M+H)^+$. $^1$H NMR (500 MHz, Methanol-d4) δ 7.33-7.26 (m, 1H), 6.91-6.85 (m, 3H), 6.62 (ddd, J=29.1, 16.8, 10.5 Hz, 1H), 6.29 (ddd, J=16.9, 7.4, 2.0 Hz, 1H), 5.76 (ddd, J=12.5, 10.4, 2.0 Hz, 1H), 4.26-4.11 (m, 1H), 4.02-3.61 (m, 3H), 3.56-3.47 (m, 1H), 2.40-2.22 (m, 1H), 2.12-1.93 (m, 1H).

(I-76)

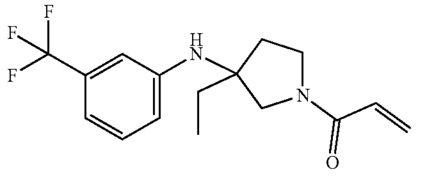

1-(3-ethyl-3-((3-(trifluoromethyl)phenyl)amino)pyrrolidin-1-yl)prop-2-en-1-one I-76 was prepared by using the similar procedure as for I-1. Tert-butyl 3-amino-3-ethylpyrrolidine-1-carboxylate was used in the first step. LC/MS (ESI) m/z=313 $(M+H)^+$.

(I-48)

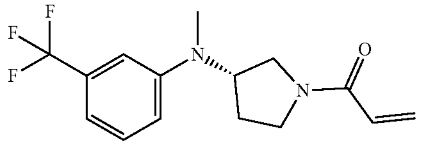

(S)-1-(3-(methyl(3-(trifluoromethyl)phenyl)amino)pyrrolidin-1-yl)prop-2-en-1-one I-48 was prepared by using the same procedure and starting material as for I-29 except for an additional methylation step below. LC/MS (ESI) m/z=299 $(M+H)^+$.

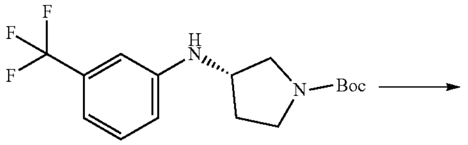

-continued

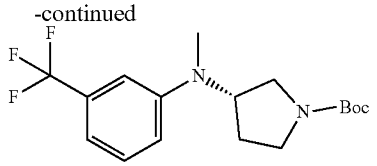

tert-butyl (S)-3-(methyl(3-(trifluoromethyl)phenyl)amino)pyrrolidine-1-carboxylate To a solution of tert-butyl (S)-3-((3-(trifluoromethyl)phenyl)amino)pyrrolidine-1-carboxylate (100 mg, 0.3 mmol) in DMF (5 mL) was NaH (60% w/t, 15 mg, 0.36 mmol) and MeI (846 mg, 0.6 mmol). The reaction mixture was stirred at 60° C. for 5 h. The mixture was quenched with water and extracted with ethyl acetate (50 mL×3). The combined organic layer was washed with brine and concentrated in vacuo. The residue was purified with silica gel column (hexane:ethyl acetate=4:1) to give the product (80 mg, 77%). LC/MS (ESI) m/z=345 $(M+H)^+$.

(I-47)

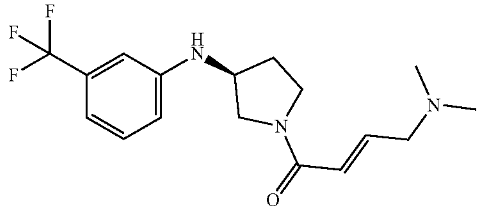

(S,E)-4-(dimethylamino)-1-(3-((3-(trifluoromethyl)phenyl)amino)pyrrolidin-1-yl)but-2-en-1-one I-47 is prepared by using the similar procedure as for I-1. (E)-4-bromobut-2-enoyl chloride was used in the last step and then react with dimethylamine in THF. LC/MS (ESI) m/z=342 $(M+H)^+$.

(I-50)

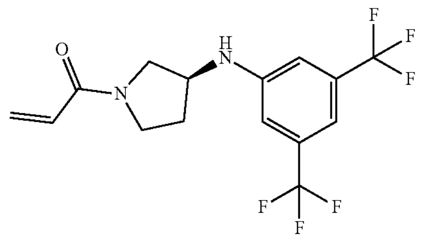

(S)-1-(3-((3,5-bis(trifluoromethyl)phenyl)amino)pyrrolidin-1-yl)prop-2-en-1-one

I-50 is prepared by using the similar procedure as for I-1. Tert-butyl (S)-3-aminopyrrolidine-1-carboxylate and 1-bromo-3,5-bis(trifluoromethyl)benzene were used in the first step. LC/MS (ESI) m/z=353 $(M+H)^+$.

(I-51)

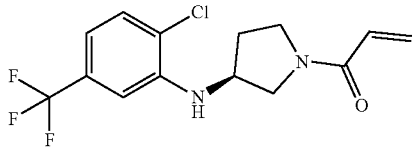

(S)-1-(3-((2-chloro-5-(trifluoromethyl)phenyl) amino)pyrrolidin-1-yl)prop-2-en-1-one I-51 is prepared by using the similar procedure as for I-1. Tert-butyl (S)-3-aminopyrrolidine-1-carboxylate and 2-bromo-1-chloro-4-(trifluoromethyl)benzene were used in the first step. LC/MS (ESI) m/z=319 $(M+H)^+$.

(I-52)

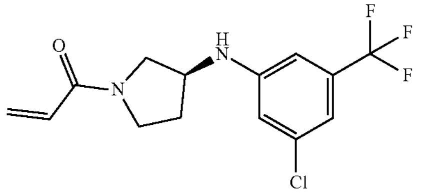

(S)-1-(3-((3-chloro-5-(trifluoromethyl)phenyl) amino)pyrrolidin-1-yl)prop-2-en-1-one I-52 is prepared by using the similar procedure as for I-1. Tert-butyl (S)-3-aminopyrrolidine-1-carboxylate and 1-bromo-3-chloro-5-(trifluoromethyl)benzene were used in the first step. LC/MS (ESI) m/z=319 $(M+H)^+$.

(I-53)

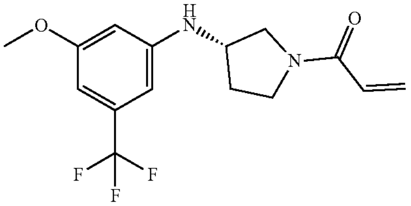

(S)-1-(3-((3-methoxy-5-(trifluoromethyl)phenyl) amino)pyrrolidin-1-yl)prop-2-en-1-one (S)-1-(3-((2-methyl-5-(trifluoromethyl)phenyl) amino)pyrrolidin-1-yl)prop-2-en-1-one I-54 is prepared by using the similar procedure as for I-1. Tert-butyl (S)-3-aminopyrrolidine-1-carboxylate and 2-bromo-1-methyl-4-(trifluoromethyl)benzene were used in the first step. LC/MS (ESI) m/z=299 $(M+H)^+$.

(I-55)

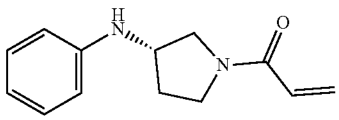

(S)-1-(3-(phenylamino)pyrrolidin-1-yl)prop-2-en-1-one

I-55 is prepared by using the similar procedure as for I-1. Tert-butyl (S)-3-aminopyrrolidine-1-carboxylate and bromobenzene were used in the first step. LC/MS (ESI) m/z=217 $(M+H)^+$.

(I-56)

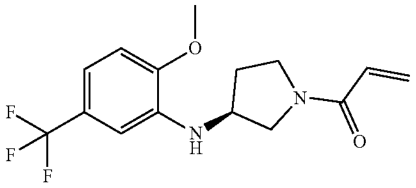

(S)-1-(3-((2-methoxy-5-(trifluoromethyl)phenyl) amino)pyrrolidin-1-yl)prop-2-en-1-one I-56 is prepared by using the similar procedure as for I-1. Tert-butyl (S)-3-aminopyrrolidine-1-carboxylate and 2-bromo-1-methoxy-4-(trifluoromethyl)benzene were used in the first step. LC/MS (ESI) m/z=315 $(M+H)^+$.

(I-57)

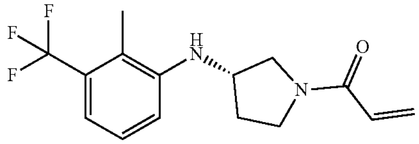

(S)-1-(3-((2-methyl-3-(trifluoromethyl)phenyl) amino)pyrrolidin-1-yl)prop-2-en-1-one I-57 is prepared by using the similar procedure as for I-1. Tert-butyl (S)-3-aminopyrrolidine-1-carboxylate and 1-bromo-2-methyl-3-(trifluoromethyl)benzene were used in the first step. LC/MS (ESI) m/z=299 $(M+H)^+$.

(I-49)

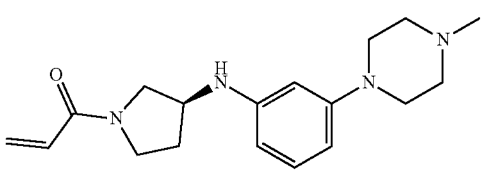

(S)-1-(3-((3-(4-methylpiperazin-1-yl)phenyl)amino) pyrrolidin-1-yl)prop-2-en-1-one I-49 is prepared by using the similar procedure as for I-1. Tert-butyl (S)-3-aminopyrrolidine-1-carboxylate and 1-(3-bromophenyl)-4-methylpiperazine were used in the first step. LC/MS (ESI) m/z=315 $(M+H)^+$.

(I-61)

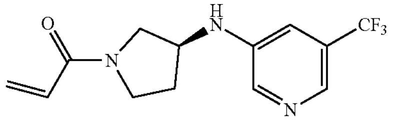

(S)-1-(3-((5-(trifluoromethyl)pyridin-3-yl)amino) pyrrolidin-1-yl)prop-2-en-1-one I-61 was prepared by using the similar procedure as for I-1. Tert-butyl (S)-3-aminopyrrolidine-1-carboxylate and 3-bromo-5-trifluoromethyl pyridine were used in the first step. LC/MS (ESI) m/z=286 $(M+H)^+$. $^1H$ NMR (500 MHz, DMSO-d6) δ 8.25 (t, J=3.4 Hz, 1H), 8.09 (d, J=1.8 Hz, 1H), 7.21 (dt, J=13.3, 2.5 Hz, 1H), 6.68 (dd, J=10.7, 7.0 Hz, 1H), 6.59 (ddd, J=20.3, 16.7, 10.3 Hz, 1H), 6.14 (ddd, J=16.8, 8.6, 2.4 Hz, 1H), 5.67 (ddd, J=17.8, 10.3, 2.4 Hz, 1H), 4.27-4.08 (m, 1H), 3.92 (dd, J=10.6, 5.9 Hz, 0.5H), 3.73-3.61 (m, 1.5H), 3.59-3.44 (m, 1H), 3.43-3.33 (m, 1H), 2.31-2.08 (m, 1H), 1.95-1.77 (m, 1H).

(I-62)

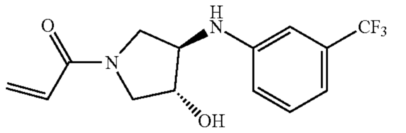

1-((3R,4R)-3-hydroxy-4-((3-(trifluoromethyl)phenyl)amino)pyrrolidin-1-yl)prop-2-en-1-one I-62 was prepared by using the similar procedure as for I-1. Tert-butyl (3R,4R)-3-amino-4-hydroxypyrrolidine-1-carboxylate was used in the first step. LC/MS (ESI) m/z=301 $(M+H)^+$. $^1H$ NMR (500 MHz, DMSO-d6) δ 7.30 (t, J=7.9 Hz, 1H), 6.96-6.75 (m, 3H), 6.58 (ddd, J=16.8, 10.3, 7.5 Hz, 1H), 6.37 (dd, J=23.7, 5.9 Hz, 1H), 6.15 (ddd, J=16.8, 4.0, 2.5 Hz, 1H), 5.68 (dt, J=10.3, 2.8 Hz, 1H), 5.46 (dd, J=39.5, 3.4 Hz, 1H), 4.07 (d, J=33.0 Hz, 0.5H), 3.95 (dd, J=10.9, 5.6 Hz, 0.5H), 3.81 (t, J=6.0 Hz, 0.5H), 3.74 (td, J=10.5, 9.9, 4.8 Hz, 1.5H), 3.57-3.38 (m, 3H).

(I-63)

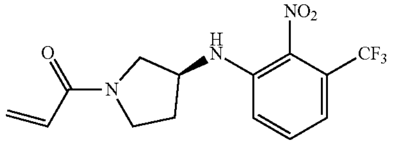

(S)-1-(3-((2-nitro-3-(trifluoromethyl)phenyl)amino) pyrrolidin-1-yl)prop-2-en-1-one I-63 was prepared by using the similar procedure as for I-1. Tert-butyl (S)-3-aminopyrrolidine-1-carboxylate and 1-chloro-2-nitro-3-(trifluoromethyl)benzene were used in the first step. LC/MS (ESI) m/z=330 $(M+H)^+$. $^1H$ NMR (500 MHz, DMSO-d6) δ 7.58 (t, J=8.2 Hz, 1H), 7.39 (dd, J=15.0, 8.6 Hz, 1H), 7.11 (d, J=7.6 Hz, 1H), 6.57 (ddd, J=27.5, 16.8, 10.3 Hz, 1H), 6.38 (dd, J=6.8, 2.9 Hz, 1H), 6.14 (ddd, J=16.8, 5.4, 2.4 Hz, 1H), 5.66 (ddd, J=13.0, 10.3, 2.4 Hz, 1H), 4.24 (dp, J=45.3, 6.0 Hz, 1H), 3.94 (dd, J=10.5, 6.5 Hz, 0.5H), 3.72 (dd, J=12.5, 6.4 Hz, 0.5H), 3.68-3.57 (m, 1H), 3.54-3.44 (m, 1H), 3.47-3.36 (m, 1H), 2.29-2.07 (m, 1H), 2.05-1.87 (m, 1H).

(I-65)

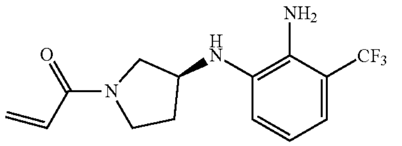

(S)-1-(3-((2-amino-3-(trifluoromethyl)phenyl) amino)pyrrolidin-1-yl)prop-2-en-1-one I-65 was prepared by using the same procedure and starting material as for I-63 except for an additional hydrogenation step below. LC/MS (ESI) m/z=300 $(M+H)^+$. $^1H$ NMR (500 MHz, DMSO-d6) δ 6.79-6.70 (m, 2H), 6.68-6.51 (m, 2H), 6.13 (ddd, J=16.8, 6.8, 2.5 Hz, 1H), 5.66 (ddd, J=14.0, 10.3, 2.5 Hz, 1H), 5.08-4.94 (m, 3H), 4.17-3.98 (m, 1H), 3.92 (dd, J=10.5, 6.0 Hz, 0.5H), 3.76-3.62 (m, 1.5H), 3.58-3.39 (m, 2H), 2.28-2.08 (m, 1H), 2.02-1.84 (m, 1H).

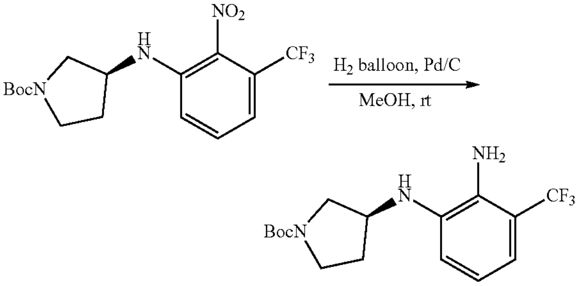

Tert-butyl (S)-3-((2-amino-3-(trifluoromethyl)phenyl)amino)pyrrolidine-1-carboxylate To a MeOH solution of tert-butyl (S)-3-((2-nitro-3-(trifluoromethyl)phenyl)amino)pyrrolidine-1-carboxylate (64 mg, 0.17 mmol) was added 10% Pd/C (35 mg) and a balloon of hydrogen was equipped. The suspension was stirred at room temperature for 4 h. The mixture was filtrated through Celite and the filtrate was concentrated to afford residue, which was directly used in the next step. LC/MS (ESI) m/z=346 $(M+H)^+$.

(I-67)

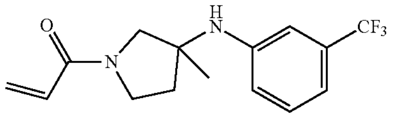

1-(3-Methyl-3-((3-(trifluoromethyl)phenyl)amino) pyrrolidin-1-yl)prop-2-en-1-one I-67 was prepared by using the similar procedure as for I-1. Tert-butyl 3-amino-3-methylpyrrolidine-1-carboxylate was used in the first step. LC/MS (ESI) m/z=299 $(M+H)^+$. $^1H$ NMR (500 MHz, DMSO-d6) δ 7.28 (t, J=8.0 Hz, 1H), 6.98-6.87 (m, 2H), 6.83 (d, J=7.4 Hz, 1H), 6.56 (ddd, J=18.1, 16.8, 10.3 Hz, 1H), 6.21 (d, J=4.3 Hz, 1H), 6.12 (ddd, J=16.8, 6.6, 2.4 Hz, 1H), 5.66 (ddd, J=10.3, 8.8, 2.4 Hz, 1H), 3.87-3.73 (m, 1H), 3.71-3.59 (m, 1.5H), 3.53-3.43 (m, 1H), 3.39 (d, J=12.3 Hz, 0.5H), 2.36-2.16 (m, 1H), 2.08-1.85 (m, 1H), 1.42 (s, 3H).

(I-9)

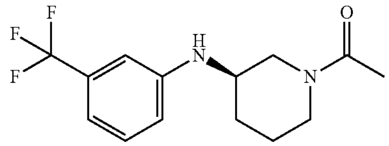

(R)-1-(3-((3-(trifluoromethyl)phenyl)amino)piperidin-1-yl)ethan-1-one

I-9 is prepared by using the similar procedure as for I-1. Acetyl chloride was used in the last step. LC/MS (ESI) m/z=287 $(M+H)^+$. 1H NMR (500 MHz, DMSO-d6) δ 7.38-7.19 (m, 1H), 7.02-6.71 (m, 3H), 4.57-4.12 (m, 1H), 3.86-3.76 (m, 1H), 3.28-2.94 (m, 3H), 2.48-2.36 (m, 1H), 2.11-1.85 (m, 4H), 1.81-1.66 (m, 1H), 1.60-1.29 (m, 2H).

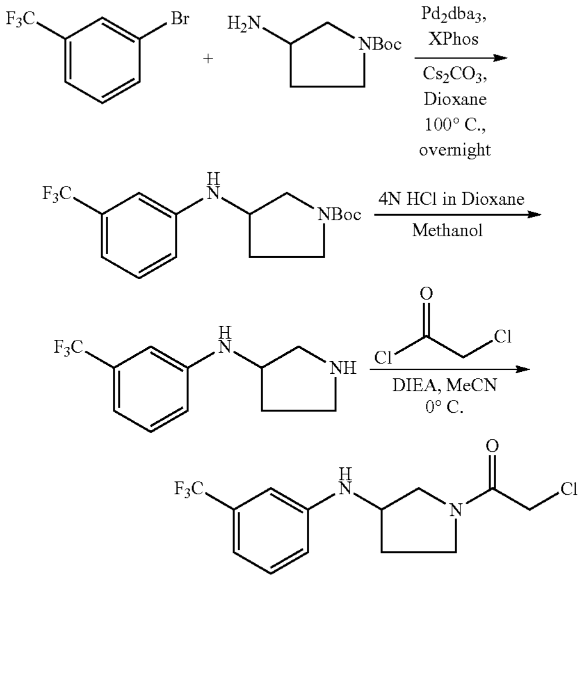

(I-10)

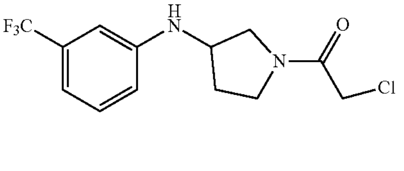

tert-butyl 3-((3-(trifluoromethyl)phenyl)amino)pyrrolidine-1-carboxylate

To a solution of 1-bromo-3-(trifluoromethyl)benzene (223 mg, 1.0 mmol) and tert-butyl 3-aminopyrrolidine-1-carboxylate (223 mg, 1.2 mmol) in 5 mL of dioxane was added $Pd_2dba_3$ (9 mg, 0.01 mmol), XPhos (14 mg, 0.03 mmol) and $Cs_2CO_3$ (652 mg, 2 mmol) under $N_2$. The mixture was stirred at 100° C. overnight. The mixture was filtered. The filtrate was concentrated in vacuo, then purified by flash chromatography on silica gel (hexane:ethyl acetate=4:1) to provide the product (230 mg, 70%). LC/MS (ESI) m/z=331 $(M+H)^+$.

N-(3-(trifluoromethyl)phenyl)pyrrolidin-3-amine

To a solution of tert-butyl 3-((3-(trifluoromethyl)phenyl)amino)pyrrolidine-1-carboxylate (230 mg, 0.7 mmol) in 3 mL of methanol was added HCl/dioxane (1 mL, 4 N) solution. The result solution was stirred at room temperature for 1 h, and then concentrated in vacuo to obtain the product as HCl salt, which was used into next step without any purification. LC/MS (ESI) m/z=231 $(M+H)^+$.

2-chloro-1-(3-((3-(trifluoromethyl)phenyl)amino)pyrrolidin-1-yl)ethan-1-one

To a solution of N-(3-(trifluoromethyl)phenyl)pyrrolidin-3-amine (23 mg, 0.1 mmol) and DIEA (33 μL, 0.2 mmol) in 1 mL of acetonitrile was added acryloyl chloride dropwise at 0° C. until the reaction completed. Then the mixture was diluted with dichloromethane, washed with 1 N $NaHCO_3$ solution and brine. The organic layer was dried over sodium sulfate, concentrated in vacuo and then purified by prep-HPLC ($MeOH/H_2O$, 0-100%) to provide I-10 (23.2 mg, 55%) as TFA salt. LC/MS (ESI) m/z=307 $(M+H)^+$. 1H NMR (500 MHz, DMSO-d6) δ 7.31 (t, J=8.1 Hz, 1H), 7.00-6.77 (m, 3H), 4.44-4.23 (m, 2H), 4.19-3.99 (m, 1H), 3.92-3.76 (m, 1H), 3.70-3.55 (m, 2H), 3.35-3.20 (m, 2H), 2.30-2.07 (m, 1H), 2.00-1.70 (m, 1H).

(I-12)

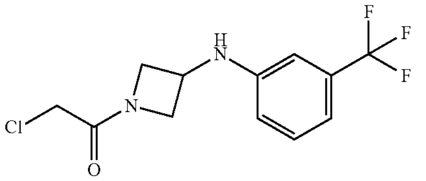

2-chloro-1-(3-((3-(trifluoromethyl)phenyl)amino)azetidin-1-yl)ethan-1-one

I-12 is prepared by using the similar procedure as for I-10. Tert-butyl 3-aminoazetidine-1-carboxylate was used in the first step. LC/MS (ESI) m/z=293 $(M+H)^+$. 1H NMR (500 MHz, DMSO-d6) δ 7.33 (t, J=8.2 Hz, 1H), 7.03-6.63 (m, 4H), 4.68-4.39 (m, 1H), 4.39-4.20 (m, 2H), 4.15 (s, 2H), 4.01-3.88 (m, 1H), 3.88-3.69 (m, 1H).

(I-14)

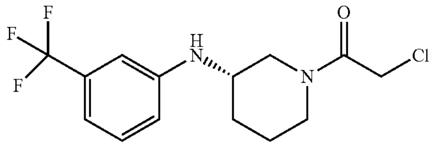

(S)-2-chloro-1-(3-((3-(trifluoromethyl)phenyl)amino)piperidin-1-yl)ethan-1-one

I-14 is prepared by using the similar procedure as for I-10. Tert-butyl (S)-3-aminopiperidine-1-carboxylate was used in the first step. LC/MS (ESI) m/z=321 $(M+H)^+$. 1H NMR (500 MHz, DMSO-d6) δ 7.29 (t, J=7.9 Hz, 1H), 6.99-6.90 (m, 1H), 6.91-6.80 (m, 2H), 4.46-4.29 (m, 2H), 4.24-3.90 (m, 1H), 3.86-3.65 (m, 1H), 3.58-3.51 (m, 1H), 3.32-3.06 (m, 1H), 3.00-2.92 (m, 1H), 2.60-2.52 (m, 1H), 2.02-1.93 (m, 1H), 1.82-1.70 (m, 1H), 1.67-1.36 (m, 2H).

(I-16)

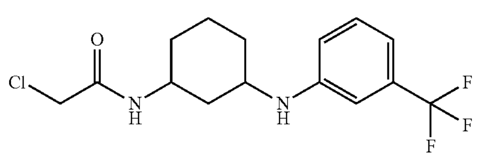

2-chloro-N-(3-((3-(trifluoromethyl)phenyl)amino)cyclohexyl)acetamide

I-16 is prepared by using the similar procedure as for I-10. Tert-butyl (3-aminocyclohexyl)carbamate was used in the first step. LC/MS (ESI) m/z=335 $(M+H)^+$. 1H NMR (500 MHz, DMSO-d6) δ 8.16 (d, J=7.8 Hz, 1H), 7.94-7.60 (m, 1H), 7.26 (t, J=7.8 Hz, 1H), 6.90-6.66 (m, 3H), 4.00 (s, 2H), 3.88-3.78 (m, 1H), 2.13-1.59 (m, 4H), 1.50-0.79 (m, 5H).

(I-19)

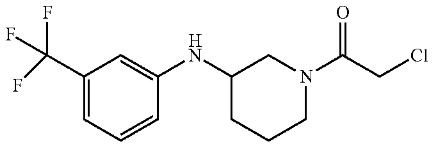

2-chloro-1-(3-((3-(trifluoromethyl)phenyl)amino)piperidin-1-yl)ethan-1-one

I-19 is prepared by using the similar procedure as for I-10. Tert-butyl 3-aminopiperidine-1-carboxylate was used in the first step. LC/MS (ESI) m/z=321 $(M+H)^+$. 1H NMR (500 MHz, DMSO-d6) δ 7.29 (t, J=7.9 Hz, 1H), 7.02-6.76 (m, 3H), 6.49-5.78 (m, 1H), 4.46-4.31 (m, 2H), 4.29-3.91 (m, 1H), 3.86-3.64 (m, 1H), 3.17-2.90 (m, 2H), 2.61-2.53 (m, 1H), 2.08-1.69 (m, 2H), 1.67-1.37 (m, 2H).

(I-24)

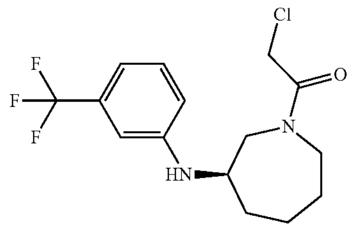

(R)-2-chloro-1-(3-((3-(trifluoromethyl)phenyl)amino)azepan-1-yl)ethan-1-one

I-24 is prepared by using the similar procedure as for I-10. Tert-butyl (R)-3-aminoazepane-1-carboxylate was used in the first step. LC/MS (ESI) n/z=335 $(M+H)^+$. 1H NMR (500 MHz, DMSO-d6) δ 7.51-7.22 (m, 1H), 7.16-6.71 (m, 3H), 4.42 (s, 2H), 4.13-3.74 (m, 5H), 3.04-2.73 (m, 1H), 1.99-0.99 (m, 6H).

(I-26)

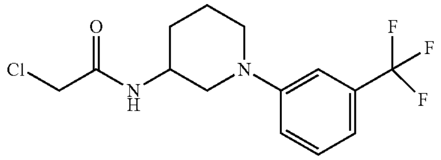

2-chloro-N-(1-(3-(trifluoromethyl)phenyl)piperidin-3-yl)acetamide

I-26 is prepared by using the similar procedure as for I-10. Tert-butyl piperidin-3-ylcarbamate was used in the first step. LC/MS (ESI) m/z=321 $(M+H)^+$. 1H NMR (500 MHz, DMSO-d6) δ 8.27 (d, J=7.4 Hz, 1H), 7.41 (t, J=8.0 Hz, 1H), 7.21 (dd, J=8.4, 2.6 Hz, 1H), 7.18-7.13 (m, 1H), 7.04 (d, J=8.3 Hz, 1H), 4.07 (s, 2H), 3.83-3.73 (m, 1H), 3.66-3.53 (m, 2H), 2.94 (ddd, J=12.9, 10.1, 3.1 Hz, 1H), 2.79 (dd, J=12.2, 9.0 Hz, 1H), 1.88-1.72 (m, 2H), 1.64-1.44 (m, 2H).

(I-27)

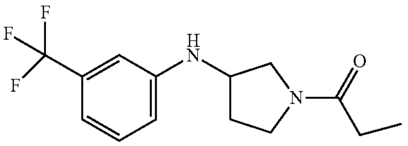

1-(3-((3-(trifluoromethyl)phenyl)amino)pyrrolidin-1-yl)propan-1-one

I-27 is prepared by using the similar procedure as for I-10. Propionyl chloride was used in last step. LC/MS (ESI) m/z=287 $(M+H)^+$. 1H NMR (500 MHz, DMSO-d6) δ 7.39-7.22 (m, 1H), 7.00-6.74 (m, 3H), 4.15-3.69 (m, 2H), 3.63-3.46 (m, 2H), 3.31-3.17 (m, 2H), 2.34-1.68 (m, 4H), 0.98 (dt, J=9.2, 7.4 Hz, 3H).

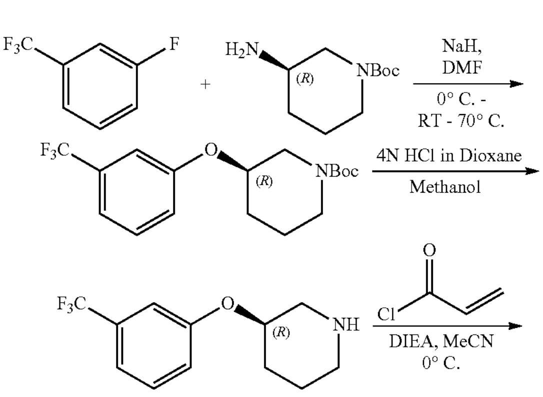

YLIU-02-174-1

-continued

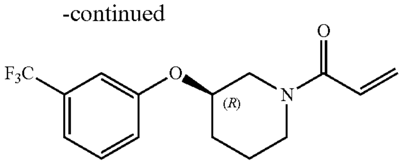

(I-21)

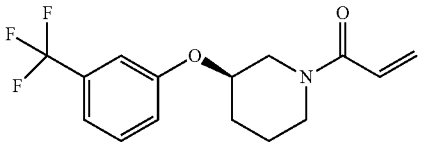

tert-butyl (R)-3-(3-(trifluoromethyl)phenoxy)piperidine-1-cloxylate

To a solution of tert-butyl (R)-3-hydroxypiperidine-1-carboxylate (504 mg, 2.4 mmol) in DMF (10 mL) was added NaH (360 mg, 9 mmol, 60% w.t. in mineral oil) at 0° C. The resulting mixture was stirred at the same temperature for 30 min, and then 1-fluoro-3-(trifluoromethyl)benzene (328 mg, 2 mmol) was added. The reaction mixture was stirred at room temperature for 30 min, and then heated up to 70° C. for another 1 h. After cooling down the mixture was diluted with water, extracted with dichloromethane (100 mL×3). The combined organic layer was washed with brine, and then concentrated in vacuo to provide crude product, which was used into next step directly. LC/MS (ESI) m/z=346 $(M+H)^+$.

(R)-3-(3-(trifluoromethyl)phenoxy)piperidine

To a solution of tert-butyl (R)-3-(3-(trifluoromethyl)phenoxy)piperidine-1-carboxylate in 10 mL of methanol was added 4N HCl/dioxane (4 mL) solution. The resulted mixture was stirred at 60° C. for 1 h, then concentrated in vacuo. The residue was purified by prep-HPLC ($MeOH/H_2O$, 0-100%) to provide the product as a TFA salt. LC/MS (ESI) m/z=246 $(M+H)^+$.

(R)-1-(3-(3-(trifluoromethyl)phenoxliperidin-1-yl) prop-2-en-1-one

To a solution of (R)-3-(3-(trifluoromethyl)phenoxy)piperidine (36 mg, 0.1 mmol) and DIEA (33 μL, 0.2 mmol) in acetonitrile (1 mL) was added acryloyl chloride dropwise at 0° C. until the reaction completed. The resulted mixture was diluted with dichloromethane, and then washed with 1 N $NaHCO_3$ solution and brine. The organic layer was dried over sodium sulfate and concentrated in vacuo. The residue was purified by prep-HPLC ($MeOH/H_2O$, 0-100%) to provide the product (18.3 mg, 45%) as TFA salt. LC/MS (ESI) m/z=300 $(M+H)^+$. $^1H$ NMR (500 MHz, DMSO-$d_6$) δ 7.22 (s, 1H), 6.84 (dd, J=16.7, 10.4 Hz, 1H), 6.58 (dd, J=16.7, 10.5 Hz, 1H), 6.12 (dd, J=16.8, 2.4 Hz, 1H), 6.03 (dd, J=16.8, 2.4 Hz, 1H), 5.70 (dd, J=10.5, 2.4 Hz, 1H), 5.54 (dd, J=10.5, 2.4 Hz, 1H), 4.03 (dd, J=12.7, 3.5 Hz, 1H), 3.83-3.67 (m, 4H), 2.04 (dt, J=11.3, 5.6 Hz, 1H), 1.95 (td, J=10.0, 5.0 Hz, 1H), 1.52 (ddt, J=10.2, 7.0, 4.0 Hz, 2H).

(I-58)

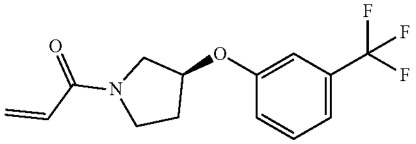

(S)-1-(3-(3-(trifluoromethyl)phenoxy)pyrrolidin-1-yl)prop-2-en-1-one

I-58 is prepared by using the similar procedure as for I-21. Tert-butyl (S)-3-aminopyrrolidine-1-carboxylate was used in the first step. LC/MS (ESI) m/z=2861+H)$^+$.

(I-20)

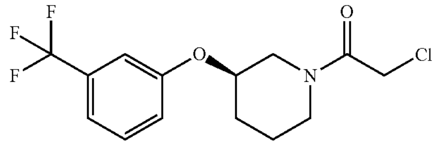

(R)-2-chloro-1-(3-(3-(trifluoromethyl)phenoxy)piperidin-1-yl)ethan-1-one

I-20 is prepared by using the similar procedure as for I-21. 2-chloroacetyl chloride was used in the last step. LC/MS (ESI) m/z=322 $(M+H)^+$. 1H NMR (500 MHz, DMSO-d6) δ 7.53 (t, J=7.5 Hz, 1H), 7.37-7.28 (m, 2H), 7.30-7.24 (m, 1H), 4.74-4.49 (m, 1H), 4.49-4.17 (m, 2H), 3.89-3.72 (m, 1H), 3.67-3.37 (m, 4H), 2.05-1.95 (m, 1H), 1.87-1.64 (m, 1H), 1.66-1.41 (m, 1H).

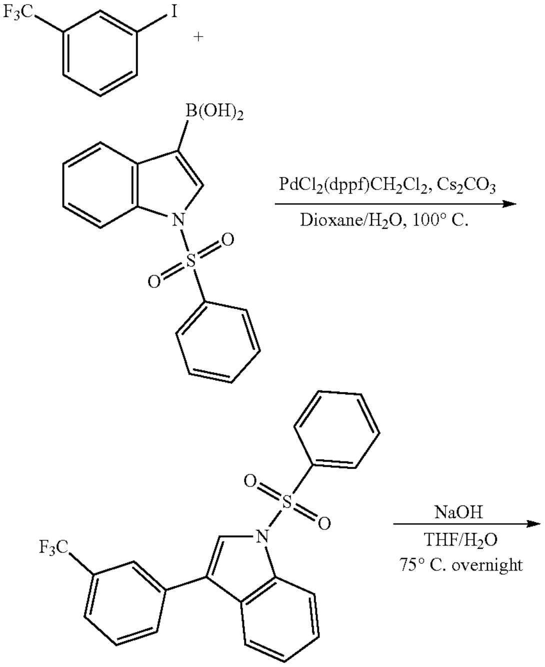

-continued

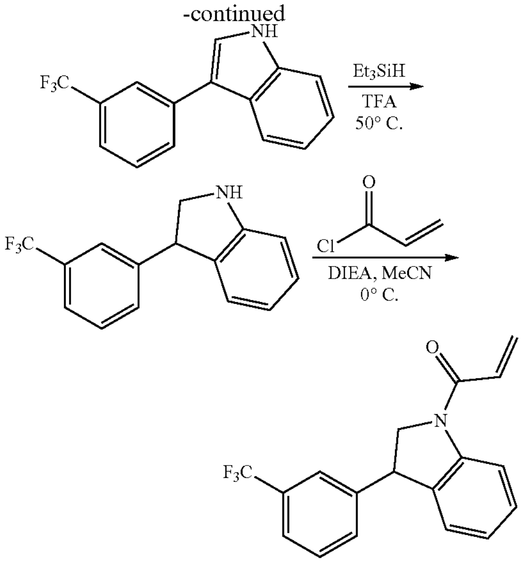

(I-34)

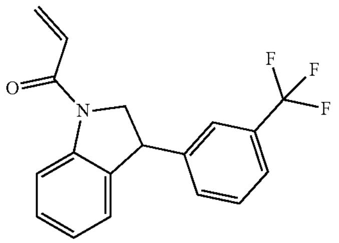

1-(phenylsulfonyl)-3-(3-(trifluoromethyl)phenyl)-1H-indole

To a solution of 1-iodo-3-(trifluoromethyl)benzene (680 mg, 2.5 mmol) and (1-(phenylsulfonyl)-1H-indol-3-yl)boronic acid (903 mg, 3 mmol) in 10 mL of dioxane/$H_2O$ (v/v=1/1) was added $PdCl_2$(dppf)$Cl_2$ (102 mg, 0.125 mmol) and $Cs_2CO_3$ (1.6 g, 5 mmol) under $N_2$. The resulted mixture was stirred at 100° C. overnight. After cooling down the mixture was filtered and the filtrate was concentrated in vacuo. The residue was purified by flash chromatography on silica gel (hexane/ethyl acetate=4/1) to provide the product (934 mg, 93%). LC/MS (ESI) m/z=402 $(M+H)^+$.

3-(3-(trifluoromethyl)phenyl)-1H-indole

To a solution of 1-(phenylsulfonyl)-3-(3-(trifluoromethyl) phenyl)-1H-indole (934 mg, 2.3 mmol) in 10 mL THF/$H_2O$ (v/v=1/1) was added NaOH (552 mg, 13.8 mmol). The resulted mixture was stirred at 75° C. overnight. After cooling down the reaction mixture was extracted with ethyl acetate (100 mL×3). The combined organic layer was washed with brine, and then concentrated in vacuo. The residue was purified with flash chromatography on silica gel (hexane/ethyl acetate=1/1) to provide the product (540 mg, 90%). LC/MS (ESI) m/z=262 $(M+H)^+$.

3-(3-(trifluoromethyl)phenyl)indoline

To a solution of 3-(3-(trifluoromethyl)phenyl)-1H-indole (261 mg, 1 mmol) in 2 mL of TFA was added $Et_3$ SiH (232 mg, 2 mmol) at 0° C. The reaction mixture was stirred at 50° C. overnight. After cooling down the mixture was concentrated in vacuo and purified with flash chromatography on silica gel (dichloromethane/methanol from 0 to 10%) to provide the product. LC/MS (ESI) m/z=264 $(M+H)^+$.

1-(3-(3-(trifluoromethyl)phenyl)indolin-1-yl)prop-2-en-1-one

To a solution of 3-(3-(trifluoromethyl)phenyl)indoline (26 mg, 0.1 mmol) and DIEA (33 μL, 0.2 mmol) in 1 mL of acetonitrile was added acryloyl chloride dropwise at 0° C. until the reaction completed. The mixture was diluted with dichloromethane and washed with 1 N $NaHCO_3$ solution and brine. The organic layer was dried over sodium sulfate, concentrated in vacuo. The residue was purified by prep-HPLC to provide the product (6.1 mg, 19%). LC/MS (ESI) m/z=318 $(M+H)^+$. $^1$H NMR (500 MHz, DMSO-$d_6$) δ 8.25 (d, J=8.0 Hz, 1H), 7.69-7.65 (m, 2H), 7.60 (t, J=7.9 Hz, 1H), 7.53 (d, J=7.7 Hz, 1H), 7.27 (t, J=7.7 Hz, 1H), 7.05 (t, J=7.5 Hz, 1H), 6.99 (d, J=7.4 Hz, 1H), 6.78 (dd, J=16.7, 10.3 Hz, 1H), 6.33 (dd, J=16.6, 2.2 Hz, 1H), 5.83 (dd, J=10.4, 2.2 Hz, 1H), 4.89 (d, J=8.1 Hz, 1H), 4.70 (t, J=10.3 Hz, 1H), 4.30-4.04 (m, 1H).

(I-35)

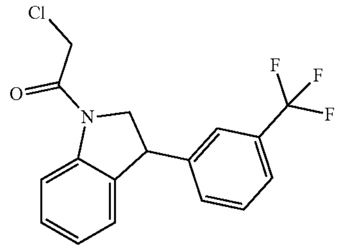

2-chloro-1-(3-(3-(trifluoromethyl)phenyl)indolin-1-yl)ethan-1-one

I-35 is prepared by using the similar procedure as for I-34. 2-chloroacetyl chloride was used in the last step. LC/MS (ESI) m/z=340 $(M+H)^+$.

(I-68)

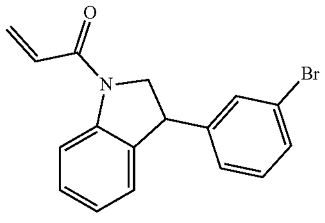

1-(3-(3-Bromophenyl)indolin-1-yl)prop-2-en-1-one

I-68 is prepared by using the similar procedure as for I-34. 1,3-dibromobenzene was used in the first step. LC/MS (ESI) m/z=328, 330 $(M+H)^+$. $^1$H NMR (500 MHz, DMSO-d6) δ 8.23 (d, J=8.0 Hz, 1H), 7.52-7.41 (m, 2H), 7.36-7.17 (m, 4H), 7.10-6.95 (m, 2H), 6.76 (dd, J=16.6, 10.4 Hz, 1H), 6.32 (dd, J=16.6, 2.2 Hz, 1H), 5.82 (dd, J=10.3, 2.2 Hz, 1H), 4.70 (dt, J=49.7, 9.7 Hz, 2H), 4.16 (dd, J=10.7, 6.4 Hz, 1H).

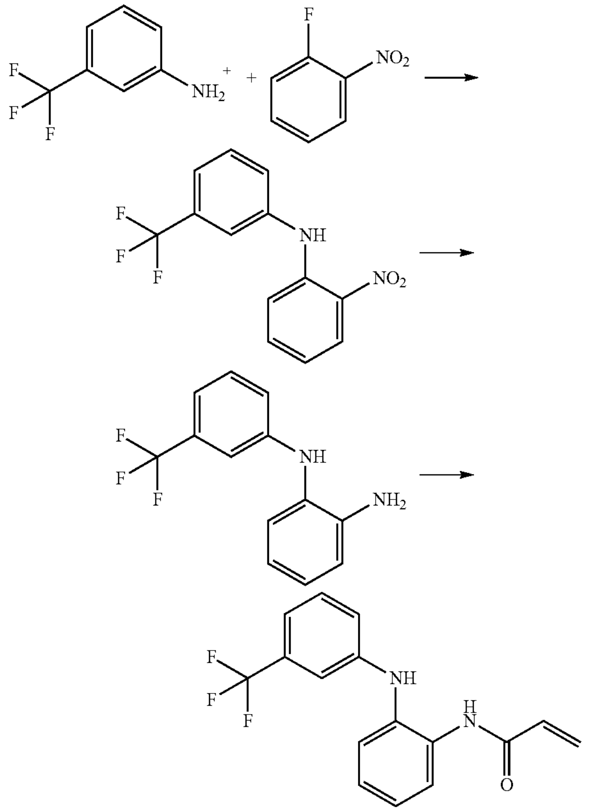

(I-22)

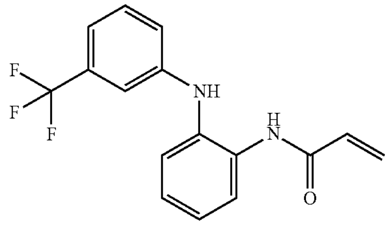

2-nitro-N-(3-(trifluoromethyl)phenyl)aniline

To a solution of 3-(trifluoromethyl)aniline (241 mg, 1.5 mmol) and 1-fluoro-2-nitrobenzene (141 mg, 1 mmol) in DMA (3 mL) was added $K_2CO_3$ (276 mg, 2 mmol). The reaction mixture was stirred at 120° C. overnight. After cooling down the mixture was diluted with water, and then extracted with ethyl acetate (100 mL×3). The combined organic layer was washed with brine, and then concentrated in vacuo. The residue was purified with flash chromatography on silica gel (hexane/ethyl acetate=4/1) to provide the product (200 mg, 71%). LC/MS (ESI) m/z=283 $(M+H)^+$.

$N^1$-(3-(trifluoromethyl)phenyl)benzene-1,2-diamine

To a solution of 2-nitro-N-(3-(trifluoromethyl)phenyl) aniline (200 mg, 0.71 mmol) in Methanol (5 mL) was added Pd/C (20 mg, 10%). The reaction mixture was stirred at room temperature for 90 min under $H_2$, and then filtered through Celite. The filtrate was concentrated in vacuo. The residue was put into next step without further purification. LC/MS (ESI) m/z=253 $(M+H)^+$.

N-(2-((3-(trifluoromethyl)phenyl)amino)phenyl) acrylamide

To a solution of $N^1$-(3-(trifluoromethyl)phenyl)benzene-1,2-diamine (10 mg, 0.04 mmol) and DIEA (16 mg, 0.12 mmol) in 1 mL of acetonitrile was added acryloyl chloride dropwise at 0° C. until the reaction completed. The mixture was diluted with dichloromethane and washed with 1 N $NaHCO_3$ solution and brine. The organic layer was dried over sodium sulfate, concentrated in vacuo. The residue was purified by prep-HPLC to provide the product (5.7 mg, 46%). LC/MS (ESI) m/z=306 $(M+H)^+$.

(I-31)

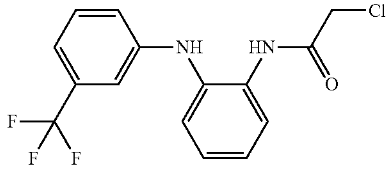

2-chloro-N-(2-((3-(trifluoromethyl)phenyl)amino) phenyl)acetamide

I-31 is prepared by using the similar procedure as for I-22. 2-chloroacetyl chloride was used in the last step. LC/MS (ESI) m/z=329 $(M+H)^+$.

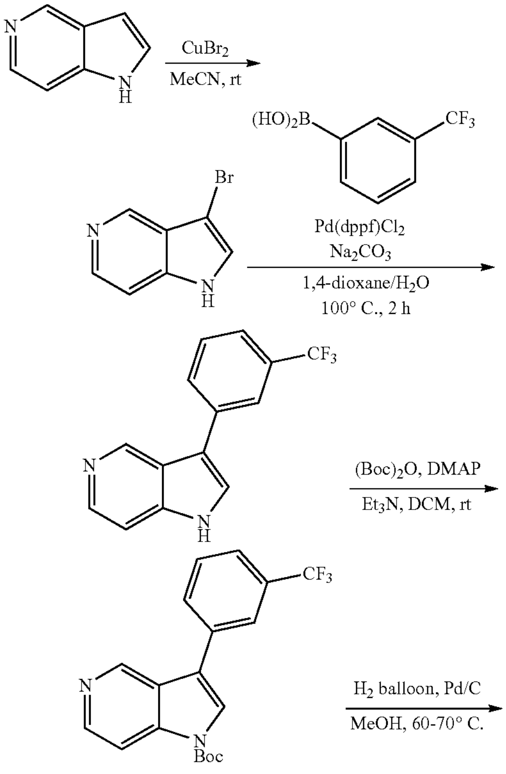

-continued

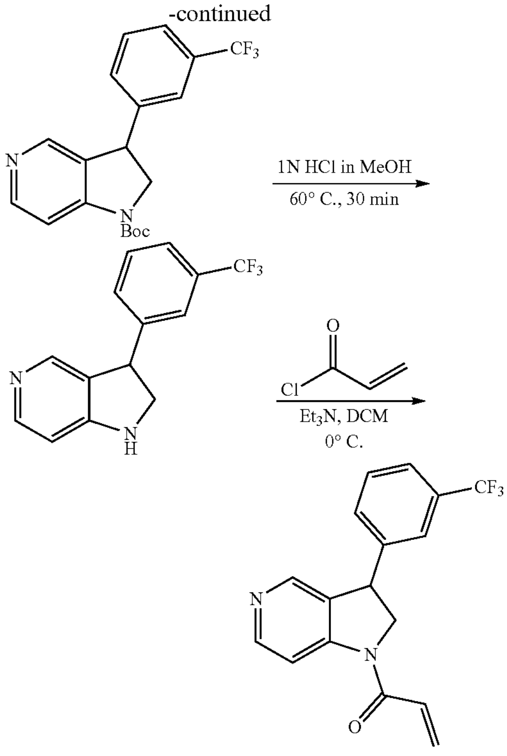

(I-64)

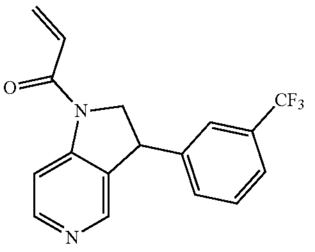

3-Bromo-1H-pyrrolo[3,2-c]pyridine 1H-pyrrolo[3,2-c]pyridine (428 mg, 3.6 mmol) was dissolved in 7 mL of MeCN and $CuBr_2$ (2.428 g, 10.9 mmol) was added in portions under stirring. The resultant mixture was stirred vigorously at room temperature for 2 h and LC-MS indicated the formation of desired product. 7M $NH_3$ in MeOH (5 mL) was added to quench the reaction and the mixture was transferred into separating funnel, to which EA and water were added. The organic phase was separated and dried over anhydrous $Na_2SO_4$ overnight. After $Na_2SO_4$ was filtrated and the organic phase was concentrated to afford off-white solid (696 mg, 3.5 mmol), which was used directly in the next step. LC/MS (ESI) m/z=197, 199 $(M+H)^+$.

3-(3-(Trifluoromethyl)phenyl)-1H-pyrrolo[3,2-c] pyridine

3-Bromo-1H-pyrrolo[3,2-c]pyridine (350 mg, 1.8 mmol), (3-(trifluoromethyl)phenyl)boronic acid (380 mg, 2.0 mmol), Pd(dppf)$Cl_2$ (132 mg, 0.18 mmol) and $Na_2CO_3$ (477 mg, 4.5 mmol) were placed in a 15 mL sealed tube and then 1,4-dioxane (4 mL) and water (1 mL) were added. The mixture was stirred and heated in 100° C. oil bath for 12 h. LC-MS indicated the formation of desired product but the bromide was not consumed completely. The mixture was diluted with EA and filtrated through Celite. After concentration, the resultant residue was purified via silica gel flash chromatography (9% MeOH in DCM) to afford desired product as pale brown solid (203 mg, 0.77 mmol). LC/MS (ESI) m/z=263 $(M+H)^+$.

Tert-butyl 3-(3-(trifluoromethyl)phenyl)-1H-pyrrolo [3,2-c]pyridine-1-carboxylate 3-(3-(Trifluoromethyl)phenyl)-1H-pyrrolo[3,2-c]pyridine (203 mg, 0.77 mmol) and DMAP (61 mg, 0.5 mmol) were dissolved i° DCM (8 mL) and then $Et_3N$ (0.28 mL, 2.0 mmol) and $(Boc)_2O$ (437 mg, 2.0 mmol) were added in sequence. The resultant mixture was stirred at room temperature for 3 h. After concentration the residue was purified via silica gel flash chromatography (48% EA in hexane) to afford desired product as colorless gum (188 mg, 0.52 mmol). LC/MS (ESI) m/z=363 $(M+H)^+$.

tert-butyl 3-(3-(trifluoromethyl)phenyl)-2,3-dihydro-1H-pyrrolo[3,2-c]pyridine-1-carboxylate To a solution of tert-butyl 3-(3-(trifluoromethyl)phenyl)-1H-pyrrolo[3,2-c]pyridine-1-carboxylate (188 mg, 0.52 mmol) in MeOH was added 10% Pd/C (100 mg) and a balloon of hydrogen was equipped. The suspension was stirred in 60-70° C. oil bath for 3 days. LC-MS indicated the formation of desired product. The mixture was filtrated through Celite and the filtrate was concentrated to afford residue, which was purified via silica gel flash chromatography (35% EA in hexane) to afford desired product as off white solid (29 mg, 0.08 mmol). LC/MS (ESI) m/z=365 $(M+H)^+$.

3-(3-(Trifluoromethyl)phenyl)-2,3-dihydro-1H-pyrrolo[3,2-c]pyridine

Tert-butyl 3-(3-(trifluoromethyl)phenyl)-2,3-dihydro-1H-pyrrolo[3,2-c]pyridine-1-carboxylate (29 mg, 0.08 mmol) was dissolved in 1M HCl in MeOH (8 mL) and the solution was heated in 60° C. oil bath for 30 min. After concentration the residue was basified by $Et_3N$ and purified via silica gel flash chromatography (15% DCM in MeOH) to afford desired product as light yellow gum (18 mg, 0.068 mmol). LC/MS (ESI) m/z=265 $(M+H)^+$.

1-(3-(3-(Trifluoromethyl)phenyl)-2,3-dihydro-1H-pyrrolo[3,2-c]pyridin-1-yl)prop-2-en-1-one To an ice-water bath cooled solution of 3-(3-(trifluoromethyl)phenyl)-2,3-dihydro-1H-pyrrolo[3,2-c]pyridine (18 mg, 0.068 mmol) and $Et_3N$ (20 μL, 0.136 mmol) in DCM was added 0.1 M solution of acryloyl chloride in DCM (0.68 mL, 0.068 mmol). The resultant solution was stirred for 2 h. After concentration the residue was purified via silica gel flash chromatography (80-90% EA in hexane) to afford desired product as light yellow gum (9 mg, 0.028 mmol). $^1H$ NMR (500 MHz, DMSO-d6) δ 8.43 (s, 1H), 8.15 (s, 1H), 8.05 (s, 1H), 7.77-7.54 (m, 5H), 6.77 (dd, J=16.7, 10.3 Hz, 1H), 6.46-6.32 (m, 1H), 5.89 (dd, J=10.2, 2.1 Hz, 1H), 4.99 (dd, J=10.3, 6.7 Hz, 1H), 4.73 (t, J=10.5 Hz, 1H), 4.24 (dd, J=10.7, 6.7 Hz, 1H).

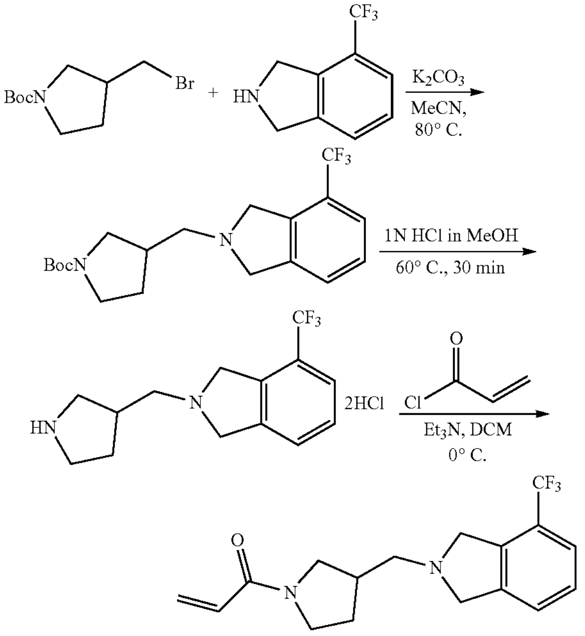

(I-66)

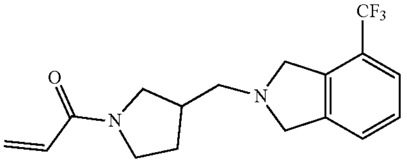

Tert-butyl 3-((4-(trifluoromethyl)isoindolin-2-yl) methyl)pyrrolidine-1-carboxylate Tert-butyl 3-(bromomethyl)pyrrolidine-1-carboxylate (158 mg, 0.6 mmol) and 4 -(trifluoromethyl)isoindoline (112 mg, 0.5 mmol) were dissolved in 2 mL of MeCN and $K_2CO_3$ (138 mg, 1.00 mmol) were added. The mixture was heated in 80° C. oil bath for 3 h. The mixture was filtered and the filtrate was concentrated. The resultant residue was purified via silica gel flash chromatography (25% EA in hexane) to afford desired product as colorless gum (112 mg, 0.3 mmol). LC/MS (ESI) m/z=371 $(M+H)^+$.

2-(Pyrrolidin-3-ylmethyl)-4-(trifluoromethyl)isoindoline dihydrochloride salt

Tert-butyl 3-((4-(trifluoromethyl)isoindolin-2-yl)methyl) pyrrolidine-1-carboxylate (112 mg, 0.3 mmol) was dissolved in 1M HCl/MeOH solution (8 mL) and heated in 60° C. oil bath for 30 min. The solution was concentrated to to afford desired product as colorless oil, which was directly used in the next step. LC/MS (ESI) m/z=271 $(M+H)^+$.

1-(3-((4-(Trifluoromethyl)isoindolin-2-yl)methyl) pyrrolidin-1-yl)prop-2-en-1-one The 2-(pyrrolidin-3-ylmethyl)-4-(trifluoromethyl)isoindoline dihydrochloride salt obtained in the last step was dissolved in DCM (2 mL) and $Et_3N$ (0.17 mL, 1.2 mmol). Then the solution was cooled in ice-water bath and 0.1 M solution of acryloyl chloride in DCM (3.6 mL, 0.36 mmol) was added. The resultant solution was stirred for 2 h. After concentration the residue was purified via silica gel flash chromatography (100% EA) to afford desired product as colorless oil (72 mg, 0.22 mmol). $^1H$ NMR (500 MHz, DMSO-d6) δ 7.63-7.49 (m, 2H), 7.44 (t, J=7.7 Hz, 1H), 6.58 (ddd, J=16.8, 10.3, 3.8 Hz, 1H), 6.11 (ddd, J=16.8, 7.0, 2.4 Hz, 1H), 5.64 (ddd, J=14.0, 10.3, 2.5 Hz, 1H), 4.12-3.86 (m, 4H), 3.77 (dd, J=10.2, 7.3 Hz, 0.5H), 3.71-3.63 (m, 0.5H), 3.60 (dd, J=12.2, 7.4 Hz, 0.5H), 3.56-3.48 (m, 1H), 3.37-3.24 (m, 1H), 3.10 (dd, J=12.2, 7.3 Hz, 0.5H), 2.78-2.65 (m, 2H), 2.57-2.34 (m, 1H), 2.13-1.94 (m, 1H), 1.78-1.51 (m, 1H).

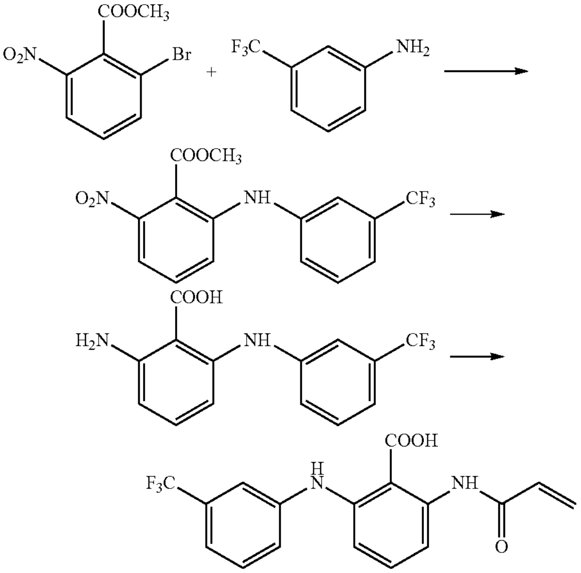

(I-4)

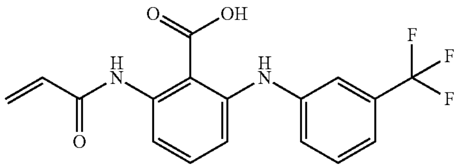

methyl 2-nitro-6-((3-(trifluoromethyl)phenyl)amino) benzoate

To a solution of methyl 2-bromo-6-nitrobenzoate (420 mg, 1.62 mmol) and 3-(trifluoromethyl)aniline (312 mg, 1.94 mmol) in 5 mL of dioxane was added $Pd_2dba_3$ (30 mg, 0.016 mmol), XPhos (47 mg, 0.049 mmol) and $Cs_2CO_3$ (1.06 g, 3.24 mmol) under $N_2$. The mixture was stirred at 100° C. overnight. The mixture was filtered. The filtrate was concentrated in vacuo, then purified by flash chromatography on silica gel (hexane:ethyl acetate=4:1) to provide the product (222 mg, 40%). LC/MS (ESI) m/z=341 $(M+H)^+$.

2-amino-6-((3-(trifluoromethyl)phenyl)amino)benzoic acid

To a solution of methyl 2-nitro-6-((3-(trifluoromethyl) phenyl)amino)benzoate (181 mg, 0.53 mmol) in i-PrOH/ water (6 mL/2 mL) was added iron powder (300 mg, 5.31 mmol) and $NH_4Cl$ (141 mg, 2.66 mmol). The reaction mixture was stirred at 60° C. fo 2 h, and then filtered. The filtrate was concentrated in vacuo. The residue was purified with prep-HPLC to give the product (101 mg, 64%). LC/MS (ESI) m/z=297 $(M+H)^+$.

2-acrylamido-6-((3-(trifluoromethyl)phenyl)amino) benzoic acid

To a solution of 2-amino-6-((3-(trifluoromethyl)phenyl) amino)benzoic acid (30 mg, 0.1 mmol) and DIEA (40 mg, 0.3 mmol) in 2 mL of acetonitrile was added acryloyl chloride dropwise at 0° C. until the reaction completed. The mixture was purified by prep-HPLC to provide the product (13.1 mg, 37%). LC/MS (ESI) m/z=351 $(M+H)^+$.

(I-3)

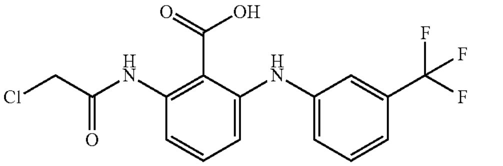

2-(2-chloroacetamido)-6-((3-(trifluoromethyl)phenyl)amino)benzoic acid

I-3 is prepared by using the similar procedure as for I-4. 2-chloroacetyl chloride was used in the last step. LC/MS (ESI) m/z=373 $(M+H)^+$.

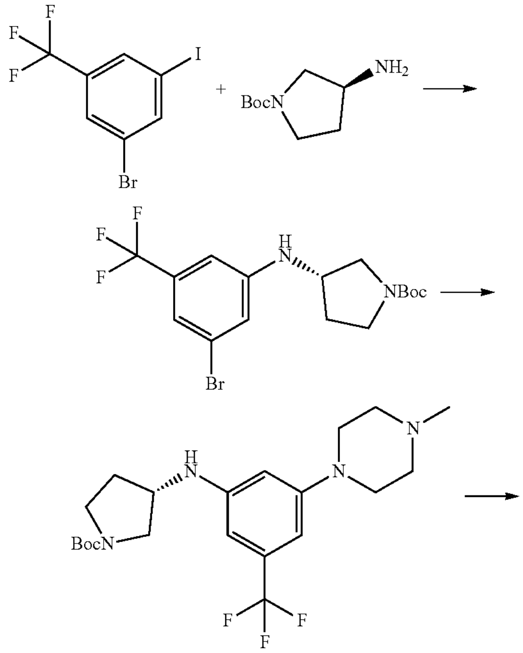

-continued

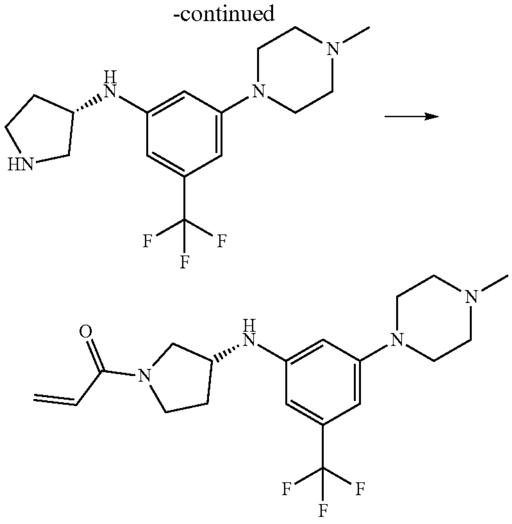

(I-59)

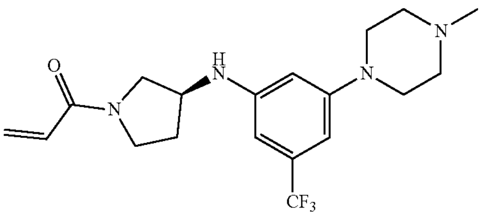

tert-butyl (S)-3-((3-bromo-5-(trifluoromethyl)phenyl)amino)pyrrolidine-1-carboxylate To a solution of 1-bromo-3-iodo-5-(trifluoromethyl)benzene (351 mg, 1 mmol) and tert-butyl (S)-3-aminopyrrolidine-1-carboxylate (186 mg, 1 mmol) in 5 mL of dioxane was added $Pd_2dba_3$ (10 mg, 0.01 mmol), XPhos (15 mg, 0.03 mmol) and $Cs_2CO_3$ (652 mg, 2 mmol) under $N_2$. The mixture was stirred at 100° C. overnight. The mixture was filtered. The filtrate was concentrated in vacuo, then purified by flash chromatography on silica gel (hexane:ethyl acetate=4:1) to provide the product (300 mg, 73%). LC/MS (ESI) m/z=409 (M+H)+.

tert-butyl (S)-3-((3-(4-methylpiperazin-1-yl)-5-(trifluoromethyl)phenyl)amino)pyrrolidine-1-carboxylate To a solution of tert-butyl (S)-3-((3-bromo-5-(trifluoromethyl)phenyl)amino)pyrrolidine-1-carboxylate (67 mg, 0.16 mmol) and 1-methylpiperazine (20 mg, 0.2 mmol) in 2 mL of dioxane was added $Pd_2dba_3$ (2 mg, 0.002 mmol), XPhos (3 mg, 0.005 mmol) and $Cs_2CO_3$ (107 mg, 0.32 mmol) under $N_2$. The mixture was stirred at 100° C. overnight. The mixture was filtered. The filtrate was concentrated in vacuo, then purified by flash chromatography on silica gel (dichloromethane:methanol=0~10%) to provide the product (56 mg, 82%). LC/MS (ESI) m/z=429 $(M+H)^+$.

(S)—N-(3-(4-methylpiperazin-1-yl)-5-(trifluoromethyl)phenyl)pyrrolidin-3-amine

To a solution of tert-butyl (S)-3-((3-(4-methylpiperazin-1-yl)-5-(trifluoromethyl)phenyl)amino)pyrrolidine-1-carboxylate (56 mg, 0.13 mmol) in 3 mL of dichloromethane was added TFA (1 mL). The result solution was stirred at room temperature for 1 h, and then concentrated in vacuo to obtain the product as TFA salt, which was used into next step without any purification. LC/MS (ESI) m/z=329 $(M+H)^+$.

(S)-1-(3-((3-(4-methylpiperazin-1-yl)-5-(trifluoromethyl)phenyl)amino)pyrrolidin-1-yl)prop-2-en-1-one To a solution of (S)—N-(3-(4-methylpiperazin-1-yl)-5-(trifluoromethyl)phenyl)pyrrolidin-3-amine (crude from last step) and DIEA (82 mg, 0.65 mmol) in 2 mL of acetonitrile was added acryloyl chloride dropwise at 0° C. until the reaction completed. Then the mixture was diluted with dichloromethane, washed with 1 N $NaHCO_3$ solution and brine. The organic layer was dried over sodium sulfate, concentrated in vacuo and then purified by prep-HPLC ($MeOH/H_2O$, 0-100%) to provide I-59 (20 mg, 31% for two steps) as TFA salt. LC/MS (ESI) m/z=383 $(M+H)^+$.

(I-60)

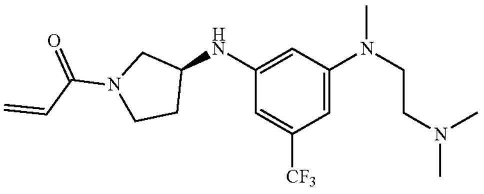

(S)-1-(3-((3-((2-(dimethylamino)ethyl)(methyl)amino)-5-(trifluoromethyl)phenyl)amino)pyrrolidin-1-yl)prop-2-en-1-one I-60 is prepared by using the similar procedure as for I-59. $N^1,N^1,N^2$-trimethylethane-1,2-diamine was used in the second step. LC/MS (ESI) m/z=385 $(M+H)^+$.

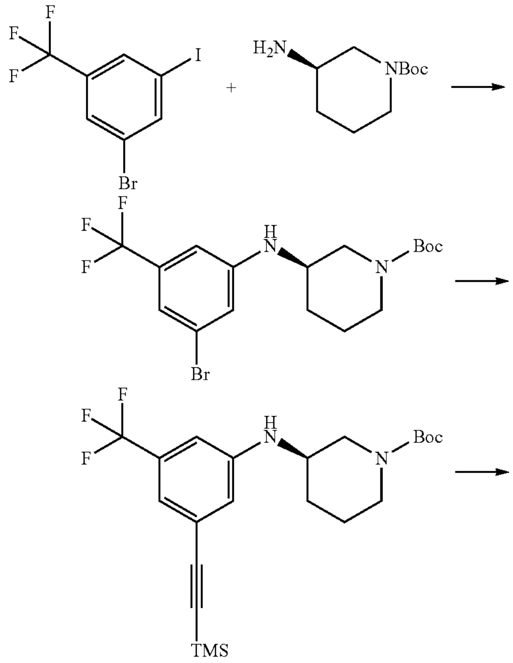

-continued

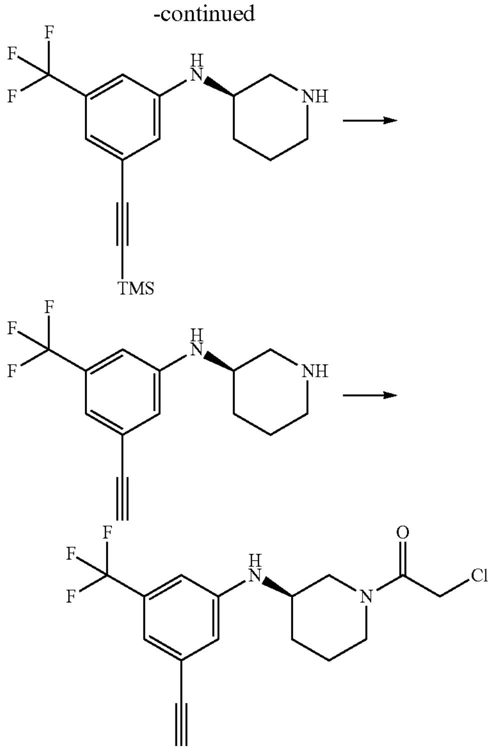

(I-18)

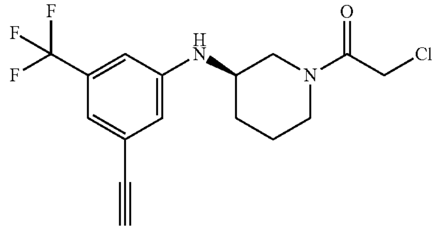

tert-butyl (R)-3-((3-bromo-5-(trifluoromethyl)phenyl)amino)piperidine-1-carboxylate To a solution of 1-bromo-3-iodo-5-Iifluoromethyl)benzene (351 mg, 1 mmol) and tert-butyl (R)-3-aminopiperidine-1-carboxylate (200 mg, 1 mmol) in 5 mL of dioxane was added $Pd_2dba_3$ (10 mg, 0.01 mmol), XPhos (15 mg, 0.03 mmol) and $Cs_2CO_3$ (652 mg, 2 mmol) under $N_2$. The mixture was stirred at 100° C. overnight. The mixture was filtered. The filtrate was concentrated in vacuo, then purified by flash chromatography on silica gel (hexane:ethyl acetate=4:1) to provide the product (300 mg, 71%). LC/MS (ESI) m/z=423 (M+H)+.

tert-butyl (R)-3-((3-(trifluoromethyl)-5-((trimethylsilyl)ethynyl)phenylIino)piperidine-1-carboxylate To a solution of tert-butyl (R)-3-((3-bromo-5-(trifluoromethyl)phenyl)amino)piperidine-1-carboxylate (260 mg, 0.63 mmol) and ethynyltrimethylsilane (245 mg, 2.5 mmol) in 5 mL of DMF was added $Pd(PPh_3)Cl_2$ (22 mg, 0.032 mmol), CuI (12 mg, 0.064 mmol) and triethylamine (250 mg, 2.5 mmol) under $N_2$. The mixture was stirred at 60° C. overnight. The mixture was filtered. The filtrate was concentrated in vacuo, then purified by flash chromatography on silica gel (hexane:ethyl acetate=4:1) to provide the product (260 mg, 93%). LC/MS (ESI) m/z=441 (M+H)+.

(R)—N-(3-(trifluoromethyl)-5-((trimetIsilyl)ethynyl) phenyl)piperidin-3-amine

A mixture of tert-butyl (R)-3-((3-(trifluoromethyl)-5-((trimethylsilyl)ethynyl)phenyl)amino)piperidine-1-carboxylate (44 mg, 0.1 mmol) in 3 mL of 4N HCl/dioxane solution was stirred at room temperature for 1 h, and then concentrated in vacuo to obtain the product as HCl salt, which was used into It step without any purification. LC/MS (ESI) m/z=341 $(M+H)^+$.

(R)—N-(3-ethynyl-5-(trifluoromethyl)phenyl)piperidin-3-amine

To a solution of (R)—N-(3-(trifluoromethyl)-5-((trimethylsilyl)ethynyl)phenyl)piperidin-3-amine (crude from last step) in 3 mL of MeOH was added $K_2CO_3$ (138 mg, 1 mmol). The reaction mixture was stirred at room temperature for 1 h, and then concentrated in vacuo. The residue was re-dissolved in DMSO and filtered. The filtrate was purified by prep-HPLC ($MeOH/H_2O$, 0-100%) to provide the product (3Ig, 91% for two steps) as TFA salt. LC/MS (ESI) m/z=269 $(M+H)^+$.

(R)-2-chloro-1-(3-((3-ethynyl-5Irifluoromethyl)phenyl)amino)piperidin-1-yl)ethan-1-one To a solution of (R)—N-(3-ethynyl-5-(trifluoromethyl) phenyl)piperidin-3-amine (35 mg, 0.09 mmol) and DIEA (60 mg, 0.46 mmol) in 2 mL of acetonitrile was added 2-chloroacetyl chloride dropwise at 0° C. until the reaction completed. Then the mixture was diluted with dichloromethane, washed with 1 N $NaHCO_3$ solution and brine. The organic layer was then dried over sodium sulfate, concentrated in vacuo and then purified by prep-HPLC ($MeOH/H_2O$, 0-100%) to provide I-18 (23 mg, 56%) as TFA salt. LC/MS (ESI) m/z=345 $(M+H)^+$.

Int-1

Aryl aldehyde (20 mmol, 1.0 eq) and nitromethane (32 mmol, 1.6 eq) were dissolved in tBuOH/THF (15 mL/15 mL) at rt. Then tBuOK (2 mmol, 0.1 eq) was added and the resulting mixture was stirred for 2 h. Next, it was poured into water and extracted 3× with ethyl acetate. The combined organic phase was then dried over anhydrous $Na_2SO_4$ and concentrated to afford crude b-hydroxyl nitroalkane, which was directly dissolved in DCM. DMAP (1 mmol, 0.05 eq) was then added, and the mixture was stirred and cooled in ice-water bath. $Ac_2O$ (22 mmol, 1.1 eq) was added dropwise before ice-water bath was removed. The mixture was stirred for additional 2 h and LC-MS indicated formation of desired nitroalkene. The mixture was poured into saturated $NaHCO_3$ and extracted 3× with DCM. The combined organic phase was dried over anhydrous $Na_2SO_4$ and concentrated to afford crude product and purified via silica gel flash chromatography.

Int-2

The nitroalkene (2 mmol, 1.0 eq) and N-(Methoxymethyl)-N-(trimethylsilylmethyl)benzylamine (2.4 mmol, 1.2 eq) were dissolved in DCM and cooled in ice-water bath, and TFA (0.24 mmol, 0.12 eq) was added dropwise. The mixture was then stirred overnight. After this time, LC-MS indicated nitroalkene was consumed completely, and the mixture was purified via silica gel flash chromatography to afford desired product.

Int-3

The Int-2 (1 mmol, 1.0 eq) was dissolved in MeOH (3 mL) and saturated $NH_4Cl$ (0.5 mL) was added. Then Zn dust (10 mmol, 10 eq) was added and the mixture was stirred at rt for 2 h. After this time, LC-MS indicated formation of amine and Int-2 was completely consumed. Then the mixture was filtered and concentrated to afford crude product, which was purified via preparative HPLC.

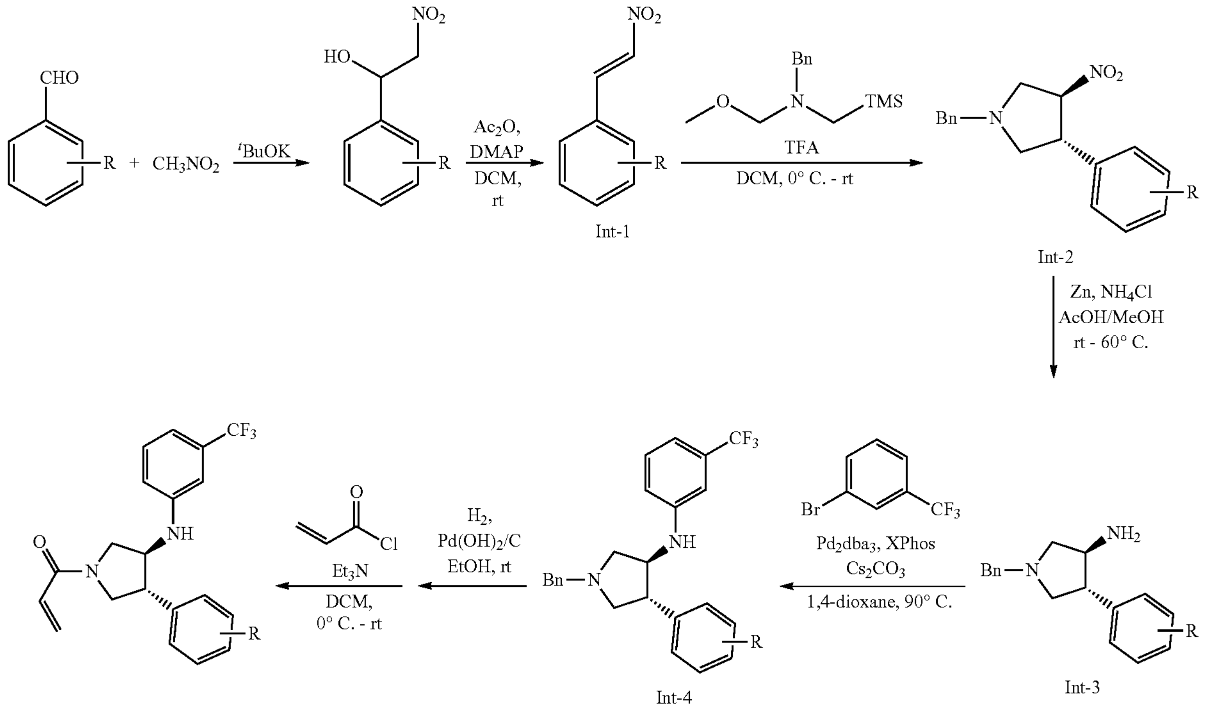

Int-4

The amine Int-3 (0.4 mmol, 1.0 eq), 3-bromotrifluoride-benzene (0.4 mmol, 1.0 eq) and $Pd_2dba_3$ (0.02 mmol, 0.05 eq), XPhos (0.04 mmol, 0.1 eq), $Cs_2CO_3$ (1.2 mmol, 3.0 eq) were placed in 10 mL vial and dioxane (3 mL) was added. The mixture was then stirred under nitrogen in 90° C. oil bath for 5 h. LC-MS indicated formation of desired product Int-4. The mixture was cooled to rt and purified via silica gel flash chromatography.

Final Product (I-109, I-110, I-74)

The Int-4 was hydrogenated in EtOH under catalysis of $Pd(OH)_2/C$ overnight. The amine product was acylated by acryl chloride in DCM with TEA. The final product was purified via preparative HPLC.

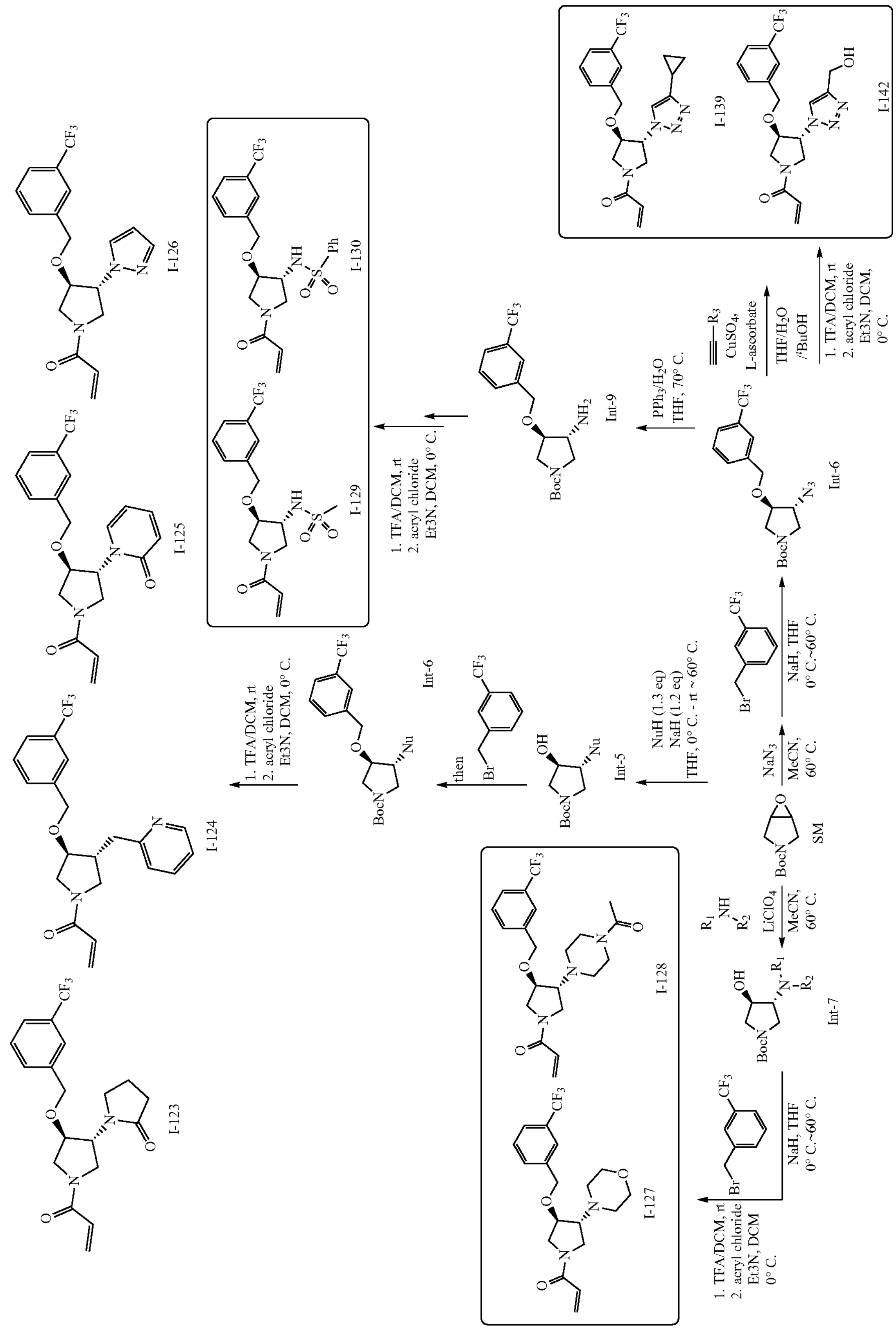
I-123
I-124
I-125
I-126
1. TFA/DCM, rt
2. acryl chloride
Et3N, DCM, 0° C.
Int-6
then
I-129
I-130
1. TFA/DCM, rt
2. acryl chloride
Et3N, DCM, 0° C.
Int-5
NuH (1.3 eq)
NaH (1.2 eq)
THF, 0° C. - rt ~ 60° C.
Int-9
PPh3/H2O
THF, 70° C.
NaN3
MeCN,
60° C.
NaH, THF
0° C.~60° C.
Int-6
SM
LiClO4
MeCN,
60° C.
Int-7
CuSO4,
L-ascorbate
THF/H2O
/tBuOH
1. TFA/DCM, rt
2. acryl chloride
Et3N, DCM,
0° C.
I-139
I-142
NaH, THF
0° C.~60° C.
1. TFA/DCM, rt
2. acryl chloride
Et3N, DCM
0° C.
I-127
I-128

Int-6

The nucleophile was deprotonated with NaH in THF under ice-water bath and then epoxide SM was added. The reaction was warmed to 60° C. and then trifluorobenzyl bromide was added. The mixture was stirred at 60° C. until Int-5 was completely consumed. The reaction was purified via silica gel flash chromatography to afford Int-6.

Final Product (I-123, I-124, I-125, I-126)

The Boc group of Int-6 was removed by stirring the compound with TFA in DCM at rt and then acylated with acryl chloride with TEA in DCM to give the final product, which was purified via preparative HPLC.

Int-7

Secondary amine and SM were mixed in MeCN and LiClO4 was added. The reaction was heated until Int-7 formed and SM was completely consumed. Then Int-7 was purified via silica gel flash chromatography.

Final Product (I-127, I-128)

The Int-7 was alkylated with benzyl bromide and deBoc and then acylated to afford final product, which was purified via preparative HPLC.

Int-8

Sodium azide and SM were mixed in MeCN and heated to 60° C. overnight to afford Int-8, which was purified via silica gel flash chromatography.

Int-9

The Int-8 was reduced by PPh3 in THF/water at 60° C. to afford amine Int-9, which was purified via preparative HPLC.

Final Product (I-129, I-130)

The Int-9 was acylated with sulfonyl chloride to afford sulfonamide. Then it was deBoc and acylated with acryl chloride in DCM to afford final product.

Final Product (I-139, I-142)

The Int-8 and alkynyl were mixed in THF/tBuOH/$H_2O$ and $CuSO_4$ and L-ascorbate were added. The cycloaddition reaction proceeded well and 1,2,3-triazole product was isolated via silica gel flash chromatography. Then 1,2,3-triazole was deBoc and acylated with acryl chloride in DCM to afford final product.

I-173, I-174, I-175, I-177 were made also follow the similar route as above.

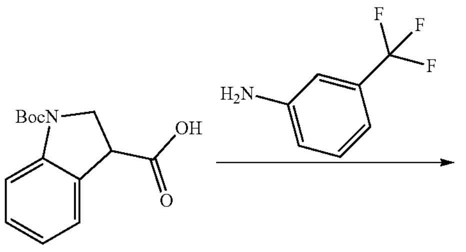

SM-1

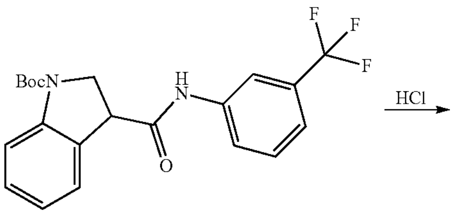

Int-1

-continued

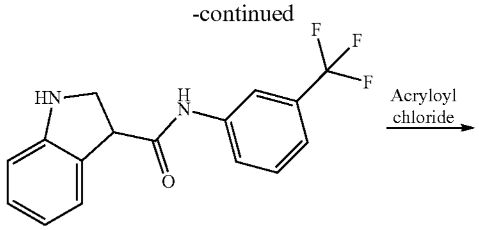

Int-2

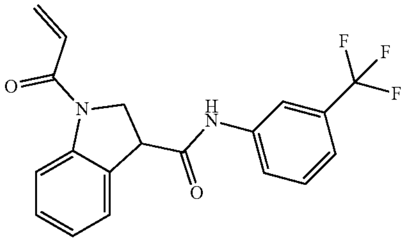

I-80

SM-1 was coupled with 3-(trifluoromethyl)aniline with HATU to provide int-1 which was deprotected with HCl. The Int-2 was converted to final product I-80 through a reaction with Acryloyl chloride.

Other analogs such as I-93, I-94 and I-95, I-131 and I-132 were made with a similar synthesis route.

Mass spectrometry data for selected compounds can be found in Table 3.

TABLE 3

Mass Spectrometry Data for Selected Compounds of the Disclosure

| Compound | LCMS [M + 1] | Compound | LCMS [M + 1] | Compound | LCMS [M + 1] |
|---|---|---|---|---|---|
| I-139 | 407 | I-128 | 426 | I-83 | 405 |
| I-141 | 329 | I-129 | 393 | I-84 | 405 |
| I-120 | 358 | I-130 | 455 | I-85 | 391 |
| I-121 | 344 | I-131 | 375 | I-86 | 375 |
| I-122 | 358 | I-132 | 405 | I-87 | 375 |
| I-123 | 383 | I-114 | 314 | I-88 | 429 |
| I-124 | 391 | I-115 | 314 | I-89 | 331 |
| I-125 | 393 | I-116 | 358 | I-90 | 367 |
| I-126 | 366 | I-117 | 344 | I-91 | 311 |
| I-108 | 528 | I-188 | 344 | I-92 | 325 |
| I-110 | 439 | I-119 | 344 | I-80 | 361 |
| I-98 | 300 | I-142 | 397 | I-81 | 405 |
| I-99 | 338 | I-93 | 377 | I-142 | 397 |
| I-100 | 300 | I-94 | 393 | I-173 | 439 |
| I-101 | 329 | I-104 | 329 | I-174 | 439 |
| I-102 | 315 | I-95 | 375 | I-175 | 444 |
| I-103 | 285 | I-97 | 356 | I-177 | 444 |
| I-127 | 385 | I-82 | 315 | | |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of any one of the formulae:

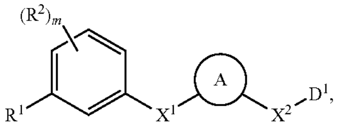

-continued

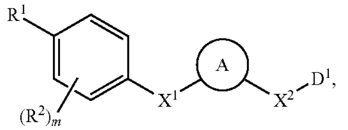

and

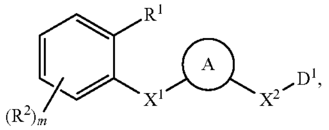

or a pharmaceutically acceptable salt, solvate, hydrate, polymorph, co-crystal, tautomer, stereoisomer, or isotopically labeled derivative thereof, wherein:

$R^1$ is —$CF_3$, halogen, optionally substituted heterocyclyl, —$OR^f$, —$N(R^f)_2$, or —$SR^f$, each occurrence of $R^f$ s independently hydrogen, optionally substituted alkyl, alkynyl, aryl;

$R^2$ is hydrogen, halogen, optionally substituted acyl, optionally substituted alkyl, haloalkyl, methyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, —$OR^c$, —$NO_2$, —$N(R^c)_2$, or —$SR^c$, wherein $R^c$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined together with $X^1$ to form an optionally substituted heterocyclic ring;

m is 0, 1, 2, 3 or 4;

A is an optionally substituted heterocyclic ring, such that: i) Ring A is an optionally substituted heterocyclic ring wherein each heteroatom is selected from nitrogen and sulfur when $X^1$ is a bond, and ii) Ring A is not indolinyl when $X^1$ is —O—, —$C(R^d)_2O$— or —$OC(R^d)_2$—;

$X^1$ is a bond, —O—, $C_{1-6}$ alkyl, —$N(R^d)$—, —$C(R^d)_2N(R^d)$—, —C(=O)$N(R^d)$—, —$N(R^d)C$(=O)—, —$C(R^d)_2O$—, or —$OC(R^d)_2$—, wherein $R^d$ is independently hydrogen or $C_{1-6}$ alkyl;

$X^2$ is a bond;

$D^1$ is:

(i-1)

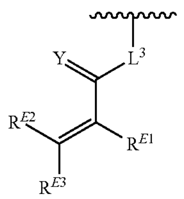

or

-continued (i-14)

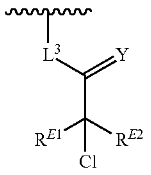

wherein:

$L^3$ is a bond or an optionally substituted $C_{1-4}$ hydrocarbon chain, optionally wherein one or more carbon units of the hydrocarbon chain are independently replaced with $—NR^{L3a}—$, wherein $R^{L3a}$ is hydrogen;

$R^{E1}$ is hydrogen;

$R^{E2}$ is selected from the group consisting of hydrogen and $—CH_2N(R^{E2a})_2$, wherein each occurrence of $R^{E2a}$ is independently alkyl; and $R^{E3}$ is hydrogen;

Y is —O—.

2. The compound of claim 1, wherein the formula is

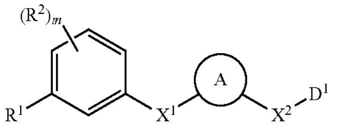

or

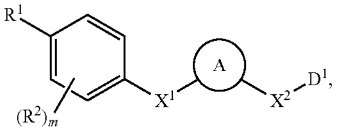

or a pharmaceutically acceptable salt, solvate, hydrate, polymorph, co-crystal, tautomer, stereoisomer, or isotopically labeled derivative thereof.

3. The compound of claim 2, wherein the compound is any one of the formulae:

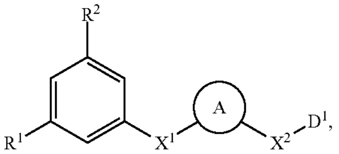

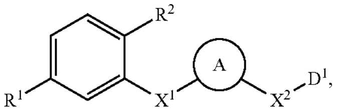

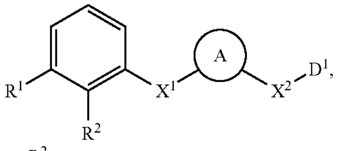

or

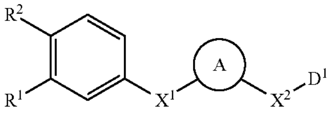

or a pharmaceutically acceptable salt, solvate, hydrate, polymorph, co-crystal, tautomer, stereoisomer, or isotopically labeled derivative thereof.

4. The compound of claim 1, wherein $R^1$ is $—CF_3$.

5. The compound of claim 1, wherein the compound is of the formula:

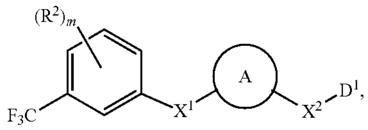

or a pharmaceutically acceptable salt, solvate, hydrate, polymorph, co-crystal, tautomer, stereoisomer, or isotopically labeled derivative thereof.

6. The compound of claim 1, or a pharmaceutically acceptable salt, solvate, hydrate, polymorph, co-crystal, tautomer, stereoisomer, or isotopically labeled derivative thereof, wherein A is of any one of the formulae:

(II-a)

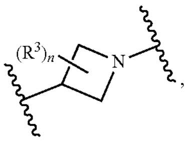

(II-b)

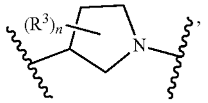

(II-c)

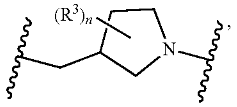

(II-d)

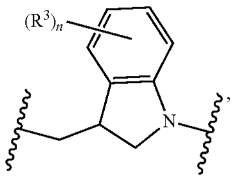

(II-e)

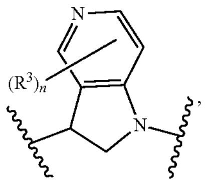

(II-g)

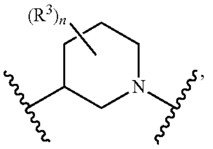

(II-h)

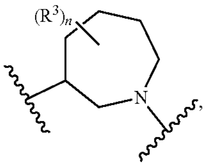

-continued (II-i)

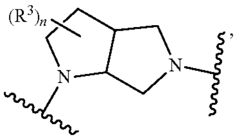

(II-j)

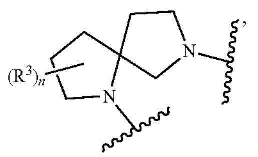

wherein:

$R^3$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —C(=O)OR$^e$, —C(=O)N(R$^e$)$_2$, —OR$^e$, —N(R$^e$)$_2$, —SR$^e$, or —N(R$^e$)SO$_2$R$^e$ wherein R$^e$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, two instances of $R^3$ can be joined together to form an optionally substituted carbocyclic or heterocyclic fused ring; and n is 0, 1, 2, 3, 4, 5, 6, 7, or 8 as valency permits.

7. The compound of claim 1, wherein the compound is of any one of the formulae:

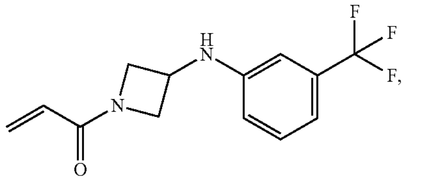

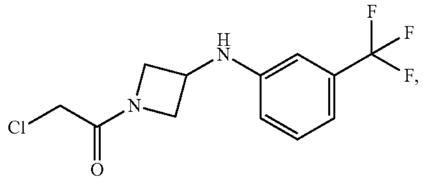

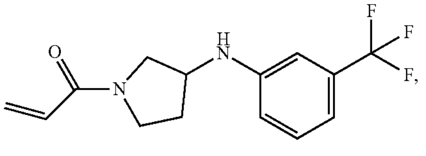

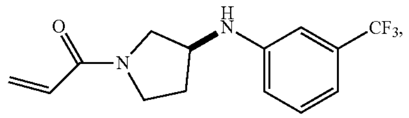

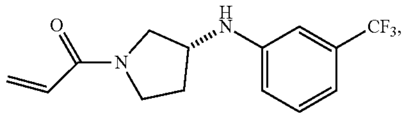

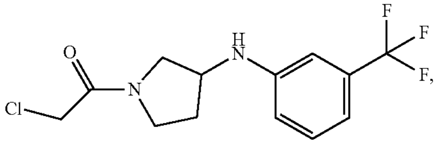

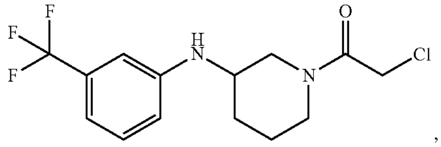

,

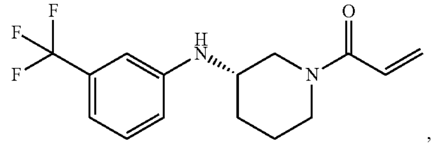

,

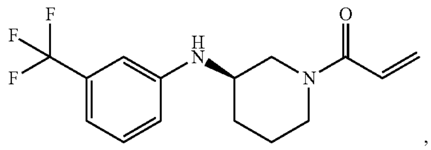

,

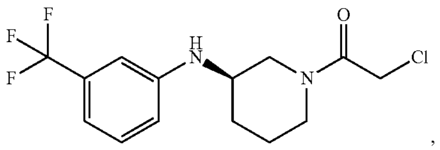

,

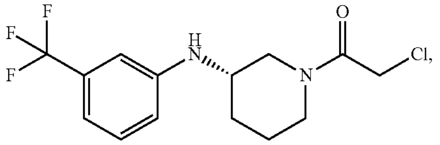

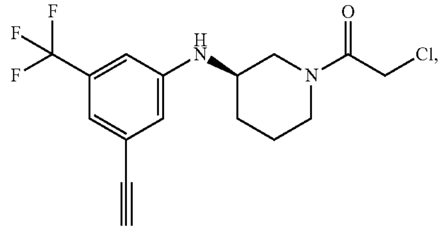

-continued
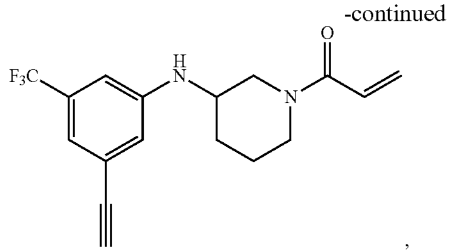
,
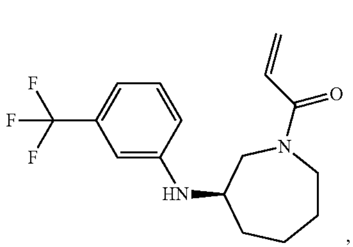
,
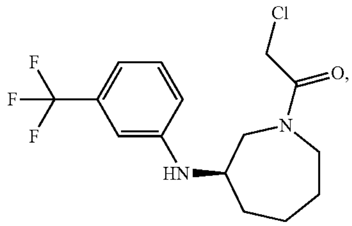
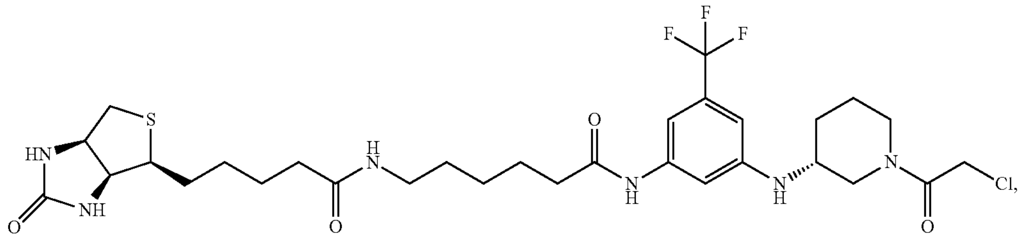
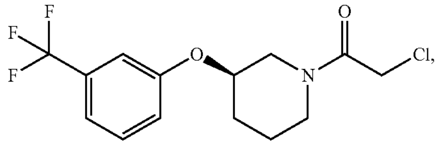
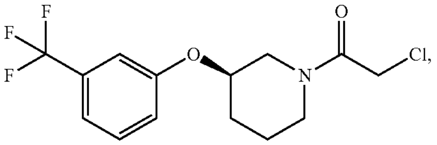
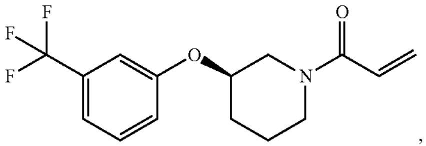
,
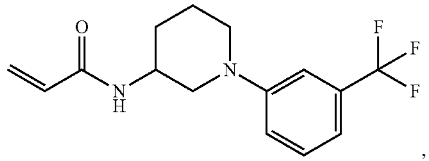
,
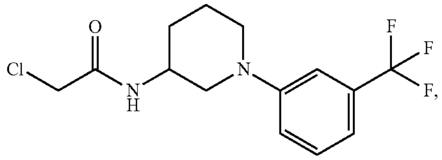
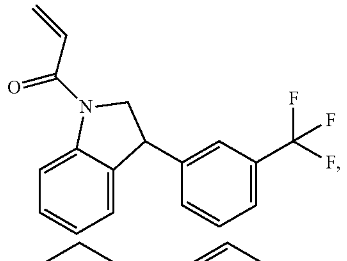
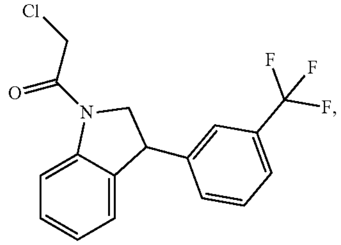
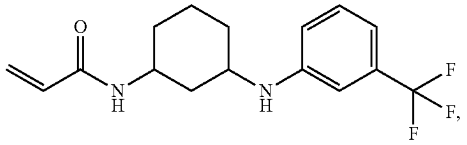
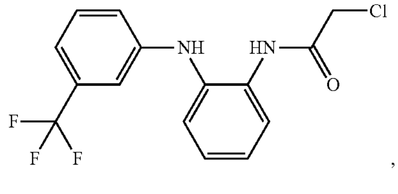
,
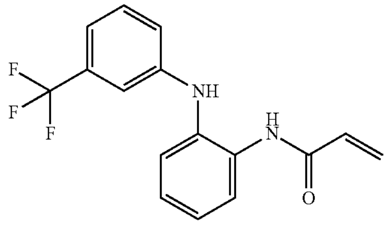
, -continued
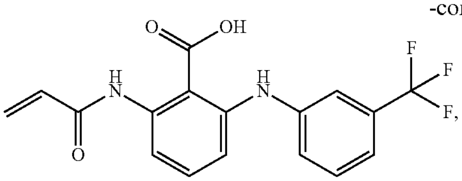
,
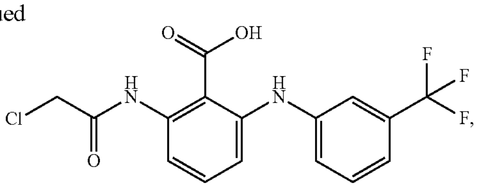
,
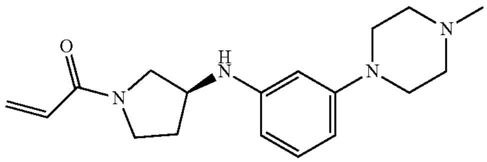
,
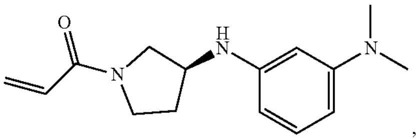
,
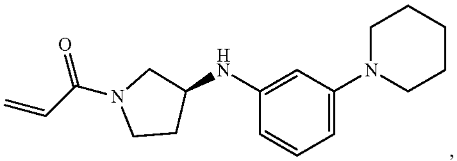
,
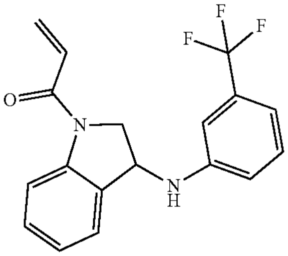
,
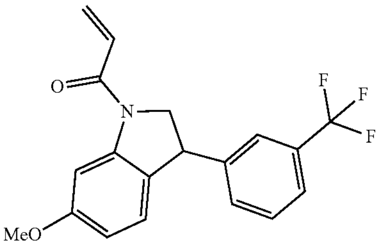
,
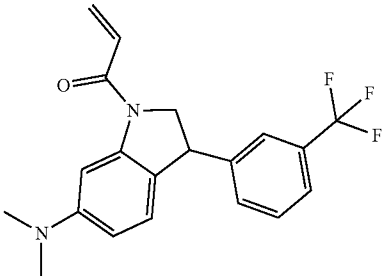
,
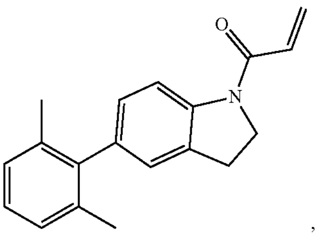
,
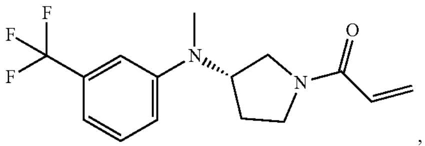
,
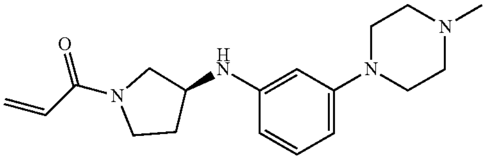
,
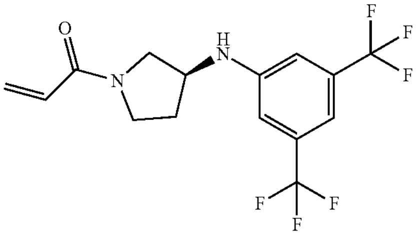
,
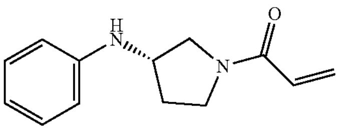
,
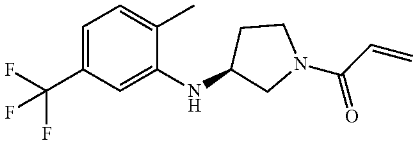
,
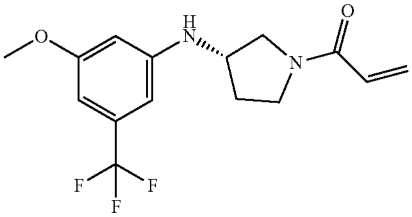
,
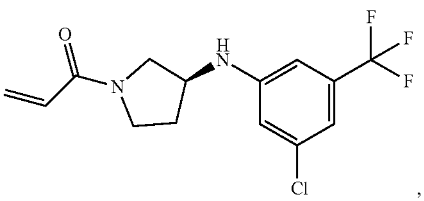
, -continued
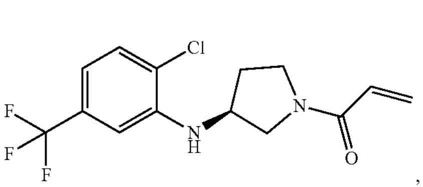,
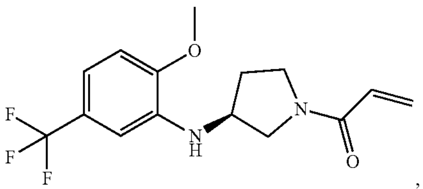,
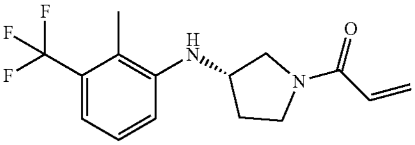,
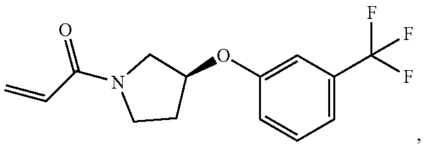,
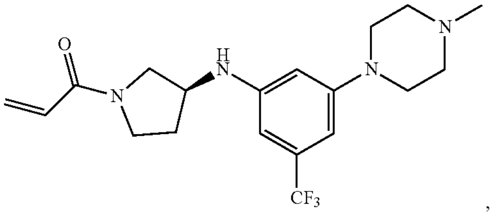,
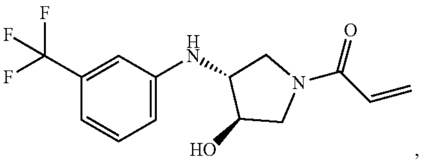,
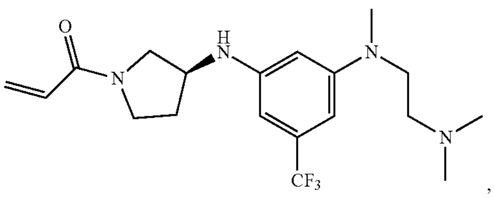,
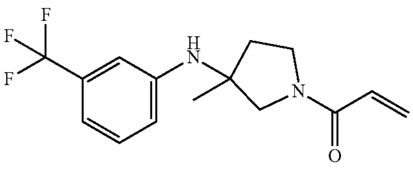,
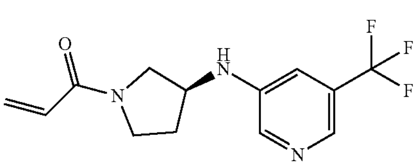,
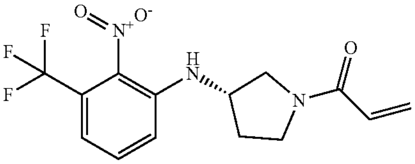,
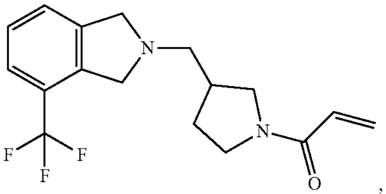,
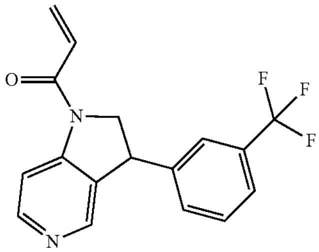,
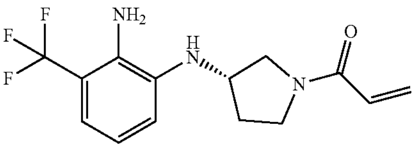,
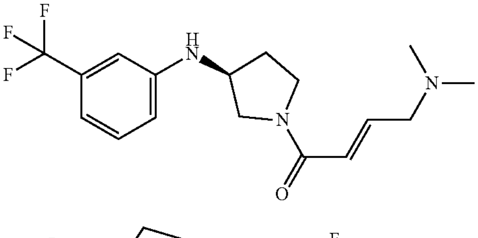,
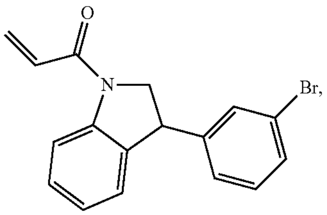,
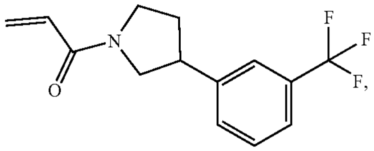, -continued
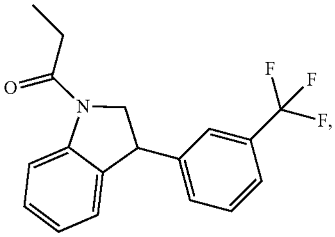,
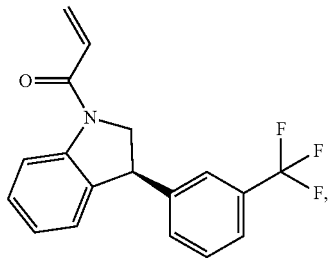,
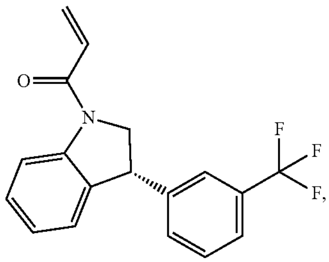,
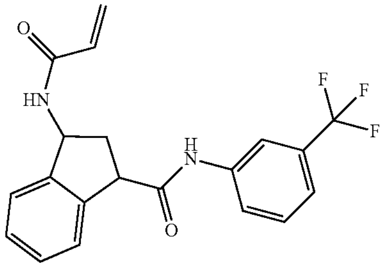,
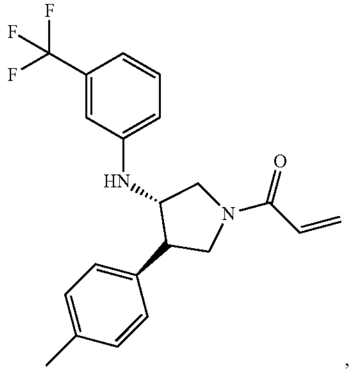,
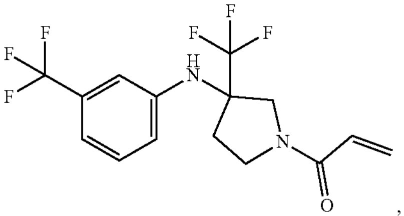,
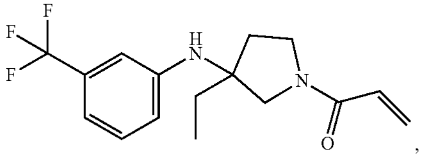,
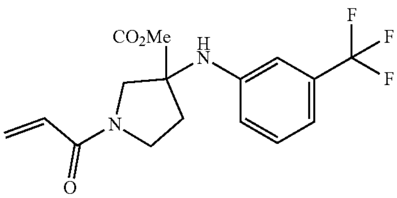,
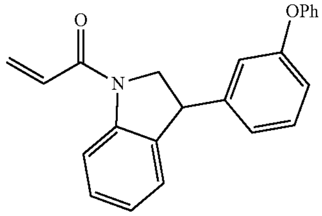,
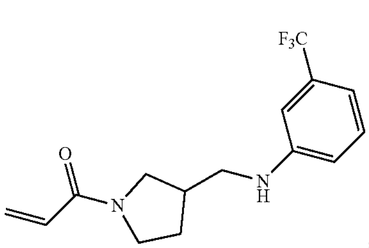,
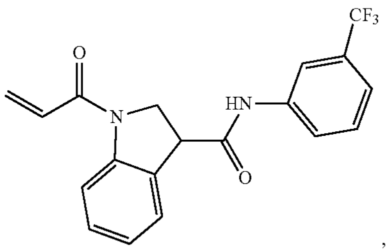,
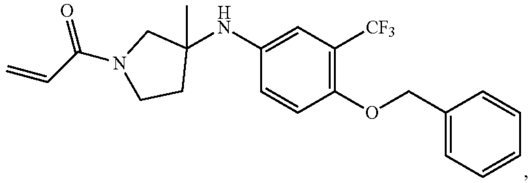,
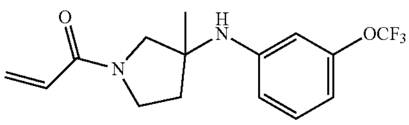, -continued
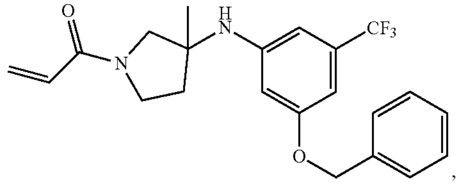
,
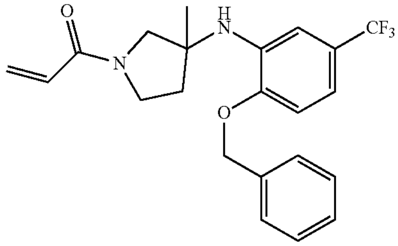
,
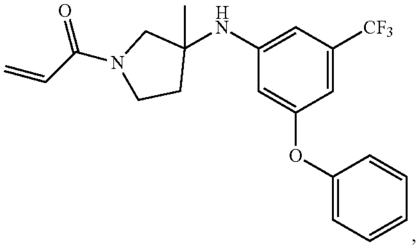
,
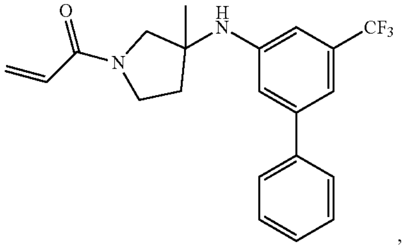
,
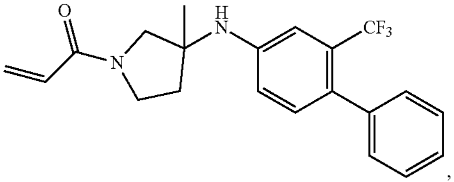
,
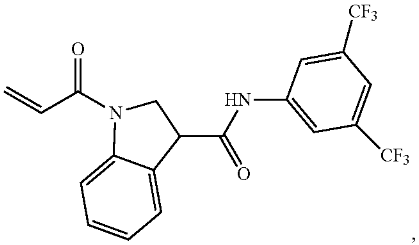
,
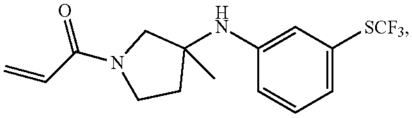
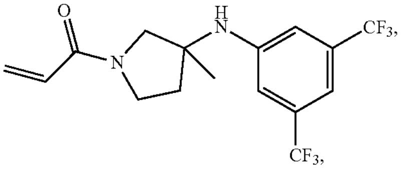
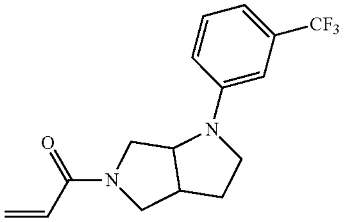
,
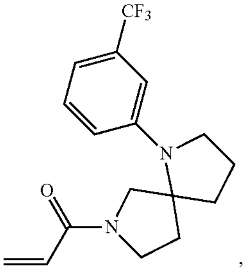
,
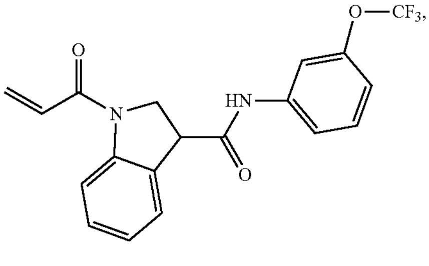
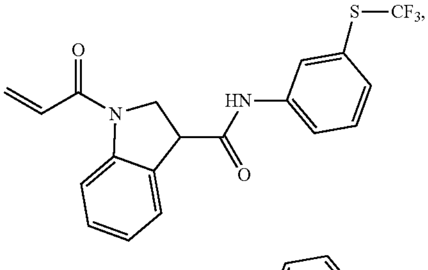
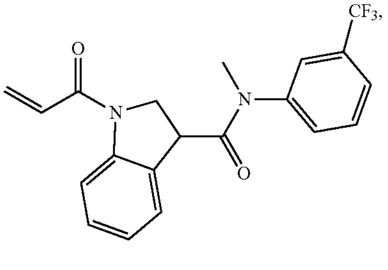
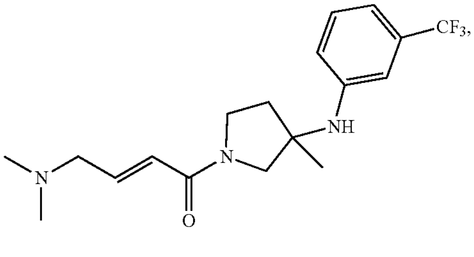

-continued
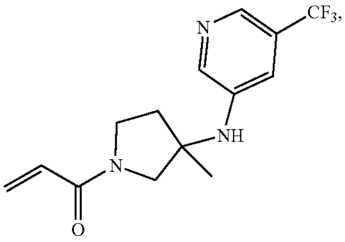
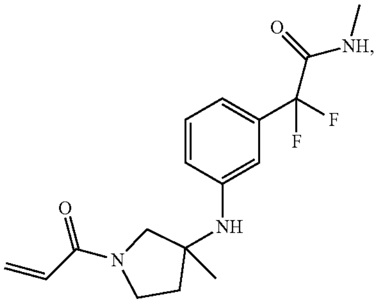
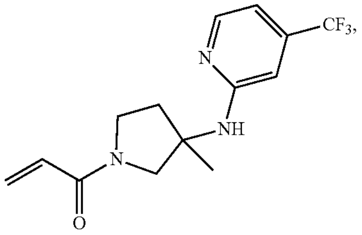
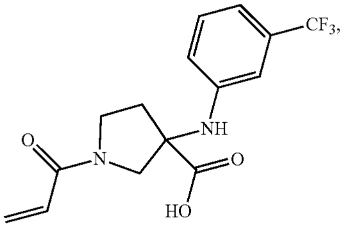
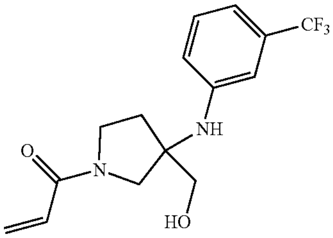
,
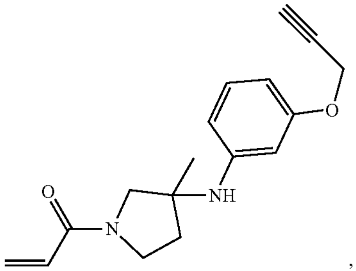
,
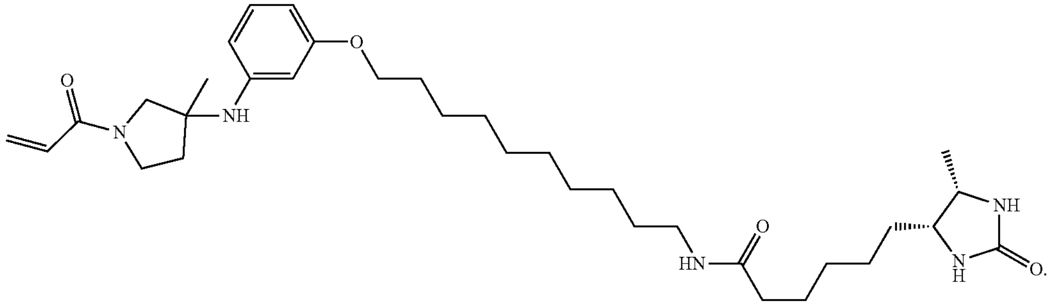
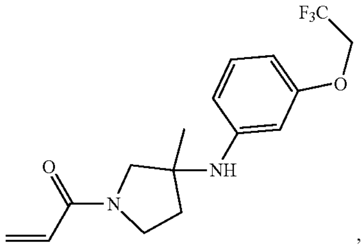
,
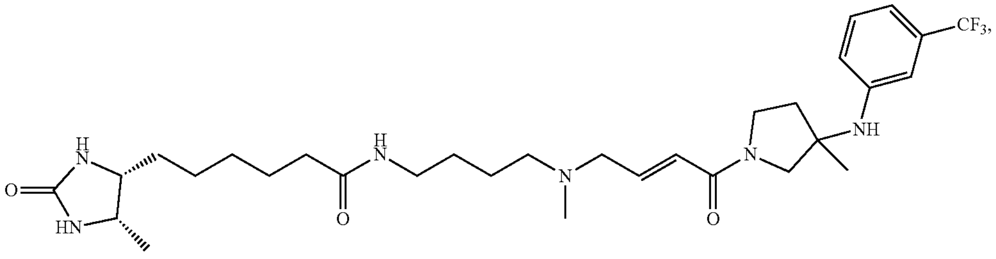

-continued
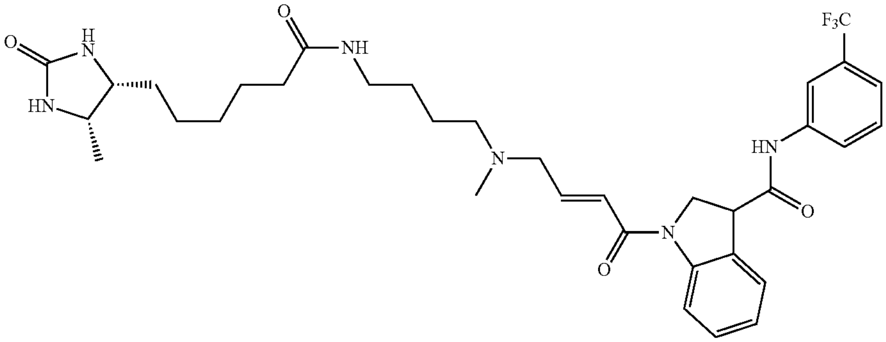
,
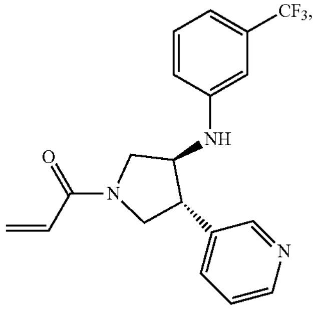
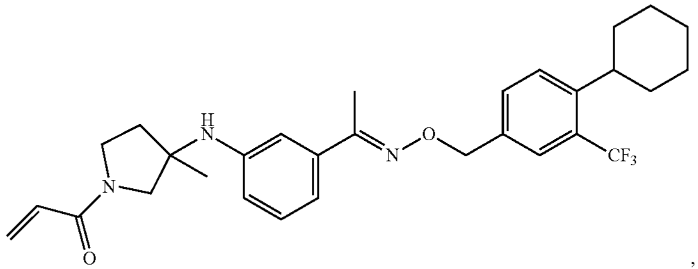
,
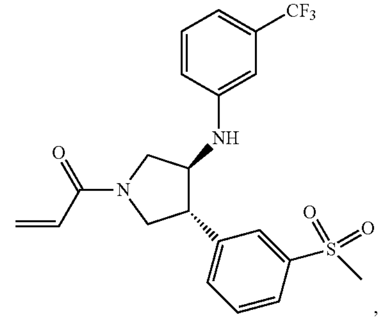
,
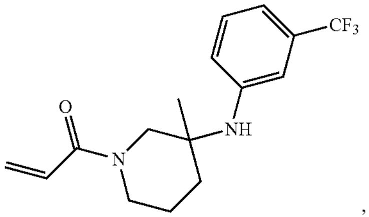
,
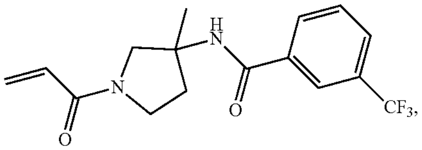
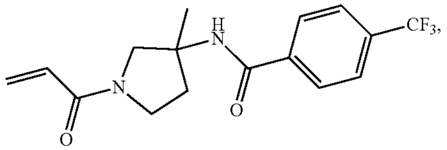
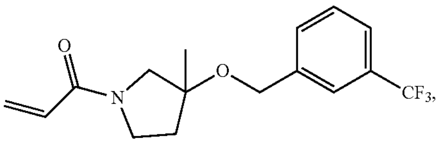
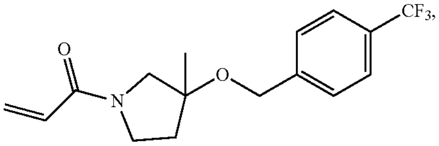

-continued
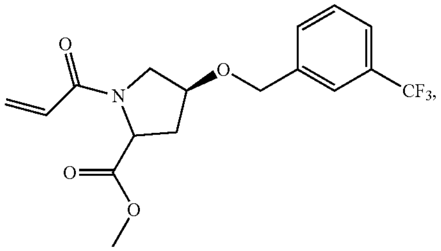
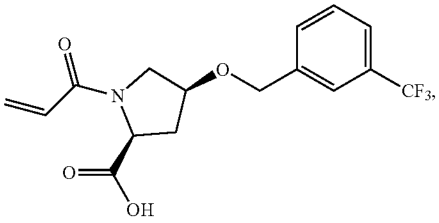
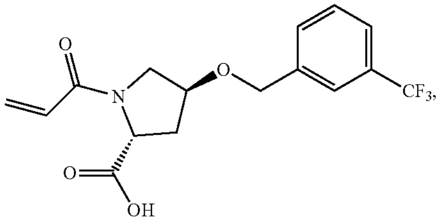
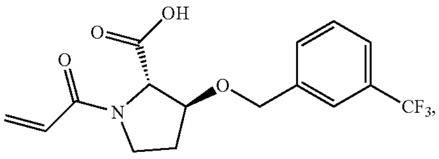
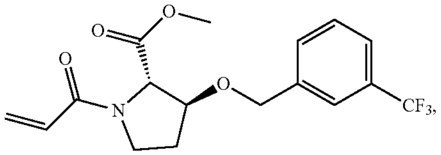
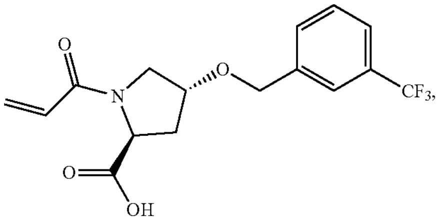
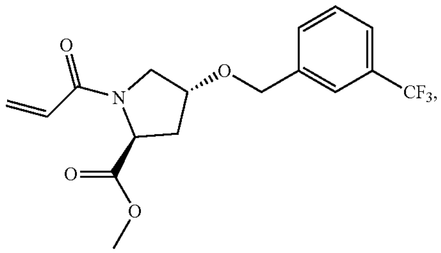
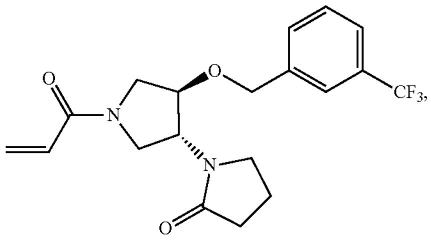
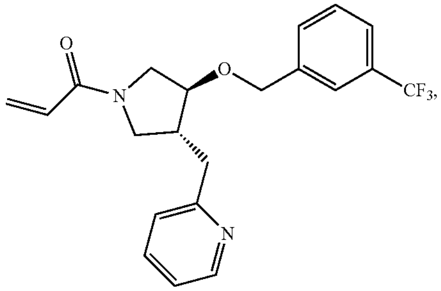
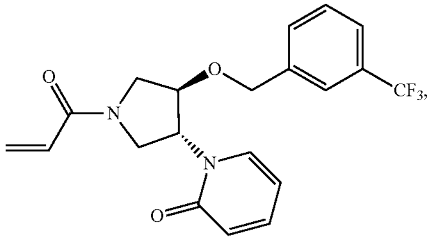
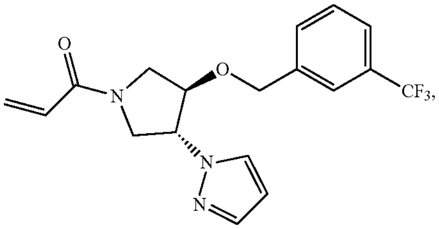
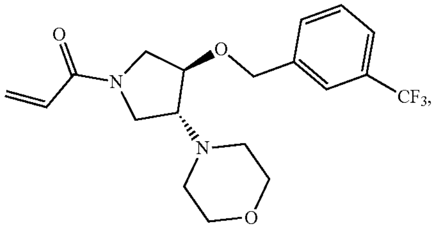

-continued
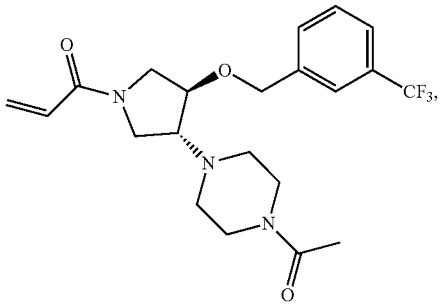
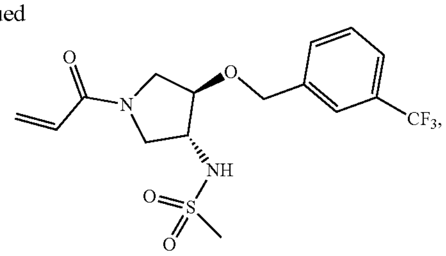
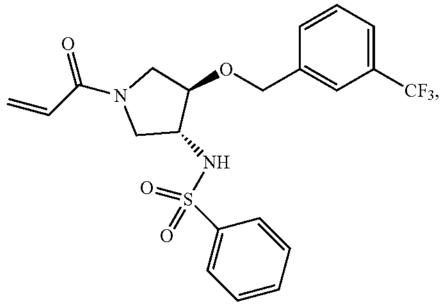
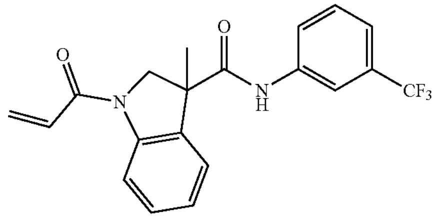
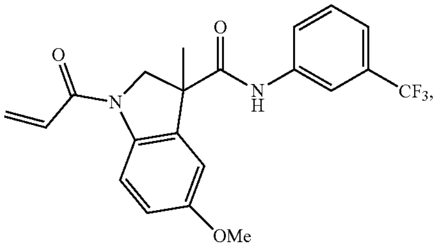
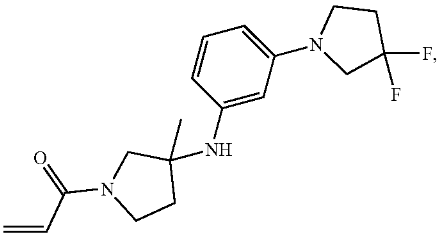
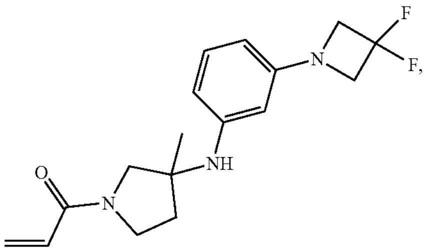
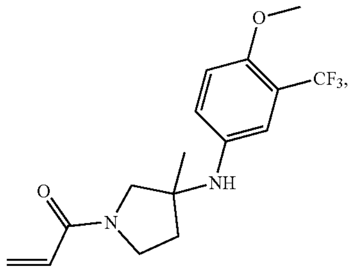
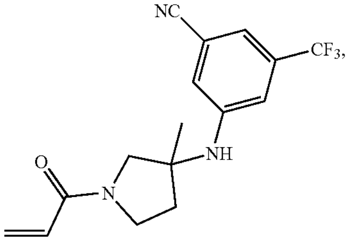
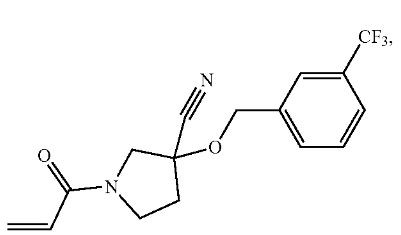
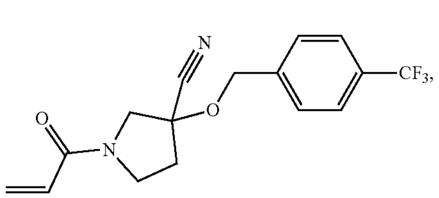
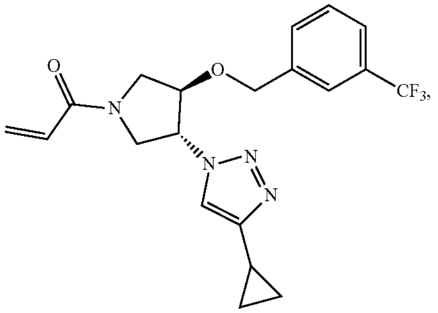

-continued
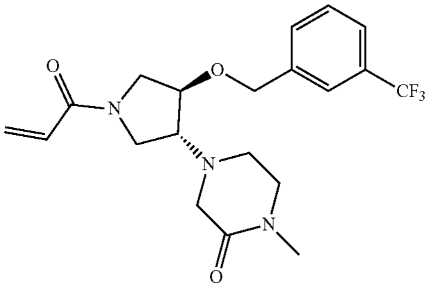
,
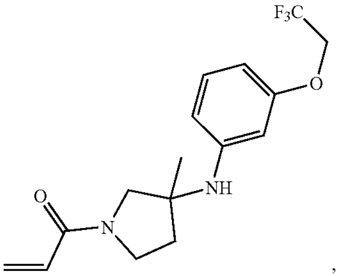
,
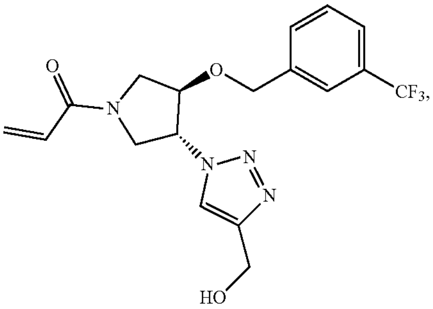
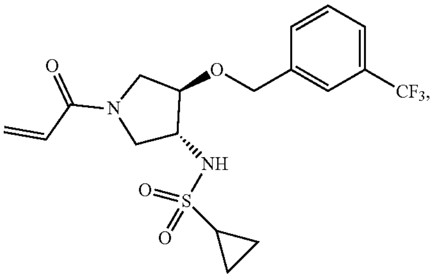
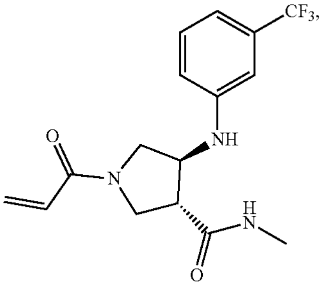
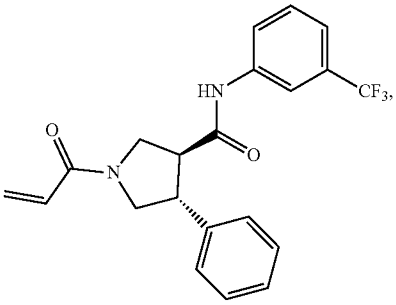
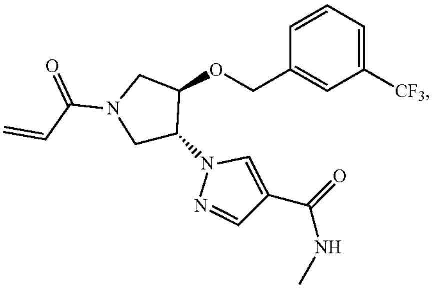
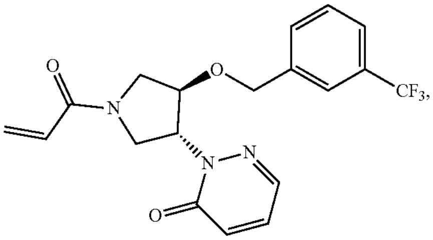
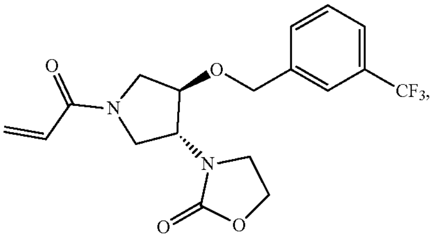
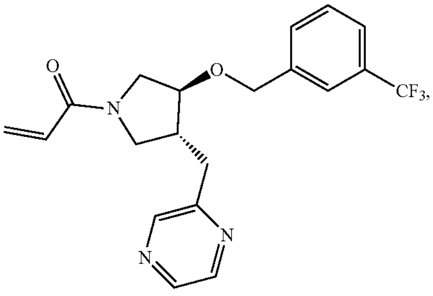

-continued
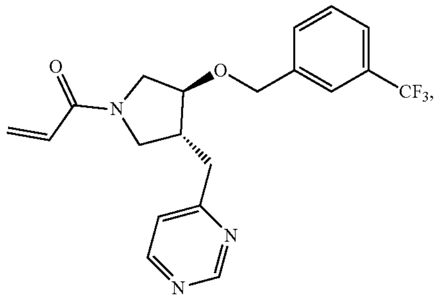
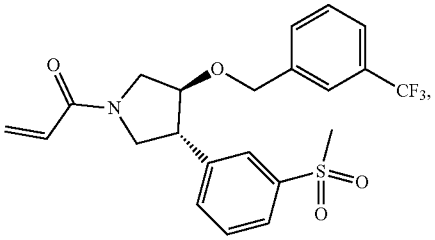
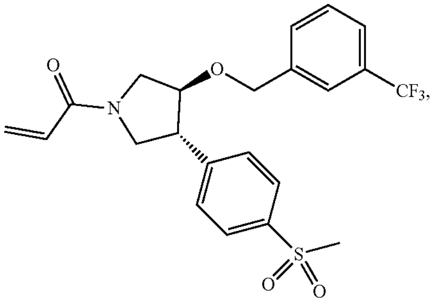
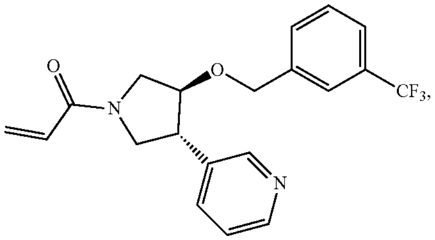
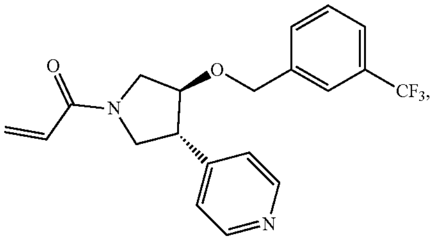
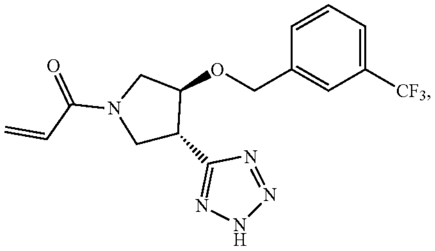
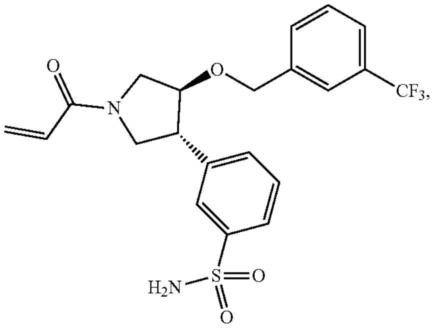
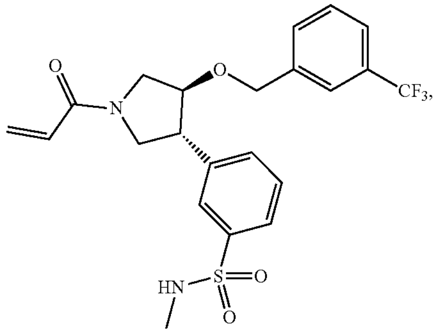
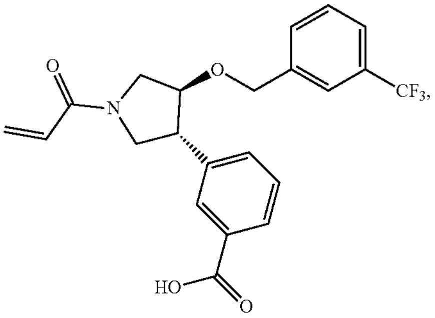

-continued
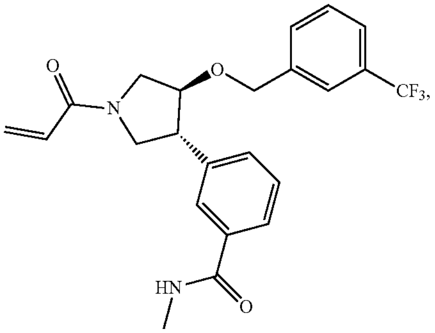
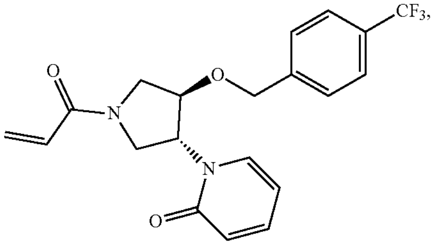
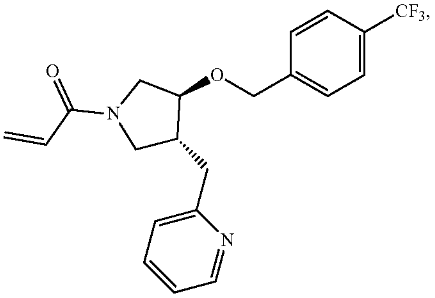
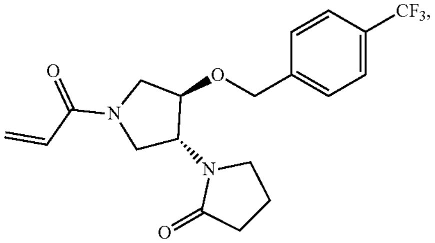
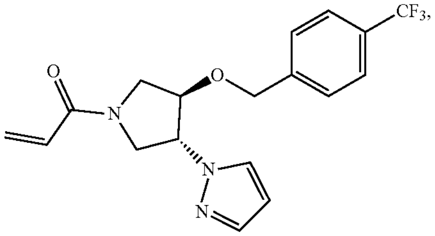
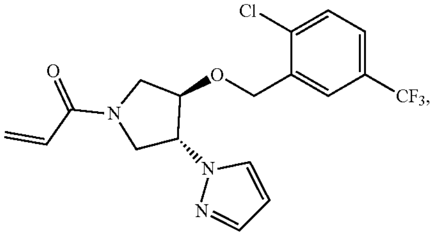
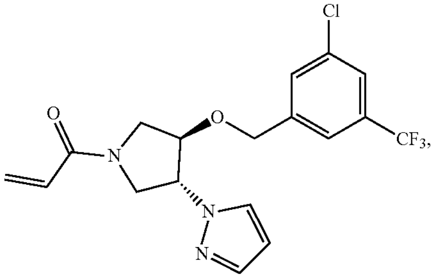
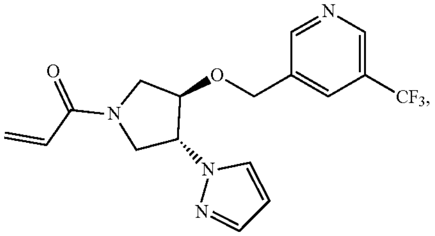
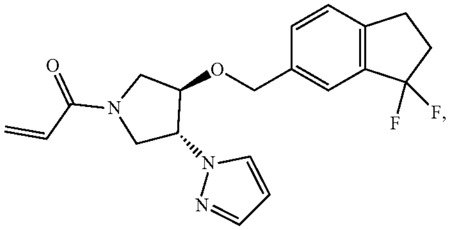
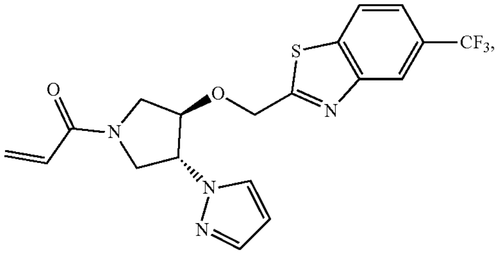

-continued
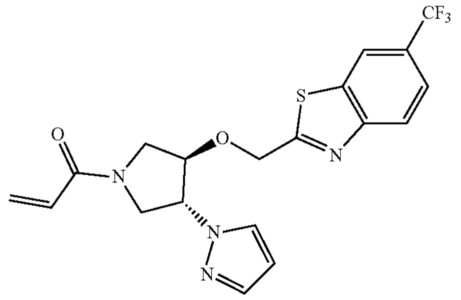
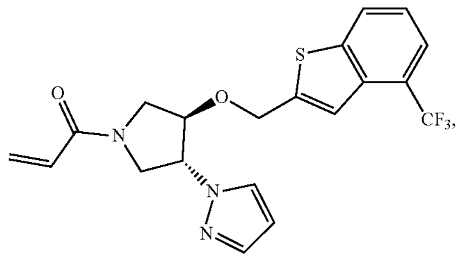
,
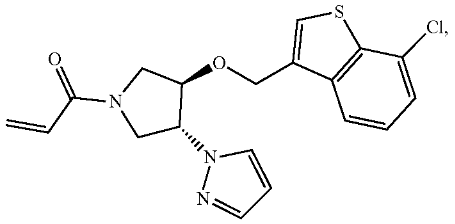
,
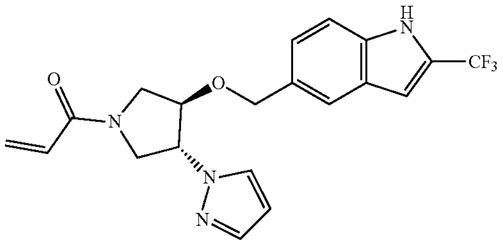
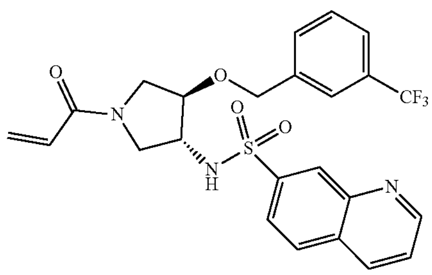
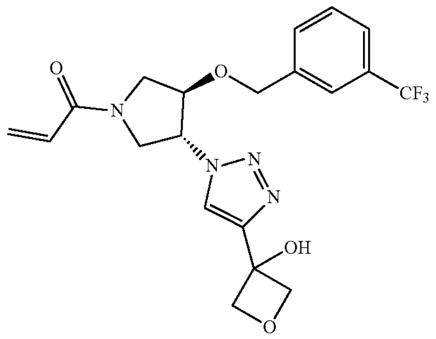
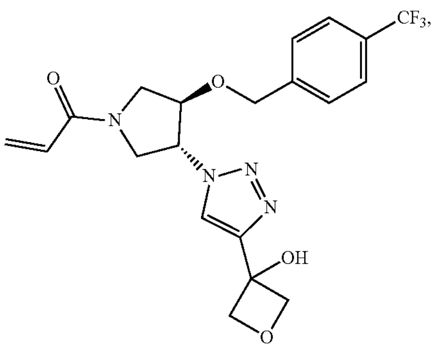
,
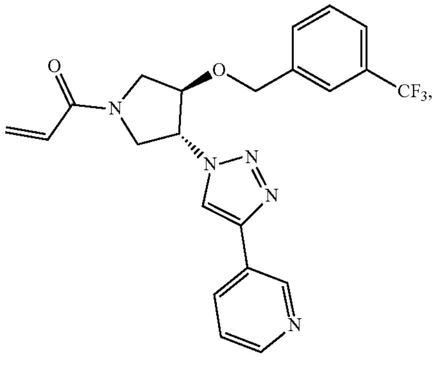
, -continued
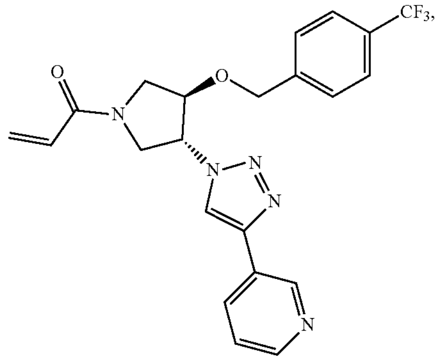
,
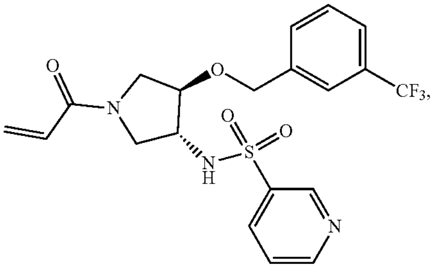
,
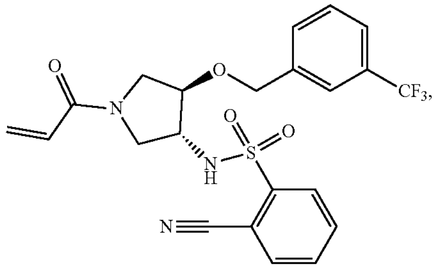
,
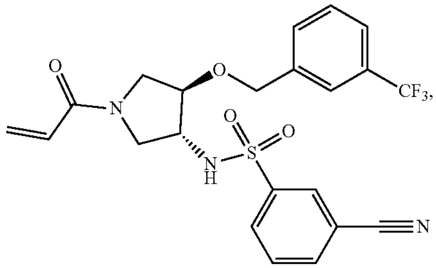
,
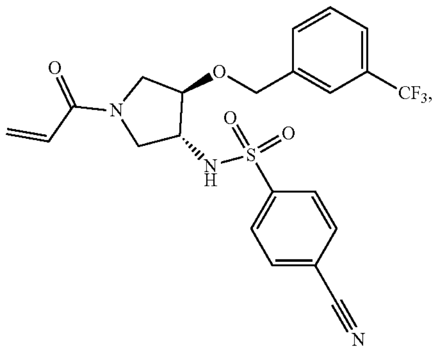
,
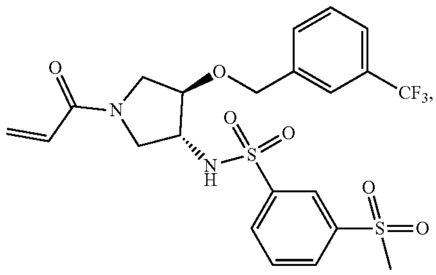
,
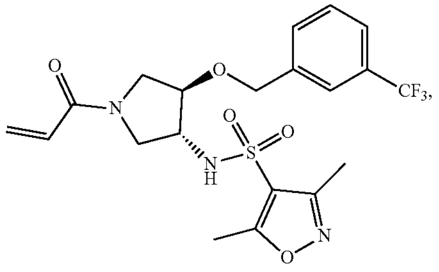
,
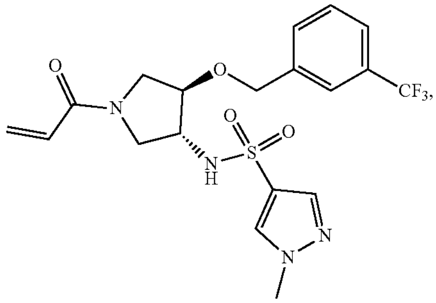
,
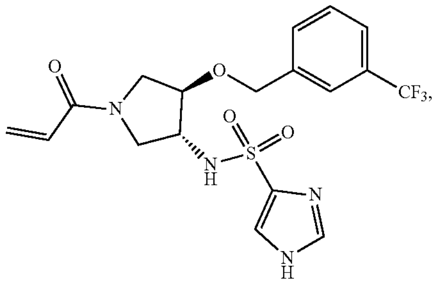
,
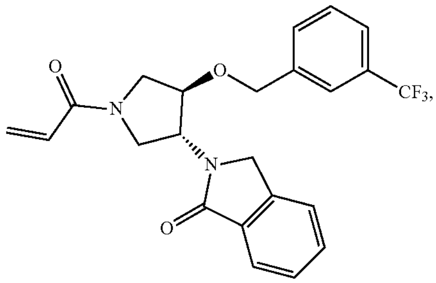
, -continued

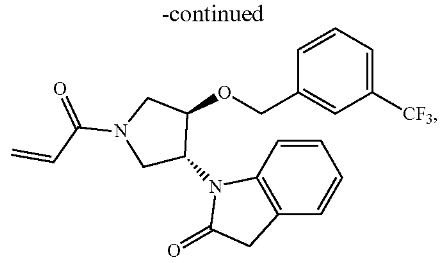

or a pharmaceutically acceptable salt, solvate, hydrate, polymorph, co-crystal, tautomer, stereoisomer, or isotopically labeled derivative thereof.

8. The compound of claim 1, wherein the compound is of the formula:

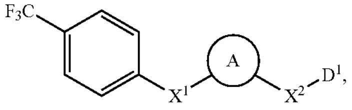

or a pharmaceutically acceptable salt, solvate, hydrate, polymorph, co-crystal, tautomer, stereoisomer, or isotopically labeled derivative thereof.

9. The compound of claim 8, or a pharmaceutically acceptable salt thereof.

10. The compound of claim 1, or a pharmaceutically acceptable salt, solvate, hydrate, polymorph, co-crystal, tautomer, stereoisomer, or isotopically labeled derivative thereof, of the formula:

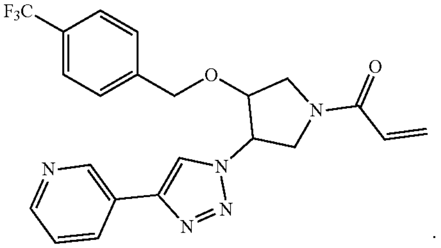 [SMILES: C=CC(=O)N1CC(OCc2ccc(C(F)(F)F)cc2)C(n2cc(-c3cccnc3)nn2)C1]

11. The compound of claim 1, wherein the compound is

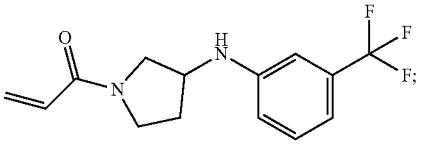 [SMILES: C=CC(=O)N1CCC(Nc2cccc(C(F)(F)F)c2)C1]

or a pharmaceutically acceptable salt, solvate, hydrate, polymorph, co-crystal, tautomer, stereoisomer, or isotopically labeled derivative thereof.

12. A compound of Formula (I-e):

(I-e)

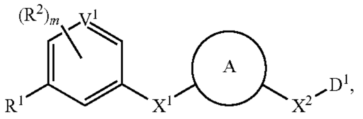

or a pharmaceutically acceptable salt, solvate, hydrate, tautomer, stereoisomer or isotopically labeled derivative thereof wherein:

$R^1$ is hydrogen, trifluoromethyl, or $N(R^a)(R^b)$, wherein $R^a$ is optionally substituted alky;

$R^b$ is optionally substituted alkyl, or $R^a$ and $R^b$ together with the nitrogen atom to which they are attached form a heterocycle;

$R^2$ is hydrogen, halogen, optionally substituted acyl, optionally substituted alkyl, haloalkyl, optionally substituted heteroalkyl, trifluoromethyl, optionally substituted alkenyl, optionally substituted alkynyl, optionally substituted carbocyclyl, optionally substituted heterocyclyl, optionally substituted aryl, optionally substituted heteroaryl, $—OR^c$, $—NO_2$, $—N(R^c)_2$, or $—SR^c$, wherein $R^c$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally, $R^2$ can be joined together with $X^1$ to form an optionally substituted heterocyclic ring;

A is an optionally substituted heterocyclic ring, such that: i) Ring A is an optionally substituted heterocyclic ring wherein each heteroatom is selected from nitrogen and sulfur when $X^1$ is a bond, and ii) Ring A is not indolinyl when $X^1$ is —O—;

$V^1$ is $—C(R^2)—$;

$X^1$ is a bond or O, S, $—CH_2N(R^d)—$, or $—N(R^d)—$, wherein $R^d$ is a bond, hydrogen, substituted or unsubstituted $C_{1-6}$ alkyl, or a nitrogen protecting group, or optionally $R^d$ can be joined together with one instance of $R^2$ to form an optionally substituted heterocyclic ring;

$X^2$ is a bond;

m is 0, 1, 2, 3 or 4;

$D^1$ is

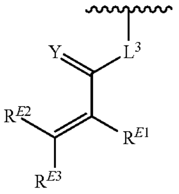

(i-1)

or

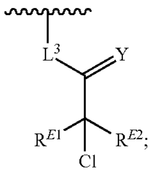

(i-14)

wherein:

$L^3$ is a bond or an optionally substituted $C_{1-4}$ hydrocarbon chain, optionally wherein one or more carbon units of the hydrocarbon chain are independently replaced with —$NR^{L3a}$—, wherein $R^{L3a}$ is hydrogen;

$R^{E1}$ is hydrogen;

$R^{E2}$ is selected from the group consisting of hydrogen and —$CH_2N(R^{E2a})_2$, wherein each occurrence of $R^{E2a}$ is independently selected from the group consisting of alkyl; and $R^{E3}$ is hydrogen;

Y is O.

13. A pharmaceutical composition comprising a compound of claim 1, or a pharmaceutically acceptable salt, solvate, hydrate, polymorph, co-crystal, tautomer, stereoisomer, or isotopically labeled derivative thereof, and a pharmaceutically acceptable excipient.

* * * * *